United States Patent
Gu et al.

(10) Patent No.: US 11,186,602 B2
(45) Date of Patent: *Nov. 30, 2021

(54) GLUCOPYRANOSYL DERIVATIVE AND USE THEREOF

(71) Applicant: SUNSHINE LAKE PHARMA CO., LTD., Guangdong (CN)

(72) Inventors: Zheng Gu, Dongguan (CN); Wuyong Wu, Dongguan (CN); Panpan Kang, Dongguan (CN); Tong Qu, Dongguan (CN); Zongyuan Zhang, Dongguan (CN); Weiming Huang, Dongguan (CN); Tianyun Wu, Dongguan (CN); Yingjun Zhang, Dongguan (CN)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/965,438

(22) PCT Filed: Jan. 29, 2019

(86) PCT No.: PCT/CN2019/073550
§ 371 (c)(1),
(2) Date: Jul. 28, 2020

(87) PCT Pub. No.: WO2019/149178
PCT Pub. Date: Aug. 8, 2019

(65) Prior Publication Data
US 2021/0054013 A1    Feb. 25, 2021

(30) Foreign Application Priority Data

Jan. 31, 2018 (CN) .......................... 201810093154.8

(51) Int. Cl.
    *C07H 9/04*     (2006.01)
    *A61P 3/10*     (2006.01)
    *A61K 31/7048*  (2006.01)
    *A61K 45/06*    (2006.01)

(52) U.S. Cl.
    CPC .......... *C07H 9/04* (2013.01); *A61K 31/7048* (2013.01); *A61K 45/06* (2013.01); *A61P 3/10* (2018.01)

(58) Field of Classification Search
    None
    See application file for complete search history.

(56) References Cited

U.S. PATENT DOCUMENTS

| | | |
|---|---|---|
| 7,635,684 B2 | 12/2009 | Fushimi et al. |
| 7,973,012 B2 | 7/2011 | Kakinuma et al. |
| 8,115,017 B2 | 2/2012 | Kakinuma et al. |
| 8,324,176 B2 | 12/2012 | Fushimi et al. |
| 8,466,113 B2 | 6/2013 | Kakinuma et al. |
| 9,018,249 B2 | 4/2015 | Jain et al. |
| 9,161,945 B2 | 10/2015 | Kakinuma et al. |
| 9,200,025 B2 | 12/2015 | Carson et al. |
| 9,688,710 B2 | 6/2017 | Carson et al. |
| 10,106,569 B2 | 10/2018 | Carson et al. |

FOREIGN PATENT DOCUMENTS

| | | |
|---|---|---|
| CN | 105461762 A | 4/2016 |
| WO | 2007/126117 A1 | 11/2007 |
| WO | 2012/023582 A1 | 2/2012 |
| WO | 2014/187365 A1 | 11/2014 |

OTHER PUBLICATIONS

Wolff, Manfred E. "Burger's Medicinal Chemistry, 5ed, Parti", John Wiley & Sons, 1995, pp. 975-977. (Year: 1995).*
Stella, Journal of Pharmaceutical Sciences, vol. 99, No. 12, Dec. 2010. (Year: 2010).*
Tsimihodimos, European Journal of Pharmacology 838 (2018) 153-156. (Year: 2018).*
Zhang, Acta Pharmaceutical Sinica B 2018;8(5): 721-732. (Year: 2018).*
Apr. 25, 2019 International Search Report issued in International Patent Application No. PCT/CN2019/073550.
Apr. 25, 2019 Written Opinion issued in International Patent Application No. PCT/CN2019/073550.

* cited by examiner

*Primary Examiner* — Layla D Berry
(74) *Attorney, Agent, or Firm* — Oliff PLC

(57) ABSTRACT

A glucopyranosyl derivative is used as an inhibitor of sodium-dependent glucose transporters (SGLTs), particularly being used as an inhibitor of sodium-dependent glucose transporter-1 (SGLT1), and a pharmaceutically acceptable salt or stereoisomer thereof, further relating to a pharmaceutical composition containing the derivative. The compound and a pharmaceutical composition is used thereof in the preparation of a drug for treating diabetes and diabetes-related diseases.

18 Claims, No Drawings

GLUCOPYRANOSYL DERIVATIVE AND USE THEREOF

CROSS-REFERENCE TO RELATED APPLICATION

This application claims the priority and benefits of Chinese Patent Application No. 201810093154.8, filed with the State Intellectual Property Office of China on Jan. 31, 2018, which is incorporated herein by reference in its entirety.

FIELD OF THE INVENTION

The present invention belongs to the field of medicine, and specifically relates to a glucopyranosyl derivative that is used as an inhibitor of sodium-dependent glucose transporter (SGLTs), particularly being used as an inhibitor of sodium-dependent glucose transporter 1 (SGLT1), their preparation methods, pharmaceutical compositions containing the derivatives, and uses of the derivatives and compositions thereof. More specifically, it relates to a compound having Formula (I), or a pharmaceutically acceptable salt, or a stereoisomer thereof, or a pharmaceutical composition containing the compound, and the uses of the compound and the pharmaceutical composition thereof in the manufacture of a medicament for the treatment of diabetes and diabetes-related diseases.

BACKGROUND OF THE INVENTION

Diabetes mellitus is a common chronic disease, characterized by hyperglycemia. The onset of diabetes associates with insulin resistance in peripheral tissue, reduction of insulin in vivo and increase of gluconeogenesis in liver. When the disease cannot be controlled effectively through diet and exercise, insulin or oral hypoglycemic drugs for treatment are needed. At present, hypoglycemic drugs comprise biguanides, sulfonylureas, insulin sensitizers, glinides, α-glucosidase inhibitors and DPP-IV (dipeptidyl peptidase IV) inhibitors, etc. However, these current hypoglycemic drugs have shortcomings. Biguanides can cause lactic acidosis. Sulfonylureas can result in severe hypoglycemia. Improper use of glinides can also cause hypoglycemia. Insulin sensitizers can lead to edema, heart failure and weight gain. α-Glucosidase inhibitors can cause abdominal bloating and diarrhea. DPP-IV inhibitors need to combine with metformin to achieve the desired effect of hypoglycemia. Therefore, there is an urgent need to develop novel, safer, and more effective hypoglycemic agents.

It has been found by research that glucose transporter proteins are a class of carrier proteins embedded in the cell membrane for transporting glucose. Glucose must be in virtue of glucose transporter protein to cross lipid bilayer structure of cell membranes. Glucose transporter proteins are divided into two categories. The first category includes sodium-dependent glucose transporters (SGLTs), and the other category includes glucose transporters (GLUTs). Two major family members of SGLTs are SGLT1 and SGLT2. SGLT1 is mainly distributed in small intestine, kidney, heart and windpipe, predominantly expressed in the intestinal brush border and the S3 segment of the renal proximal tubule, and a few expressed in heart and windpipe, and transports glucose and galactose with a sodium to glucose ratio of 2:1. While SGLT2 is mainly distributed in kidney, predominantly expressed in the S1 segment of the renal proximal tubule, and transports glucose with a sodium to glucose ratio of 1:1. In biological bodies, glucose is transported by SGLTs through active transport against a concentration gradient with simultaneous energy consumption. While glucose is transported by GLUTs through facilitated diffusion along a concentration gradient without energy consumption in the transport process. Research indicates that normally plasma glucose is filtered in the kidney glomeruli in which 90% of glucose in the early S1 segment of the renal tubule is actively transported to epithelial cells by SGLT2 and 10% of glucose in the distal S3 segment of the renal tubule is actively transported to epithelial cells by SGLT1, and then transported to peripheral capillary network by GLUT of epithelial basement membrane accomplishing reabsorption of glucose by renal tubules. Hence, SGLTs is the first stage in regulation of glucose metabolism in cells, and an ideal target for treating diabetes effectively. Inhibiting SGLTs would not influence the normal anti-regulatory mechanism of glucose and cause the risk of hypoglycemia. Meanwhile, lowering blood glucose through an increase of renal glucose excretion could promote weight loss in obese patients. It has also been found by research that the mechanism of action of SGLTs inhibitors is independent of pancreatic β cell dysfunction or the degree of insulin resistance. Therefore, the efficacy of SGLTs inhibitors will not decrease with the severe insulin resistance or β-cell failure. SGLTs inhibitors could be used alone or in combination with other hypoglycemic agents, through mechanism complementation to better exert hypoglycemic effect. Therefore, SGLTs inhibitors are ideal and novel hypoglycemic agents.

In addition, it has also been found by research that SGLTs inhibitors can be used for treating diabetes-related complications. Such as retinopathy, neuropathy, kidney disease, insulin resistance caused by glucose metabolic disorder, hyperinsulinemia, hyperlipidemia, obesity, and so on. Meanwhile, SGLTs inhibitors can also be used in combination with current treatment regimens, such as sulphonamides, thiazolidinedione, metformin, and insulin, etc, which can reduce the dose without impacting on the effectiveness of the medicine, and thereby avoid or reduce side effects, and improve patient compliance.

At present, research is mainly focused on the discovery of selective SGLT2 inhibitors. Most SGLTs inhibitors currently in clinical trials, such as dapagliflozin, canagliflozin and empagliflozin, are selective SGLT2 inhibitors. However, recent clinical trial results indicate that SGLT1 inhibitors can exhibit greater benefits provided by inhibiting glucose reabsorption (US Patent Application Publication No. US20110218159). According to reports, patients with congenital SGLT1 abnormalities have insufficient absorption of glucose and galactose, which provides a factual basis for reducing carbohydrate absorption by inhibiting SGLT1 activity. In addition, in OLETF rats and rats suffering from streptease-induced diabetes symptoms, the mRNA and protein of SGLT1 are increased, and glucose absorption is accelerated. Therefore, blocking SGLT1 activity can inhibit the absorption of carbohydrates such as glucose in the small intestine, and subsequently prevent the rise of blood glucose levels. In particular, delaying the absorption of glucose based on the above mechanism can effectively normalize postprandial hyperglycemia. In addition, SGLT1 inhibitors have the ability to increase glucagon-like peptide-1 (GLP-1) levels (Moriya, R. et al., Am J Physiol Endorinol Metab, 297: E1358-E1365 (2009)).

In summary, SGLT1 inhibitors have a good prospect as novel antidiabetic drugs.

SUMMARY OF THE INVENTION

The present invention provides a class of compounds with significant/excellent SGLTs inhibitory activity, especially SGLT1 inhibitory activity, for improving the intestinal environment; or for the treatment of diabetes, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders related to blood concentration, constipation, high blood pressure and their complication. The present invention also provides methods of preparing these compounds, pharmaceutical compositions comprising these compounds, and methods of using these compounds and compositions to prepare medicaments for the above-mentioned diseases in mammals, especially humans. Compared with the existing similar compounds, the compounds of the present invention not only have better pharmacological activity, but also have better in vivo metabolic kinetic properties and in vivo pharmacodynamic properties. Specifically, the compounds of the present invention have excellent SGLT1 inhibitory activity, and therefore have excellent blood glucose lowering and urinary glucose excretion effects. Therefore, the compound provided by the present invention has better druggability compared with the existing similar compounds.

In one aspect, the invention relates to a compound having Formula (I) or a stereoisomer, a geometric isomer, a tautomer, an N-oxide, a solvate, a metabolite, a pharmaceutically acceptable salt, a dimer, a trimer or a prodrug thereof,

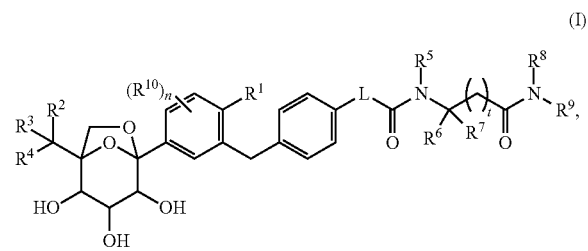

(I)

wherein,

L is $-(CR^aR^b)_q-$, $-CH=CH-(CR^aR^b)_p-$, $-O-(CR^aR^b)_p-$, $-NH-(CR^aR^b)_p-$, $-S-(CR^aR^b)_p-$, $-S(=O)-(CR^aR^b)_p-$ or $-S(=O)_2-(CR^aR^b)_p-$;

q is 1, 2, 3, 4, 5 or 6;

p is 0, 1, 2, 3, 4, 5 or 6;

each $R^a$ and $R^b$ is independently H, D, F, Cl, Br, I, CN, NO$_2$, OH, NH$_2$, $-C(=O)$ OH, $-SH$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino, $C_{1-6}$ haloalkoxy, $C_{3-6}$ cycloalkyl or 3-6 membered heterocyclyl; or, $R^a$ and $R^b$ together with the carbon atom to which they are attached, form a $C_{3-6}$ carbocycle or a 3-6 membered heterocycle;

$R^1$ is H, D, F, Cl, Br, I, OH, CN, NO$_2$, NH$_2$, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ haloalkyl, $C_{1-6}$ haloalkoxy, $C_{1-6}$ alkylamino, $C_{1-6}$ alkylthio, $C_{3-6}$ cycloalkyl or $C_{3-6}$ cycloalkyl-$C_{1-4}$ alkylene, wherein each of $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ haloalkyl, $C_{1-6}$ haloalkoxy, $C_{1-6}$ alkylamino, $C_{1-6}$ alkylthio, $C_{3-6}$ cycloalkyl and $C_{3-6}$ cycloalkyl-$C_{1-4}$ alkylene is independently unsubstituted or substituted with 1, 2, 3 or 4 substituents, and the substituent is independently selected from D, F, Cl, Br, I, CN, NO$_2$, OH, NH$_2$, $-C(=O)$ OH, $-SH$, $C_{1-6}$ alkyl, $C_{1-6}$ haloalkyl, $C_{1-6}$ alkoxy, $C_{1-6}$ alkylamino or $C_{1-6}$ haloalkoxy;

each of $R^2$ and $R^3$ is independently H, D, CN, OH, NH$_2$, $-SH$, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ alkylamino, $C_{3-6}$ cycloalkyl or 3-6 membered heterocyclyl, wherein each $C_{1-6}$ alkyl, $C_{2-6}$ alkenyl, $C_{2-6}$ alkynyl, $C_{1-6}$ alkoxy, $C_{1-6}$ alkylthio, $C_{1-6}$ alkylamino, $C_{3-6}$ cycloalkyl and 3-6 membered heterocyclyl is independently unsubstituted or substituted with 1, 2, 3 or 4 substituents, and the substituent is independently selected from D, F, Cl, Br, I, CN, NO$_2$, OH, NH$_2$, $-C(=O)$ OH, $-SH$, $=O$, $C_{1-6}$ alkyl, $C_{1-6}$ haloalkyl, $C_{1-6}$ alkoxy, $C_{1-6}$ alkylamino or $C_{1-6}$ haloalkoxy;

or, $R^2$ and $R^3$ together with the carbon atom to which they are attached, form carbonyl, or $R^2$ and $R^3$, together with the carbon atom to which they are attached form a $C_{3-6}$ carbocycle or a 3-6 membered heterocycle, wherein each of $C_{3-6}$ carbocycle and 3-6 membered heterocycle is independently unsubstituted or substituted with 1, 2, 3 or 4 substituents, and the substituent is independently selected from D, F, Cl, Br, I, CN, NO$_2$, OH, NH$_2$, $-C(=O)$ OH, $-SH$, $=O$, $C_{1-6}$ alkyl, $C_{1-6}$ haloalkyl, $C_{1-6}$ alkoxy, $C_{1-6}$ alkylamino or $C_{1-6}$ haloalkoxy;

$R^4$ is H, D, $-OR^{4a}$ or $-SR^{4b}$;

each of $R^{4a}$ and $R^{4b}$ is independently H, D, $C_{1-6}$ alkyl, $C_{3-6}$ cycloalkyl, $C_{3-6}$ cycloalkyl-$C_{1-4}$ alkylene, 5-6 membered heterocyclyl, (5-6 membered heterocyclyl)-$C_{1-4}$ alkylene, $C_{6-10}$ aryl, $C_{6-10}$ aryl-$C_{1-4}$ alkylene, 5-6 membered heteroaryl or (5-6 membered heteroaryl)-$C_{1-4}$ alkylene, wherein each $C_{1-6}$ alkyl, $C_{3-6}$ cycloalkyl, $C_{3-6}$ cycloalkyl-$C_{1-4}$ alkylene, 5-6 membered heterocyclyl, (5-6 membered heterocyclyl)-$C_{1-4}$ alkylene, $C_{6-10}$ aryl, $C_{6-10}$ aryl-$C_{1-4}$ alkylene, 5-6 membered heteroaryl and (5-6 membered heteroaryl)-$C_{1-4}$ alkylene is independently unsubstituted or substituted with 1, 2, 3 or 4 substituents, and the substituent is independently selected from D, F, Cl, Br, I, CN, NO$_2$, OH, NH$_2$, $-C(=O)$ OH, $-SH$, $=O$, $C_{1-6}$ alkyl, $C_{1-6}$ haloalkyl, $C_{1-6}$ alkoxy, $C_{1-6}$ alkylamino or $C_{1-6}$ haloalkoxy;

each $R^{10}$ is H, D, F, Cl, Br, I, OH, CN, NO$_2$, NH$_2$, $C_{1-6}$ alkyl or $C_{1-6}$ alkoxy;

$R^5$ is H, D, $C_{1-6}$ alkyl, $C_{1-6}$ haloalkyl, $C_{3-8}$ cycloalkyl, 3-8 membered heterocyclyl, $C_{6-10}$ aryl or 5-8 membered heteroaryl, wherein each of $C_{1-6}$ alkyl, $C_{1-6}$ haloalkyl, $C_{3-8}$ cycloalkyl, 3-8 membered heterocyclyl, $C_{6-10}$ aryl and 5-8 membered heteroaryl is independently unsubstituted or substituted with 1, 2, 3 or 4 substituents, and the substituent is independently selected from D, F, Cl, Br, I, CN, NO$_2$, OH, NH$_2$, $=O$, $-C(=O)$ OH, $-C(=O)$ NH$_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino, $C_{1-6}$ haloalkoxy, $C_{3-6}$ cycloalkyl, 5-6 membered heterocyclyl, $C_{6-10}$ aryl or 5-6 membered heteroaryl;

each of $R^6$ and $R^7$ is independently H, D, F, Cl, Br, I, CN, NO$_2$, OH, NH$_2$, $C_{1-6}$ alkyl, $C_{1-6}$ alkoxy, $C_{1-6}$ alkylamino, $C_{1-6}$ haloalkyl, $C_{1-6}$ haloalkoxy, $C_{3-8}$ cycloalkyl, 3-8 membered heterocyclyl, $C_{6-10}$ aryl or 5-8 membered heteroaryl, wherein each $C_{1-6}$ alkyl, $C_{1-6}$ alkoxy, $C_{1-6}$ alkylamino, $C_{1-6}$ haloalkyl, $C_{1-6}$ haloalkoxy, $C_{3-8}$ cycloalkyl, 3-8 membered heterocyclyl, $C_{6-10}$ aryl and 5-8 membered heteroaryl is independently unsubstituted or substituted with 1, 2, 3 or 4 substituents, and the substituent is independently selected from D, F, Cl, Br, I, CN, NO$_2$, OH, NH$_2$, $=O$, $-C(=O)$ OH, $-C(=O)$ NH$_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino, $C_{1-6}$ haloalkoxy, $C_{3-6}$ cycloalkyl, 5-6 membered heterocyclyl, $C_{6-10}$ aryl or 5-6 membered heteroaryl;

or, $R^6$ and $R^7$ together with the carbon atom to which are attached, form a $C_{3-8}$ carbocycle, a 3-8 membered heterocycle, a $C_{6-10}$ aromatic ring or a 5-8 membered heteroaromatic ring, wherein each of $C_{3-8}$ carbocycle, 3-8 membered heterocycle, $C_{6-10}$ aromatic ring and 5-8 membered heteroaromatic ring is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

or $R^5$ and $R^6$ together with the atom to which they are attached, or $R^5$ and $R^7$ together with the atom to which they are attached, form a 3-8 membered heterocycle or a 5-8 membered heteroaromatic ring, wherein each 3-8 membered heterocycle and 5-8 membered heteroaromatic ring is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

each of $R^8$ and $R^9$ is independently H, D, $R^eO$—$C_{1-4}$ alkylene, $R^dR^cN$—$C_{1-4}$ alkylene, $C_{1-8}$ alkyl, $C_{1-6}$ haloalkyl, $C_{3-8}$ cycloalkyl, $C_{3-8}$ cycloalkyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-8 membered heteroaryl or (5-8 membered heteroaryl)-$C_{1-4}$ alkylene, wherein each $C_{1-8}$ alkyl, $C_{1-6}$ haloalkyl, $C_{3-8}$ cycloalkyl, $C_{3-8}$ cycloalkyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-8 membered heteroaryl and (5-8 membered heteroaryl)-$C_{1-4}$ alkylene is independently unsubstituted or substituted with 1, 2, 3 or 4 substituents, and the substituent is independently selected from D, F, Cl, Br, I, CN, $NO_2$, =O, —$OR^e$, —$NR^cR^d$, —C(=O)$OR^e$, —C(=O) $NHR^f$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

or, $R^8$ and $R^9$ together with the nitrogen atom to which they are attached, form a 3-8 membered heterocycle or a 5-8 membered heteroaromatic ring, wherein each of 3-8 membered heterocycle and 5-8 membered heteroaromatic ring is independently unsubstituted or substituted with 1, 2, 3 or 4 substituents, and the substituent is independently selected from D, F, Cl, Br, I, CN, $NO_2$, =O, —$OR^e$, —$NR^cR^d$, —C(=O)$OR^e$, —C(=O)$NHR^f$, $C_{1-6}$ alkyl, $C_{2-6}$ alkenyl, $C^{2-6}$ alkynyl, $C_{1-6}$ haloalkyl, $C_{1-6}$ alkoxy, $C_{1-6}$ alkylamino or $C_{1-6}$ haloalkoxy;

each $R^c$, $R^d$, $R^e$ and $R^f$ is independently H, D, $C_{1-6}$ alkyl, $C_{1-6}$ haloalkyl, $C_{3-8}$ cycloalkyl, $C_{3-8}$ cycloalkyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-8 membered heteroaryl or (5-8 membered heteroaryl)-$C_{1-4}$ alkylene, wherein each $C_{1-6}$ alkyl, $C_{1-6}$ haloalkyl, $C_{3-8}$ cycloalkyl, $C_{3-8}$ cycloalkyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-8 membered heteroaryl and (5-8 membered heteroaryl)-$C_{1-4}$ alkylene is independently unsubstituted or substituted with 1, 2, 3 or 4 substituents, and the substituent is independently selected from D, F, Cl, Br, I, CN, $NO_2$, OH, —$NH_2$, =O, —C(=O) OH, —C(=O)$NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

or, $R^c$ and $R^d$ together with the nitrogen atom to which they are attached, form a 3-8 membered heterocycle or a 5-8 membered heteroaromatic ring, wherein each of 3-8 membered heterocycle and 5-8 membered heteroaromatic ring is independently unsubstituted or substituted with 1, 2, 3 or 4 substituents, and the substituent is independently selected from D, F, Cl, Br, I, CN, $NO_2$, =O, OH, —$NH_2$, —C(=O) OH, —C(=O)$NH_2$, $C_{1-6}$ alkyl, $C_{2-6}$ alkenyl, $C^{2-6}$ alkynyl, $C_{1-6}$ haloalkyl, $C_{1-6}$ alkoxy, $C_{1-6}$ alkylamino or $C_{1-6}$ haloalkoxy;

n is 0, 1, 2 or 3;

t is 0, 1, 2, 3, 4, 5 or 6; with the proviso that when $R^5$ and $R^8$ are both H, and $R^9$ is

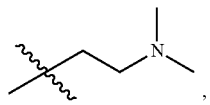

t is not 0.

In other embodiments, the present invention relates to a compound having formula (II), or a stereoisomer, a geometric isomer, a tautomer, an N-oxide, a solvate, a metabolite, a pharmaceutically acceptable salt, a dimer, a trimer or a prodrug thereof,

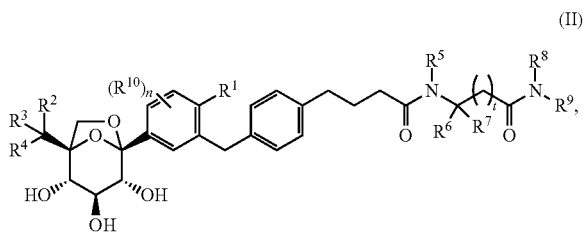

wherein $R^1$, $R^2$, $R^3$, $R^4$, $R^5$, $R^6$, $R^7$, $R^8$, $R^9$, $R^{10}$, n and t have the definitions described in the present invention.

In other embodiments, $R^1$ is H, D, F, Cl, Br, I, OH, CN, $NO_2$, $NH_2$, methyl, ethyl, n-propyl, isopropyl, propenyl, propynyl, methoxy, ethoxy, hydroxymethyl, trifluoromethyl, trifluoroethyl, monofluoromethyl, trifluoromethoxy, difluoromethoxy, methylamino, cyclopropyl, cyclobutyl, cyclopentyl, cyclohexyl or cyclopropyl-methylene, wherein each of methyl, ethyl, n-propyl, isopropyl, propenyl, propynyl, methoxy, ethoxy, hydroxymethyl, trifluoroethyl, monofluoromethyl, difluoromethoxy, methylamino, cyclopropyl, cyclobutyl, cyclopentyl, cyclohexyl and cyclopropyl-methylene is independently unsubstituted or substituted with 1, 2, 3, or 4 substituents, and the substituent is independently selected from D, F, Cl, Br, I, CN, $NO_2$, OH, $NH_2$, —C(=O) OH, —SH, methyl, ethyl, n-propyl, isopropyl, trifluoromethyl, methoxy, ethoxy, methylamino, trifluoromethoxy or difluoromethoxy.

In some embodiments, each of $R^2$ and $R^3$ is independently H, D, CN, OH, $NH_2$, —SH, methyl, ethyl, n-propyl, isopropyl, vinyl, propynyl, methoxy, ethoxy, methylthio, methylamino, cyclopropyl, cyclobutyl, cyclopentyl, cyclohexyl or 5-6 membered heterocyclyl, wherein each methyl, ethyl, n-propyl, isopropyl, vinyl, propynyl, methoxy, ethoxy, methylthio, methylamino, cyclopropyl, cyclobutyl, cyclopentyl, cyclohexyl and 5-6 membered heterocyclyl is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, methyl, ethyl, n-propyl, isopropyl, trifluoromethyl, methoxy, ethyloxy, methylamino, trifluoromethoxy or difluoromethoxy;

or, $R^2$ and $R^3$, together with the carbon atom to which they are attached, form carbonyl;

or, $R^2$ and $R^3$ together with the carbon atom to which they are attached, form cyclopropane, cyclobutane, cyclopentane, cyclohexane or a 5-6 membered heterocycle, wherein each of cyclopropane, cyclobutane, cyclopentane, cyclohexane and a 5-6 membered heterocycle is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, methyl, ethyl, n-propyl, isopropyl, trifluoromethyl, methoxy, ethoxy, methylamino, trifluoromethoxy or difluoromethoxy.

In some embodiments, $R^4$ is H, D, —$OR^{4a}$ or —$SR^{4b}$;

each of $R^{4a}$ and $R^{4b}$ is independently H, D, methyl, ethyl, n-propyl, isopropyl, cyclopropyl, cyclobutyl, cyclopentyl, cyclohexyl, $C_{3-6}$ cycloalkyl-$C_{1-2}$ alkylene, tetrahydrofuranyl, tetrahydrothienyl, tetrahydropyranyl, piperidinyl, morpholinyl, thiomorpholinyl, piperazinyl, (5-6 membered heterocyclyl)-$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl or (5-6 membered heteroaryl)-$C_{1-2}$ alkylene, wherein each methyl, ethyl, n-propyl, isopropyl, cyclopropyl, cyclobutyl, cyclopentyl, cyclohexyl, $C_{3-6}$ cycloalkyl-$C_{1-2}$ alkylene, tetrahydrofuranyl, tetrahydrothienyl, tetrahydropyranyl, piperidinyl, morpholinyl, thiomorpholinyl, piperazinyl, (5-6 membered heterocyclyl)-$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl and (5-6 membered heteroaryl)-$C_{1-2}$ alkylene is independently unsubstituted or substituted with 1, 2, 3, or 4 substituents, and the substituent is independently selected from D, F, Cl, Br, I, CN, $NO_2$, OH, $NH_2$, —C(=O) OH, —SH, =O, methyl, ethyl, n-propyl, isopropyl, trifluoromethyl, methoxy, ethoxy, methylamino, trifluoromethoxy or difluoromethoxy.

In other embodiments, $R^{10}$ is H, D, F, Cl, Br, I, OH, CN, $NO_2$, $NH_2$, methyl, ethyl, n-propyl, isopropyl, methoxy or ethoxy.

In other embodiments, $R^5$ is H, D, $C_{1-4}$ alkyl, $C_{1-4}$ haloalkyl, $C_{3-6}$ cycloalkyl, 5-6 membered heterocyclyl, $C_{6-10}$ aryl or 5-6 membered heteroaryl, wherein each of $C_{1-4}$ alkyl, $C_{1-4}$ haloalkyl, $C_{3-6}$ cycloalkyl, 5-6 membered heterocyclyl, $C_{6-10}$ aryl and 5-6 membered heteroaryl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino, $C_{1-4}$ haloalkoxy, $C_{3-6}$ cycloalkyl, 5-6 membered heterocyclyl, $C_{6-10}$ aryl or 5-6 membered heteroaryl;

each of $R^6$ and $R^7$ is independently H, D, F, Cl, Br, I, CN, $NO_2$, OH, $NH_2$, $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl, 5-6 membered heterocyclyl, $C_{6-10}$ aryl or 5-6 membered heteroaryl, wherein each $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl, 5-6 membered heterocyclyl, $C_{6-10}$ aryl and 5-6 membered heteroaryl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino, $C_{1-4}$ haloalkoxy, $C_{3-6}$ cycloalkyl, 5-6 membered heterocyclyl, $C_{6-10}$ aryl or 5-6 membered heteroaryl;

or, $R^6$ and $R^7$ together with the carbon atom to which they are attached, form a $C_{3-6}$ carbocycle, a 5-6 membered heterocycle, a $C_{6-10}$ aromatic ring or a 5-6 membered heteroaromatic ring, wherein each of $C_{3-6}$ carbocycle, 5-6 membered heterocycle, $C_{6-10}$ aromatic ring and 5-6 membered heteroaromatic ring is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy;

or $R^5$ and $R^6$ together with the atom to which they are attached, or $R^5$ and $R^7$ together with the atom to which they are attached, form a 3-6 membered heterocycle or a 5-6 membered heterocycle, wherein each 3-6 membered heterocycle and 5-6 membered heterocycle is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy.

In still other embodiments, $R^5$ is H, D, methyl, ethyl, n-propyl, isopropyl, n-butyl, isobutyl, tert-butyl, trifluoromethyl, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each of methyl, ethyl, n-propyl, isopropyl, n-butyl, isobutyl, tert-butyl, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy, difluoromethoxy, cyclopropyl, cyclobutyl, cyclopentyl or phenyl;

each of $R^6$ and $R^7$ is independently H, D, F, Cl, Br, I, CN, $NO_2$, OH, $NH_2$, methyl, ethyl, n-propyl, isopropyl, n-butyl, isobutyl, tert-butyl, methoxy, ethoxy, methylamino, trifluoromethyl, trifluoromethoxy, difluoromethoxy, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each methyl, ethyl, n-propyl, isopropyl, n-butyl, isobutyl, tert-butyl, methoxy, ethoxy, methylamino, difluoromethoxy, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy, difluoromethoxy, cyclopropyl, cyclobutyl, cyclopentyl or phenyl;

or, $R^6$ and $R^7$ together with the carbon atom to which they are attached, form cyclopropane, cyclobutane, cyclopentane, cyclohexane, pyrrolidine, tetrahydrofuran, tetrahydrothiophene, tetrahydropyran, tetrahydrothiopyran, piperidine, morpholine, thiomorpholine, piperazine, benzene ring, furan, pyrrole, pyridine, pyrazole, imidazole, triazole, tetrazole, oxazole, oxadiazole, 1,3,5-triazine, thiazole, thiophene, pyrazine, pyridazine or pyrimidine, wherein each of cyclopropane, cyclobutane, cyclopentane, cyclohexane, pyrrolidine, tetrahydrofuran, tetrahydrothiophene, tetrahydropyran, tetrahydrothiopyran, piperidine, morpholine, thiomorpholine, piperazine, benzene ring, furan, pyrrole, pyridine, pyrazole, imidazole, triazole, tetrazole, oxazole, oxadiazole, 1,3,5-triazine, thiazole, thiophene, pyrazine, pyridazine and pyrimidine is independently unsubstituted or substituted with 1, 2, 3, or 4 substituents, and the substituent is independently selected from D, F, Cl, Br, I, CN, $NO_2$, OH, $NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy or difluoromethoxy;

or $R^5$ and $R^6$ together with the atom to which they are attached, or $R^5$ and $R^7$ together with the atom to which they are attached, form aziridine, azetidine, pyrrolidine, pyrazolidine, imidazolidine, oxazolidine, thiazolidine, piperidine, morpholine, thiomorpholine, piperazine, pyrrole, pyridine, pyrazole, imidazole, triazole, tetrazole, oxazole, oxadiazole, 1,3,5-triazine, thiazole, pyrazine, pyridazine or pyrimidine, wherein each aziridine, azetidine, pyrrolidine, pyrazolidine, imidazolidine, oxazolidine, thiazolidine, piperidine, morpholine, thiomorpholine, piperazine, pyrrole, pyridine, pyrazole, imidazole, triazole, tetrazole, oxazole, oxadiazole, 1,3,5-triazine, thiazole, pyrazine, pyridazine and pyrimidine is independently unsubstituted or substituted with 1, 2, 3, or 4 substituents, and the substituent is independently selected from D, F, Cl, Br, I, CN, $NO_2$, OH, $NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy or difluoromethoxy.

In other embodiments, each of $R^8$ and $R^9$ is independently H, D, $R^cO$—$C_{1-4}$ alkylene, $R^dR^cN$—$C_{1-4}$ alkylene, $C_{1-6}$ alkyl, $C_{1-4}$ haloalkyl, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene, wherein each $C_{1-6}$ alkyl, $C_{1-4}$ haloalkyl, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl and (5-6 membered heteroaryl)-$C_{1-2}$ alkylene is independently unsubstituted or substituted with 1, 2, 3 or 4 substituents, and the substituent is independently selected from D, F, Cl, Br, I, CN, $NO_2$, =O, —$OR^e$, —$NR^cR^d$, —C(=O)$OR^e$, —C(=O) $NHR^f$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy;

or, $R^8$ and $R^9$ together with the nitrogen atom to which they are attached, form a 3-6 membered heterocycle or a 5-6 membered heteroaromatic ring, wherein each of 3-6 membered heterocycle and 5-6 membered heteroaromatic ring is independently unsubstituted or substituted with 1, 2, 3 or 4 substituents, and the substituent is independently selected from D, F, Cl, Br, I, CN, $NO_2$, =O, —$OR^e$, —$NR^cR^d$, —C(=O)$OR^e$, —C(=O)$NHR^f$, $C_{1-4}$ alkyl, $C_{2-4}$ alkenyl, $C^{2-4}$ alkynyl, $C_{1-4}$ haloalkyl, $C_{1-4}$ alkoxy, $C_{1-4}$ alkylamino or $C_{1-4}$ haloalkoxy.

In still other embodiments, each of $R^8$ and $R^9$ is independently H, D, $R^dR^cN$—$C_{1-4}$ alkylene, methyl, ethyl, n-propyl, isopropyl, n-butyl, isobutyl, tert-butyl, n-pentyl, n-hexyl, trifluoromethyl, cyclopropyl, cyclobutyl, cyclopentyl, cyclohexyl, $C_{3-6}$ cycloalkyl-$C_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl)-$C_{1-2}$ alkylene, phenyl, $C_{6-10}$ aryl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl or (5-6 membered heteroaryl)-$C_{1-2}$ alkylene, wherein each methyl, ethyl, n-propyl, isopropyl, n-butyl, isobutyl, tert-butyl, n-pentyl, n-hexyl, cyclopropyl, cyclobutyl, cyclopentyl, cyclohexyl, $C_{3-6}$ cycloalkyl-$C_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl)-$C_{1-2}$ alkylene, phenyl, $C_{6-10}$ aryl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl and (5-6 membered heteroaryl)-$C_{1-2}$ alkylene is independently unsubstituted or substituted with 1, 2, 3, or 4 substituents, and the substituent is independently selected from D, F, Cl, Br, I, CN, $NO_2$, =O, —OH, —$NR^cR^d$, —C(=O)OH, —C(=O) $NH_2$, methyl, ethyl, n-propyl, vinyl, ethynyl, trifluoromethyl, methoxy, ethoxy, methylamino, trifluoromethoxy or difluoromethoxy;

or, $R^8$ and $R^9$ together with the nitrogen atom to which they are attached, form aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine or pyrimidine, wherein each of aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine and pyrimidine is independently unsubstituted or substituted with 1, 2, 3, or 4 substituents, and the substituent is independently selected from D, F, Cl, Br, I, CN, $NO_2$, =O, —OH, —$NR^cR^d$, —C(=O) OH, —C(=O) $NH_2$, methyl, ethyl, n-propyl, vinyl, ethynyl, trifluoromethyl, methoxy, ethoxy, methylamino, trifluoromethoxy or difluoromethoxy.

In some embodiments, each $R^c$, $R^d$, $R^e$ and $R^f$ is independently H, D, $C_{1-4}$ alkyl, $C_{1-4}$ haloalkyl, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene, wherein each $C_{1-4}$ alkyl, $C_{1-4}$ haloalkyl, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl and (5-6 membered heteroaryl)-$C_{1-2}$ alkylene is independently unsubstituted or substituted with 1, 2, 3 or 4 substituents, and the substituent is independently selected from D, F, Cl, Br, I, CN, $NO_2$, OH, —$NH_2$, =O, —C(=O)OH, —C(=O)$NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy;

or, $R^c$ and $R^d$ together with the nitrogen atom to which they are attached, form a 3-6 membered heterocycle or a 5-6 membered heteroaromatic ring, wherein each of 3-6 membered heterocycle and 5-6 membered heteroaromatic ring is independently unsubstituted or substituted with 1, 2, 3 or 4 substituents, and the substituent is independently selected from D, F, Cl, Br, I, CN், NO$_2$, =O, OH, —NH$_2$, —C(=O) OH, —C(=O)NH$_2$, C$_{1-4}$ alkyl, C$_{2-4}$ alkenyl, C$^{24}$ alkynyl, C$_{1-4}$ haloalkyl, C$_{1-4}$ alkoxy, C$_{1-4}$ alkylamino or C$_{1-4}$ haloalkoxy.

In still other embodiments, each $R^c$, $R^d$, $R^e$ and $R^f$ is independently H, D, methyl, ethyl, n-propyl, isopropyl, n-butyl, isobutyl, tert-butyl, trifluoromethyl, cyclopropyl, cyclobutyl, cyclopentyl, cyclohexyl, C$_{3-6}$ cycloalkyl-C$_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl)-C$_{1-2}$ alkylene, phenyl, phenyl-C$_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl or (5-6 membered heteroaryl)-C$_{1-2}$ alkylene, wherein each methyl, ethyl, n-propyl, isopropyl, n-butyl, isobutyl, tert-butyl, cyclopropyl, cyclobutyl, cyclopentyl, cyclohexyl, C$_{3-6}$ cycloalkyl-C$_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl)-C$_{1-2}$ alkylene, phenyl, phenyl-C$_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl and (5-6 membered heteroaryl)-C$_{1-2}$ alkylene is independently unsubstituted or substituted with 1, 2, 3, or 4 substituents, and the substituent is independently selected from D, F, Cl, Br, I, CN, NO$_2$, OH, —NH$_2$, =O, —C(=O) OH, —C(=O) NH$_2$, methyl, ethyl, n-propyl, isopropyl, vinyl, ethynyl, trifluoromethyl, methoxy, ethoxy, methylamino, trifluoromethoxy or difluoromethoxy;

or, $R^c$ and $R^d$ together with the nitrogen atom to which they are attached, form aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine or pyrimidine, wherein each of aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine and pyrimidine is independently unsubstituted or substituted with 1, 2, 3, or 4 substituents, and the substituent is independently selected from D, F, Cl, Br, I, CN, NO$_2$, OH, NH$_2$, =O, —C(=O) OH, —C(=O) NH$_2$, methyl, ethyl, n-propyl, isopropyl, vinyl, ethynyl, trifluoromethyl, methoxy, ethoxy, methylamino, trifluoromethoxy or difluoromethoxy.

In other aspect, provided herein is a pharmaceutical composition comprising the compound disclosed herein.

In some embodiments, the pharmaceutical composition of the present invention further comprises a pharmaceutically acceptable carrier, excipient, adjuvant, vehicle or a combination thereof.

In some embodiments, the pharmaceutical composition of the present invention further comprises one or more other additional therapeutic agents, wherein the other additional therapeutic agent is selected from an anti-diabetic drug, an anti-hyperglycemic drug, an anti-obesity drug, an anti-hypertensive drug, an appetite suppressant drug, a lipid-lowering drug, or a combination thereof.

In other embodiments, each anti-diabetic and anti-hyperglycemic drug of the present invention is independently selected from a SGLT2 inhibitor, a biguanide drug, a sulfonylurea drug, a glucosidase inhibitor, a PPAR agonist (peroxisome proliferator-activated receptor agonist), a αP2 inhibitor (fat cell fatty Acid binding protein inhibitor), a PPARα/γ dual activator (peroxisome proliferator-activated receptor α/γ dual activator), a dipeptidyl peptidase IV inhibitor, a glinides drug, an insulin, a glucagon-like peptide-1 inhibitor, a PTP1B inhibitor (protein tyrosine phosphatase 1B inhibitor), a glycogen phosphorylase inhibitor, a glucose-6-phosphatase inhibitor or a combination thereof.

In other embodiments, the anti-obesity drug of the present invention is selected from a central anti-obesity drug, a MCH (black pigment concentrating hormone) receptor antagonist, a neuropeptide Y receptor antagonist, a cannabinoid receptor antagonist, a cerebrointestinal peptide antagonist, a lipase inhibitor, a β3 agonist, a 11β-HSD1 (11β hydroxysteroid dehydrogenase 1) inhibitor, a DGAT-1 (diacylglycerol acyltransferase 1) inhibitor, a peptide appetite inhibitor, a cholecystokinin agonist, a feeding inhibitor or a combination thereof.

In other embodiments, the lipid-lowering drug of the present invention is selected from a MTP inhibitor (microsomal triglyceride transfer protein inhibitor), a HMG-CoA reductase inhibitor (hydroxymethylglutaryl coenzyme A reductase inhibitor), a squalene synthase inhibitor, a betinic acid-type hypolipidemic drug (also known as fibrate hypolipidemic drug), an ACAT inhibitor (acetylcholesterol acetyltransferase inhibitor), a lipoxygenase inhibitor, a cholesterol absorption inhibitor, an ileum sodium ion/bile acid co-transporter inhibitor, an up-regulator of LDL receptor activity, a nicotinic hypolipidemic drug, a bile acid chelate, or a combination thereof.

In still other embodiments, the lipid-lowering drug is pravastatin, simvastatin, atorvastatin, fluvastatin, cerivastatin, atavastatin, rosuvastatin or a combination thereof.

In other aspect, provided herein is use of the compound or the pharmaceutical composition disclosed herein in the manufacture of a medicament for inhibiting SGLT1.

In other aspect, provided herein is use of the compound or the pharmaceutical composition disclosed herein in the manufacture of a medicament for improving the intestinal environment.

In other aspect, provided herein is use of the compound or the pharmaceutical composition disclosed herein in the manufacture of a medicament for preventing or treating a disease, lessening a disease symptom or delaying the progression or onset of a disease, wherein the disease is diabetes, diabetic complication, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders related to blood concentration, constipation, or high blood pressure.

In another aspect, provided herein is a method of inhibiting SGLT1, comprising administering a therapeutically effective amount of the compound of the invention or the pharmaceutical composition of the invention to a subject.

In another aspect, provided herein is a method of improving the intestinal environment, comprising administering a therapeutically effective amount of the compound of the invention or the pharmaceutical composition of the invention to a subject.

In another aspect, provided herein is a method of preventing or treating a disease, lessening a disease symptom or delaying the progression or onset of a disease in a subject comprising administering to the subject a therapeutically effective amount of the compound of the invention or the pharmaceutical composition of the invention, wherein the disease is diabetes, diabetic complication, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders related to blood concentration, constipation, or high blood pressure.

In other aspect, provided herein is the compound or the pharmaceutical composition disclosed herein for use in inhibiting SGLT1.

In other aspect, provided herein is the compound or the pharmaceutical composition disclosed herein for use in improving the intestinal environment.

In other aspect, provided herein is the compound or the pharmaceutical composition disclosed herein for use in preventing or treating a disease, lessening a disease symptom or delaying the progression or onset of a disease, wherein the disease is diabetes, diabetes complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders related to blood concentration, constipation, or high blood pressure.

In some embodiments, the diabetic complication is diabetic retinopathy, diabetic neuropathy or diabetic nephropathy.

In some embodiments, the hyperlipidemia is hypertriglyceridemia.

The foregoing merely summarizes certain aspects disclosed herein and is not intended to be limiting in nature. These aspects and other aspects and embodiments are described more fully below.

DETAILED DESCRIPTION OF THE INVENTION

The present invention provides a glucopyranosyl derivative, preparation processes and pharmaceutical uses thereof. Skilled in the art can learn from this article to properly improve the process parameters. Of particular note is that all similar substitutions and modifications to the skilled person is obvious, and they are deemed to be included in the present invention.

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention. One skilled in the art will recognize many methods and materials similar or equivalent to those described herein, which could be used in the practice of the present invention. The present invention is by no means limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety. As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and Smith et al., "March's Advanced Organic Chemistry", John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles used herein refer to one or more than one (i.e. at least one) articles of the grammatical objects. By way of example, "a component" means one or more components, and thus, possibly, more than one component is contemplated and may be employed or used in an implementation of the described embodiments.

Unless otherwise stated, the terms used in the specification and claims of the present invention have the following definitions.

The term "comprise" is an open expression, it means comprising the contents disclosed herein, but don't exclude other contents.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". The term "optionally" or "optional" means that the subsequently described event or condition can but does not necessarily occur, and the description includes the situation in which the event or condition occurs, and the situation in which the event or condition does not occur. In general, the term "optionally" whether or not preceding the term "substituted" means that one or more hydrogen atoms in a given structure are unsubstituted or substituted with a specific substituent. Unless otherwise indicated, an optionally substituted group may have a substituent at each substitutable position of the group. When more than one position in a given structure can be substituted with more than one substituent selected from a specified group, the substituent may be either the same or different at each position. The substituents described herein may be, but not limited to, D, F, Cl, Br, I, CN, $NO_2$, OH, $NH_2$, oxo (=O), —C(=O) OH, —C(=O) $NH_2$, —SH, —$OR^e$, —$NR^cR^d$, —C(=O)$OR^e$, —C(=O)$NHR^f$, alkyl, haloalkyl, alkoxy, alkylamino, alkylthio, haloalkoxy, alkenyl, alkynyl, hydroxyalkyl, cycloalkyl, cycloalkyl-alkylene, carbocyclyl, carbocyclyl-alkylene, heterocyclyl, heterocyclyl-alkylene, aryl, aryl-alkylene, heteroaryl or heteroaryl-alkylene, wherein $R^c$, $R^d$, $R^e$ and $R^f$ have the definitions described in this invention.

Furthermore, what need to be explained is that the phrases "each . . . is independently" and "each of . . . and . . . is independently", unless otherwise stated, should be broadly understood, which can mean that the specific options expressed by the same symbol are independent of each other in different groups; or the specific options expressed by the same symbol are independent of each other in same groups.

At each part of the present specification, substitutes of compounds disclosed herein are disclosed in groups or in ranges. It is specifically intended that the invention includes each and every individual subcombination of the members of such groups and ranges. For example, the term "$C_{1-8}$ alkyl" especially refers to independently disclosed $C_1$ alkyl (methyl), $C_2$ alkyl (ethyl), $C_3$ alkyl, $C_4$ alkyl, $C_5$ alkyl, $C_6$ alkyl, $C_7$ alkyl and $C_8$ alkyl; "$C_{3-8}$ cycloalkyl" means independently disclosed $C_3$ cycloalkyl (cyclopropyl), $C_4$ cycloalkyl (cyclobutyl), $C_5$ cycloalkyl (cyclopentyl), $C_6$ cycloalkyl (cyclohexyl), $C_7$ cycloalkyl (cycloheptyl) and $C_8$ cycloalkyl (cyclooctyl); "3-8 membered heterocycle (radical)" refers to independently disclosed 3 membered heterocycle, 4 membered heterocycle, 5 membered heterocycle, 6 membered heterocycle, 7 membered heterocycle and 8 membered heterocycle.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" as used herein refers to a saturated linear or branched monovalent hydrocarbon radical containing 1 to 20 carbon atoms. Unless otherwise specified, the alkyl group contains 1-20 carbon atoms. In some embodiments, the alkyl group contains 1-12 carbon atoms. In some embodiments, the alkyl group contains 1-10 carbon atoms. In other embodiments, the alkyl group contains 1-9 carbon atoms. In other embodiments, the alkyl group contains 1-8 carbon atoms. In other embodiments, the alkyl group contains 1-6 carbon atoms, i.e., $C_{1-6}$ alkyl. In still other embodiments, the alkyl group contains 1-4 carbon atoms, i.e., $C_{1-4}$ alkyl. In yet other embodiments, the alkyl group contains 1-3 carbon atoms, i.e., $C_{1-3}$ alkyl. In still yet other embodiments, the alkyl group contains 1-2 carbon atoms, i.e., $C_{1-2}$ alkyl.

Some non-limiting examples of the alkyl group include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, n-heptyl and n-octyl, etc. Wherein, the alkyl group may be optionally substituted with one or more substituents disclosed herein.

The term "alkyl" or the prefix "alk-" used in the present invention is inclusive of both straight chain and branched saturated carbon chain.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In some embodiments, the alkylene group contains 1-8 carbon atoms. In other embodiments, the alkylene group contains 1-6 carbon atoms. In other embodiments, the alkylene group contains 1-4 carbon atoms, i.e., $C_{1-4}$ alkylene. In still other embodiments, the alkylene group contains 1-3 carbon atoms, i.e., $C_{1-3}$ alkylene. In yet other embodiments, the alkylene group contains 1-2 carbon atoms, i.e., $C_{1-2}$ alkylene. Such examples include methylene (—CH$_2$—), ethylene (including —CH$_2$CH$_2$— or —CH(CH$_3$)—), isopropylidene (including —CH(CH$_3$)CH$_2$— or —C(CH$_3$)$_2$—), n-propylene (including —CH$_2$CH$_2$CH$_2$—, —CH(CH$_2$CH$_3$)— or —CH$_2$CH(CH$_3$)—), n-butylene (including —CH$_2$(CH$_2$)$_2$CH$_2$—, —CH(CH$_2$CH$_2$CH$_3$)—, —CH$_2$CH(CH$_2$CH$_3$)—, —CH$_2$CH$_2$CH(CH$_3$)— or —CH(CH$_3$)CH(CH$_3$)—), tert-butylene (including —CH(CH(CH$_3$)$_2$)—, —CH$_2$CH(CH$_3$)CH$_2$— or —CH$_2$C(CH$_3$)$_2$—), pentylene (e.g., —CH$_2$(CH$_2$)$_3$CH$_2$—), hexylene (e.g., —CH$_2$(CH$_2$)$_4$CH$_2$—) and so on. wherein, the alkylene group may be optionally substituted with one or more substituents disclosed herein.

The term "alkenyl" refers to linear or branched-chain monovalent hydrocarbon radical of 2 to 12 carbon atoms with at least one site of unsaturation, i.e., a carbon-carbon, sp$^2$ double bond, wherein the alkenyl radical may be optionally substituted with one or more substituents described herein, and includes radicals having "cis" and "trans" orientations, or alternatively, "E" and "Z" orientations. In some embodiments, the alkenyl contains 2 to 8 carbon atoms. In other embodiments, the alkenyl contains 2 to 6 carbon atoms, i.e., $C_{2-6}$ alkenyl. In still other embodiments, the alkenyl contains 2 to 4 carbon atoms, i.e., $C_{2-4}$ alkenyl. Examples of the alkenyl group include, but are not limited to, vinyl (—CH=CH$_2$), propenyl (—CH$_2$CH=CH$_2$, —CH=CHCH$_3$), butenyl (—CH=CHCH$_2$CH$_3$, —CH$_2$CH=CHCH$_3$, —CH$_2$CH$_2$CH=CH$_2$, —CH=C(CH$_3$)$_2$, —CH=C(CH$_3$)$_2$, —CH$_2$C(CH$_3$)=CH$_2$), pentenyl (—CH$_2$CH$_2$CH$_2$CH=CH$_2$, —CH$_2$CH$_2$CH=CHCH$_3$, —CH$_2$CH$_2$CH=CHCH$_3$, —CH$_2$CH=CHCH$_2$CH$_3$, —CH=CHCH$_2$CH$_2$CH$_3$, —CH$_2$CH$_2$C(CH$_3$)=CH$_2$, —CH$_2$CH=C(CH$_3$)$_2$, —CH=CHCH(CH$_3$)$_2$, —C(CH$_2$CH$_3$)=CHCH$_3$, —CH(CH$_2$CH$_3$)CH=CH$_2$), etc.

The term "alkynyl" refers to a linear or branched monovalent hydrocarbon radical of 2 to 12 carbon atoms with at least one site of unsaturation, i.e., a carbon-carbon, sp triple bond. In some embodiments, the alkynyl contains 2 to 8 carbon atoms. In other embodiments, the alkynyl contains 2 to 6 carbon atoms, i.e., $C_{2-6}$ alkynyl. In still other embodiments, the alkynyl contains 2 to 4 carbon atoms, i.e., $C_{2-4}$ alkynyl. Some non-limiting examples of the alkynyl group include ethynyl (—C≡CH), propynyl (including 1-propynyl (—C≡C—CH$_3$) and propargyl (—CH$_2$C≡CH)), 1-butynyl, 2-butynyl, 1-pentynyl, 2-pentynyl, 3-methyl-1-butynyl, 1-hexynyl, 1-heptynyl and 1-octynyl, etc. The alkynyl group may be independently and optionally substituted by one or more substituents disclosed herein.

The term "alkoxy" or "alkyloxy" refers to an alkyl group, as previously defined, attached to parent molecular moiety via an oxygen atom, i.e., alkyl-O—. In some embodiments, the alkoxy group contains 1-20 carbon atoms. In some embodiments, the alkoxy group contains 1-10 carbon atoms. In other embodiments, the alkoxy group contains 1-8 carbon atoms. In other embodiments, the alkoxy group contains 1-6 carbon atoms, i.e., $C_{1-6}$ alkoxy. In other embodiments, the alkoxy group contains 1-4 carbon atoms, i.e., $C_{1-4}$ alkoxy. In still other embodiment, the alkoxy group contains 1-3 carbon atoms, i.e., $C_{1-3}$ alkoxy. In yet other embodiment, the alkoxy group contains 1-2 carbon atoms, i.e., $C_{1-2}$ alkoxy.

Some non-limiting examples of the alkoxy group include, but are not limited to, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH (CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH (CH$_3$)CH$_2$CH$_3$), and the like, wherein the alkoxy group may be independently unsubstituted or substituted with one or more substituents described in the present invention.

The term "alkylthio" refers to an alkyl group, as previously defined, attached to parent molecular moiety via a sulfur atom, i.e., alkyl-S—. In some embodiments, the alkylthio group contains 1-6 carbon atoms, i.e., $C_{1-6}$ alkylthio. In other embodiments, the alkylthio group contains 1-4 carbon atoms, i.e., $C_{1-4}$ alkylthio. In other embodiments, the alkylthio group contains 1-3 carbon atoms, i.e., $C_{1-3}$ alkylthio. In still other embodiment, the alkylthio group contains 1-2 carbon atoms, i.e., $C_{1-2}$ alkylthio. Some non-limiting examples of the alkylthio group include methylthio and ethylthio, etc. The alkylthio group may be optionally substituted with one or more substituents disclosed herein.

The term "alkylamino" refers to "N-alkylamino" and "N,N-dialkylamino" wherein the amino group is independently substituted with one alkyl radical or two alkyl radicals, respectively. In some embodiments, the alkylamino group is lower alkylamino group having one or two alkyl groups of 1 to 6 carbon atoms attached to nitrogen atom. In other embodiments, the alkylamino group is lower alkylamino group having 1 to 4 carbon atoms. In other embodiments, the alkylamino group is lower alkylamino group having 1 to 3 carbon atoms. In other embodiments, the alkylamino group is lower alkylamino group having 1 to 2 carbon atoms. Some non-limiting examples of suitable alkylamino radical include mono or dialkylamino. Such examples include, but are not limited to, methylamino (N-methylamino), ethylamino (N-ethylamino), N, N-dimethylamino, N, N-diethylamino, and the like. The alkylamino group may be optionally substituted with one or more substituents disclosed herein.

The term "haloalkyl" refers to an alkyl group substituted with one or more halogen atoms. In some embodiments, the haloalkyl group contains 1-10 carbon atoms. In some embodiments, the haloalkyl group contains 1-8 carbon atoms. In other embodiments, the haloalkyl group contains 1-6 carbon atoms, i.e., $C_{1-6}$ haloalkyl. In other embodiments, the haloalkyl group contains 1-4 carbon atoms, i.e., $C_{1-4}$ haloalkyl. In still other embodiment, the haloalkyl group contains 1-3 carbon atoms, i.e., $C_{1-3}$ haloalkyl. In yet other embodiment, the haloalkyl group contains 1-2 carbon atoms, i.e., $C_{1-2}$ haloalkyl. Examples of haloalkyl include, but are not limited to, monofluoromethyl (—CH$_2$F), difluoromethyl (—CHF$_2$), trifluoromethyl (—CF$_3$), fluoroethyl (—CHFCH$_3$, —CH$_2$CH$_2$F), difluoroethyl (—CF$_2$CH$_3$, —CFHCFH$_2$, —CH$_2$CHF$_2$), perfluoroethyl, fluoropropyl (—CHFCH$_2$CH$_3$, —CH$_2$CHFCH$_3$, —CH$_2$CH$_2$CH$_2$F), difluoropropyl (—CF$_2$CH$_2$CH$_3$, —CFHCFHCH$_3$, —CH$_2$CH$_2$CHF$_2$, —CH$_2$CF$_2$CH$_3$, —CH$_2$CHFCH$_2$F), trifluoropropyl, 1,1-dichloroethyl, 1,2-dichloropropyl, etc. Wherein, the haloalkyl group may be optionally substituted with one or more substituents disclosed herein.

The term "haloalkoxy" refers to an alkoxy group substituted with one or more halogen atoms. In some embodiments, the haloalkoxy group contains 1-10 carbon atoms. In some embodiments, the haloalkoxy group contains 1-8 carbon atoms. In other embodiments, the haloalkoxy group contains 1-6 carbon atoms, i.e., $C_{1-6}$ haloalkoxy. In other embodiments, the haloalkoxy group contains 1-4 carbon atoms, i.e., $C_{1-4}$ haloalkoxy. In still other embodiment, the haloalkoxy group contains 1-3 carbon atoms, i.e., $C_{1-6}$ haloalkoxy. In yet other embodiment, the haloalkoxy group contains 1-2 carbon atoms, i.e., $C_{1-2}$ haloalkoxy. Some non-limiting examples of the haloalkoxy group include trifluoromethoxy, difluoromethoxy, etc. Wherein, the haloalkoxy group may be optionally substituted with one or more substituents disclosed herein.

The term "hydroxyalkyl" refers to an alkyl group substituted with one or more hydroxy, wherein the alkyl group is as defined herein. In some embodiments, the hydroxyalkyl contains 1-6 carbon atoms, i.e., $C_{1-6}$ hydroxyalkyl. In other embodiments, the hydroxyalkyl contains 1-4 carbon atoms, i.e., $C_{1-4}$ hydroxyalkyl. In other embodiments, the hydroxyalkyl contains 1-3 carbon atoms, i.e., $C_{1-3}$ hydroxyalkyl. In still other embodiment, the hydroxyalkyl contains 1-2 carbon atoms, i.e., $C_{1-2}$ hydroxyalkyl. Examples of hydroxyalkyl include, but are not limited to, hydroxymethyl, 2-hydroxyethyl (—CH$_2$CH$_2$OH), 1-hydroxyethyl (—CHOHCH$_3$), 1,2-dihydroxyethyl (—CHOHCH$_2$OH), 2,3-dihydroxypropyl (—CH$_2$CHOHCH$_2$OH), 1-hydroxypropyl (—CH$_2$CH$_2$CH$_2$OH), 2-hydroxypropyl, 3-hydroxypropyl, hydroxybutyl, etc. Wherein, the hydroxyalkyl group may be optionally substituted with one or more substituents disclosed herein.

The term "cycloalkyl" refers to a monocyclic, bicyclic or tricyclic ring system with one or more attachment points connected to the rest of the molecule, saturated, containing 3-12 ring carbon atoms. Wherein, in some embodiments, cycloalkyl is a ring system containing 3-10 ring carbon atoms; in other embodiments, cycloalkyl is a ring system containing 3-8 ring carbon atoms, i.e., $C_{3-8}$ cycloalkyl; in other embodiments, cycloalkyl is a ring system containing 5-8 ring carbon atoms; in other embodiments, cycloalkyl is a ring system containing 3-6 ring carbon atoms, i.e., $C_{3-6}$ cycloalkyl; in other embodiments, cycloalkyl is a ring system containing 5-6 ring carbon atoms. Examples of the cycloalkyl group include, but are not limited to, cyclopropyl, cyclobutyl, cyclopentyl, cyclohexyl and the like. The cycloalkyl group may be optionally substituted with one or more substituents disclosed herein.

The term "carbocyclyl" may be used alone or as a large part of "carbocyclylalkyl" or "carbocyclylalkoxy", meaning a non-aromatic carbocyclic system saturated or containing one or more unsaturated units and containing 3-14 ring carbon atoms, and does not contain any aromatic ring. The term "carbocycle", "carbocyclyl" or "carbocyclic group" is used interchangeably herein. In some embodiments, the number of ring carbon atoms of carbocycle is 3-12; in other embodiments, the number of ring carbon atoms of carbocycle is 3-10; in other embodiments, the number of ring carbon atoms of carbocycle is 3-8, i.e., $C_{3-8}$ carbocycle (radical); in other embodiments, the number of ring carbon atoms of carbocycle is 3-6, i.e., $C_{3-6}$ carbocycle (radical); in some other embodiments, the number of ring carbon atoms of carbocycle is 5-6; in other embodiments, the number of ring carbon atoms of carbocycle is 5-8. In other embodiments, the number of ring carbon atoms of carbocycle is 6-8.

This "carbocyclyl" includes monocyclic, bicyclic or polycyclic fused, spiro or bridged carbocyclic ring systems, and also includes polycyclic ring systems in which the carbocycle can be fused with one or more non-aromatic carbocycles or one or more aromatic rings or a combination thereof, wherein the attached atomic group or point is on the carbocycle. Bicyclic carbocyclyl includes bridged bicyclic carbocyclyl, fused bicyclic carbocyclyl and spiro bicyclic carbocyclyl. The "fused" bicyclic ring system contains two rings sharing two adjacent ring atoms. Bridged bicyclic groups include two rings that share 2, 3, or 4 adjacent ring atoms. Spiro ring systems share one ring atom. Some non-limiting examples of the carbocyclic group include cycloalkyl, cycloalkenyl and cycloalkynyl. Further examples of carbocyclyl include, but are in no way limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like, Bridged carbocyclyl groups include, but are not limited to, bicyclo [2.2.2] octyl, bicyclo [2.2.1] heptyl, bicyclo [3.3.1] nonyl, bicyclo [3.2.3] nonyl, etc. The carbocyclyl group can be optionally substituted with one or more substituents described herein.

The term "heterocyclyl" can be used alone or as a large part of "heterocyclylalkyl" or "heterocyclylalkoxy", referring to a saturated or partially unsaturation, nonaromatic ring having 3 to 12 ring atoms as a monocyclic, bicyclic, or tricyclic ring system, in which at least one ring member is selected from nitrogen, sulfur and oxygen. Wherein, the heterocyclic group is non-aromatic and does not contain any aromatic ring, and the ring system has one or more connection points connected to the rest of the molecule. The term "heterocyclyl" includes monocyclic, bicyclic or polycyclic fused, spiro or bridged heterocyclic ring systems. Bicyclic heterocyclic groups include bridged bicyclic heterocyclyl, fused bicyclic heterocyclyl and spiro bicyclic heterocyclyl. The terms "heterocyclyl", "heterocyclic group" and "heterocycle" are used interchangeably herein. Unless otherwise specified, the heterocyclyl group may be carbon or nitrogen linked, and a —CH$_2$— group can be optionally replaced by a —C(=O)— group. In which, the sulfur can be optionally oxygenized to S-oxide. and the nitrogen can be optionally oxygenized to N-oxide. In some embodiments, the heterocyclyl is a ring system composed of 3-8 ring atoms; in some embodiments, the heterocyclyl is a ring system composed of 3-6 ring atoms; in some embodiments, the heterocyclyl is a ring system composed of 5-7 ring atoms; in some embodiments, the heterocyclyl is a ring system composed of 5-10 ring atoms; in some embodiments, the heterocyclyl is a ring system composed of 5-8 ring atoms; in other embodiments, the heterocyclyl is a ring system composed of 6-8 ring atoms; in other embodiments, the heterocyclyl is a ring system composed of 5-6 ring atoms; in other embodiments, the heterocyclyl is a ring system composed of 4 ring atoms; in other embodiments, the heterocyclyl is a ring system composed of 5 ring atoms; in other embodiments, the heterocyclyl is a ring system composed of 6 ring atoms; in other embodiments, the heterocyclyl is a ring system composed of 7 ring atoms; in other embodiments, the heterocyclyl is a ring system composed of 8 ring atoms.

Examples of the heterocyclyl group include, but are not limited to, oxiranyl, aziridinyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, oxazolidine, thiazolidine, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, tetrahydropyrrolyl, dihydropyrrolyl, tetrahydropyridinyl, tetrahydropyrimidinyl, tetrahydropyrazinyl, tetrahydropyridazinyl. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limited examples of heterocyclyl wherein the ring sulfur atom is oxidized is sulfolanyl and 1,1-dioxo-thiomorpholinyl. Bridged heterocyclyl groups include, but are not limited to, 2-oxabicyclo [2.2.2] octyl, 1-azabicyclo [2.2.2] octyl, 3-azabicyclo [3.2.1] octyl, etc. The heterocyclyl group may be optionally substituted with one or more substituents disclosed herein.

The term "m membered", where m is an integer typically describes the number of ring-forming atoms in a moiety where the number of ring-forming atoms is m. For example, piperidinyl is an example of a heterocyclic group consisting of 6 ring atoms and 1,2,3,4-tetrahydronaphthyl is an example of a carbocyclic group consisting of 10 ring atoms.

The term "aryl" used alone or as a substantial part of "arylalkyl" or "arylalkoxy", refers to monocyclic, bicyclic and tricyclic aromatic carbocyclic ring systems having a total of six to fourteen ring atoms, or six to twelve ring atoms, or six to ten ring atoms, wherein each ring in the system contains 3 to 7 ring members and that has a single point or multipoint of attachment to the rest of the molecule. The term "aryl" may be used interchangeably with the term "aryl ring" or "aromatic ring". Some non-limiting examples of the aryl group include phenyl, naphthyl and anthracene. The aryl group may be optionally substituted with one or more substituents disclosed herein.

The term "heteroaryl" used alone or as a major part of "heteroarylalkyl" or "heteroarylalkoxy" refers to monocyclic, bicyclic and tricyclic aromatic systems having a total of five to sixteen ring members, wherein at least one ring contains one or more heteroatoms, wherein each ring contains 5 to 7 ring members, wherein at least one ring system is aromatic, that has a single point or multipoint of attachment to the rest of the molecule. Unless otherwise stated, the heteroaryl group may be connected to the rest of the molecule (such as the host structure in the general formula) through any reasonable position (which may be C in CH or N in NH). When a —CH$_2$— group is present in the heteroaryl group, the —CH$_2$— group may be optionally replaced by —C(=O)—. The term "heteroaryl" and "heteroaromatic ring" or "heteroaromatic compound" can be used interchangeably herein. In some embodiments, the heteroaryl group is a 5-14 membered heteroaryl comprising 1, 2, 3 or 4 heteroatoms independently selected from O, S and N. In other embodiments, the heteroaryl group is a 5-12 membered heteroaryl comprising 1, 2, 3 or 4 heteroatoms independently selected from O, S and N. In other embodiments, the heteroaryl group is a 5-10 membered heteroaryl comprising 1, 2, 3 or 4 heteroatoms independently selected from O, S and N. In other embodiments, the heteroaryl group is a 5-8 membered heteroaryl comprising 1, 2, 3 or 4 heteroatoms independently selected from O, S and N. In other embodiments, the heteroaryl group is a 5-7 membered heteroaryl comprising 1, 2, 3 or 4 heteroatoms independently selected from O, S and N. In other embodiments, the heteroaryl group is a 5-6 membered heteroaryl comprising 1, 2, 3 or 4 heteroatoms independently selected from O, S and N. In other embodiments, the heteroaryl group is a 5 membered heteroaryl comprising 1, 2, 3 or 4 heteroatoms independently selected from O, S and N. In other embodiments, the heteroaryl group is a 6 membered heteroaryl comprising 1, 2, 3 or 4 heteroatoms independently selected from O, S and N.

In other embodiments, some non-limiting examples of heteroaryl include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl, 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiodiazolyl, 1,3,4-thiodiazolyl, 1,2,5-thiodiazolyl, pyrazinyl, 1,3,5-triazinyl, and the following bi- or tricyclic groups: indolinyl, 1,2,3,4-tetrahydroisoquinolinyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), isoquinolinyl (e.g., 1-isoquinolinyl, 3-isoquinolinyl or 4-isoquinolinyl), phenoxothiyl, dibenzimidazolyl, dibenzofuranyl, dibenzothienyl, etc. The heteroaryl group is optionally substituted with one or more substituents disclosed herein.

The term "heteroatom" refers to one or more of oxygen, sulfur, nitrogen, phosphorus and silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl, R is the substituent described in the present invention).

The term "halogen" refers to fluoro (F), chloro (Cl), bromo (Br), or iodo (I).

The term "nitro" refers to —NO$_2$.

The term "mercapto" refers to —SH.

The term "hydroxy" refers to —OH.

The term "amino" refers to —NH$_2$.

The term "cyano" refers to —CN.

The term "carboxylic acid" or "carboxy" refers to —C(=O)OH.

The term "carbonyl", whether used alone or in conjunction with other terms, means —(C=O)—.

The term "D" refers to deuteration, i.e., $^2$H.

As described in the present invention, a ring system formed by drawing a bond to connect a substituent to the center of the ring represents that the substituent can be substituted at any substitutable position on the ring system. For example, formula a represents that any position on ring A that may be substituted may be optionally substituted with n R; when ring A has a bicyclic structure, R may be substituted at any substitutable position on any ring; for example, formula b represents that the substituent R may be substituted at any position on the benzene ring that may be substituted, as shown in formulas b-1 to b-3:

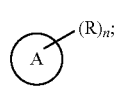

formula a

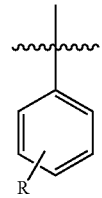

formula b

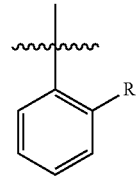

formula b-1 formula b-2

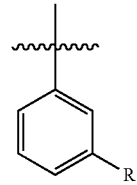

formula b-3

The term "protecting group" or "PG" refers to a substituent group used to block or protect a specific functionality when other functional groups in the compound react. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include, but are not limited to, acetyl, benzoyl, benzyl, p-methoxybenzyl, silane, and the like. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl) ethoxy-methyl, 2-(p-toluenesulfonyl) ethyl, 2-(p-nitrophenylsulfonyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

The term "leaving group" or "LG" refers to an atom or functional group that is detached from a larger molecule in a chemical reaction, and is a term used in nucleophilic substitution reactions and elimination reactions. In the nucleophilic substitution reaction, the reactant attacked by the nucleophilic reagent is called a substrate, and the atom or atomic group that breaks out with a pair of electrons from the substrate molecule is called a leaving group. Common leaving groups are, for example, but not limited to, halogen atoms, ester groups, sulfonate groups, nitro groups, azide groups, or hydroxy.

The term "pharmaceutically acceptable" means that the substance or composition must be chemically and/or toxicologically compatible with the other ingredients comprising the formulation and/or the mammal being treated with it. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" includes any solvent, dispersion medium, coating material, surfactant, antioxidant, preservative (e.g., antibacterial agent, antifungal agent), isotonic agent, salt, drug stabilizer, binder, excipient, dispersing agent, lubricant, sweetener, flavoring agent, coloring agent, or a combination thereof, these carriers are known to those skilled in the art (e.g., Remington's Pharmaceutical Sciences, 18th Ed. Mack Printing Company, 1990, pp. 1289-1329). Except where any conventional carrier is incompatible with the active ingredient, its use in therapeutic or pharmaceutical compositions is covered.

The term "pharmaceutical composition" refers to a mixture of one or more of the compounds described herein, or physiologically/pharmaceutically acceptable salts or prodrugs thereof, and other chemical components, such as physiologically/pharmaceutically acceptable carriers, excipients, diluents, adhesives, fillers, and other additional therapeutic agents, such as anti-diabetic agents, antihyperglycemic agents, antiadipositas agents, antihypertensive agents, antiplatelet agents, antiatherosclerotic agents, lipid-lowering agents, etc. The purpose of the pharmaceutical composition is to facilitate administration of a compound to an organism.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in Higuchi et al., Pro-drugs as Novel Delivery Systems, Vol. 14, A.C.S. Symposium Series; Roche, et al. ed., Bioreversible Carriers in Drug Design, American Pharmaceutical Association and Pergamon Press, 1987; Rautio et al., Prodrugs: Design and Clinical Applications, Nature Reviews Drug Discovery, 2008, 7, 255-270, and Hecker et al., Prodrugs of Phosphates and Phosphonates, J. Med. Chem., 2008, 51, 2328-2345, all of which are incorporated herein by reference in their entireties.

The term "metabolite" refers to a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

The term "pharmaceutically acceptable salt" refers to organic or inorganic salts of a compound disclosed herein. Pharmaceutically acceptable salts are well known in the art. For example, the pharmaceutically acceptable salts are described in detail in Berge et al., J. Pharmacol Sci, 1977, 66: 1-19, which is incorporated herein by reference in its entirety. Some non-limiting examples of the pharmaceutically salts include salts of an amino group formed with inorganic acids such as hydrochloric acid, hydrobromic acid, phosphoric acid, metaphosphoric acid, sulfuric acid, nitric acid and perchloric acid or with organic acids such as methanesulfonic acid, ethanesulfonic acid, acetic acid, trifluoroacetic acid, glycolic acid, 2-hydroxyethanesulfonic acid, oxalic acid, maleic acid, tartaric acid, citric acid, succinic acid, malonic acid, benzenesulfonic acid, p-toluenesulfonic acid, malic acid, fumaric acid, lactic acid and lactobionic acid or salts obtained by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, laurate, laurylsulfate, malonate, 2-naphthalenesulfonate, nicotinate, nitrate, oleate, palmitate, pamoate, pectinate, persulfate, 3-phenylpropionate, picrate, pivalate, propionate, stearate, thiocyanate, undecanoate, valerate, and the like. Salts derived from appropriate bases include alkali metal, alkaline earth metal, ammonium and $N^+(C_{1-4}$ alkyl)4 salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include appropriate and nontoxic ammonium, quaternary ammonium, and amine cations formed using counterions, such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

The term "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, Advanced Organic Chemistry, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (m-CPBA), for example, in an inert solvent such as dichloromethane.

Any asymmetric atom (e.g., carbon or the like) of the compound(s) disclosed herein can be present in racemic or enantiomerically enriched, for example the (R)-, (S)-, (R, S)- or (S, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. If possible, the substituent on the atom having an unsaturated double bond may exist in the form of -(Z)- or -(E)-.

Therefore, as described in the present invention, the compound of the present invention may exist in one form or a mixture of possible isomers, rotamers, atropisomers, tautomers, e.g., in the form of substantially pure geometric (cis or trans) isomers, diastereomers, optical isomers (enantiomers), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aubé, Elsevier, Oxford, U K, 2012); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972);

The present invention also includes isotopically labeled compounds of the present invention, which are the same as those described in the present invention except for the fact that one or more atoms are replaced by atoms having an atomic mass or mass number different from the atomic mass or mass number common in nature. Examples of isotopes that can be incorporated into compounds of the invention include isotopes of hydrogen, carbon, nitrogen, oxygen, phosphorous, sulfur, fluorine, and chlorine, such as $^2H$, $^3H$, $^{13}C$, $^{14}C$, $^{15}N$, $^{16}O$, $^{17}O$, $^{31}P$, $^{32}P$, $^{36}S$, $^{18}F$ and $^{37}Cl$.

Compounds of the invention containing the aforementioned isotopes and/or other isotopes of other atoms and pharmaceutically acceptable salts of the compounds are included within the scope of the invention. Isotopically-labeled compounds of the present invention, for example those into which radioactive isotopes such as $^3H$ or $^{14}C$ are incorporated, are useful in drug and/or substrate tissue distribution assays. Due to ease of preparation and detection, tritiated, i.e., $^3H$, and carbon-14, i.e., $^{14}C$, isotopes are particularly preferred. In addition, substitution with heavy isotopes, such as deuterium, i.e., $^2H$, may provide some therapeutic advantages derived from greater metabolic stability, such as increased half-life in the body or reduced dosage requirements. Therefore, it may be preferable in some cases.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that these stereoisomers are mirror images of each other. A specific stereoisomer is referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Depending on the choice of the starting materials and procedures, the compounds can be present in the form of one of the possible stereoisomers or as mixtures thereof, such as pure optical isomers, or as a mixture of isomers, or as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

The compounds disclosed herein may contain asymmetric or chiral centers, and therefore exist in different stereoisomeric forms. It is expected that all stereoisomeric forms of the compounds of the invention, including but not limited to diastereomers, enantiomers, atropisomers, geometric (or conformational) isomers and their mixtures, such as racemic mixtures, are within the scope of the present invention.

Unless otherwise indicated, the structures described in the present invention also include all isomers (e.g., enantiomers, diastereomers, atropisomers, and geometric (or conformational)) forms including this structure; for example, the R and S configurations of each asymmetric center, (Z) and (E) double bond isomers, and (Z) and (E) conformational isomers. Therefore, single stereochemical isomers of the compounds of the present invention as well as mixtures of enantiomers, diastereomers and mixtures of geometric isomers (or conformers) are within the scope of the present invention.

The term "tautomer" or "tautomeric form" refers to structural isomers of different energies which are interconvertible via a low energy barrier. Where tautomerization is possible (e.g. in solution), a chemical equilibrium of tautomers can be reached. For example, protontautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)- one tautomerism. Unless otherwise stated, all tautomeric forms of the compounds disclosed herein are within the scope of the invention.

The term "geometric isomers" also called "cis-trans isomers" refers to isomers caused by double bonds (including double bonds of olefins, C=N double bonds and N=N double bonds) or single bonds of ring carbon atoms that cannot rotate freely.

The term "dimer" refers to substances of the same or the same kind, appearing in a double form, and may have properties or functions that are not available in a single state. Common examples include dicyclopentadiene, cuprous dichloride, sucrose, and so on.

The term "trimer" refers to three substances of the same or the same kind that are polymerized into a new molecule. The new molecule is a trimer and is a low molecular weight polymer.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the terms "subject" and "patient" are used interchangeably. The terms "subject" and "patient" refer to animals (e.g., birds or mammals such as chickens, quails, or turkeys), especially "mammals" including non-primates (e.g., cattle, pigs, horses, sheep, rabbits, guinea pigs, rats, cats, dogs, and mice) and primates (e.g., monkeys, chimpanzees, and humans), and more particularly humans. In one embodiment, the subject is a non-human animal, such as a domestic animal (e.g., horse, cow, pig, or sheep) or a pet (e.g., dog, cat, guinea pig, or rabbit). In other embodiments, "patient" refers to a human.

The term "syndrome X", also known as conditions, diseases of metabolic syndrome, the disorders are detailed in Johannsson et al., J. Clin. Endocrinol. Metab., 1997; 82, 727-734, which is incorporated herein by reference.

The term "intestinal improvement" refers to increasing beneficial bacteria such as Bifidobacterium, Lactobacillus, etc., increasing organic acids in the intestine, and reducing spoilage products in the intestine.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Additionally, unless otherwise stated, structures depicted herein are also meant to include compounds that differ only in the presence of one or more isotopically enriched atoms.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

DESCRIPTION OF COMPOUNDS OF THE INVENTION

The present invention provides a compound with excellent SGLTs inhibitory activity, especially compound with excellent SGLT1 inhibitory activity, used for the preparation of drugs for improving the intestinal environment; or for the preparation of drugs for treating diabetes, diabetes complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders related to blood concentration, constipation, or high blood pressure. The present invention also provides methods of preparing these compounds, pharmaceutical compositions comprising these compounds, and methods of using these compounds and compositions to prepare medicaments for the above-mentioned diseases in mammals, especially humans. Compared with the existing similar compounds, the compounds of the present invention not only have better pharmacological activity, but also have better in vivo metabolic kinetic properties and in vivo pharmacodynamic properties. At the same time, the preparation method is simple and easy, and the technological method is stable, which is suitable for industrial production. Therefore, the compound provided by the present invention has better druggability compared with the existing similar compounds.

Specifically:

in one aspect, the invention relates to a compound having Formula (I) or a stereoisomer, a geometric isomer, a tautomer, an N-oxide, a solvate, a metabolite, a pharmaceutically acceptable salt, a dimer, a trimer or a prodrug thereof,

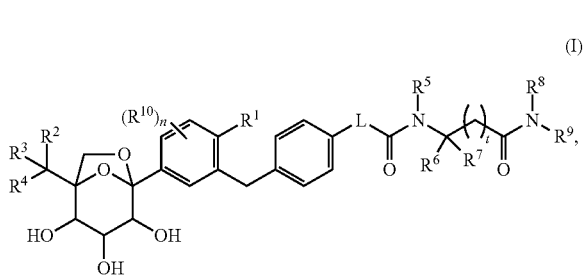

wherein $R^1$, $R^2$, $R^3$, $R^4$, $R^5$, $R^6$, $R^7$, $R^8$, $R^9$, $R^{10}$, L, n and t have the definition as described in the present invention, with the proviso that when $R^5$ and $R^8$ are both H and $R^9$ is

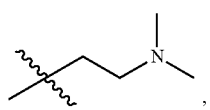 [SMILES: *CCN(C)C]

t is not 0.

In some embodiments, L is —$(CR^aR^b)_q$—, —CH=CH—$(CR^aR^b)_p$—, —O—$(CR^aR^b)_p$—, —NH—$(CR^aR^b)_p$—, —S—$(CR^aR^b)_p$—, —S(=O)—$(CR^aR^b)_p$— or —S(=O)$_2$—$(CR^aR^b)_p$—;

q is 1, 2, 3, 4, 5 or 6;

p is 0, 1, 2, 3, 4, 5 or 6;

each $R^a$ and $R^b$ is independently H, D, F, Cl, Br, I, CN, $NO_2$, OH, $NH_2$, —C(=O) OH, —SH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino, $C_{1-6}$ haloalkoxy, $C_{3-6}$ cycloalkyl or 3-6 membered heterocyclyl; or, $R^a$ and $R^b$ together with the carbon atom to which they are attached, form a $C_{3-6}$ carbocycle or a 3-6 membered heterocycle;

$R^1$ is H, D, F, Cl, Br, I, OH, CN, $NO_2$, $NH_2$, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ haloalkyl, $C_{1-6}$ haloalkoxy, $C_{1-6}$ alkylamino, $C_{1-6}$ alkylthio, $C_{3-6}$ cycloalkyl or $C_{3-6}$ cycloalkyl-$C_{1-4}$ alkylene, wherein each of $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ haloalkyl, $C_{1-6}$ haloalkoxy, $C_{1-6}$ alkylamino, $C_{1-6}$ alkylthio, $C_{3-6}$ cycloalkyl and $C_{3-6}$ cycloalkyl-$C_{1-4}$ alkylene is independently unsubstituted or substituted with 1, 2, 3 or 4 substituents, and the substituent is independently selected from D, F, Cl, Br, I, CN, $NO_2$, OH, $NH_2$, —C(=O) OH, —SH, $C_{1-6}$ alkyl, $C_{1-6}$ haloalkyl, $C_{1-6}$ alkoxy, $C_{1-6}$ alkylamino or $C_{1-6}$ haloalkoxy;

each of $R^2$ and $R^3$ is independently H, D, CN, OH, $NH_2$, —SH, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ alkylamino, $C_{3-6}$ cycloalkyl or 3-6 membered heterocyclyl, wherein each $C_{1-6}$ alkyl, $C_{2-6}$ alkenyl, $C_{2-6}$ alkynyl, $C_{1-6}$ alkoxy, $C_{1-6}$ alkylthio, $C_{1-6}$ alkylamino, $C_{3-6}$ cycloalkyl and 3-6 membered heterocyclyl is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

or, $R^2$ and $R^3$ together with the carbon atom to which they are attached, form carbonyl, or, $R^2$ and $R^3$ together with the carbon atom to which they are attached, form a $C_{3-6}$ carbocycle or a 3-6 membered heterocycle, wherein each of $C_{3-6}$ carbocycle and 3-6 membered heterocycle is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

$R^4$ is H, D, —$OR^{4a}$ or —$SR^{4b}$;

each of $R^{4a}$ and $R^{4b}$ is independently H, D, $C_{1-6}$ alkyl, $C_{3-6}$ cycloalkyl, $C_{3-6}$ cycloalkyl-$C_{1-4}$ alkylene, 5-6 membered heterocyclyl, (5-6 membered heterocyclyl)-$C_{1-4}$ alkylene, $C_{6-10}$ aryl, $C_{6-10}$ aryl-$C_{1-4}$ alkylene, 5-6 membered heteroaryl or (5-6 membered heteroaryl)-$C_{1-4}$ alkylene, wherein each $C_{1-6}$ alkyl, $C_{3-6}$ cycloalkyl, $C_{3-6}$ cycloalkyl-$C_{1-4}$ alkylene, 5-6 membered heterocyclyl, (5-6 membered heterocyclyl)-$C_{1-4}$ alkylene, $C_{6-10}$ aryl, $C_{6-10}$ aryl-$C_{1-4}$ alkylene, 5-6 membered heteroaryl and (5-6 membered heteroaryl)-$C_{1-4}$ alkylene is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

$R^{10}$ is H, D, F, Cl, Br, I, OH, CN, $NO_2$, $NH_2$, $C_{1-6}$ alkyl or $C_{1-6}$ alkoxy;

$R^5$ is H, D, $C_{1-6}$ alkyl, $C_{1-6}$ haloalkyl, $C_{3-8}$ cycloalkyl, 3-8 membered heterocyclyl, $C_{6-10}$ aryl or 5-8 membered heteroaryl, wherein each of $C_{1-6}$ alkyl, $C_{1-6}$ haloalkyl, $C_{3-8}$ cycloalkyl, 3-8 membered heterocyclyl, $C_{6-10}$ aryl and 5-8 membered heteroaryl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino, $C_{1-6}$ haloalkoxy, $C_{3-6}$ cycloalkyl, 5-6 membered heterocyclyl, $C_{6-10}$ aryl or 5-6 membered heteroaryl;

each of $R^6$ and $R^7$ is H, D, F, Cl, Br, I, CN, $NO_2$, OH, $NH_2$, $C_{1-6}$ alkyl, $C_{1-6}$ alkoxy, $C_{1-6}$ alkylamino, $C_{1-6}$ haloalkyl, $C_{1-6}$ haloalkoxy, $C_{3-8}$ cycloalkyl, 3-8 membered heterocyclyl, $C_{6-10}$ aryl or 5-8 membered heteroaryl, wherein each $C_{1-6}$ alkyl, $C_{1-6}$ alkoxy, $C_{1-6}$ alkylamino, $C_{1-6}$ haloalkyl, $C_{1-6}$ haloalkoxy, $C_{3-8}$ cycloalkyl, 3-8 membered heterocyclyl, $C_{6-10}$ aryl and 5-8 membered heteroaryl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino, $C_{1-6}$ haloalkoxy, $C_{3-6}$ cycloalkyl, 5-6 membered heterocyclyl, $C_{6-10}$ aryl or 5-6 membered heteroaryl;

or, $R^6$ and $R^7$ together with the carbon atom to which they are attached, form a $C_{3-8}$ carbocycle, a 3-8 membered heterocycle, a $C_{6-10}$ aromatic ring or a 5-8 membered heteroaromatic ring, wherein each of $C_{3-8}$ carbocycle, 3-8 membered heterocycle, $C_{6-10}$ aromatic ring and 5-8 membered heteroaromatic ring is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

or $R^5$ and $R^6$ together with the atom to which they are attached, or $R^5$ and $R^7$ together with the atom to which they are attached, form a 3-8 membered heterocycle or a 5-8 membered heteroaromatic ring, wherein each 3-8 membered heterocycle and 5-8 membered heteroaromatic ring is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

each of $R^8$ and $R^9$ is independently H, D, $R^eO$—$C_{1-4}$ alkylene, $R^dR^cN$—$C_{1-4}$ alkylene, $C_{1-8}$ alkyl, $C_{1-6}$ haloalkyl, $C_{3-8}$ cycloalkyl, $C_{3-8}$ cycloalkyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-8 membered heteroaryl or (5-8 membered heteroaryl)-$C_{1-4}$ alkylene, wherein each $C_{1-8}$ alkyl, $C_{1-6}$ haloalkyl, $C_{3-8}$ cycloalkyl, $C_{3-8}$ cycloalkyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-8 membered heteroaryl and (5-8 membered heteroaryl)-$C_{1-4}$ alkylene is independently unsubstituted or substituted with 1, 2, 3 or 4 substituents, and the substituent is independently selected from D, F, Cl, Br, I, CN, $NO_2$, =O, —$OR^e$, —$NR^cR^d$, —C(=O)$OR^e$, —C(=O) $NHR^f$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

or, $R^8$ and $R^9$ together with the nitrogen atom to which they are attached, form a 3-8 membered heterocycle or a 5-8 membered heteroaromatic ring, wherein each of 3-8 membered heterocycle and 5-8 membered heteroaromatic ring is independently unsubstituted or substituted with 1, 2, 3 or 4 substituents, and the substituent is independently selected from D, F, Cl, Br, I, CN, $NO_2$, =O, —$OR^e$, —$NR^cR^d$, —C(=O)OR$^e$, —C(=O)NHR$^f$, C$_{1-6}$ alkyl, C$_{2-6}$ alkenyl, C$^{2-6}$ alkynyl, C$_{1-6}$ haloalkyl, C$_{1-6}$ alkoxy, C$_{1-6}$ alkylamino or C$_{1-6}$ haloalkoxy;

each R$^c$, R$^d$, R$^e$ and R$^f$ is independently H, D, C$_{1-6}$ alkyl, C$_{1-6}$ haloalkyl, C$_{3-8}$ cycloalkyl, C$_{3-8}$cycloalkyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-8 membered heteroaryl or (5-8 membered heteroaryl)-C$_{1-4}$ alkylene, wherein each C$_{1-6}$ alkyl, C$_{1-6}$ haloalkyl, C$_{3-8}$ cycloalkyl, C$_{3-8}$ cycloalkyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-8 membered heteroaryl and (5-8 membered heteroaryl)-C$_{1-4}$ alkylene is independently unsubstituted or substituted with 1, 2, 3 or 4 substituents, and the substituent is independently selected from D, F, Cl, Br, I, CN, NO$_2$, OH, —NH$_2$, =O, —C(=O) OH, —C(=O)NH$_2$, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ alkylamino or C$_{1-6}$ haloalkoxy;

or, R$^c$ and R$^d$ together with the nitrogen atom to which they are attached, form a 3-8 membered heterocycle or a 5-8 membered heteroaromatic ring, wherein each of 3-8 membered heterocycle and 5-8 membered heteroaromatic ring is independently unsubstituted or substituted with 1, 2, 3 or 4 substituents, and the substituent is independently selected from D, F, Cl, Br, I, CN, NO$_2$, =O, OH, —NH$_2$, —C(=O) OH, —C(=O)NH$_2$, C$_{1-6}$ alkyl, C$_{2-6}$ alkenyl, C$^{2-6}$ alkynyl, C$_{1-6}$ haloalkyl, C$_{1-6}$ alkoxy, C$_{1-6}$ alkylamino or C$_{1-6}$ haloalkoxy;

n is 0, 1, 2 or 3;

t is 0, 1, 2, 3, 4, 5 or 6; with the proviso that when R$^5$ and R$^8$ are both H and R$^9$ is

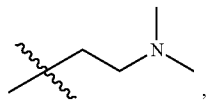 [SMILES: *CCN(C)C]

is not 0.

In other embodiments, the present invention relates to a compound having formula (I-a) or a stereoisomer, a geometric isomer, a tautomer, an N-oxide, a solvate, a metabolite, a pharmaceutically acceptable salt, a dimer, a trimer or a prodrug thereof,

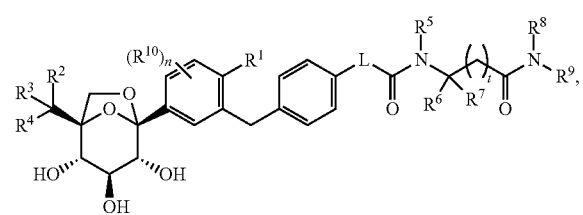

(I-a)

wherein R$^1$, R$^2$, R$^3$, R$^4$, R$^5$, R$^6$, R$^7$, R$^8$, R$^9$, R$^{10}$, L n and t are as defined herein.

In other embodiments, the present invention relates to a compound having formula (II), or a stereoisomer, a geometric isomer, a tautomer, an N-oxide, a solvate, a metabolite, a pharmaceutically acceptable salt, a dimer, a trimer or a prodrug thereof,

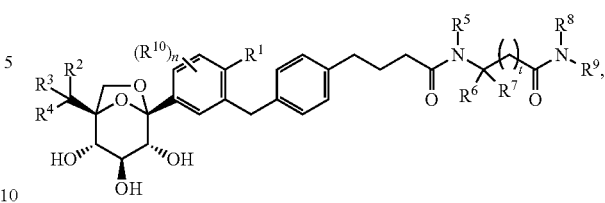

(II)

wherein R$^1$, R$^2$, R$^3$, R$^4$, R$^5$, R$^6$, R$^7$, R$^8$, R$^9$, R$^{10}$, n and t are as defined herein.

In other embodiments, R$^1$ is H, D, F, Cl, Br, I, OH, CN, NO$_2$, NH$_2$, C$_{1-4}$ alkyl, C$_{2-4}$ alkenyl, C$_{2-4}$ alkynyl, C$_{1-4}$ alkoxy, C$_{1-4}$ hydroxyalkyl, C$_{1-4}$ haloalkyl, C$_{1-4}$ haloalkoxy, C$_{1-4}$ alkylamino, C$_{1-4}$ alkylthio, C$_{3-6}$ cycloalkyl or C$_{3-6}$ cycloalkyl-C$_{1-2}$ alkylene, wherein each of C$_{1-4}$ alkyl, C$_{2-4}$ alkenyl, C$_{2-4}$ alkynyl, C$_{1-4}$ alkoxy, C$_{1-4}$ hydroxyalkyl, C$_{1-4}$ haloalkyl, C$_{1-4}$ haloalkoxy, C$_{1-4}$ alkylamino, C$_{1-4}$ alkylthio, C$_{3-6}$ cycloalkyl and C$_{3-6}$ cycloalkyl-C$_{1-2}$ alkylene is independently unsubstituted or substituted with 1, 2, 3 or 4 substituents, and the substituent is independently selected from D, F, Cl, Br, I, CN, NO$_2$, OH, NH$_2$, —C(=O) OH, —SH, C$_{1-4}$ alkyl, C$_{1-4}$ haloalkyl, C$_{1-4}$ alkoxy, C$_{1-4}$ alkylamino or C$_{1-4}$ haloalkoxy.

In still other embodiments, R$^1$ is H, D, F, Cl, Br, I, OH, CN, NO$_2$, NH$_2$, methyl, ethyl, n-propyl, isopropyl, propenyl, propynyl, methoxy, ethoxy, hydroxymethyl, trifluoromethyl, trifluoroethyl, monofluoromethyl, trifluoromethoxy, difluoromethoxy, methylamino, cyclopropyl, cyclobutyl, cyclopentyl, cyclohexyl or cyclopropyl-methylene, wherein each of methyl, ethyl, n-propyl, isopropyl, propenyl, propynyl, methoxy, ethoxy, hydroxymethyl, trifluoroethyl, monofluoromethyl, difluoromethoxy, methylamino, cyclopropyl, cyclobutyl, cyclopentyl, cyclohexyl and cyclopropyl-methylene is independently unsubstituted or substituted with 1, 2, 3, or 4 substituents, and the substituent is independently selected from D, F, Cl, Br, I, CN, NO$_2$, OH, NH$_2$, —C(=O) OH, —SH, methyl, ethyl, n-propyl, isopropyl, trifluoromethyl, methoxy, ethoxy, methylamino, trifluoromethoxy or difluoromethoxy.

In other embodiments, each of R$^2$ and R$^3$ is independently H, D, CN, OH, NH$_2$, —SH, C$_{1-4}$ alkyl, C$_{2-4}$ alkenyl, C$_{2-4}$ alkynyl, C$_{1-4}$ alkoxy, C$_{1-4}$ alkylthio, C$_{1-4}$ alkylamino, C$_{3-6}$ cycloalkyl or 5-6 membered heterocyclyl, wherein each C$_{1-4}$ alkyl, C$_{2-4}$ alkenyl, C$_{2-4}$ alkynyl, C$_{1-4}$ alkoxy, C$_{1-4}$ alkylthio, C$_{1-4}$ alkylamino, C$_{3-6}$ cycloalkyl and 5-6 membered heterocyclyl is independently unsubstituted or substituted with 1, 2, 3 or 4 substituents, and the substituent is independently selected from D, F, Cl, Br, I, CN, NO$_2$, OH, NH$_2$, —C(=O) OH, —SH, =O, C$_{1-4}$ alkyl, C$_{1-4}$ haloalkyl, C$_{1-4}$ alkoxy, C$_{1-4}$ alkylamino or C$_{1-4}$ haloalkoxy.

In still other embodiments, each of R$^2$ and R$^3$ is independently H, D, CN, OH, NH$_2$, —SH, methyl, ethyl, n-propyl, isopropyl, vinyl, propynyl, methoxy, ethoxy, methylthio, methylamino, cyclopropyl, cyclobutyl, cyclopentyl, cyclohexyl or 5-6 membered heterocyclyl, wherein each methyl, ethyl, n-propyl, isopropyl, vinyl, propynyl, methoxy, ethoxy, methylthio, methylamino, cyclopropyl, cyclobutyl, cyclopentyl, cyclohexyl and 5-6 membered heterocyclyl is independently unsubstituted or substituted with 1, 2, 3 or 4 substituents, and the substituent is independently selected from D, F, Cl, Br, I, CN, NO$_2$, OH, NH$_2$, —C(=O) OH, —SH, =O, methyl, ethyl, n-propyl, isopropyl, trifluoromethyl, methoxy, ethyloxy, methylamino, trifluoromethoxy or difluoromethoxy.

In other embodiments, $R^2$ and $R^3$ together with the carbon atom to which they are attached, form carbonyl.

In other embodiments, $R^2$ and $R^3$ together with the carbon atom to which they are attached, form a $C_{3-6}$ carbocycle or a 5-6 membered heterocycle, wherein each of $C_{3-6}$ carbocycle and 5-6 membered heterocycle is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, $R^2$ and $R^3$ together with the carbon atom to which they are attached, form cyclopropane, cyclobutane, cyclopentane, cyclohexane or a 5-6 membered heterocycle, wherein each of cyclopropane, cyclobutane, cyclopentane, cyclohexane and a 5-6 membered heterocycle is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, methyl, ethyl, n-propyl, isopropyl, trifluoromethyl, methoxy, ethoxy, methylamino, trifluoromethoxy or difluoromethoxy.

In other embodiments, $R^4$ is H, D, —$OR^{4a}$ or —$SR^{4b}$; each of $R^{4a}$ and $R^{4b}$ is independently H, D, $C_{1-4}$ alkyl, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene, wherein each $C_{1-4}$ alkyl, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl and (5-6 membered heteroaryl)-$C_{1-2}$ alkylene is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, $R^4$ is H, D, —$OR^{4a}$ or —$SR^{4b}$; each of $R^{4a}$ and $R^{4b}$ is independently H, D, methyl, ethyl, n-propyl, isopropyl, cyclopropyl, cyclobutyl, cyclopentyl, cyclohexyl, $C_{3-6}$ cycloalkyl-$C_{1-2}$ alkylene, tetrahydrofuranyl, tetrahydrothienyl, tetrahydropyranyl, piperidinyl, morpholinyl, thiomorpholinyl, piperazinyl, (5-6 membered heterocyclyl)-$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl or (5-6 membered heteroaryl)-$C_{1-2}$ alkylene, wherein each methyl, ethyl, n-propyl, isopropyl, cyclopropyl, cyclobutyl, cyclopentyl, cyclohexyl, $C_{3-6}$ cycloalkyl-$C_{1-2}$ alkylene, tetrahydrofuranyl, tetrahydrothienyl, tetrahydropyranyl, piperidinyl, morpholinyl, thiomorpholinyl, piperazinyl, (5-6 membered heterocyclyl)-$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl and (5-6 membered heteroaryl)-$C_{1-2}$ alkylene is independently unsubstituted or substituted with 1, 2, 3, or 4 substituents, and the substituent is independently selected from D, F, Cl, Br, I, CN, $NO_2$, OH, $NH_2$, —C(=O) OH, —SH, =O, methyl, ethyl, n-propyl, isopropyl, trifluoromethyl, methoxy, ethoxy, methylamino, trifluoromethoxy or difluoromethoxy.

In other embodiments, $R^{10}$ is H, D, F, Cl, Br, I, OH, CN, $NO_2$, $NH_2$, $C_{1-4}$ alkyl or $C_{1-4}$ alkoxy.

In still other embodiments, $R^{10}$ is H, D, F, Cl, Br, I, OH, CN, $NO_2$, $NH_2$, methyl, ethyl, n-propyl, isopropyl, methoxy or ethoxy.

In other embodiments, $R^5$ is H, D, $C_{1-4}$ alkyl, $C_{1-4}$ haloalkyl, $C_{3-6}$ cycloalkyl, 5-6 membered heterocyclyl, $C_{6-10}$ aryl or 5-6 membered heteroaryl, wherein each of $C_{1-4}$ alkyl, $C_{1-4}$ haloalkyl, $C_{3-6}$ cycloalkyl, 5-6 membered heterocyclyl, $C_{6-10}$ aryl and 5-6 membered heteroaryl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino, $C_{1-4}$ haloalkoxy, $C_{3-6}$ cycloalkyl, 5-6 membered heterocyclyl, $C_{6-10}$ aryl or 5-6 membered heteroaryl.

In still other embodiments, $R^5$ is H, D, methyl, ethyl, n-propyl, isopropyl, n-butyl, isobutyl, tert-butyl, trifluoromethyl, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each of methyl, ethyl, n-propyl, isopropyl, n-butyl, isobutyl, tert-butyl, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy, difluoromethoxy, cyclopropyl, cyclobutyl, cyclopentyl or phenyl.

In other embodiments, each of $R^6$ and $R^7$ is independently H, D, F, Cl, Br, I, CN, $NO_2$, OH, $NH_2$, $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl, 5-6 membered heterocyclyl, $C_{6-10}$ aryl or 5-6 membered heteroaryl, wherein each $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl, 5-6 membered heterocyclyl, $C_{6-10}$ aryl and 5-6 membered heteroaryl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino, $C_{1-4}$ haloalkoxy, $C_{3-6}$ cycloalkyl, 5-6 membered heterocyclyl, $C_{6-10}$ aryl or 5-6 membered heteroaryl.

In still other embodiments, each of $R^6$ and $R^7$ is independently H, D, F, Cl, Br, I, CN, $NO_2$, OH, $NH_2$, methyl, ethyl, n-propyl, isopropyl, n-butyl, isobutyl, tert-butyl, methoxy, ethoxy, methylamino, trifluoromethyl, trifluoromethoxy, difluoromethoxy, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each methyl, ethyl, n-propyl, isopropyl, n-butyl, isobutyl, tert-butyl, methoxy, ethoxy, methylamino, difluoromethoxy, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents, and the substituent is independently selected from D, F, Cl, Br, I, CN, NO$_2$, OH, NH$_2$, =O, —C(=O) OH, —C(=O) NH$_2$, methyl, ethyl, n-propyl, isopropyl, vinyl, ethynyl, trifluoromethyl, methoxy, ethoxy, methylamino, trifluoromethoxy, difluoromethoxy, cyclopropyl, cyclobutyl, cyclopentyl or phenyl.

In other embodiments, $R^6$ and $R^7$ together with the carbon atom to which they are attached, form a $C_{3-6}$ carbocycle, a 5-6 membered heterocycle, a $C_{6-10}$ aromatic ring or a 5-6 membered heteroaromatic ring, wherein each of $C_{3-6}$ carbocycle, 5-6 membered heterocycle, $C_{6-10}$ aromatic ring and 5-6 membered heteroaromatic ring is independently unsubstituted or substituted with 1, 2, 3 or 4 substituents, and the substituent is independently selected from D, F, Cl, Br, I, CN, NO$_2$, OH, NH$_2$, =O, —C(=O) OH, —C(=O) NH$_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy.

In still other embodiments, $R^6$ and $R^7$ together with the carbon atom to which they are attached, form cyclopropane, cyclobutane, cyclopentane, cyclohexane, pyrrolidine, tetrahydrofuran, tetrahydrothiophene, tetrahydropyran, tetrahydrothiopyran, piperidine, morpholine, thiomorpholine, piperazine, benzene ring, furan, pyrrole, pyridine, pyrazole, imidazole, triazole, tetrazole, oxazole, oxadiazole, 1,3,5-triazine, thiazole, thiophene, pyrazine, pyridazine or pyrimidine, wherein each of cyclopropane, cyclobutane, cyclopentane, cyclohexane, pyrrolidine, tetrahydrofuran, tetrahydrothiophene, tetrahydropyran, tetrahydrothiopyran, piperidine, morpholine, thiomorpholine, piperazine, benzene ring, furan, pyrrole, pyridine, pyrazole, imidazole, triazole, tetrazole, oxazole, oxadiazole, 1,3,5-triazine, thiazole, thiophene, pyrazine, pyridazine and pyrimidine is independently unsubstituted or substituted with 1, 2, 3, or 4 substituents, and the substituent is independently selected from D, F, Cl, Br, I, CN, NO$_2$, OH, NH$_2$, =O, —C(=O) OH, —C(=O) NH$_2$, methyl, ethyl, n-propyl, isopropyl, vinyl, ethynyl, trifluoromethyl, methoxy, ethoxy, methylamino, trifluoromethoxy or difluoromethoxy.

In other embodiments, $R^5$ and $R^6$ together with the atom to which they are attached, or $R^5$ and $R^7$ together with the atom to which they are attached, form a 3-6 membered heterocycle or a 5-6 membered heteroaromatic ring, wherein each 3-6 membered heterocycle and 5-6 membered heteroaromatic ring is independently unsubstituted or substituted with 1, 2, 3 or 4 substituents, and the substituent is independently selected from D, F, Cl, Br, I, CN, NO$_2$, OH, NH$_2$, =O, —C(=O) OH, —C(=O) NH$_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy.

In still other embodiments, $R^5$ and $R^6$ together with the atom to which they are attached, or $R^5$ and $R^7$ together with the atom to which they are attached, form aziridine, azetidine, pyrrolidine, pyrazolidine, imidazolidine, oxazolidine, thiazolidine, piperidine, morpholine, thiomorpholine, piperazine, pyrrole, pyridine, pyrazole, imidazole, triazole, tetrazole, oxazole, oxadiazole, 1,3,5-triazine, thiazole, pyrazine, pyridazine or pyrimidine, wherein each aziridine, azetidine, pyrrolidine, pyrazolidine, imidazolidine, oxazolidine, thiazolidine, piperidine, morpholine, thiomorpholine, piperazine, pyrrole, pyridine, pyrazole, imidazole, triazole, tetrazole, oxazole, oxadiazole, 1,3,5-triazine, thiazole, pyrazine, pyridazine and pyrimidine is independently unsubstituted or substituted with 1, 2, 3, or 4 substituents, and the substituent is independently selected from D, F, Cl, Br, I, CN, NO$_2$, OH, NH$_2$, =O, —C(=O) OH, —C(=O) NH$_2$, methyl, ethyl, n-propyl, isopropyl, vinyl, ethynyl, trifluoromethyl, methoxy, ethoxy, methylamino, trifluoromethoxy or difluoromethoxy.

In other embodiments, each of $R^8$ and $R^9$ is independently H, D, $R^eO$—$C_{1-4}$ alkylene, $R^dR^cN$—$C_{1-4}$ alkylene, $C_{1-6}$ alkyl, $C_{1-4}$ haloalkyl, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene, wherein each $C_{1-6}$ alkyl, $C_{1-4}$ haloalkyl, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl and (5-6 membered heteroaryl)-$C_{1-2}$ alkylene is independently unsubstituted or substituted with 1, 2, 3 or 4 substituents, and the substituent is independently selected from D, F, Cl, Br, I, CN, NO$_2$, =O, —OR$^e$, —NR$^cR^d$, —C(=O)OR$^e$, —C(=O) NHR$^f$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy.

In still other embodiments, each of $R^8$ and $R^9$ is independently H, D, $R^dR^cN$—$C_{1-4}$ alkylene, methyl, ethyl, n-propyl, isopropyl, n-butyl, isobutyl, tert-butyl, n-pentyl, n-hexyl, trifluoromethyl, cyclopropyl, cyclobutyl, cyclopentyl, cyclohexyl, $C_{3-6}$ cycloalkyl-$C_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl)-$C_{1-2}$ alkylene, phenyl, $C_{6-10}$ aryl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl or (5-6 membered heteroaryl)-$C_{1-2}$ alkylene, wherein each methyl, ethyl, n-propyl, isopropyl, n-butyl, isobutyl, tert-butyl, n-pentyl, n-hexyl, cyclopropyl, cyclobutyl, cyclopentyl, cyclohexyl, $C_{3-6}$ cycloalkyl-$C_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl)-$C_{1-2}$ alkylene, phenyl, $C_{6-10}$ aryl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl and (5-6 membered heteroaryl)-$C_{1-2}$ alkylene is independently unsubstituted or substituted with 1, 2, 3, or 4 substituents, and the substituent is independently selected from D, F, Cl, Br, I, CN, NO$_2$, =O, —OH, —NR$^cR^d$, —C(=O)OH, —C(=O) NH$_2$, methyl, ethyl, n-propyl, vinyl, ethynyl, trifluoromethyl, methoxy, ethoxy, methylamino, trifluoromethoxy or difluoromethoxy.

In other embodiments, $R^8$ and $R^9$ together with the nitrogen atom to which they are attached, form a 3-6 membered heterocycle or a 5-6 membered heteroaromatic ring, wherein each of 3-6 membered heterocycle and 5-6 membered heteroaromatic ring is independently unsubstituted or substituted with 1, 2, 3 or 4 substituents, and the substituent is independently selected from D, F, Cl, Br, I, CN, NO$_2$, =O, —OR$^e$, —NR$^cR^d$, —C(=O)OR$^e$, —C(=O)NHR$^f$, $C_{1-4}$ alkyl, $C_{2-4}$ alkenyl, $C^{2-4}$ alkynyl, $C_{1-4}$ haloalkyl, $C_{1-4}$ alkoxy, $C_{1-4}$ alkylamino or $C_{1-4}$ haloalkoxy.

In still other embodiments, $R^8$ and $R^9$ together with the nitrogen atom to which they are attached, form aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine or pyrimidine, wherein each of aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine and pyrimidine is independently unsubstituted or substituted with 1, 2, 3, or 4 substituents, and the substituent is independently selected from D, F, Cl, Br, I, CN, $NO_2$, =O, —OH, —$NR^cR^d$, —C(=O) OH, —C(=O) $NH_2$, methyl, ethyl, n-propyl, vinyl, ethynyl, trifluoromethyl, methoxy, ethoxy, methylamino, trifluoromethoxy or difluoromethoxy.

In other embodiments, each $R^c$, $R^d$, $R^e$ and $R^f$ is independently H, D, $C_{1-4}$ alkyl, $C_{1-4}$ haloalkyl, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene, wherein each $C_{1-4}$ alkyl, $C_{1-4}$ haloalkyl, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl and (5-6 membered heteroaryl)-$C_{1-2}$ alkylene is independently unsubstituted or substituted with 1, 2, 3 or 4 substituents, and the substituent is independently selected from D, F, Cl, Br, I, CN, $NO_2$, OH, —$NH_2$, =O, —C(=O)OH, —C(=O)$NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy.

In still other embodiments, each $R^c$, $R^d$, $R^e$ and $R^f$ is independently H, D, methyl, ethyl, n-propyl, isopropyl, n-butyl, isobutyl, tert-butyl, trifluoromethyl, cyclopropyl, cyclobutyl, cyclopentyl, cyclohexyl, $C_{3-6}$ cycloalkyl-$C_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl)-$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl or (5-6 membered heteroaryl)-$C_{1-2}$ alkylene, wherein each methyl, ethyl, n-propyl, isopropyl, n-butyl, isobutyl, tert-butyl, cyclopropyl, cyclobutyl, cyclopentyl, cyclohexyl, $C_{3-6}$ cycloalkyl-$C_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl)-$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl and (5-6 membered heteroaryl)-$C_{1-2}$ alkylene is independently unsubstituted or substituted with 1, 2, 3, or 4 substituents, and the substituent is independently selected from D, F, Cl, Br, I, CN, $NO_2$, OH, —$NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy or difluoromethoxy.

In other embodiments, $R^c$ and $R^d$ together with the nitrogen atom to which they are attached, form a 3-6 membered heterocycle or a 5-6 membered heteroaromatic ring, wherein each of 3-6 membered heterocycle and 5-6 membered heteroaromatic ring is independently unsubstituted or substituted with 1, 2, 3 or 4 substituents, and the substituent is independently selected from D, F, Cl, Br, I, CN, $NO_2$, =O, OH, —$NH_2$, —C(=O)OH, —C(=O)$NH_2$, $C_{1-4}$ alkyl, $C_{2-4}$ alkenyl, $C^{2-4}$ alkynyl, $C_{1-4}$ haloalkyl, $C_{1-4}$ alkoxy, $C_{1-4}$ alkylamino or $C_{1-4}$ haloalkoxy.

In still other embodiments, $R^c$ and $R^d$ together with the nitrogen atom to which they are attached, form aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine or pyrimidine, wherein each of aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine and pyrimidine is independently unsubstituted or substituted with 1, 2, 3, or 4 substituents, and the substituent is independently selected from D, F, Cl, Br, I, CN, $NO_2$, OH, $NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy or difluoromethoxy.

In some embodiments, the present invention relates to one of the following structures, or a stereoisomer, geometric isomers, a tautomer, an N-oxide, a solvate, a metabolite, a pharmaceutically acceptable salt, a dimer, a trimer or a prodrug thereof, (1)

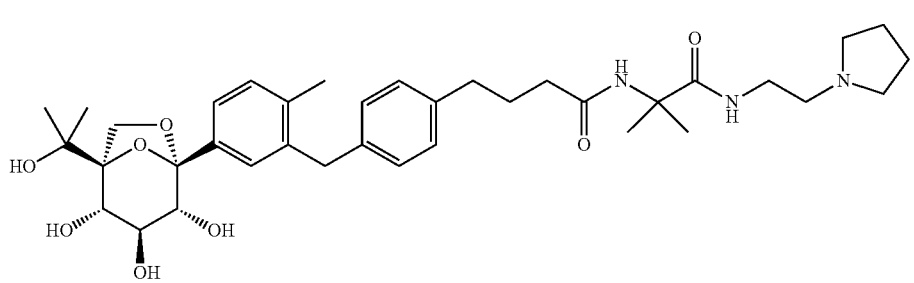

,

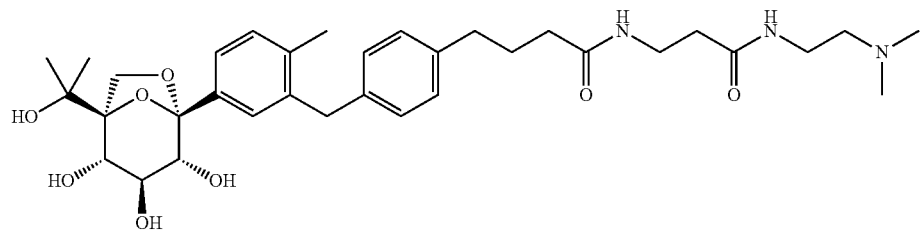
(2)
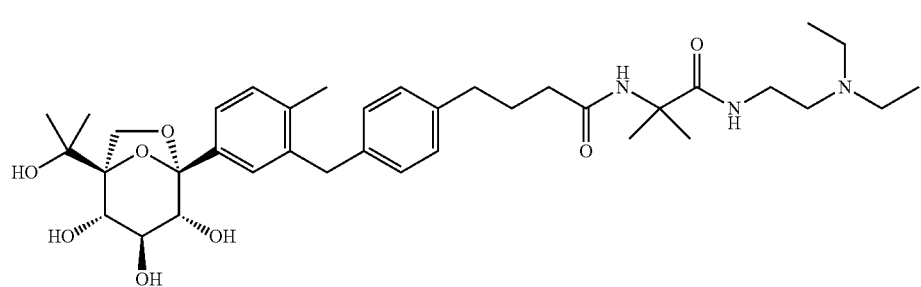
(3)
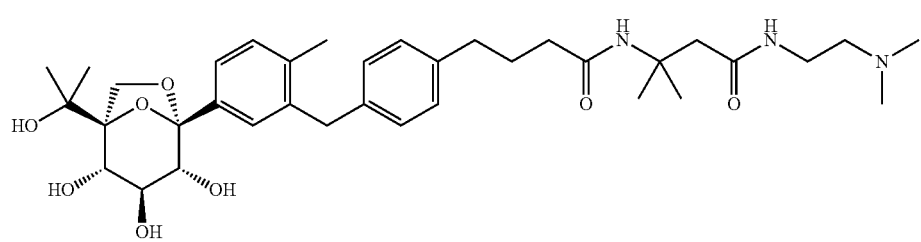
(4)
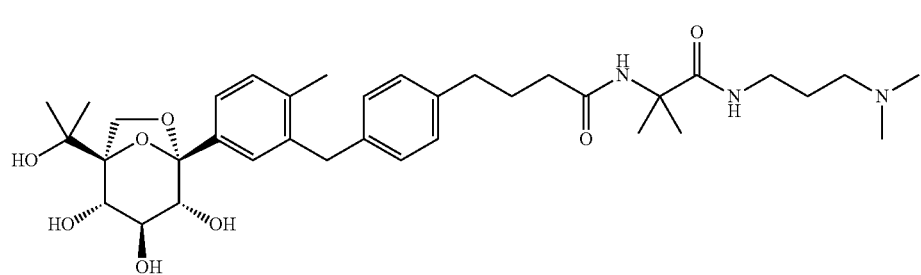
(5)
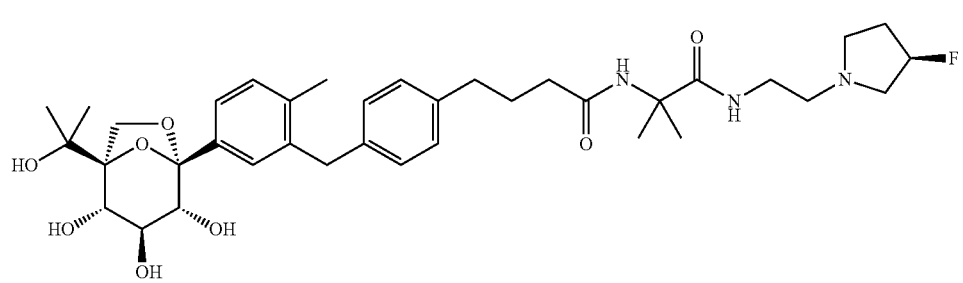
(6)
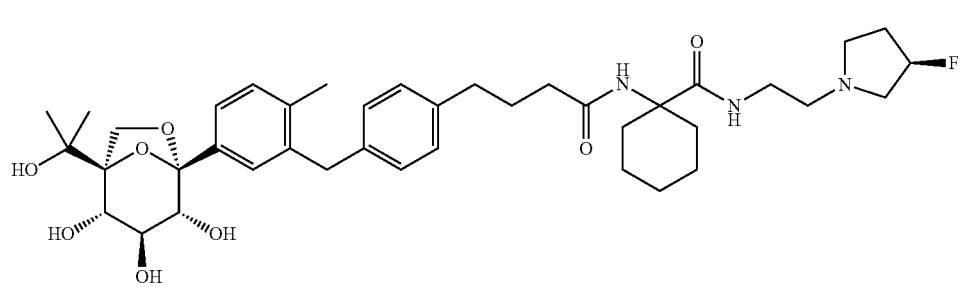
(7)

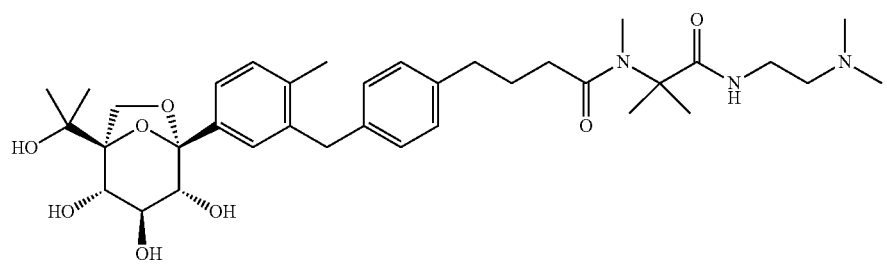
(8)
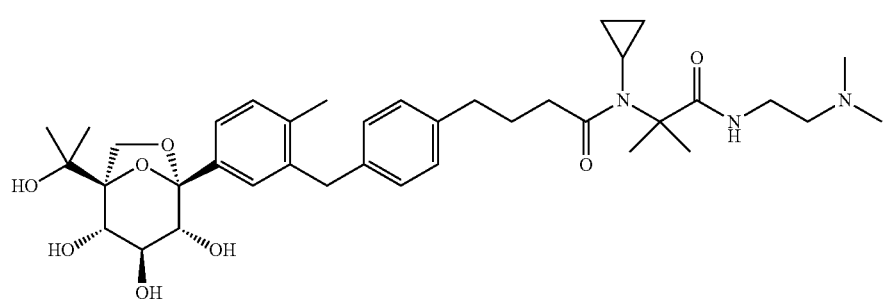
(9)
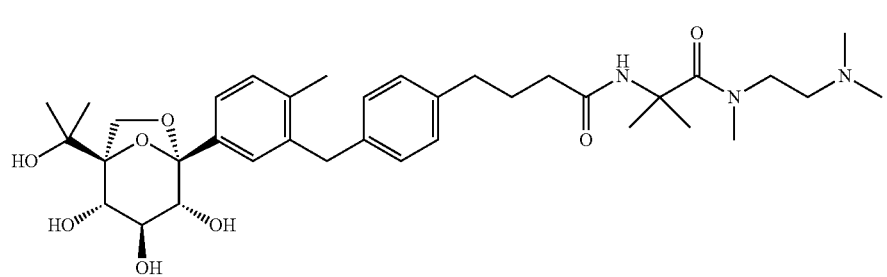
(10)
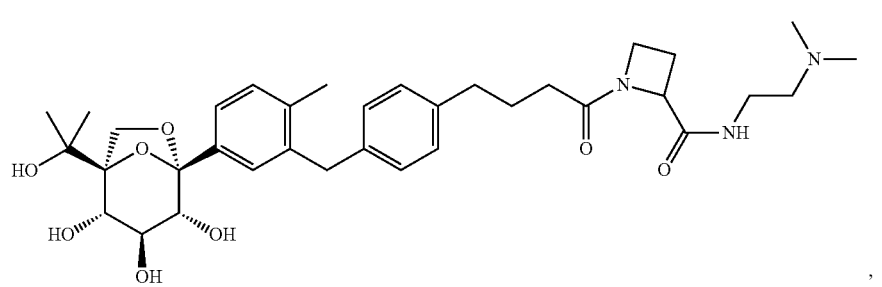
(11)
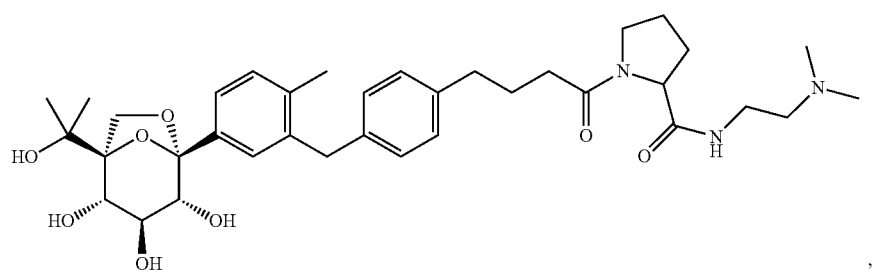
(12)

-continued
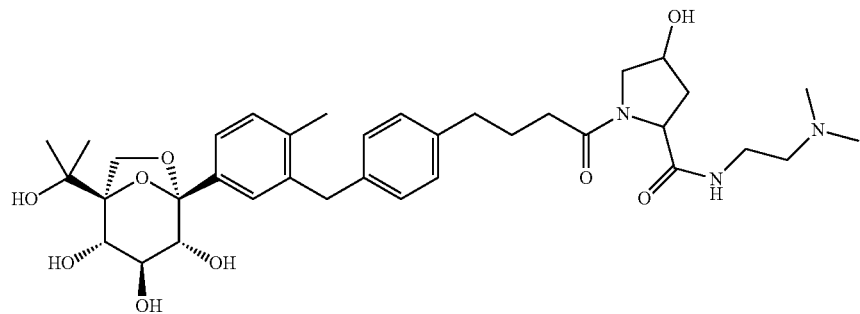
(13)
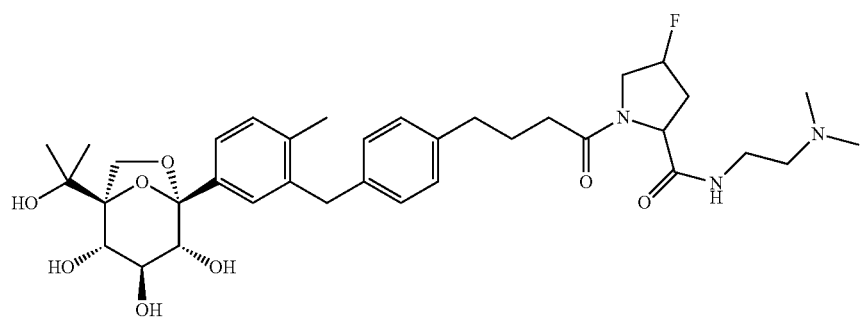
(14)
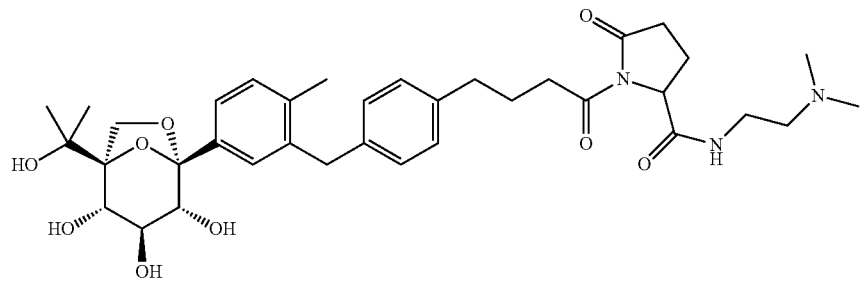
(15)
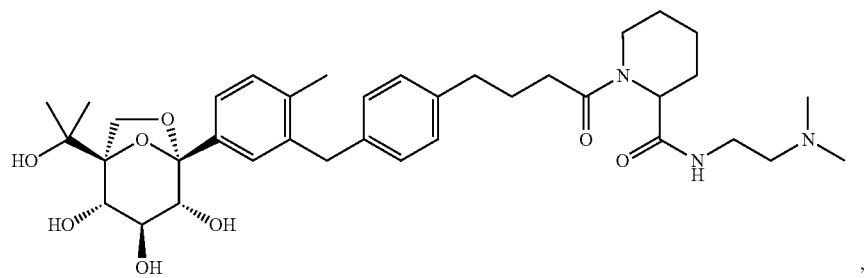
(16)
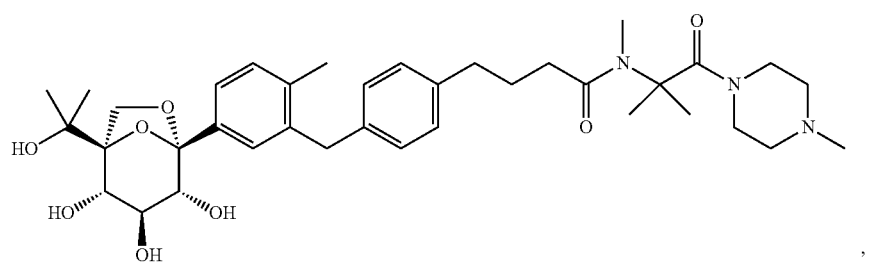
(17)

-continued
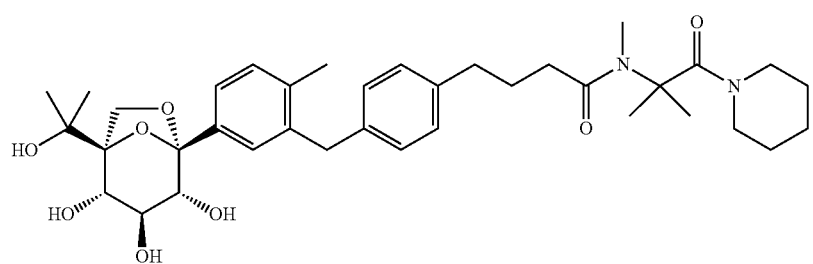
(18)
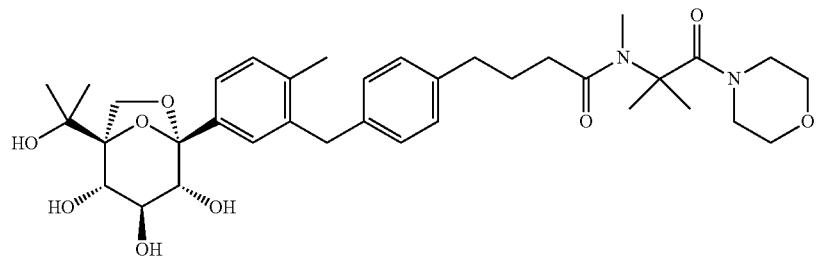
(19)
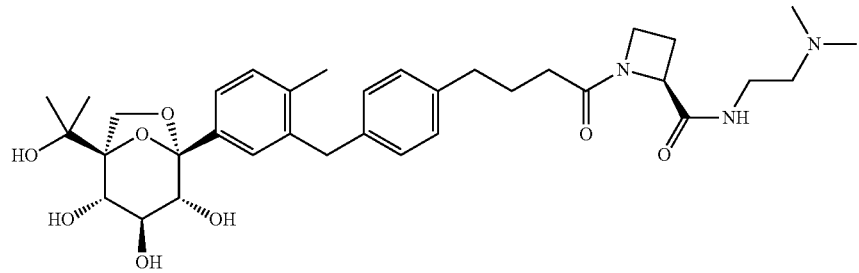
(20)
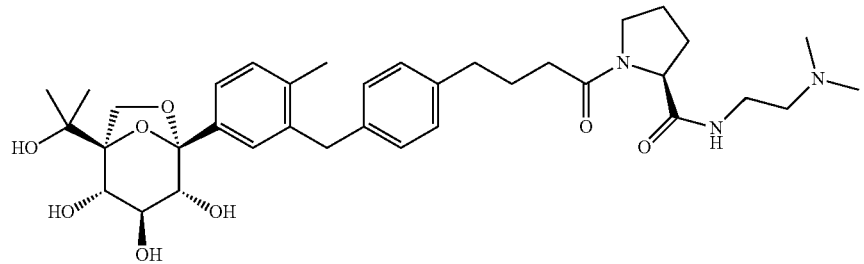
(21)
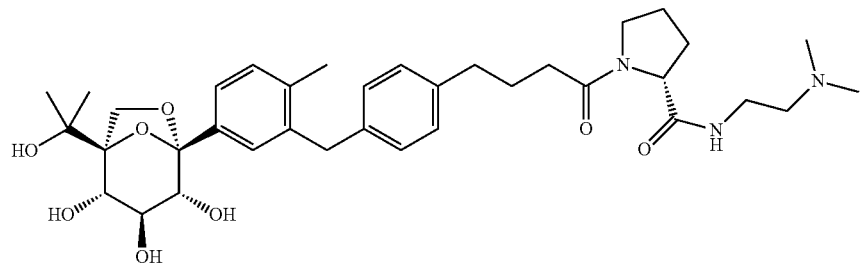
(22)

-continued

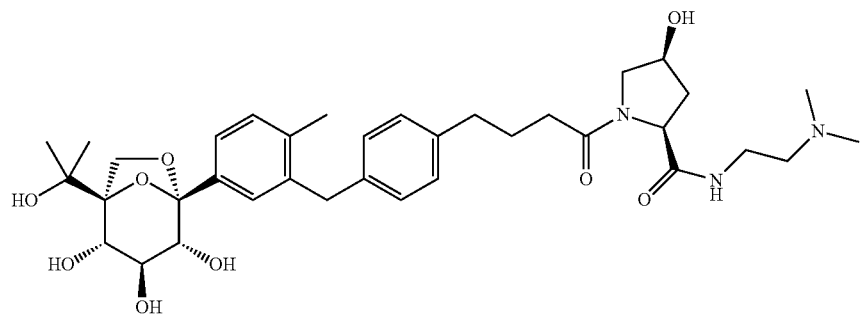

(23)

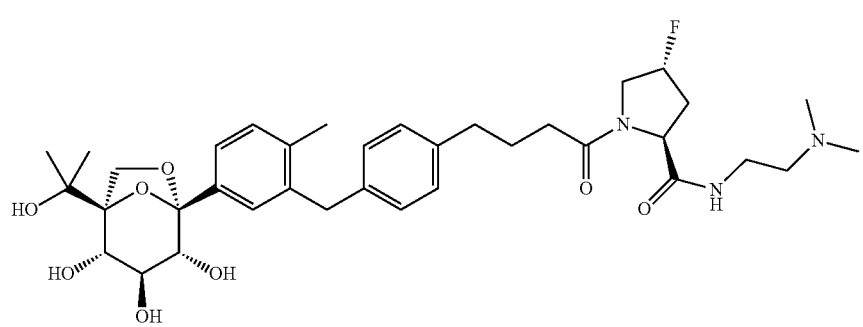

(24)

or

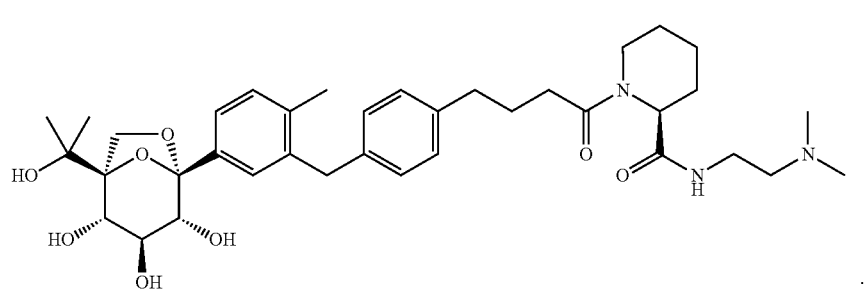

(25)

.

In other aspect, provided herein is a pharmaceutical composition comprising the compound disclosed herein.

In some embodiments, the pharmaceutical composition of the present invention further comprises a pharmaceutically acceptable carrier, excipient, adjuvant, vehicle or a combination thereof.

In some embodiments, the pharmaceutical composition of the present invention further comprises one or more other additional therapeutic agents, wherein the other additional therapeutic agent is selected from an anti-diabetic drug, an anti-hyperglycemic drug, an anti-obesity drug, an anti-hypertensive drug, an appetite suppressant drug, a lipid-lowering drug, or a combination thereof.

In some embodiments, the pharmaceutical composition of the present invention can be in the form of a liquid, solid, semi-solid, gel or spray.

In other embodiments, each anti-diabetic and anti-hyperglycemic drug of the present invention is independently selected from a SGLT2 inhibitor, a biguanide drug, a sulfonylurea drug, a glucosidase inhibitor, a PPAR agonist (peroxisome proliferator-activated receptor agonist), a αP2 inhibitor (fat cell fatty acid binding protein inhibitor), a PPARα/γ dual activator (peroxisome proliferator-activated receptor α/γ dual activator), a dipeptidyl peptidase IV inhibitor, a glinides drug, an insulin, a glucagon-like peptide-1 inhibitor, a PTP1B inhibitor (protein tyrosine phosphatase 1B inhibitor), a glycogen phosphorylase inhibitor, a glucose-6-phosphatase inhibitor or a combination thereof.

In other embodiments, the anti-obesity drug of the present invention is selected from a central anti-obesity drug, a MCH (black pigment concentrating hormone) receptor antagonist, a neuropeptide Y receptor antagonist, a cannabinoid receptor antagonist, a cerebrointestinal peptide antagonist, a lipase inhibitor, a β3 agonist, a 11β-HSD1 (11β hydroxysteroid dehydrogenase 1) inhibitor, a DGAT-1 (diacylglycerol acyltransferase 1) inhibitor, a peptide appetite inhibitor, a cholecystokinin agonist, a feeding inhibitor or a combination thereof.

In other embodiments, the antihypertensive drug of the present invention is selected from an angiotensin converting enzyme inhibitor, an angiotensin II receptor antagonist, a calcium channel antagonist, a potassium channel opener, a diuretic, or a combination thereof.

In other embodiments, the lipid-lowering drug of the present invention is selected from a MTP inhibitor (microsomal triglyceride transfer protein inhibitor), a HMG-CoA reductase inhibitor (hydroxymethylglutaryl coenzyme A reductase inhibitor), a squalene synthase inhibitor, a betinic acid-type hypolipidemic drug (also known as fibrate hypolipidemic drug), an ACAT inhibitor (acetylcholesterol acetyltransferase inhibitor), a lipoxygenase inhibitor, a cholesterol absorption inhibitor, an ileum sodium ion/bile acid co-transporter inhibitor, an up-regulator of LDL receptor activity, a nicotinic hypolipidemic drug, a bile acid chelate, or a combination thereof.

In still other embodiments, the lipid-lowering drug is pravastatin, simvastatin, atorvastatin, fluvastatin, cerivastatin, atavastatin, rosuvastatin or a combination thereof.

In other aspect, provided herein is use of the compound or the pharmaceutical composition disclosed herein in the manufacture of a medicament for inhibiting SGLT1 in humans or animals.

In other aspect, provided herein is use of the compound or the pharmaceutical composition disclosed herein in the manufacture of a medicament for improving the intestinal environment.

In other aspect, provided herein is use of the compound or the pharmaceutical composition disclosed herein in the manufacture of a medicament for preventing or treating a disease, lessening a disease symptom or delaying the progression or onset of a disease, wherein the disease is diabetes, diabetic complication, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders related to blood concentration, constipation, or high blood pressure.

In some embodiments, the diabetic complication is diabetic retinopathy, diabetic neuropathy or diabetic nephropathy.

In some embodiments, the hyperlipidemia is hypertriglyceridemia.

In another aspect, provided herein is a method of inhibiting SGLT1 activity comprising administering to the patient a therapeutically effective amount of the compound or the pharmaceutical composition disclosed herein.

In another aspect, provided herein is a method of improving the intestinal environment comprising administering to the patient a therapeutically effective amount of the compound or the the pharmaceutical composition disclosed herein.

In another aspect, provided herein is a method of preventing or treating a disease comprising administering to the patient a therapeutically effective amount of the compound or the the pharmaceutical composition disclosed herein, wherein the disease is diabetes, diabetes complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders related to blood concentration, constipation, or high blood pressure. Moreover, the above-mentioned compound or pharmaceutical composition provided by the present invention can be co-administered with other therapies or therapeutic agents. The mode of administration can be simultaneous, sequential or at certain time intervals.

The dosage of the compound or pharmaceutical composition required for the implementation of treatment, prevention or delay is usually dependent on the specific compound administered, the patient, the specific disease or condition and its severity, the route and frequency of administration, etc., and it needs to be determined by the attending physician according to the specific situation. For example, when the compound or pharmaceutical composition provided by the present invention is administered by an intravenous route, it can be administered once a week or even longer intervals.

In other aspect, provided herein is the compound or the pharmaceutical composition disclosed herein for use in inhibiting SGLT1.

In another aspect, provided herein is the compound or the pharmaceutical composition disclosed herein for use in improving the intestinal environment.

In other aspect, provided herein is the compound or the pharmaceutical composition disclosed herein for use in preventing or treating a disease, lessening a disease symptom or delaying the progression or onset of a disease, wherein the disease is diabetes, diabetes complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders related to blood concentration, constipation, or high blood pressure.

In some embodiments, the salt refers to a pharmaceutically acceptable salt. The term "pharmaceutically acceptable" means that the substance or composition must be chemically and/or toxicologically compatible with the other ingredients comprising the formulation and/or the mammal being treated with it.

The compound of the present invention also includes other salt of such compound, which is not necessarily pharmaceutically acceptable salt, and can be used as an intermediate for preparing and/or purifying the compound of the invention and/or for separating an enantiomer of the compound of the present invention.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, lauryl sulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, p-toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have the structure depicted by the general formula given herein, except that one or more atoms are replaced by the atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^{2}H$, $^{3}H$, $^{11}C$, $^{13}C$, $^{14}C$, $^{15}N$, $^{18}F$, $^{31}P$, $^{32}P$, $^{36}S$, $^{37}Cl$ or $^{125}I$, respectively.

In another aspect, the compounds of the invention include isotopically enriched compounds as defined herein, for example those into which radioactive isotopes, such as 3H, 14c and $^{18}F$, or those into which non-radioactive isotopes, such as $^{2}H$ and $^{13}C$ are present. Such isotopically enriched compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. An $^{18}F$-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability. For example, increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g., $D_2O$, $d_6$-acetone, DMSO-$d_6$.

The foregoing merely summarizes certain aspects disclosed herein and is not intended to be limiting in nature. These aspects and other aspects and embodiments are described more fully below.

Composition of the Compound of the Invention and Preparations and Administration The present invention relates to a pharmaceutical composition comprising the compound of the present invention or the compound of the structure shown in the examples, or a stereoisomer, a geometric isomer, a tautomer, an N-oxide, a solvate, a metabolite, a dimer, a trimer, a pharmaceutically acceptable salt or a prodrug thereof. The pharmaceutical composition further comprises at least one pharmaceutically acceptable carrier, excipient, adjuvant, vehicle or a combination thereof, and, optionally, other therapeutic and/or prophylactic ingredients. The amount of the compound in the pharmaceutical compositions disclosed herein is an effective and detectable amount for inhibiting sodium-dependent glucose transporters (SGLTs), especially SGLT1 activity.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

Pharmaceutically acceptable carriers may contain inert ingredients that do not unduly inhibit the biological activity of the compound. The pharmaceutically acceptable carrier should be biocompatible, for example, non-toxic, non-inflammatory, non-immunogenic or once administered to the patient without other adverse reactions or side effects. Standard pharmaceutical technology can be used.

As described above, the pharmaceutical compositions or pharmaceutically acceptable compositions disclosed herein further comprise a pharmaceutically acceptable carrier, an adjuvant, or a vehicle, which, as used herein, includes any and all solvents, diluents, liquid vehicle, dispersion or suspension aids, surface active agents, isotonic agents, thickening or emulsifying agents, preservatives, solid binders, lubricants and the like, as suited to the particular dosage form desired. Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, any other conventional carrier medium and its use are also contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as Tween 80, phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, methyl cellulose, hydroxypropyl methyl cellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds or compositions of the present invention can be administered by any suitable means, and the compounds and the pharmaceutically acceptable compositions described above can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofuryl alcohol, polyethylene glycols and fatty acid esters of sorbitan, and mixtures thereof. In addition to the inert diluent, the oral compositions may also contain adjuvants such as wetting agents, emulsifying or suspending agents, sweetening agents, flavoring agents and fragrances.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. The acceptable vehicles and solvents that include water, Ringer's solution, U. S. P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound or a composition described herein, it is often desirable to slow the absorption of the compound from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolic acid. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

The solid dosage forms for oral administration include capsules, tablets, pills, powders and granules. In such solid dosage forms, the active compounds are mixed with at least one pharmaceutically acceptable inert excipients or carriers, such as sodium citrate or calcium phosphate and/or (a) fillers or swelling agents such as starch, lactose, sucrose, glucose, mannitol and silicic acid; (b) adhesives such as carboxymethylcellulose, alginates, gelatin, polyethylene pyrrole ketone, sucrose and gum arabic; (c) moisturizing agents such as glycerol; (d) disintegrating agents such as agar, calcium carbonate, potato starch or tapioca starch, alginic acid, certain silicates and sodium carbonate; (e) blocker solution, such as paraffin; (f) absorption promoter such as quaternary ammonium compounds; (g) wetting agents such as cetyl alcohol and glycerol monostearate; (h) absorbents such as kaolin and bentonite, (i) lubricants such as talc, calcium stearate, magnesium stearate, solid polyethylene glycol, laurylsodium sulfate, and mixtures thereof. In the case of capsules, tablets and pills, the pharmaceutical compositions may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, controlled release coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the pharmaceutical compositions may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active ingredient is admixed under sterile conditions with a pharmaceutically acceptable carrier and any necessary preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carrier compounds for topical administration of the present invention include, but are not limited to, mineral oil, petrolatum oil, white petrolatum, propylene glycol, polyoxyethylene, polyoxypropylene compounds, emulsified waxes and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Compounds disclosed herein can be administered as the sole pharmaceutical agent or in combination with one or more other additional therapeutic (pharmaceutical) agents where the combination causes no unacceptable adverse effects. This may be of particular relevance for the treatment of diabetes, diabetic complications and other related diseases. Some non-limiting examples of these diseases include diabetes mellitus type I, diabetes type II, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, diabetic complications, atherosclerosis, cardiovascular disease, congestive heart failure, hypomagnesemia, hyponatremia, renal failure, disorders related to blood concentration, constipation, or hypertension. The "additional therapeutic agent" used in the present invention includes an anti-diabetic drug, an anti-hyperglycemic drug, an anti-obesity drug, an anti-hypertensive drug, an appetite suppressing drug, a lipid-lowering drug, or a combination thereof.

Wherein, the anti-diabetic agent includes, but is not limited to, a SGLT2 inhibitor (e.g., dapagliflozin, canagliflozin, tofogliflozin, ipragliflozin, luseogliflozin, empagliflozin), a biguanide drug (e.g., phenformin, metformin), a sulfonylurea drug (e.g., acetohexamide, chlorpropamide, glibenclamide, glipizide, gliclazide, glimepiride, glipentide, gliquidone, tolazamide, tolbutamide and meglitinide), a glinides drug (e.g., repaglinide and nateglinide), an α-glucoside hydrolase inhibitor (e.g., acarbose), an α-glucosidase inhibitor (e.g., adiposine, camiglibose, emiglitate, miglitol, voglibose, pradimicin, salbostatin), a PPAR agonist (e.g., bagliglitazone, ciglitazone, darglitazone, englitazone, isaglitazone, pioglitazone, rosiglitazone and troglitazone), a PPARα/γ dual agonist (such as CLX-0940, GW-1536, GW-1929, GW-2433, KRP-297, L-796449, LR-90, MK-0767 and SB-219994), a dipeptidyl peptidase IV (DPP-IV) inhibitor (e.g., sitagliptin, vidagliptin, alogliptin, linagliptin and saxagliptin), a glucagon-like peptide-1(GLP-1) agonist (e.g., exendin-3 and exendin-4), a protein tyrosine phosphatases-1B (PTP-1B) inhibitor (e.g., trodusquemine, hyrtiosal extract and compounds are disclosed by Zhang, S. et al., Drug Discovery Today, 12(9/10), 373-381, 2007), insulin, an insulin mimetic, a glycogen phosphorylase inhibitor, a VPAC2 receptor agonist, a glucokinase activator, a glycogen phosphorylase inhibitor, a glucose-6-phosphatase inhibitor, an αP2 inhibitor, an acetyl-CoA carboxylase-2 (ACC-2) inhibitor, a phosphodiesterase (PDE)-10 inhibitor, a diacylglycerol acyltransferase (DGAT) 1 or 2 inhibitor, a glucose transporter 4 (GLUT4) regulator and a glutamine-fructose-6-phosphate amidotransferase (GFAT) inhibitor.

Wherein, the antihyperglycemic agent includes, but is not limited to, a SGLT2 inhibitor (e.g., dapagliflozin, canagliflozin, tofogliflozin, ipragliflozin, luseogliflozin, empagliflozin), a biguanide drug (e.g., phenformin and metformin), a sulfonylurea drug (e.g., acetohexamide, chlorpropamide, glibenclamide, glipizide, gliclazide, glimepiride, glipentide, gliquidone, tolazamide, tolbutamide and meglitinide), a glinides drug (e.g., repaglinide, nateglinide), an α-glucoside hydrolase inhibitor (e.g., acarbose), an α-glucosidase inhibitor (e.g., adiposine, camiglibose, emiglitate, miglitol, voglibose, pradimicin and salbostatin), a PPAR agonist (e.g., balaglitazone, ciglitazone, darglitazone, englitazone, isaglitazone, pioglitazone, rosiglitazone and troglitazone), a PPARα/γ dual agonist (such as CLX-0940, GW-1536, GW-1929, GW-2433, KRP-297, L-796449, LR-90, MK-0767 and SB-219994), a dipeptidyl peptidase IV (DPP-IV) inhibitor (e.g., sitagliptin, vidagliptin, alogliptin and saxagliptin), a glucagon-like peptide-1(GLP-1) agonist (e.g., exendin-3 and exendin-4), a protein tyrosine phosphatases-1B (PTP-1B) inhibitor (e.g., trodusquemine, hyrtiosal extract and compounds are disclosed by Zhang, S. et al., Drug Discovery Today, 12(9/10), 373-381, 2007), insulin, an insulin mimetic, a glycogen phosphorylase inhibitor, a VPAC2 receptor agonist, a glucokinase activator, a glycogen phosphorylase inhibitor, a glucose-6-phosphatase inhibitor, an αP2 inhibitor, an acetyl-CoA carboxylase-2 (ACC-2) inhibitor, a phosphodiesterase (PDE)-10 inhibitor, a diacylglycerol acyltransferase (DGAT) 1 or 2 inhibitor, a glucose transporter 4 (GLUT4) regulator and a glutamine-fructose-6-phosphate amidotransferase (GFAT) inhibitor.

Wherein, the anti-obesity drug of the present invention includes, but is not limited to a central anti-obesity drug (such as dexfenfluramine, fenfluramine, phentermine, sibutramine, amfepramone, d-amphetamine, mazidol, phenylpropanolamine, clobenzorex, a MCH receptor antagonist (e.g., compounds described in WO06035967, SB-568849; SNAP-7941, T-226296), a neuropeptide Y receptor antagonist (e.g., CP-422935), a cannabinoid receptor antagonist (e.g., rimonabant, SR-147778), a cerebrointestinal peptide antagonist, a lipase inhibitor (e.g., orlistat, ATL-962), a β3 agonist (e.g., AJ-9677, AZ40140), a 11β-HSD1 inhibitor (e.g., BVT-3498, INCB13739), a DGAT-1 inhibitor, peptide appetite suppressants (e.g., leptin, CNTF (ciliary neurotrophic factor)), a cholecystokinin agonist (e.g., lintitript)) and a feeding inhibitor (e.g., P-57).

Wherein, the lipid-lowering agent includes, but is not limited to, an MTP inhibitor, an HMGCoA reductase inhibitor, a squalene synthase inhibitor, a fibrate hypolipidemic drug (betinic acid-type hypolipidemic drug), an ACAT inhibitor, a lipoxygenase inhibitor, a cholesterol absorption inhibitor, an ileal Na(+)/bile acid cotransporter inhibitor, an upregulators of LDL receptor activity, a bile acid sequestrant or a nicotinic acid hypolipidemic drug In some embodiments, the lipid-lowering agent is selected from pravastatin, simvastatin, atorvastatin, fluvastatin, cerivastatin, atavastatin and rosuvastatin. Wherein, the anti-obesity agent includes a CB-1 antagonist (such as rimonabant, taranabant, surinabant, otenabant, SLV319 and AVE1625), a gut-selective MTP inhibitor (such as dirlotapide, mitratapide and implitapide), a CCKa agonist, a 5-HT2c agonist (such as lorcaserin), a MCR4 agonist, a lipase inhibitor (such as cetilistat), PYY3-36, an opioid antagonist (such as naltrexone), oleoyl-estrone, obinepitide, pramlintide, tesofensine, leptin, liraglutide, bromocriptine, orlistat, exenatide, AOD-9604 and sibutramide.

Wherein, the suitable anti-inflammatory agent includes genital tract/urinary tract infection preventative and treatment. Exemplary agent includes cranberry (*Vaccinium macrocarpon*) and cranberry derivative, such as cranberry juice, cranberry extract or flavonol of cranberry. Moreover, other suitable anti-inflammatory agent includes, but is not limited to, aspirin, a non-steroidal anti-inflammatory drug, glucocorticosteroid, sulfasalazine and a selective cyclooxygenase-2 inhibitor, etc.

Use of the Compounds and Pharmaceutical Compositions

The amount of the compound or the compound in the compositions disclosed herein is an effective and detectable amount for inhibiting sodium-dependent glucose transporters (SGLTs) activity, especially SGLT1 activity. Hence, the compound of the invention would be used for preventing and treating diabetes and related diseases or improving symptoms of these diseases.

Compounds disclosed herein would be useful for, but are not limited to, preventing or treating diabetes or related diseases, or lessening diabetes or related diseases, or delaying the progression or onset of diabetes or related diseases or increasing HDL levels in a patient by administering to the patient a compound or a composition disclosed herein in an effective amount. Such diseases include, but are not limited to diabetes, especially type 2 diabetes, and insulin resistance, hyperglycemia, hyperinsulinemia, hyperlipidemia such as hypertriglyceridemia, diabetic complications such as diabetic retinopathy, diabetic neuropathy or diabetic nephropathy, obesity, syndrome X, atherosclerosis, cardiovascular disease, congestive heart failure, hypomagnesemia, hyponatremia, renal failure, disorders related to blood concentration, constipation or high blood pressure.

The compound of the present invention has an excellent intestinal environment improvement effect, which can increase the beneficial bacteria of bifidobacteria, *Lactobacillus*, etc., increase the organic acid in the intestine, and reduce the spoilage products in the intestine. By covering the intestinal environment, diseases associated with changes in the intestinal environment can be improved. The "disease associated with changes in the intestinal environment" includes, but is not limited to, chronic kidney disease, pseudomembranous enteritis/hemorrhagic enteritis, infectious enteritis, ulcerative colitis, Crohn's disease, irritable bowel syndrome, obesity, arteriosclerosis, hypertension, Guillain-Barré syndrome, allergic diseases, diabetes, multiple sclerosis, autoimmune diseases, alcoholic liver dysfunction, nonalcoholic fatty liver disease, nonalcoholic fatty hepatitis, non-steroidal anti-inflammatory drug-induced enteritis, stress, depression, influenza, periodontal disease, cancer, hay fever, functional dyspepsia, pruritus, etc.

Moreover, compounds or pharmaceutical compositions disclosed herein also suit for preventing or treating the damage of diabetes in later stages, such as kidney disease, retinopathy, neuropathy, myocardial infarction, peripheral arterial disease, thrombosis, arteriosclerosis, inflammation, immunological diseases, autoimmune diseases such as AIDS, asthma, osteoporosis, cancer, psoriasis, Alzheimer's disease, schizophrenia and infectious diseases.

An "effective amount" or "effective dose" of the compound or pharmaceutically acceptable composition is an amount that is effective in treating or lessening the severity of one or more of the aforementioned disorders. The compounds and pharmaceutically acceptable compositions are effective administered in a fairly wide dose range. For example, the daily dose is from about 0.1 mg to 1000 mg per person, the compounds or pharmaceutically acceptable compositions can be administered in a single dose or in several divided doses a day. The compounds and compositions, according to the method disclosed herein, may be administered using any amount and any route of administration which is effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents as discussed above.

General Synthesis and Detection Methods

To describe the invention, the following examples are listed. However, it should be understood that the present invention is not limited to these embodiments, but merely provides a method for practicing the present invention.

In the present invention, if the chemical name of the compound doesn't match the corresponding structure, the compound is characterized by the corresponding structure.

Generally, the compounds disclosed herein may be prepared by methods described herein, wherein the substituents are as defined for Formula (I), Formula (I-a) or Formula (II) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

The structures of the compounds were identified by nuclear magnetic resonance (e.g., $^1$H-NMR, $^{13}$C-NMit or/and $^{19}$F-NMR). $^1$H-NMR, $^{13}$C-NMit or/and $^{19}$F-NMR chemical shifts (δ) were recorded as ppm ($10^{-6}$). $^1$H-NMR, $^{13}$C-NMR, and $^{19}$F-NMit were measured with Bruker Ultrashield-400 nuclear magnetic resonance spectrometer and Bruker Avance III HD 600 nuclear magnetic resonance spectrometer. The determination solvent is deuterated chloroform ($CDCl_3$), deuterated methanol ($CD_3OD$ or MeOH-$d_4$) or deuterated dimethyl sulfoxide (DMSO-$d_6$). TMS (0 ppm) or chloroform (7.25 ppm) was used as the reference standard. When peak multiplicities are reported, the following abbreviations are used: s (singlet), d (doublet), t (triplet), m (multiplet), br (broadened), dd (doublet of doublets), dt (doublet of triplets), td (triplet of doublets), brs (broadened singlet). Coupling constants J, when given, were reported in Hertz (Hz).

Novasep pump 250 high performance liquid chromatograph was generally used for preparative purification or preparative resolution.

LC-MS spectra were determined on Agilen-6120 Quadrupole LC/MS mass spectrometer;

The silica gel used in column chromatography generally was Qingdao Ocean Chemical Factory 300 to 400 mesh silica gel.

The staring materials of the present invention were known or purchased from Shanghai Accela Company, Energy Company, J&K, Alfa Company and the like, or they could be prepared by the conventional synthesis methods in the prior art.

Unless otherwise stated, the reactions disclosed herein were carried out in a nitrogen atmosphere.

The term "nitrogen atmosphere" refers to such an atmosphere that a reaction flask was equipped with a balloon or a stainless steel autoclave filled with about 1 L nitrogen.

The term "hydrogen atmosphere" refers to such an atmosphere that a reaction flask was equipped with a balloon or a stainless steel autoclave filled with about 1 L hydrogen.

Unless otherwise stated, the solution used in the examples disclosed herein was an aqueous solution.

Unless otherwise stated, the reaction temperature was room temperature.

Unless otherwise stated, the room temperature was from 20° C. to 30° C.

The reaction process in the examples was monitored by thin layer chromatography (TLC). The solvent system for development of a TLC plate comprised dichloromethane and methanol, dichloromethane and ethyl acetate, petroleum ether and ethyl acetate. The volume ratio of the solvents in the solvent system was adjusted according to the polarity of the compounds.

The elution system of column chromatography comprised: A: petroleum ether and ethyl acetate, B: dichloromethane and ethyl acetate, C: dichloromethane and methanol. The volume ratio of the solvents in the elution system was adjusted according to the polarity of the compounds, and sometimes it was also adjusted by adding a basic agent such as aqueous ammonia or an acidic agent such as acetic acid.

The following abbreviations are used throughout the specification:

| | | | | | |
|---|---|---|---|---|---|
| DMSO-$d_6$: | deuterated dimethyl sulfoxide; | $CDCl_3$: | chloroform-d; | $CD_3OD$: | methanol-d; |
| $D_2O$: | deuterated water | Allyl: | allyl; | Br: | bromine; |
| Mg: | magnesium; | Cbz: | benzyloxycarbonyl; | Ac: | acetyl; |
| Bn: | benzyl; | Et: | ethyl; | Me: | methyl; |
| Ms: | methanesulfonyl; | Boc: | tert-butoxycarbonyl; | PMB: | p-methoxybenzyl; |
| HCl: | hydrogen chloride; | MeOH: | methanol; | mL: | milliliter; |
| μL: | microliter; | M, mol/L: | mole/liter; | mmol: | millimoles; |
| g: | gram; | mol: | mole; | h: | hour; |
| $H_2$: | hydrogen; | min: | minute; | $N_2$: | nitrogen; |
| MPa: | megapascal; | atm: | standard atmospheric pressure; | DCM: | methylene chloride; |
| HBTU: | O-benzotriazole-tetramethylurea hexafluorophosphate; | | | | |
| HATU: | O-(7-azabenzotriazol-1-yl)-N,N,N,N-tetramethylurea hexafluorophosphate; | | | | |
| DBU: | 1,8-diazabicyclo[5.4.0]undec-7-ene. | | | | |

General Synthetic Procedures

The typical synthetic steps for preparing the compounds disclosed in the present invention are shown in the following synthetic schemes 1 to 6. Unless otherwise stated, $R^2$, $R^3$, $R^6$, $R^7$, $R^c$, $X^d$ and t are as defined herein.

Synthetic scheme 1

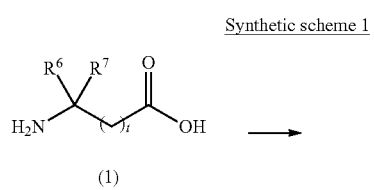

(1)

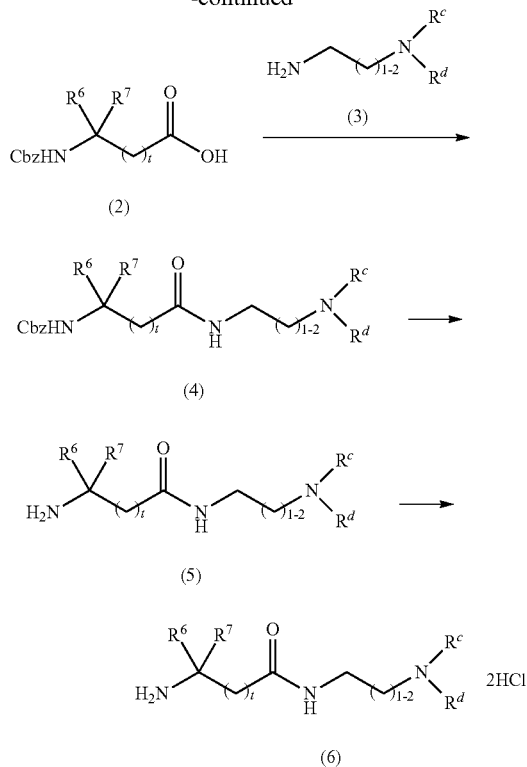

The intermediate having formula (6) can be synthesized by the method disclosed in synthesis scheme 1. First, compound (1) can react with benzyl chloroformate to give compound (2). Compound (2) and compound (3) can be subjected to a condensation reaction to give compound (4). Then, compound (4) can remove the Cbz protecting group on the amino group by catalytic hydrogenation to produce compound (5). Finally, compound (5) can form a salt with hydrogen chloride to give compound (6).

Synthetic scheme 2

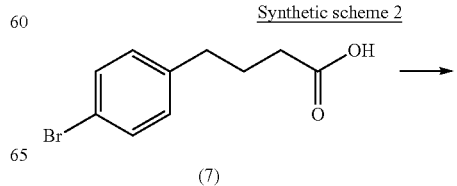

(7)

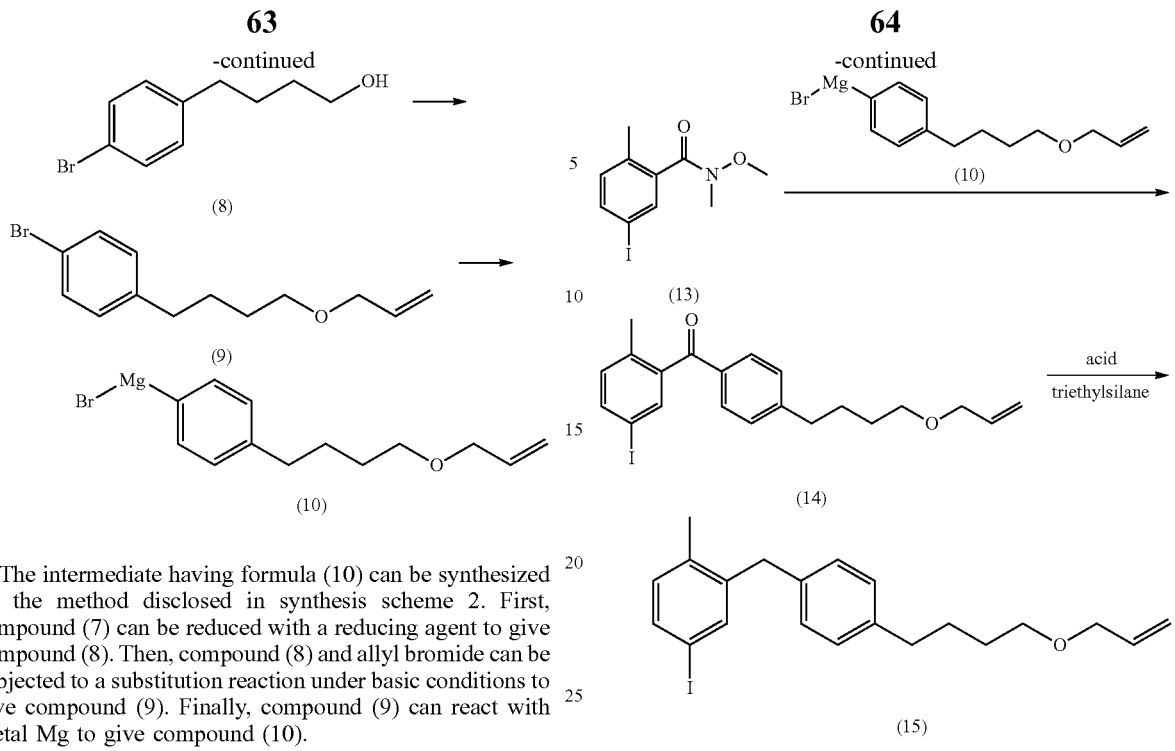

The intermediate having formula (10) can be synthesized by the method disclosed in synthesis scheme 2. First, compound (7) can be reduced with a reducing agent to give compound (8). Then, compound (8) and allyl bromide can be subjected to a substitution reaction under basic conditions to give compound (9). Finally, compound (9) can react with metal Mg to give compound (10).

Synthetic scheme 3

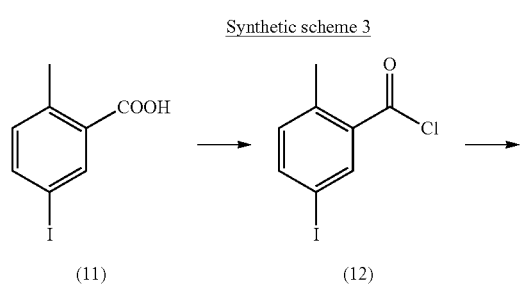

The intermediate having formula (15) can be synthesized by the method disclosed in synthesis scheme 3. First, compound (11) can react with oxalyl chloride to give compound (12).

Then, compound (12) can react with dimethylolamine hydrochloride under basic conditions to give compound (13). Next, compound (13) and the compound (10) can be subjected to Grignard reaction to give compound (14). Finally, compound (14) can be subjected to a reduction reaction in the presence of acid and triethylsilane to give compound (15).

Synthetic scheme 4

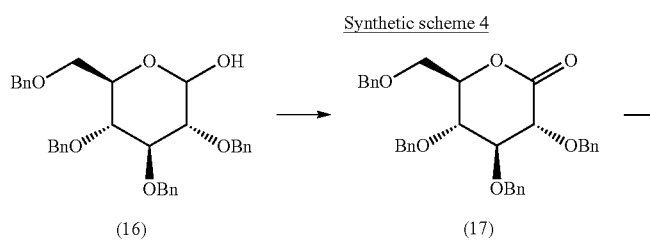

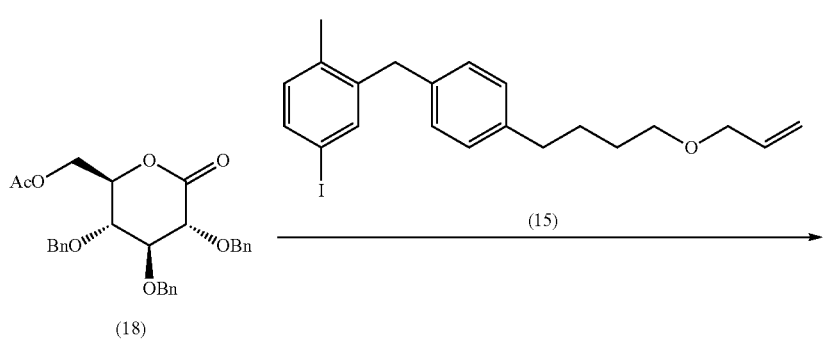

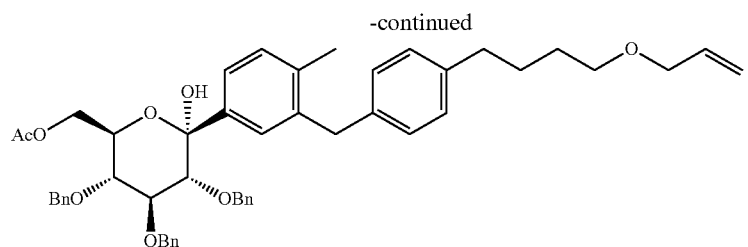
(19)
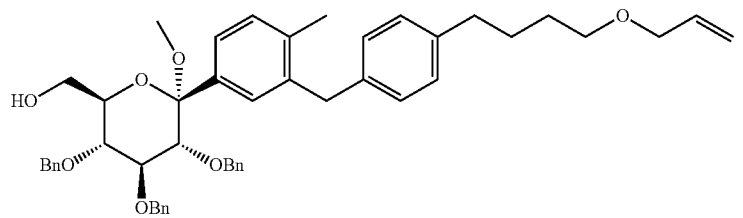
(20)
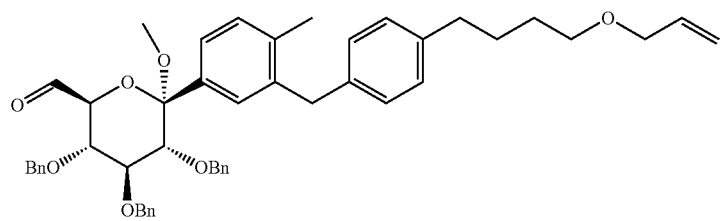
(21)
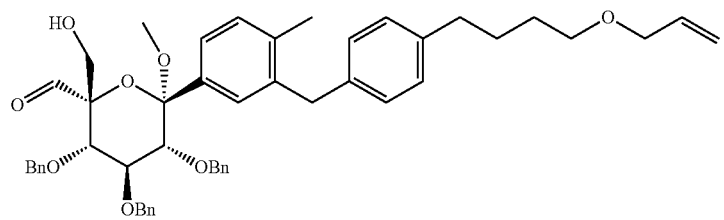
(22)
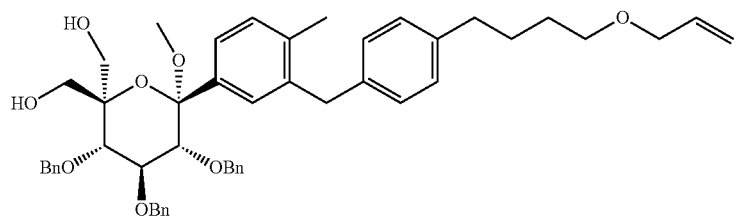
(23)
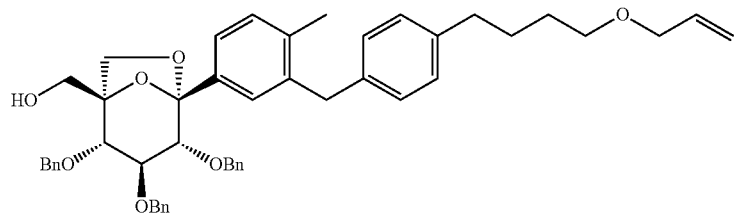
(24)

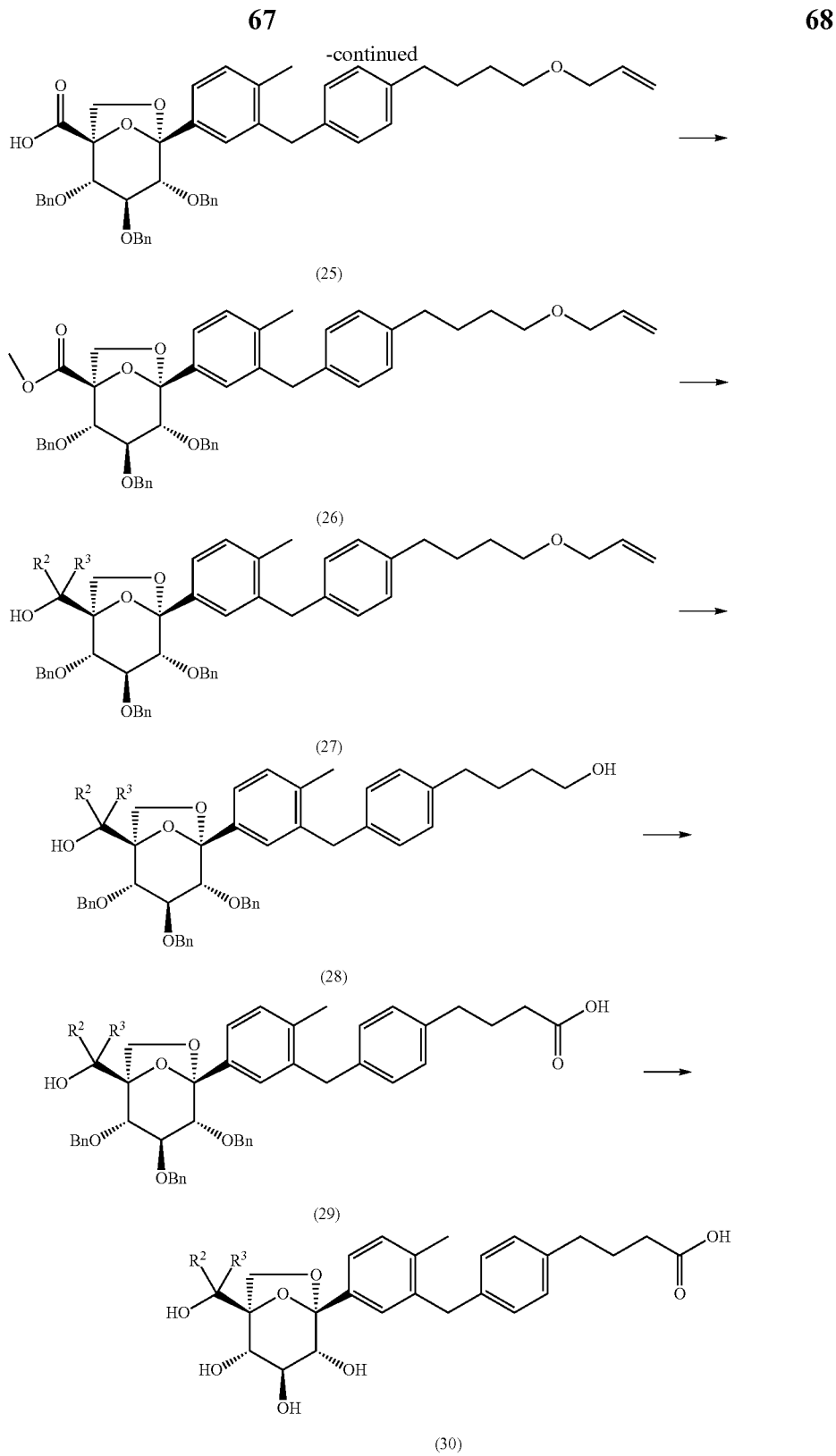

The intermediate having formula (29) or (30) can be synthesized by the method disclosed in synthesis scheme 4. First, compound (16) can be subjected to catalytic oxidation in the presence of 2,2,6,6-tetramethylpiperidine oxide to give compound (17). Compound (17) can react with acetic anhydride to give compound (18). Compound (15) can react with isopropylmagnesium chloride and then react with compound (18) through Grignard reaction to form compound (19). Compound (19) can react with methanol under acidic conditions to give compound (20). Compound (20) can be oxidized by oxidant to give compound (21). Compound (21) can react with formaldehyde in the presence of DBU to give compound (22). Then, compound (22) can be subjected to a reduction reaction with sodium borohydride to give compound (23). Compound (23) can be subjected to a ring closing reaction under acidic conditions to give compound (24). Compound (24) can be oxidized with Dess Martin oxidant to give compound (25). Compound (25) can react with methanol under acidic conditions to give compound (26). Next, compound (26) can react with Grignard reagent under low temperature to give compound (27). Compound (27) can remove the hydroxy protecting group allyl in the presence of a catalyst to give compound (28). Finally, compound (28) can be oxidized with iodobenzene diacetic acid in the presence of catalyst 2,2,6,6-tetramethylpiperidine oxide to give compound (29). Compound (29) can be removed the hydroxy protecting group Bn by catalytic hydrogenation to give compound (30).

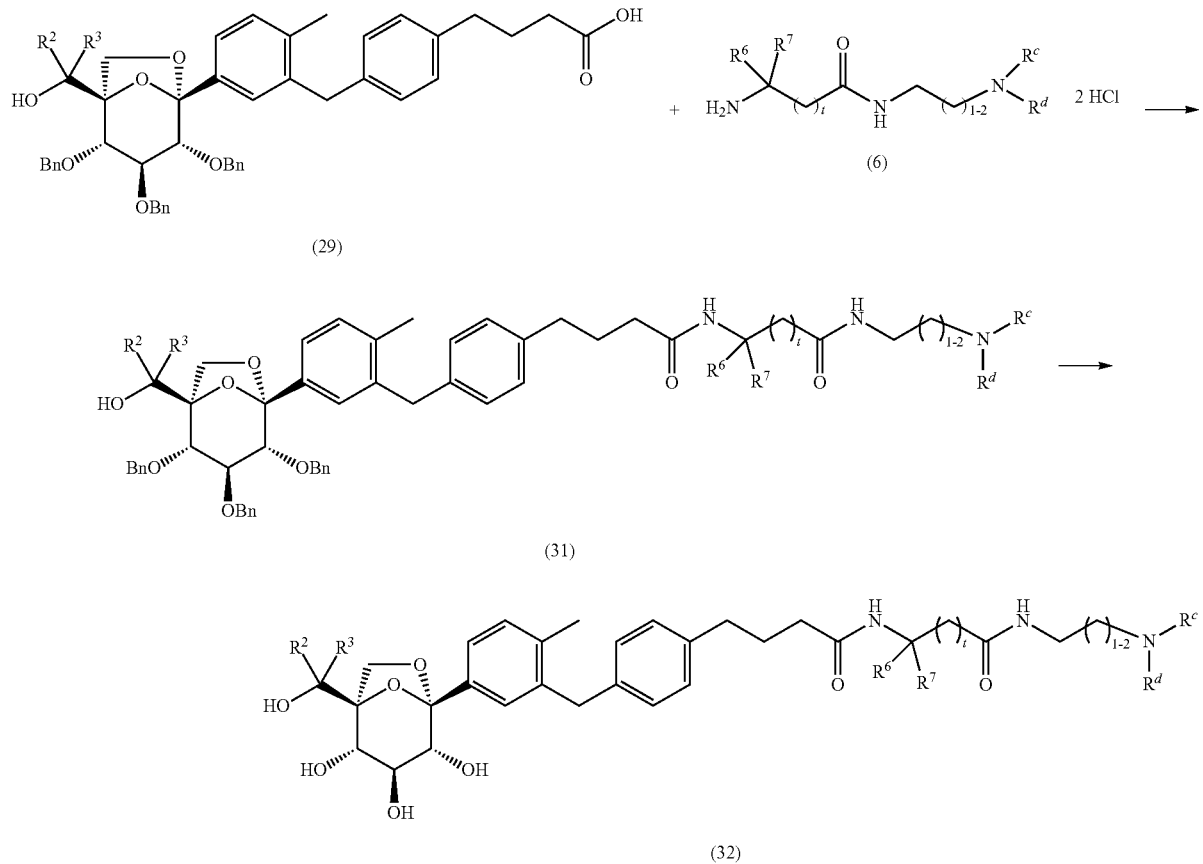

(29)

(31)

(32)

The compound having formula (32) can be synthesized by the method disclosed in synthesis scheme 5. First, compound (29) and compound can be subjected to a condensation reaction to give compound (31). Then, compound (31) can be removed the hydroxy protecting group Bn by catalytic hydrogenation to give compound (32).

Synthetic scheme 6

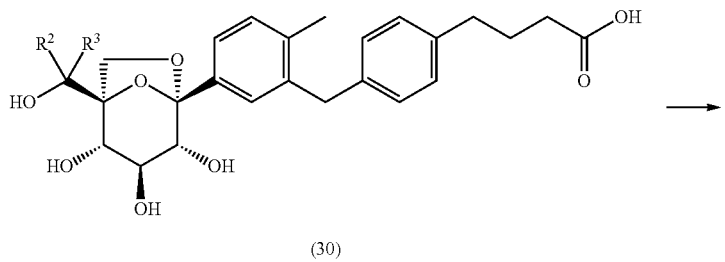

(30)

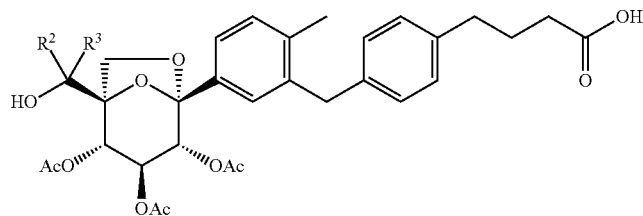

(33)

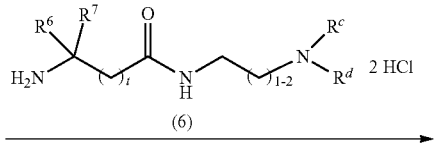

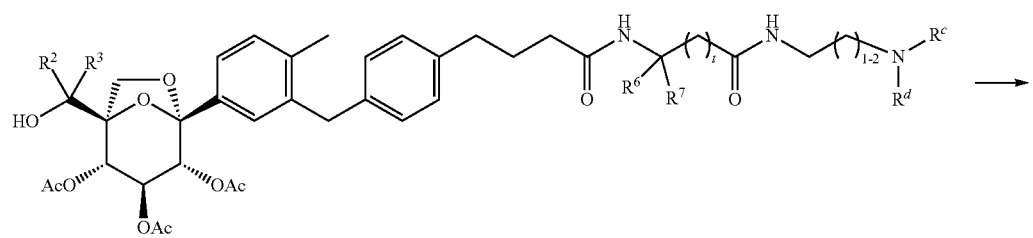

(34)

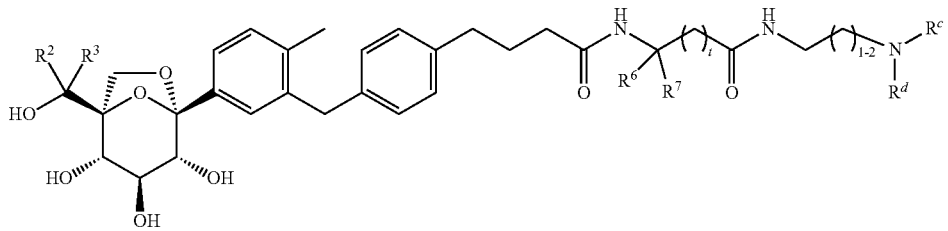

(32)

The compound having formula (32) can also be synthesized by the method disclosed in synthesis scheme 6. First, compound (30) can react with acetic anhydride under basic conditions to give compound (33). Next, compound (33) and compound can be subjected to a condensation reaction to give compound 04). Finally, compound (34) can be removed hydroxy protecting group Ac under basic conditions to give compound (32).

EXAMPLES

Example 1 2-Methyl-2-[4-[4-[[2-methyl-5-[(1S,2S, 3S,4R,5S)-2,3,4-trihydroxy-1-(1-hydroxy-1-methylethyl)-6,8-dioxabicyclo[3.2.1]octan-5-yl]phenyl] methyl]phenyl]butyryl amino]-N-(2-pyrrolidin-1-ylethyl)propionamide

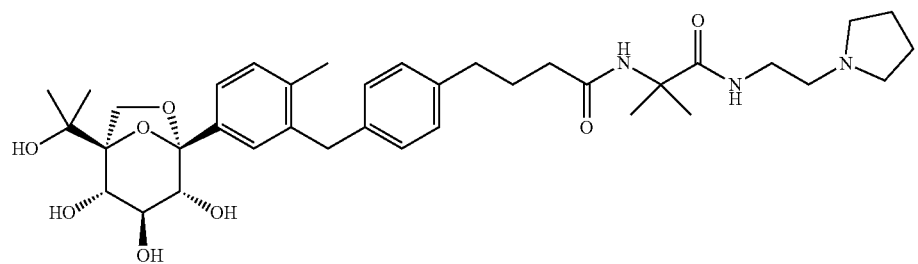 [SMILES: Cc1ccc([C@]23OC[C@](C(C)(C)O)(O2)[C@@H](O)[C@H](O)[C@H]3O)cc1Cc1ccc(CCCC(=O)NC(C)(C)C(=O)NCCN2CCCC2)cc1]

Step 1: Benzyl N-[1,1-dimethyl-2-oxo-2-(2-pyrrolidin-1-ylethylamino)ethyl]carbamate

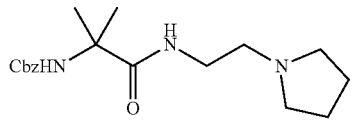 [SMILES: CC(C)(NC(=O)OCc1ccccc1)C(=O)NCCN1CCCC1]

2-(Benzyloxycarbonylamino)-2-methyl-propionic acid (3.0 g, 13 mmol) was dissolved in dichloromethane (30 mL) at room temperature. The mixture was cooled to 0° C., and HATU (5.6 g, 14 mmol) and N,N-diisopropylethylamine (7.0 mL, 40 mmol) were added. The resulting mixture was stirred for 20 minutes. 2-Pyrrolidin-1-ylethylamine (1.9 g, 17 mmol) was added, and the mixture was warmed to room temperature and stirred overnight. The resulting mixture was washed with water (20 mL), dried over anhydrous sodium sulfate, and filtered with suction. The filtrate was concentrated in vacuo and the residue was purified by silica gel column chromatography (DCM/anhydrous MeOH (v/v)=30/1) to give the title compound (2.2 g, yellow oil) in 52% yield.

MS (ESI, pos. ion) m/z: 334.4 [M+H]$^+$.

Step 2: 2-Amino-2-methyl-N-(2-pyrrolidin-1-yl-ethyl)propanamide

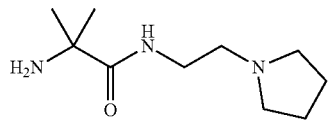

To a mixed solution of benzyl N-[1,1-dimethyl-2-oxo-2-(2-pyrrolidin-1-ylethylamino)ethyl]carbamate (2.0 g, 6.0 mmol) in tetrahydrofuran (2 mL) and anhydrous methanol (20 mL) was added 10% Palladium/carbon (0.20 g, 0.18 mmol) at room temperature. The mixture was stirred overnight under a hydrogen atmosphere. The mixture was filtered with suction and concentrated in vacuo to give the title compound (1.2 g, yellow oil) in 99% yield.

Step 3: 2-Amino-2-methyl-N-(2-pyrrolidin-1-yl-ethyl)propionamide dihydrochloride

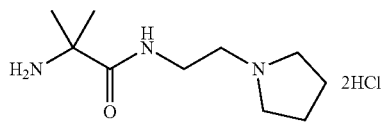

To a solution of 2-amino-2-methyl-N-(2-pyrrolidin-1-yl-ethyl)propanamide (1.2 g, 6.0 mmol) in ethyl acetate (20 mL) was added HCl isopropanol solution (4 mL, 5 M) at room temperature. The mixture was stirred for 1 hour. The mixture was filtered with suction, the filter cake was washed with ethyl acetate (20 mL), and dried in vacuo to give the title compound (1.2 g, white solid) in 73% yield.

MS (ESI, pos. ion) m/z: 200.3 [M+H]$^+$.

$^1$H NMR (400 MHz, D$_2$O) δ (ppm): 3.65 (m, 2H), 3.56 (t, 2H), 3.33 (t, 2H), 3.06 (m, 2H), 2.08 (m, 2H), 1.95 (m, 2H), 1.54 (s, 6H).

Step 4: 4-(4-bromophenyl)butyl-1-ol

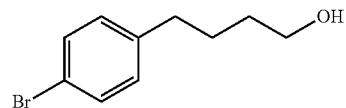

4-(4-Bromophenyl)butanoic acid (50.0 g, 150 mmol) was dissolved in tetrahydrofuran (250 mL) at room temperature, The mixture was cooled to −10° C. under a nitrogen atmosphere, then a solution of borane in tetrahydrofuran (1.0 M, 300 mL, 300 mmol) was added. The resulting mixture was warmed to room temperature and stirred for 2 hours. The mixture was poured into ice water (500 mL) and extracted with ethyl acetate (500 mL). The organic phases were washed with saturated brine (200 mL), dried over anhydrous sodium sulfate, filtered with suction and concentrated in vacuo to obtain the title compound (47.0 g, colorless oil) in 98% yield.

Step 5: 1-(4-allyloxybutyl)-4-bromo-benzene

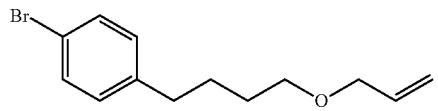

4-(4-Bromophenyl)butyl-1-ol (47.0 g, 205 mmol) was dissolved in tetrahydrofuran (500 mL) at room temperature. The mixture was cooled to −10° C. under a nitrogen atmosphere, and sodium hydride (11.0 g, 275 mmol) was added in portions. The mixture was continued stirring for 30 minutes, then allyl bromide (33.6 g, 288 mmol) was added dropwise. The resulting mixture was warmed to room temperature and stirred overnight. The mixture was poured into ice water (1.0 L) to quench the reaction. The resulting mixture was extracted with EA (500 mL). The organic phases were washed with saturated brine (200 mL), dried over anhydrous sodium sulfate, filtered with suction, and concentrated in vacuo. The residue was purified by silica gel column chromatography [ethyl acetate/petroleum ether (v/v)=1/40] to give the title compound (33.0 g, colorless oil) in 60% yield.

Step 6: [4-(4-allyloxybutyl)phenyl]-magnesium bromide

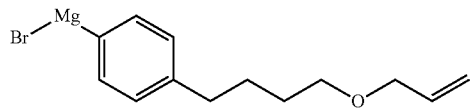

To a reaction flask were added magnesium bar (6.4 g, 0.26 mol) and iodine (0.6 g, 2 mmol) in sequence at room temperature. 1-(4-allyloxybutyl)-4-bromo-benzene (59.0 g, 219 mmol) was dissolved in tetrahydrofuran (300 mL), and 10 mL of the solution was added to the mixture in the reaction flask under a nitrogen atmosphere. The resulting mixture was heated until the reaction started (the color of iodine disappeared), then the remaining solution was added dropwise, and the mixture was stirred at 65° C. for 20 minutes to obtain the title compound (65 g, brown solution), which was directly used in the next step. The yield was calculated as 100%.

Step 7: 5-iodo-2-methyl-benzoyl chloride

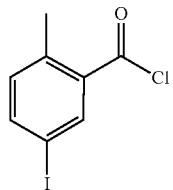

5-Iodo-2-methyl-benzoic acid (50.0 g, 191 mmol) was dissolved in dichloromethane (500 mL) at room temperature. The mixture was cooled to −10° C. under a nitrogen atmosphere, and oxalyl chloride (25 mL, 0.29 mol) and N,N-dimethylformamide (1.5 mL, 19 mmol) were added in turn. The resulting mixture was stirred overnight at room temperature. The mixture was concentrated in vacuo to give the title compound (53 g, yellow solid) in 100% yield.

Step 8: 5-idodo-N-methoxy-N,2-dimethyl-benzamide

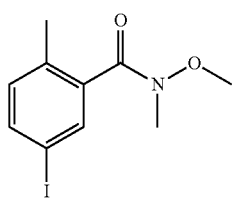

To a reaction flask were added 5-iodo-2-methyl-benzoyl chloride (53.0 g, 189 mmol), dimethylolamine hydrochloride (37.0 g, 379 mmol) and dichloromethane (500 mL) at room temperature. The mixture was cooled to 0° C. under a nitrogen atmosphere, and triethylamine (106 mL, 761 mmol) was added dropwise. The resulting mixture was stirred at room temperature for 3.5 hours. The mixture was washed with saturated brine (500 mL), dried over anhydrous sodium sulfate, and filtered with suction. The filtrate was concentrated in vacuo to give the title compound (54 g, yellow oil) in 93% yield.

MS (ESI, pos. ion) m/z: 306.0 [M+H]$^+$.

Step 9: [4-(4-allyloxybutyl)phenyl]-5-iodo-2-methyl-phenyl)methyl ketone

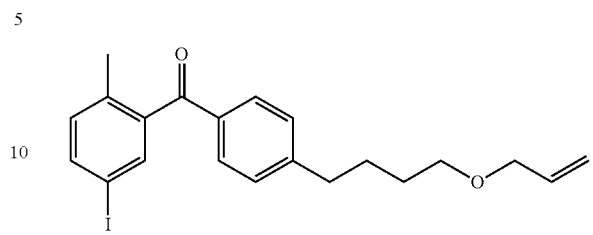

At room temperature, a solution of 5-iodo-N-methoxy-N,2-dimethyl-benzamide (50.0 g, 164 mmol) in tetrahydrofuran (200 mL) was cooled to −20° C. under a nitrogen atmosphere, then [4-(4-allyloxybutyl)phenyl]-magnesium bromide (63.0 g, 215 mmol) was added dropwise. The mixture was stirred at −20° C. for 1 hour, and stirred at room temperature overnight. The mixture was cooled to 0° C., quenched dropwise with saturated ammonium chloride solution (400 mL), extracted with ethyl acetate (300 mL×2), and the combined organic phases were washed with saturated brine (300 mL), dried over a hydrous sodium sulfate and filtered with suction. The filtrate was concentrated in vacuo, and the residue was purified by silica gel column chromatography [ethyl acetate/petroleum ether (v/v)=1/30] to give the title compound (59.0 g, colorless oil) in 83% yield.

Step 10: 2-[[4-(4-allyloxybutyl)phenyl]methyl]-4-iodo-1-methyl-benzene

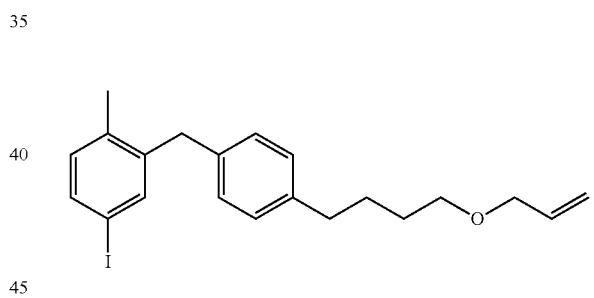

To a reaction flask were added [4-(4-allyloxybutyl)phenyl]-5-iodo-2-methyl-phenyl) methyl ketone (59.0 g, 136 mmol) and trifluoroacetic acid (150 mL) in turn at room temperature. The mixture was cooled to 0° C. under a nitrogen atmosphere, and then triethylsilane (174 mL, 1.09 mol) and trifluoromethanesulfonic acid (12.5 mL, 141 mmol) were added dropwise in turn. The mixture was stirred at room temperature for 1 hour. The mixture was concentrated in vacuo, and the residue was dissolved in ethyl acetate (600 mL), washed with water (500 mL), saturated sodium bicarbonate solution (500 mL) and saturated brine (500 mL) in turn, dried over anhydrous sodium sulfate, and filtered with suction. After concentration, the residue was purified by silica gel column chromatography [petroleum ether] to obtain the title compound (57 g, yellow oil) in 99% yield.

$^1$H NMR (400 MHz, CDCl$_3$) δ (ppm): 7.52-7.47 (m, 2H), 7.13 (d, 2H), 7.04 (d, 2H), 6.92 (d, 1H), 5.95 (m, 1H), 5.30 (dd, 1H), 5.20 (dd, 1H), 4.02-3.97 (m, 2H), 3.91 (s, 2H), 3.48 (t, 2H), 2.64 (t, 2H), 2.21 (s, 3H), 1.76-1.63 (m, 4H).

Step 11: (3R,4S,5R,6R)-3,4,5-tribenzyloxy-6-(benzyloxymethyl)tetrahydropyran-2-one

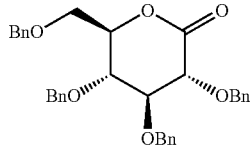 [SMILES: O=C1O[C@H](COCc2ccccc2)[C@@H](OCc2ccccc2)[C@H](OCc2ccccc2)[C@H]1OCc1ccccc1]

To a reaction flask were added (3R,4S,5R,6R)-3,4,5-tribenzyloxy-6-(benzyloxymethyl)tetrahydropyran-2-ol (130 g, 240 mmol), sodium bicarbonate (80.0 g, 952 mmol), dichloromethane (1000 mL) and water (800 mL) in turn at room temperature. The mixture was cooled to 0° C., potassium bromide (18.0 g, 151 mmol) and 2,2,6,6-tetramethylpiperidine oxide (5.6 g, 36 mmol) were added, and then sodium hypochlorite solution (360 g, available chlorine 6.2%, available chlorine 629 mmol) was added in one portion. The mixture was stirred for 20 minutes. The layers were separated, and the organic phases were washed with saturated brine (500 mL), dried over anhydrous sodium sulfate, filtered with suction, and concentrated in vacuo to obtain the title compound (129 g, yellow oil) in 100% yield.

Step 12: Methyl [(2R,3R,4S,5R)-3,4,5-tribenzyloxy-6-oxo-tetrahydropyran-2-yl] acetate

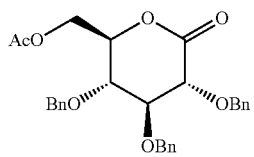

To a solution of (3R,4S,5R,6R)-3,4,5-tribenzyloxy-6-(benzyloxymethyl)tetrahydropyran-2-one (130 g, 241 mmol) in acetic anhydride (200 mL, 2.12 mol) was added glacial acetic acid (350 mL) at room temperature. The mixture was cooled to −15° C. under the nitrogen atmosphere, then concentrated sulfuric acid (14.0 mL, 263 mmol) was added dropwise. The temperature was controlled at −15° C.~−10° C. The mixture was stirred for 2.5 hours. The mixture was poured into ice water (1.5 L) and extracted with ethyl acetate (1.0 L). The organic phases were washed successively with water (500 mL), saturated sodium bicarbonate solution (1.0 L) and saturated brine (500 mL), dried over anhydrous sodium sulfate, filter with suction, and concentrated in vacuo. The residue was purified by silica gel column chromatography [ethyl acetate/petroleum ether (v/v)=1/4] to give the title compound (85 g, colorless oil) with a yield of 71%.

Step 13: Methyl [(2R,3R,4S,5R,6S)-6-[3-[[4-(4-allyloxybutyl)phenyl]methyl]-4-methyl-phenyl]-3,4,5-tribenzyloxy-6-hydroxy-tetrahydropyran-2-yl] acetate

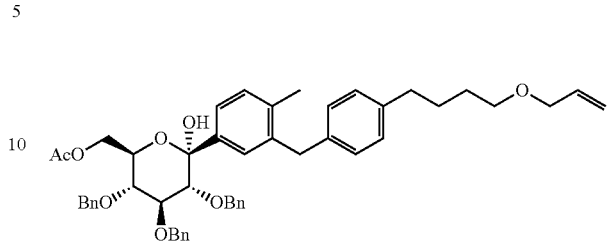

2-[[4-(4-Allyloxybutyl)phenyl]methyl]-4-iodo-1-methylbenzene (30.0 g, 71.4 mmol) was dissolved in tetrahydrofuran (150 mL) at room temperature. The mixture was cooled to −10° C. under a nitrogen atmosphere, and a solution of isopropyl magnesium chloride in tetrahydrofuran (39 mL, 78 mmol, 2.0 M) was added dropwise. The mixture was stirred for 1.5 hours, and was added dropwise to a solution of methyl [(2R,3R,4S,5R)-3,4,5-tribenzyloxy-6-oxo-tetrahydropyran-2-yl] acetate (25.0 g, 50.9 mmol) in tetrahydrofuran (150 mL). The resulting mixture was stirred for 2.5 hours. The reaction mixture was quenched with saturated aqueous ammonium chloride (200 mL). The resulting mixture was extracted with ethyl acetate (300 mL×2). The combined organic layers were washed with saturated brine (500 mL), dried over a hydrous sodium sulfate and filtered with suction. The filtrate was concentrated in vacuo, and the residue was purified by silica gel column chromatography [ethyl acetate/petroleum ether (v/v)=1/4] to give the title compound (32.1 g, yellow oil) in 80% yield.

Step 14: [(2R,3R,4S,5R,6S)-6-[3-[[4-(4-Allyloxybutyl)phenyl]methyl]-4-methyl-phenyl]-3,4,5-tribenzyloxy-6-methoxy-tetrahydropyran-2-yl]methanol

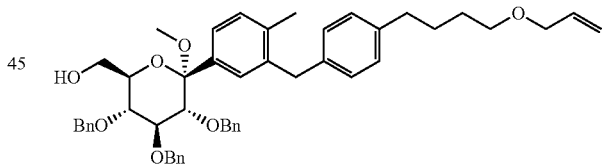

Methyl [(2R,3R,4S,5R,6S)-6-[3-[[4-(4-allyloxybutyl)phenyl]methyl]-4-methyl-phenyl]-3,4,5-tribenzyloxy-6-hydroxy-tetrahydropyran-2-yl] acetate (28.0 g, 35.6 mmol) was dissolved in anhydrous methanol (300 mL) at room temperature. Then concentrated hydrochloric acid (9.0 mL, 0.11 mol) was added and the mixture was stirred for 3 hours. The mixture was added with ethyl acetate (500 mL), washed successively with water (500 mL), saturated sodium bicarbonate solution (200 mL) and saturated brine (200 mL), dried over anhydrous sodium sulfate, filtered by suction, concentrated, and the residue was purified by silica gel column chromatography [ethyl acetate/petroleum ether (v/v)=1/4] to give the title compound (23.0 g, colorless oil) in 85% yield.

$^1$H NMR (400 MHz, CDCl$_3$) δ (ppm): 7.46-7.27 (m, 15H), 7.20-7.05 (m, 7H), 5.99 (m, 1H), 5.35 (dd, 1H), 5.25 (t, 1H), 5.02 (dt, 3H), 4.81 (d, 1H), 4.53 (d, 1H), 4.30 (t, 1H), 4.14-3.75 (m, 10H), 3.55-3.44 (m, 3H), 3.24 (s, 3H), 2.67 (t, 2H), 2.34 (s, 3H), 1.79-1.67 (m, 4H).

Step 15: [(2S,3S,4S,5R,6S)-6-[3-[[4-(4-Allyloxybutyl)phenyl]methyl]-4-methyl-phenyl]-3,4,5-tribenzyloxy-6-methoxy-tetrahydropyran-2-yl]carbaldehyde

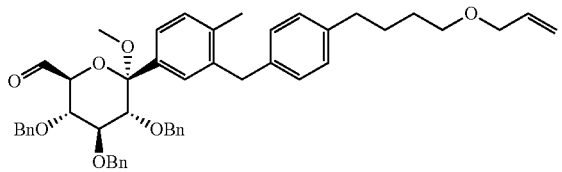 [SMILES: C=CCOCCCCc1ccc(Cc2cc([C@]3(OC)O[C@H](C=O)[C@@H](OCc4ccccc4)[C@H](OCc4ccccc4)[C@H]3OCc3ccccc3)ccc2C)cc1]

To a reaction flask were added [(2R,3R,4S,5R,6S)-6-[3-[[4-(4-allyloxybutyl)phenyl]methyl]-4-methyl-phenyl)-3,4,5-tribenzyloxy-6-methoxy-tetrahydropyran-2-yl]methanol (23.0 g, 30.4 mmol), sodium bicarbonate (16.0 g, 190 mmol), dichloromethane (250 mL) and water (160 mL) in turn at room temperature. The mixture was cooled to 0° C., then potassium bromide (2.4 g, 20 mmol), 2,2,6,6-tetramethylpiperidine oxide (0.75 g, 4.8 mmol) and sodium hypochlorite solution (52 g, available chlorine 5.53%, available chlorine 81 mmol) were added in turn. The mixture was stirred for 15 minutes. The layers were separated, and the organic phases were washed with saturated brine (200 mL), dried over anhydrous sodium sulfate, filtered by suction and concentrated to obtain the title compound (22 g, yellow oil) in 96% yield.

Step 16: (2R,3S,4S,5R,6S)-6-[3-[[4-(4-Allyloxybutyl)phenyl]methyl]-4-methyl-phenyl]-3,4,5-tribenzyloxy-2-(hydroxymethyl)-6-methoxy-tetrahydropyran-2-carbaldehyde

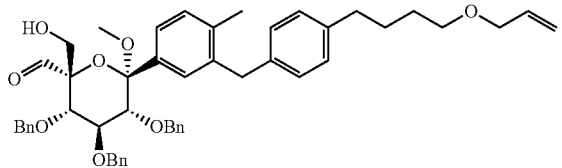 [SMILES: C=CCOCCCCc1ccc(Cc2cc([C@]3(OC)O[C@](C=O)(CO)[C@@H](OCc4ccccc4)[C@H](OCc4ccccc4)[C@H]3OCc3ccccc3)ccc2C)cc1]

[(2S,3S,4S,5R,6S)-6-[3-[[4-(4-Allyloxybutyl)phenyl]methyl]-4-methyl-phenyl]-3,4,5-tribenzyloxy-6-methoxy-tetrahydropyran-2-yl]carbaldehyde (23.0 g, 30.4 mmol) was dissolved in N,N-dimethylformamide (200 mL) at room temperature, then the mixture was cooled to 0° C. 37% Formaldehyde solution (62.0 g, 764 mmol) and DBU (3.1 g, 20 mmol) were added. The resulting mixture was warmed to room temperature and stirred overnight. The mixture was added with ethyl acetate (300 mL), washed successively with water (400 mL) and saturated brine (200 mL), dried over anhydrous sodium sulfate, filtered by suction and concentrated to obtain the title compound (23.0 g, yellow oil) in 96% yield.

Step 17: [(3S,4S,5R,6S)-6-[3-[[4-(4-Allyloxybutyl)phenyl]methyl]-4-methyl-phenyl]-3,4,5-tribenzyloxy-2-(hydroxymethyl)-6-methoxy-tetrahydropyran-2-yl]methanol

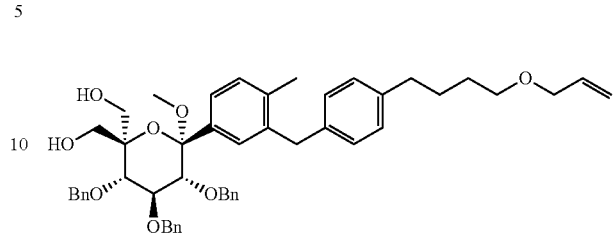

(2R,3S,4S,5R,6S)-6-[3-[[4-(4-Allyloxybutyl)phenyl]methyl]-4-methyl-phenyl]-3,4,5-tribenzyloxy-2-(hydroxymethyl)-6-methoxy-tetrahydropyran-2-carbaldehyde (23.0 g, 29.3 mmol) was dissolved in methanol (200 mL) at room temperature. Then the mixture was cooled to 0° C., and sodium borohydride (2.8 g, 74 mmol) was added in portions. The resulting mixture was continued stirring for 10 minutes. The mixture was added with ethyl acetate (500 mL), washed successively with water (500 mL) and saturated brine (200 mL), dried over anhydrous sodium sulfate, filtered by suction and concentrated to obtain the title compound (23.0 g, yellow oil) in 100% yield.

Step 18: [(1S,2S,3S,4R,5S)-5-[3-[[4-(4-Allyloxybutyl)phenyl]methyl]-4-methyl-phenyl]-2,3,4-tribenzyloxy-6,8-dioxabicyclo[3.2.1]octan-1-yl]methanol

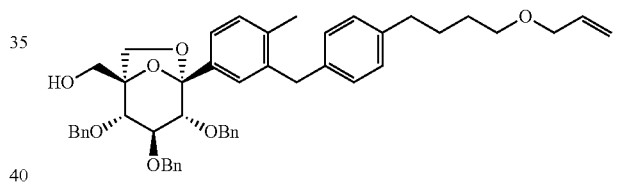

[(3S,4S,5R,6S)-6-[3-[[4-(4-Allyloxybutyl)phenyl]methyl]-4-methyl-phenyl]-3,4,5-tribenzyloxy-2-(hydroxymethyl)-6-methoxy-tetrahydropyran-2-yl]methanol (23.0 g, 29.2 mmol) was dissolved in tetrahydrofuran (150 mL) at room temperature, then p-toluenesulfonic acid monohydrate (7.0 g, 37 mmol) was added. The resulting mixture was stirred overnight. The mixture was concentrated in vacuo, and the residue was purified by silica gel column chromatography [ethyl acetate/petroleum ether (v/v)=1/8)] to give the title compound (12.5 g, yellow oil) in 57% yield.

Step 19: (1S,2S,3S,4R,5S)-5-[3-[[4-(4-Allyloxybutyl)phenyl]methyl]-4-methyl-phenyl]-2,3,4-tribenzyloxy-6,8-di oxabicyclo[3.2.1]octane-1-carboxylic acid

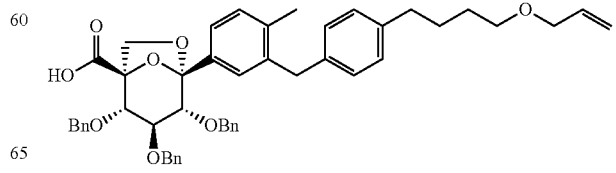

[(1S,2S,3S,4R,5S)-5-[3-[[4-(4-Allyloxybutyl)phenyl]methyl]-4-methyl-phenyl]-2,3,4-tribenzyloxy-6,8-dioxabicyclo[3.2.1]octan-1-yl]methanol (12.5 g, 16.6 mmol) was dissolved in dichloromethane (130 mL) at room temperature, then the mixture was cooled to 0° C. Dess Martin oxidant (50.0 g, 117 mmol) was added. The resulting mixture was heated to 40° C. and reacted for 2 hours. The mixture was concentrated in vacuo, and the residue was purified by silica gel column chromatography [ethyl acetate/petroleum ether (v/v)=1/2] to give the title compound (10 g, white solid) in 78% yield.

Step 20: Methyl (1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-carboxylate

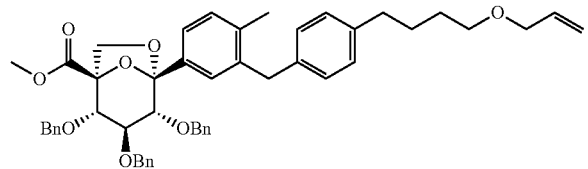 [SMILES: C=CCOCCCCc1ccc(Cc2cc([C@]34OC[C@](C(=O)OC)(O3)[C@@H](OCc3ccccc3)[C@H](OCc3ccccc3)[C@H]4OCc3ccccc3)ccc2C)cc1]

(1S,2S,3S,4R,5S)-5-[3-[[4-(4-Allyloxybutyl)phenyl]methyl]-4-methyl-phenyl]-2,3,4-tribenzyloxy-6,8-dioxabicyclo[3.2.1]octane-1-carboxylic acid (10.0 g, 13.0 mmol) was dissolved in anhydrous methanol (100 mL) at room temperature, then concentrated sulfuric acid (1.0 mL, 19 mmol) was added. The mixture was heated to 40° C. and stirred overnight. The mixture was added with ethyl acetate (200 mL), washed successively with water (300 mL) and saturated sodium bicarbonate solution (100 mL), dried over anhydrous sodium sulfate, filtered by suction, concentrated, and the residue was purified by silica gel column chromatography [ethyl acetate/petroleum ether (v/v)=1/10] to give the title compound (7.5 g, colorless oil) in 74% yield.

Step 21: 2-[(1S,2S,3S,4R,5S)-5-[3-[[4-(4-Allyloxybutyl)phenyl]methyl]-4-methyl-phenyl]-2,3,4-tribenzyloxy-6,8-di oxabicyclo[3.2.1]octan-1-yl]propane-2-ol

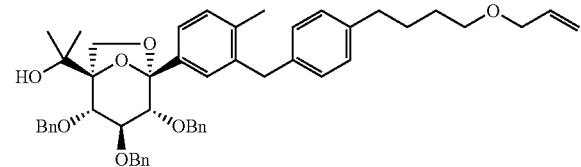 [SMILES: C=CCOCCCCc1ccc(Cc2cc([C@]34OC[C@](C(C)(C)O)(O3)[C@@H](OCc3ccccc3)[C@H](OCc3ccccc3)[C@H]4OCc3ccccc3)ccc2C)cc1]

Methyl (1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-carboxylate (7.5 g, 9.6 mmol) was dissolved in tetrahydrofuran (80 mL) at room temperature. The mixture was cooled to 0° C. under a nitrogen atmosphere, and methyl magnesium bromide ether solution (20 mL, 60 mmol, 3.0 M) was added dropwise. The resulting mixture was warmed to room temperature and stirred for 4 hours. The mixture was cooled to 0° C., quenched by dropwise addition of saturated ammonium chloride solution (100 mL), extracted with ethyl acetate (100 mL×2), and the combined organic phases were washed with saturated brine (100 mL), dried over anhydrous sodium sulfate, filtered by suction and concentrated to obtain the title compound (7.5 g, colorless oil) in 99% yield.

Step 22: 4-[4-[[2-Methyl-5-[(1S,2S,3S,4R,5S)-2,3,4-tribenzyloxy-1-(1-hydroxy-1-methyl-ethyl)-6,8-dioxabicyclo[3.2.1]octan-5-yl]phenyl]methyl]phenyl]butane-1-ol

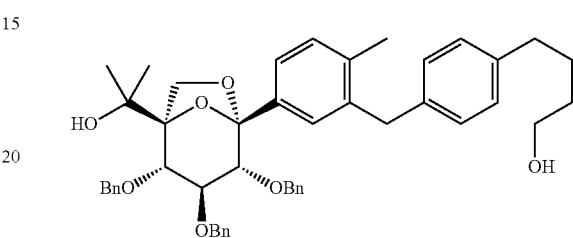

2-[(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octan-1-yl]propane-2-ol (7.0 g, 8.9 mmol) was dissolved in anhydrous methanol (80 mL) at room temperature, then palladium dichloride (1.0 g, 5.6 mmol) was added, and the mixture was stirred at room temperature for 2 hours under a nitrogen atmosphere. The mixture was filtered by suction, concentrated, and the residue was purified by silica gel column chromatography [ethyl acetate/petroleum ether (v/v)=1/2] to obtain the title compound (5.1 g, colorless oil) in 77% yield.

Step 23: 4-[4-[[2-Methyl-5-[(1S,2S,3S,4R,5S)-2,3,4-tribenzyloxy-1-(1-hydroxy-1-methyl-ethyl)-6,8-dioxabicyclo[3.2.1]octan-5-yl]phenyl]methyl]phenyl]butyric acid

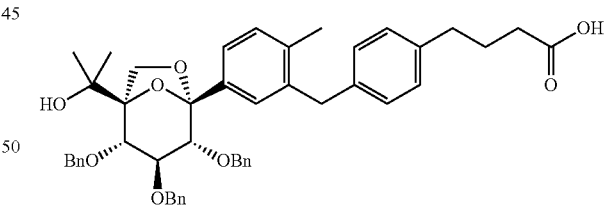

4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octan-5-yl]phenyl]methyl]phenyl]butan-1-ol (2.0 g, 2.7 mmol) was dissolved in dichloromethane (20 mL) at room temperature, then water (4 mL), 2,2,6,6-tetramethylpiperidine oxide (0.13 g, 0.79 mmol) and (diacetoxyiodo)benzene (2.2 g, 6.7 mmol) were added. The mixture was stirred overnight. The layers were separated, and the organic phases were dried over anhydrous sodium sulfate, filtered by suction, concentrated, and the residue was purified by silica gel column chromatography [ethyl acetate/petroleum ether (v/v)=1/2] to give the title compound (1.7 g, white solid) in 83% yield.

Step 24: 2-Methyl-2-[4-[4-[[2-methyl-5-[(1S,2S,3S, 4R,5S)-2,3,4-tribenzyloxy-1-(1-hydroxy-1-methyl-ethyl)-6,8-dioxabicyclo[3.2.1]octan-5-yl]phenyl] methyl]phenyl]butyrylamino]-N-(2-pyrrolidin-1-ylethyl)propionamide

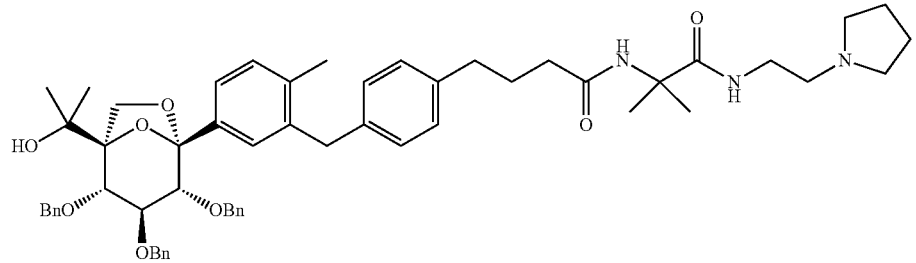 [SMILES: Cc1ccc([C@]23OC[C@](C(C)(C)O)(O2)[C@@H](OCc2ccccc2)[C@H](OCc2ccccc2)[C@H]3OCc2ccccc2)cc1Cc1ccc(CCCC(=O)NC(C)(C)C(=O)NCCN2CCCC2)cc1]

4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octan-5-yl]phenyl]methyl]phenyl]butyric acid (0.80 g, 1.05 mmol) was dissolved in N,N-dimethylformamide (6 mL) at room temperature, then the mixture was cooled to 0° C. HBTU (0.50 g, 1.3 mmol) and N,N-diisopropylethylamine (1.0 mL, 5.7 mmol) were added. The mixture was stirred for 20 minutes. 2-amino-2-methyl-N-(2-pyrrolidin-1-ylethyl) propionamide dihydrochloride (0.38 g, 1.4 mmol) was added to the mixture. The resulting mixture was stirred overnight. The mixture was added with water (60 mL) and extracted with ethyl acetate (100 mL×3). The combined organic phases were washed with saturated brine (100 mL), dried over anhydrous sodium sulfate, filtered by suction, concentrated, and the residue was purified to silica gel column chromatography [dichloromethane/anhydrous methanol (v/v)=30/1] to give the title compound (0.99 g, colorless oil) in 99% yield.

Step 25: 2-Methyl-2-[4-[4-[[2-methyl-5-[(1S,2S,3S, 4R,5S)-2,3,4-trihydroxy-1-0-hydroxy-1-methyl-ethyl)-6,8-dioxabicyclo[3.2.1]octan-5-yl]phenyl] methyl]phenyl]butyrylamino]-N-(2-pyrrolidin-1-ylethyl)propionamide

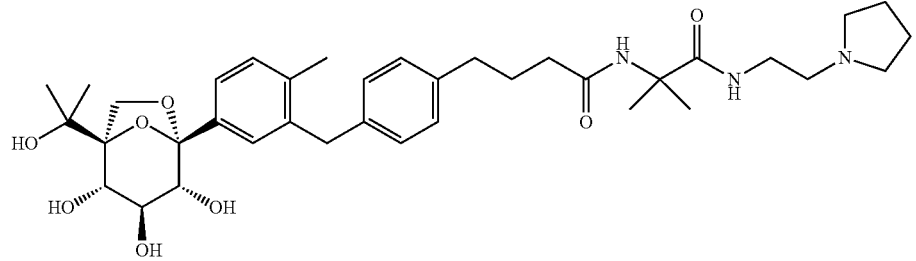 [SMILES: Cc1ccc([C@]23OC[C@](C(C)(C)O)(O2)[C@@H](O)[C@H](O)[C@H]3O)cc1Cc1ccc(CCCC(=O)NC(C)(C)C(=O)NCCN2CCCC2)cc1]

2-Methyl-2-[4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octan-5-yl]phenyl]methyl]phenyl]butyrylamino]-N-(2-pyrrolidin-1-ylethyl)propionamide (0.90 g, 0.96 mmol) was dissolved in anisole (30 mL) at room temperature, then the mixture was cooled to 0° C., and anhydrous aluminum trichloride (1.3 g, 9.7 mmol) was slowly added. The mixture was stirred for 5 minutes, then warmed to room temperature and stirred for 3 hours. The mixture was poured into ice water (50 mL), extracted with ethyl acetate (30 mL×6), and the combined organic phases were washed successively with saturated sodium bicarbonate solution (100 mL) and saturated brine (100 mL), dried over anhydrous sodium sulfate, filtered by suction, concentrated, and the residue was purified by silica gel column chromatography [dichloromethane/anhydrous methanol (v/v)=7/1] to obtain the title compound (0.28 g, white solid) in 44% yield.

MS (ESI, pos. ion) m/z: 668.5[M+H]$^+$.

$^1$H NMR (400 MHz, DMSO-d$_6$) δ (ppm): 8.65 (br.s, 1H), 8.40 (s, 1H), 7.89 (t, 1H), 7.29 (s, 1H), 7.23 (d, 1H), 7.12-7.04 (m, 5H), 5.50 (d, 1H), 5.32 (t, 1H), 5.02 (d, 1H), 4.89 (d, 1H), 4.21 (s, 1H), 4.03 (d, 1H), 3.91 (s, 2H), 3.81 (d, 1H), 3.72 (d, 1H), 3.50 (m, 2H), 3.19 (m, 2H), 3.02 (s, 2H), 2.18 (s, 3H), 2.13 (t, 2H), 2.04-1.95 (m, 4H), 1.88-1.69 (m, 4H), 1.29 (s, 6H), 1.21 (s, 3H), 1.15 (s, 3H).

Example 2 N-[3-(2-Methylaminoethylamino)-3-oxo-propyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butanamide

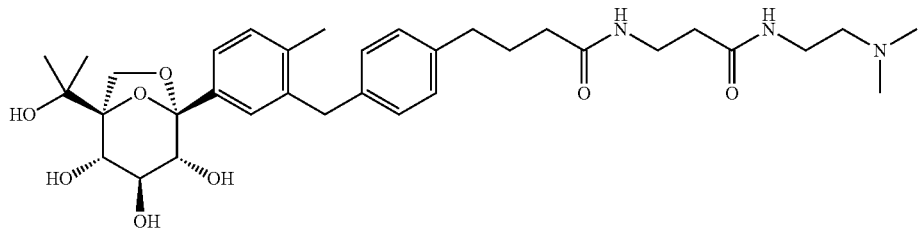 [SMILES: Cc1ccc([C@]23OC[C@](C(C)(C)O)(O2)[C@@H](O)[C@H](O)[C@H]3O)cc1Cc1ccc(CCCC(=O)NCCC(=O)NCCN(C)C)cc1]

Step 1: 3-(Benzyloxycarbonylamino)propionic acid

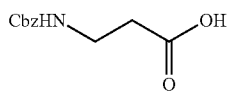 [SMILES: O=C(O)CCNC(=O)OCc1ccccc1]

3-Aminopropionic acid (3.0 g, 34 mmol) was dissolved in dioxane (20 mL) at room temperature, then sodium carbonate (11.0 g, 104 mmol) and water (60 mL) were added. The mixture was cooled to 0° C., then benzyl chloroformate (6.0 mL, 41 mmol) was added. The resulting mixture was warmed to room temperature and stirred overnight. The mixture was washed with n-hexane (100 mL), the aqueous phase was adjusted to pH=1 with dilute hydrochloric acid (1 M), extracted with ethyl acetate (100 mL×2), and the combined organic phases were washed with saturated brine (100 mL), dried over anhydrous sodium sulfate, filtered by suction and concentrated to obtain the title compound (6.9 g, colorless oil) in 92% yield.

Step 2: N-[3-(2-Dimethylaminoethylamino)-3-oxo-propyl]carbamic acid benzyl ester

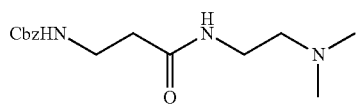 [SMILES: CN(C)CCNC(=O)CCNC(=O)OCc1ccccc1]

3-(Benzyloxycarbonylamino)propionic acid (3.0 g, 13 mmol) was dissolved in dichloromethane (30 mL) at room temperature, and the mixture was cooled to 0° C. Then HATU (5.9 g, 15 mmol) and N,N-diisopropylethylamine (7.0 mL, 40 mmol) were added. The mixture was stirred for 20 minutes. N,N-Dimethyl-1,2-ethylenediamine (1.5 g, 17 mmol) was added, and the resulting mixture was warmed to room temperature and stirred overnight. The mixture was washed with water (20 mL), the organic phases were concentrated in vacuo, and the residue was purified by silica gel column chromatography [dichloromethane/anhydrous methanol (v/v)=30/1] to give the title compound (2.0 g, yellow oil) in 51% yield.

Step 3: 3-Amino-N-(2-dimethylaminoethyl)propanamide

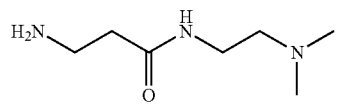

To a mixed solution of benzyl N-[3-(2-dimethylaminoethylamino)-3-oxo-propyl] carbamate (2.0 g, 6.0 mmol) in tetrahydrofuran (2 mL) and anhydrous methanol (20 mL) was added 10% palladium/carbon (0.20 g, 0.19 mmol) at room temperature, and the mixture was stirred overnight under a hydrogen atmosphere. The mixture was filtered with suction and concentrated to give the title compound (1.1 g, yellow oil) in 99% yield.

Step 4: 3-Amino-N-(2-dimethylaminoethyl)propionamide dihydrochloride

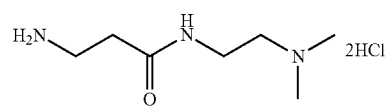

To a solution of 3-amino-N-(2-dimethylaminoethyl) propionamide (1.1 g, 6.9 mmol) in ethyl acetate (20 mL) was added HCl isopropanol solution (4 mL, 5 M) at room temperature, and the mixture was stirred for 1 hour. The mixture was filtered with suction, the filter cake was washed with ethyl acetate (20 mL), and dried in vacuo to give the title compound (1.2 g, white solid) in 75% yield.

MS (ESI, pos. ion) m/z: 160.2[M+H]$^+$.

$^1$H NMR (400 MHz, D$_2$O) δ (ppm): 3.56 (t, 2H), 3.24 (dt, 4H), 2.88 (s, 6H), 2.67 (t, 2H).

Step 5: 4-[4-[[2-Methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyric acid

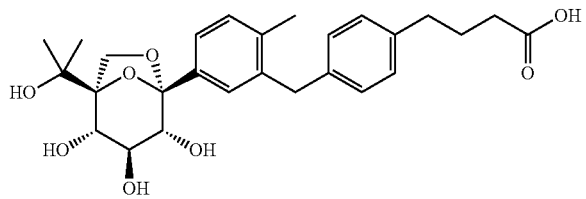 [SMILES: Cc1ccc([C@]23OC[C@](C(C)(C)O)(O2)[C@@H](O)[C@H](O)[C@H]3O)cc1Cc1ccc(CCCC(=O)O)cc1]

To a mixed solution of 4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octan-5-yl]phenyl]methyl]phenyl]butyric acid (1.3 g, 1.7 mmol) in tetrahydrofuran (2 mL) and anhydrous methanol (20 mL) was added 10% palladium hydroxide/carbon (1.2 g, 0.84 mmol) at room temperature, and the mixture was stirred overnight under a hydrogen atmosphere. The mixture was filtered by suction and concentrated, and the residue was purified by silica gel column chromatography [ethyl acetate] to obtain the title compound (0.52 g, white solid) in 53% yield.

Step 6: 4-[4-[[2-Methyl-5-[(1S,2S,3S,4R,5S)-2,3,4-triacetoxy-1-(1-hydroxy-1-methyl-ethyl)-6,8-dioxabicyclo[3.2.1]octan-5-yl]phenyl]methyl]phenyl]butyric acid

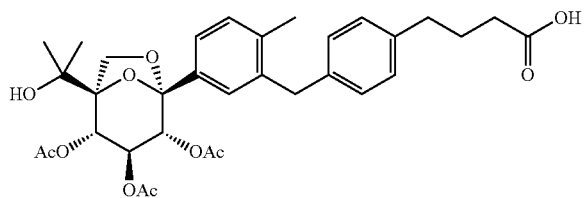 [SMILES: CC(=O)O[C@@H]1[C@@H](OC(C)=O)[C@@]2(c3ccc(C)c(Cc4ccc(CCCC(=O)O)cc4)c3)OC[C@](C(C)(C)O)(O2)[C@H]1OC(C)=O]

4-[4-[[2-Methyl-5-[(1S,2S,3S,4R,5S)-2,3,4-trihydroxy-1-(1-hydroxy-1-methyl-ethyl)-6, 8-dioxabicyclo[3.2.1]octan-5-yl]phenyl]methyl]phenyl]butyric acid (0.40 g, 0.82 mmol) was dissolved in tetrahydrofuran (10 mL) at room temperature, and the mixture was cooled to 10° C. 4-dimethylaminopyridine (5 mg, 0.04 mmol), acetic anhydride (0.70 mL, 7.5 mmol) and triethylamine (1.0 mL, 7.2 mmol) were added and the resulting mixture was stirred for 3 hours. The mixture was added with dilute hydrochloric acid (1 M) to adjust to pH=3, and extracted with ethyl acetate (60 mL×3). The combined organic phases were washed with saturated brine (80 mL), dried over anhydrous sodium sulfate, filtered by suction, concentrated, and the residue was purified by silica gel column chromatography [ethyl acetate/petroleum ether (v/v)=1/1] to obtain the title compound (0.35 g, white solid) in 69% yield.

MS (ESI, pos. ion) m/z: 635.5 [M+Na]$^+$.

Step 7: [(1S,2S,3S,4R,5S)-2,4-Diacetoxy-5-[3-[[4-[4-[[3-(2-methylaminoethylamino)-3-oxo-propyl]amino]-butyl]phenyl]methyl]-4-methyl-phenyl]-1-(1-hydroxy-1-methyl-ethyl)-6,8-dioxabicyclo[3.2.1]octan-3-yl]acetate

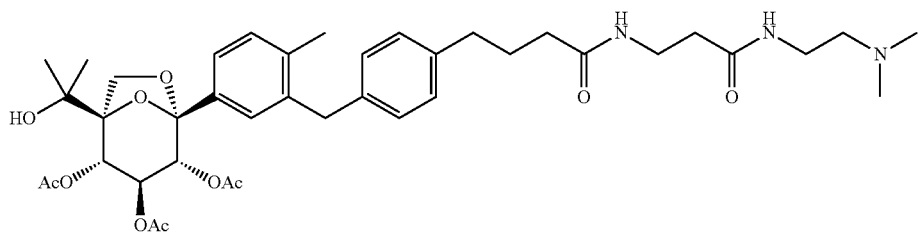 [SMILES: CC(=O)O[C@@H]1[C@@H](OC(C)=O)[C@@]2(c3ccc(C)c(Cc4ccc(CCCC(=O)NCCC(=O)NCCN(C)C)cc4)c3)OC[C@](C(C)(C)O)(O2)[C@H]1OC(C)=O]

4-[4-[[2-methyl-5-[(1S,2S,3S,4R,5S)-2,3,4-triacetoxy-1-(1-hydroxy-1-methyl-ethyl)-6,7,8-dioxabicyclo[3.2.1]octan-5-yl]phenyl]methyl]phenyl]butyric acid (0.15 g, 0.25 mmol) was dissolved in dichloromethane (5 mL) at room temperature. The mixture was cooled to 0° C., then HATU (0.12 g, 0.29 mmol) and N,N-diisopropylethylamine (0.22 mL, 1.3 mmol) were added. The resulting mixture was stirred for 20 minutes. 3-amino-N-(2-dimethylaminoethyl)propionamide dihydrochloride (74 mg, 0.32 mmol) was added, and the mixture was stirred overnight. The mixture was added with water (20 mL) and extracted with dichloromethane (40 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=8/1] to obtain the title compound (0.11 g, white solid) in 60% yield.

MS (ESI, pos. ion) m/z: 754.6[M+H]$^+$.

Step 8: N-[3-(2-Methyl aminoethylamino)-3-oxo-propyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl] butanamide

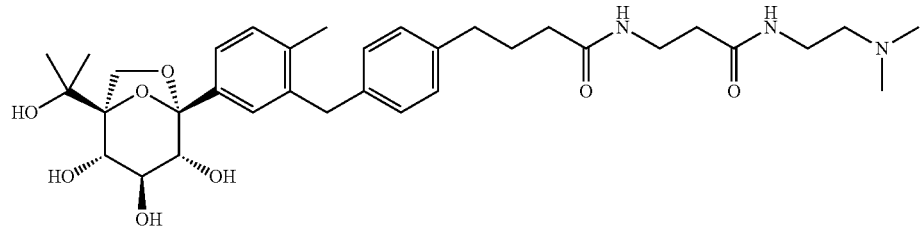 [SMILES: Cc1ccc([C@]23OC[C@](C(C)(C)O)(O2)[C@@H](O)[C@H](O)[C@H]3O)cc1Cc1ccc(CCCC(=O)NCCC(=O)NCCN(C)C)cc1]

To a solution of [(1S,2S,3S,4R,5S)-2,4-diacetoxy-5-[3-[[4-[4-[[3-(2-methylaminoethylamino)-3-oxo-propyl]amino]-butyl]phenyl]methyl]-4-methyl-phenyl]-1-(1-hydroxy-1-methyl-ethyl)-6,8-dioxabicyclo[3.2.1]octan-3-yl] acetate (0.11 g, 0.15 mmol) in anhydrous methanol (2 mL) was added sodium methoxide solid (41 mg, 0.75 mmol) at room temperature, and the mixture was stirred for 2 hours. The mixture was concentrated, and the residue was directly purified by preparative TLC [DCM/MeOH (v/v)=2/1] to give the title compound (60 mg, white solid) in 65% yield.

MS (ESI, pos. ion) m/z: 628.3[M+H]⁺.

¹H NMR (400 MHz, DMSO-d₆) δ (ppm): 8.09 (s, 1H), 7.89 (t, 1H), 7.29 (s, 1H), 7.23 (d, 1H), 7.11-7.03 (m, 5H), 5.50 (d, 1H), 5.32 (t, 1H), 5.02 (d, 1H), 4.89 (d, 1H), 4.21 (s, 1H), 4.03 (d, 1H), 3.91 (s, 2H), 3.81 (d, 1H), 3.72 (d, 1H), 3.47 (m, 2H), 3.24 (m, 2H), 2.90 (m, 2H), 2.60 (s, 6H), 2.45 (t, 2H), 2.26 (t, 2H), 2.18 (s, 3H), 2.02 (t, 2H), 1.75 (m, 2H), 1.21 (s, 3H), 1.15 (s, 3H).

Example 3 N-(2-Diethylaminoethyl)-2-methyl-2-[4-[4-[[2-methyl-5-[(1S,2S,3S,4R,5S)-2,3,4-trihydroxy-1-(1-hydroxy-1-methyl-ethyl)-6,8-dioxabicyclo [3.2.1]octan-5-yl]phenyl]methyl]phenyl] butyrylamino] propionamide

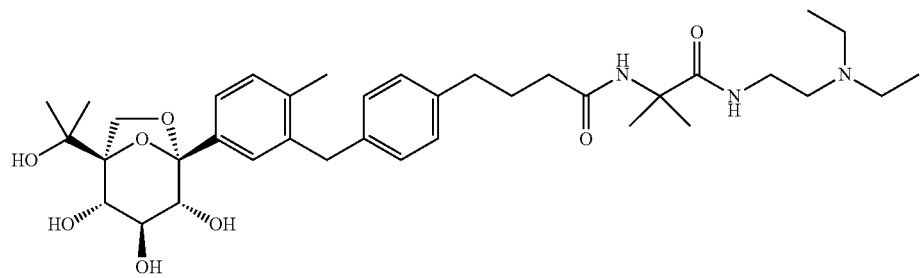 [SMILES: CCN(CC)CCNC(=O)C(C)(C)NC(=O)CCCc1ccc(Cc2cc([C@]34OC[C@](C(C)(C)O)(O3)[C@@H](O)[C@H](O)[C@H]4O)ccc2C)cc1]

Step 1: Benzyl N-[2-(2-diethylaminoethylamino)-1,1-dimethyl-2-oxo-ethyl]carbamate

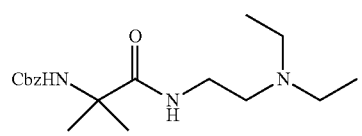 [SMILES: CCN(CC)CCNC(=O)C(C)(C)NC(=O)OCc1ccccc1]

2-(Benzyloxycarbonylamino)-2-methyl-propionic acid (3.0 g, 13 mmol) was dissolved in dichloromethane (30 mL) at room temperature. The mixture was cooled to 0° C., and HATU (5.6 g, 14 mmol) and N,N-diisopropylethylamine (7.0 mL, 40 mmol) were added. The resulting mixture was stirred for 20 minutes. N,N-Diethyl-1,2-ethylenediamine (1.9 g, 16 mmol) was added and the mixture was stirred overnight. The mixture was washed with water (20 mL), dried over anhydrous sodium sulfate, filtered by suction, concentrated, and the residue was purified by silica gel column chromatography [dichloromethane/anhydrous methanol (v/v)=30/1] to give the title compound (3.8 g, yellow oil) in 90% yield.

MS (ESI, pos. ion) m/z: 336.4[M+H]⁺.

Step 2: 2-Amino-N-(2-diethylaminoethyl)-2-methyl-propionamide

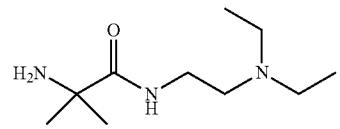

To a solution of benzyl N-[2-(2-diethylaminoethyl-amino)-1,1-dimethyl-2-oxo-ethyl] carbamate (1.0 g, 3.0 mmol) in anhydrous methanol (20 mL) was added 10% palladium/carbon catalyst (0.20 g, 0.18 mmol) at room temperature, and the mixture was stirred for 5 hours under a hydrogen atmosphere. The mixture was filtered with suction and concentrated in vacuo to give the title compound (0.6 g, yellow oil) in 99% yield.

Step 3: 2-Amino-N-(2-diethylaminoethyl)-2-methyl-propionamide dihydrochloride

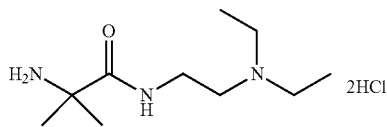

To a solution of 2-amino-N-(2-diethylaminoethyl)-2-methyl-propionamide (0.50 g, 2.5 mmol) in ethyl acetate (20 mL) was added HCl isopropanol solution (2 mL, 5 M) at room temperature, and the mixture was stirred for 1 hour. The mixture was filtered with suction, the filter cake was washed with ethyl acetate (20 mL), and dried in vacuo to give the title compound (0.6 g, white solid) in 90% yield.

MS (ESI, pos. ion) m/z: 202.4 [M+H]$^+$.

Step 4: [(1S,2S,3S,4R,5S)-2,4-Diacetoxy-5-[3-[[4-[4-[[2-(2-diethylaminoethylamino)-1,1-dimethyl-2-oxoethyl]amino]-4-oxo-butyl]phenyl]methyl]-4-methyl-phenyl]-1-(1-hydroxy-1-methyl-ethyl)-6,8-dioxabicyclo[3.2.1]octan-3-yl]acetate

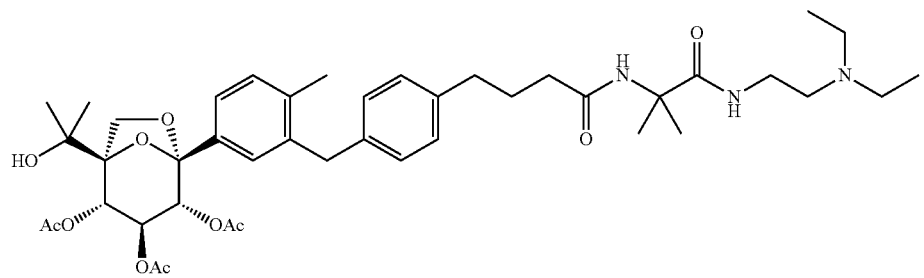 [SMILES: CCN(CC)CCNC(=O)C(C)(C)NC(=O)CCCc1ccc(Cc2cc([C@]34OC[C@](C(C)(C)O)(O3)[C@@H](OC(C)=O)[C@H](OC(C)=O)[C@H]4OC(C)=O)ccc2C)cc1]

4-[4-[[2-Methyl-5-[(1S,2S,3S,4R,5S)-2,3,4-triacetoxy-1-(1-hydroxy-1-methyl-ethyl)-6,8-dioxabicyclo[3.2.1]octan-5-yl]phenyl]methyl]phenyl]butyric acid (0.15 g, 0.25 mmol) was dissolved in methyl chloride (5 mL) at room temperature, then the mixture was cooled to 0° C. HATU (0.12 g, 0.29 mmol) and N,N-diisopropylethylamine (0.22 mL, 1.3 mmol) were added and the mixture was stirred for 20 minutes. 2-Amino-N-(2-diethylaminoethyl)-2-methyl-propionamide dihydrochloride (88 mg, 0.32 mmol) was added and the mixture was stirred overnight. The mixture was added with water (20 mL) and extracted with dichloromethane (40 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=8/1] to give the title compound (90 mg, white solid) in 46% yield.

MS (ESI, pos. ion) m/z: 796.3 [M+H]$^+$.

Step 5: N-(2-Diethylaminoethyl)-2-methyl-2-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyrylamino]propionamide To a solution of [(1S,2S,3S,4R,5S)-2,4-diacetoxy-5-[3-[[4-[4-[[2-(2-diethylaminoethylamino)-1,1-dimethyl-2-oxo-ethyl]amino]-4-oxo-butyl]phenyl]methyl]-4-methyl-phenyl]-1-(1-hydroxy-1-methyl-ethyl)-6,8-dioxabicyclo[3.2.1]octan-3-yl]acetate (90 mg, 0.11 mmol) in anhydrous methanol (2 mL) was added solid sodium methoxide (30 mg, 0.55 mmol), and the mixture was stirred for 2 hours. The mixture was concentrated, and the residue was directly purified by thin layer chromatography [DCM/MeOH (v/v)=2/1] to give the title compound (60 mg, white solid) in 79% yield.

MS (ESI, pos. ion) m/z: 670.3 [M+H]$^+$.

$^1$H NMR (400 MHz, DMSO-d$_6$) δ (ppm): 9.02 (br.s, 1H), 08.23 (s, 1H), 7.93 (t, 1H), 7.29 (s, 1H), 7.23 (d, 1H), 7.17-6.99 (m, 5H), 5.53 (d, 1H), 5.04 (d, 1H), 4.89 (d, 1H), 4.21 (s, 1H), 4.04 (d, 1H), 3.91 (s, 2H), 3.81 (d, 1H), 3.72 (m, 1H), 3.53-3.36 (m, 5H), 3.11 (t, 2H), 3.05 (m, 4H), 2.18 (s, 3H), 2.13 (t, 2H), 1.75 (m, 2H), 1.29 (s, 6H), 1.24 (s, 3H), 1.21 (s, 3H), 1.16 (s, 6H).

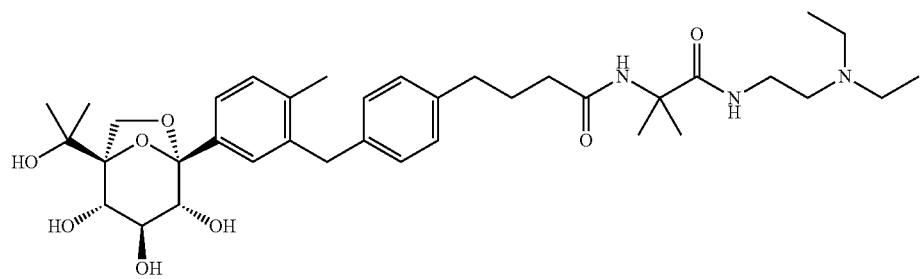 [SMILES: CCN(CC)CCNC(=O)C(C)(C)NC(=O)CCCc1ccc(Cc2cc([C@]34OC[C@](C(C)(C)O)(O3)[C@@H](O)[C@H](O)[C@H]4O)ccc2C)cc1]

Example 4 N-(2-Dimethylaminoethyl)-3-methyl-3-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyrylamino]butanamide

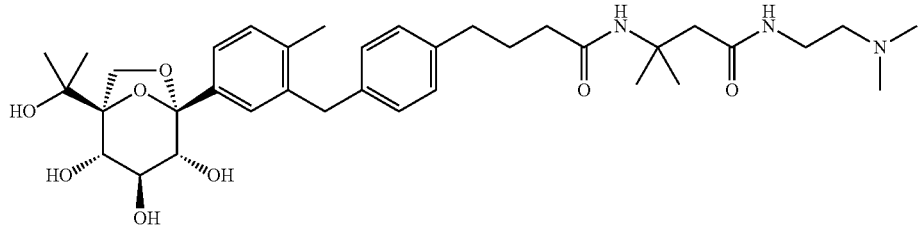 [SMILES: Cc1ccc([C@]23OC[C@](C(C)(C)O)(O2)[C@@H](O)[C@H](O)[C@H]3O)cc1Cc1ccc(CCCC(=O)NC(C)(C)CC(=O)NCCN(C)C)cc1]

Step 1: 3(benzyloxycarbonylamino)-3-methyl-butyric acid

3-Amino-3-methyl-butyric acid (3.0 g, 26 mmol) was dissolved in dioxane (20 mL) at room temperature, then sodium carbonate (8.1 g, 76 mmol) and water (60 mL) were added. The mixture was cooled to 0° C., then benzyl chloroformate (4.5 mL, 30 mmol) was added. The resulting mixture was warmed to room temperature and stirred overnight. The mixture was washed with n-hexane (100 mL), the aqueous phases were adjusted to pH=1 with dilute hydrochloric acid (1 M), extracted with ethyl acetate (100 mL×2), and the combined organic phases were washed with saturated brine (100 mL), dried over anhydrous sodium sulfate, filtered by suction, and concentrated to obtain the title compound (5.4 g, colorless oil) in 84% yield.

Step 2: N-[3-(2-Dimethylaminoethylamino)-1,1-dimethyl-3-oxo-propyl]carbamic acid benzyl ester

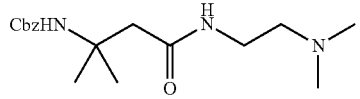 [SMILES: CN(C)CCNC(=O)CC(C)(C)NC(=O)OCc1ccccc1]

3-(Benzyloxycarbonylamino)-3-methyl-butyric acid (3.0 g, 12 mmol) was dissolved in dichloromethane (30 mL) at room temperature, and the mixture was cooled to 0° C. Then HATU (5.3 g, 13 mmol) and N,N-diisopropylethylamine (7.0 mL, 40 mmol) were added, and the mixture was stirred for 20 minutes. N,N-dimethyl-1,2-ethylenediamine (1.4 g, 16 mmol) was added, and the resulting mixture was warmed to room temperature and stirred overnight. The mixture was washed with water (20 mL), the organic phases were concentrated in vacuo, and the residue was purified by silica gel column chromatography [dichloromethane/anhydrous methanol (v/v)=30/1] to give the title compound (3.0 g, yellow oil) in 78% yield.

Step 3: 3-Amino-N-(2-dimethylaminoethyl)-3-methyl-butanamide

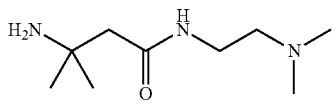

To a solution of benzyl N-[3-(2-dimethylaminoethylamino)-1,1-dimethyl-3-oxo-propyl] carbamate (3.0 g, 9.3 mmol) in anhydrous methanol (30 mL) was added 10% palladium/carbon (0.30 g, 0.28 mmol) at room temperature, and the mixture was stirred overnight under a hydrogen atmosphere. The mixture was filtered with suction and concentrated in vacuo to give the title compound (1.7 g, yellow oil) in 97% yield.

Step 4: 3-Amino-N-(2-dimethyl aminoethyl)-3-methyl-butanamide dihydrochloride

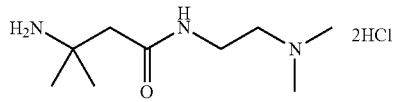

To a solution of 3-amino-N-(2-dimethylaminoethyl)-3-methyl-butanamide (1.7 g, 9.1 mmol) in ethyl acetate (20 mL) was added HCl isopropanol solution (5 mL, 5 M) at room temperature, and the mixture was stirred for 1 hour. The mixture was filtered with suction, the filter cake was washed with ethyl acetate (20 mL), and dried in vacuo to give the title compound (2.0 g, white solid) in 85% yield.

MS (ESI, pos. ion) m/z: 188.2 [M+H]$^+$.

$^1$H NMR (400 MHz, D$_2$O) δ (ppm): 3.53 (t, J=6.2 Hz, 2H), 3.24 (t, J=6.1 Hz, 2H), 2.84 (s, 6H), 2.55 (s, 2H), 1.32 (s, 6H).

Step 5: [(1S,2S,3S,4R,5S)-2,4-diacetoxy-5-[3-[[4-[4-[[3-(2-methylaminoethylamino)-1,1-dimethyl-3-oxo-propyl]amino]-4-oxo-butyl]phenyl]methyl]-4-methyl-phenyl]-1-(1-hydroxy-1-methyl-ethyl)-6,8-dioxabicyclo[3.2.1]octan-3-yl]acetate

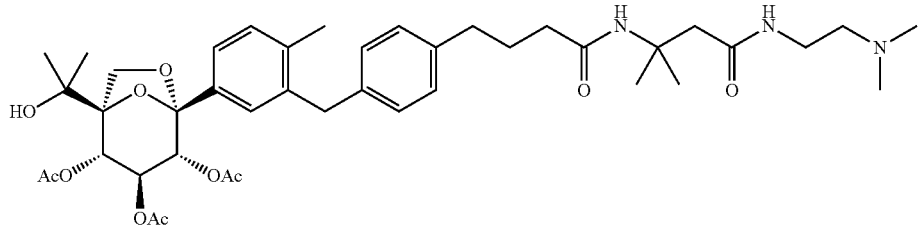 [SMILES: CC(=O)O[C@@H]1[C@@H](OC(C)=O)[C@@]2(c3ccc(C)c(Cc4ccc(CCCC(=O)NC(C)(C)CC(=O)NCCN(C)C)cc4)c3)OC[C@](C(C)(C)O)(O2)[C@H]1OC(C)=O]

4-[4-[[2-Methyl-5-[(1S,2S,3S,4R,5S)-2,3,4-triacetoxy-1-(1-hydroxy-1-methyl-ethyl)-6,8-dioxabicyclo[3.2.1]octan-5-yl]phenyl]methyl]phenyl]butyric acid (0.15 g, 0.25 mmol) was dissolved in dichloromethane (5 mL) at room temperature, then the mixture was cooled to 0° C. HATU (0.12 g, 0.29 mmol) and N,N-diisopropylethylamine (0.22 mL, 1.3 mmol) were added and the mixture was stirred for 20 minutes. 3-Amino-N-(2-dimethylaminoethyl)-3-methyl-butanamide dihydrochloride (83 mg, 0.32 mmol) was added and the mixture was stirred overnight. The mixture was added with water (20 mL) and extracted with dichloromethane (40 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=8/1] to obtain the title compound (0.12 g, white solid) in 63% yield.

MS (ESI, pos. ion) m/z: 782.7[M+H]$^+$.

Step 6: N-(2-Dimethylaminoethyl)-3-methyl-3-[4-[4-[[2-methyl-5-[(1S,2S,3S,4R,5S)-2,3,4-trihydroxy-1-(1-hydroxy-1-methyl-ethyl)6,8-dioxabicyclo[3.2.1]octan-5-yl]phenyl]methyl]phenyl]butyrylamino]butanamide

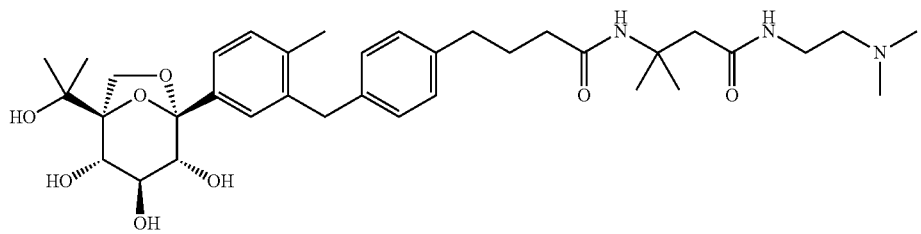 [SMILES: Cc1ccc([C@]23OC[C@](C(C)(C)O)(O2)[C@@H](O)[C@H](O)[C@H]3O)cc1Cc1ccc(CCCC(=O)NC(C)(C)CC(=O)NCCN(C)C)cc1]

To a solution of [(1S,2S,3S,4R,5S)-2,4-diacetoxy-5-[3-[[4-[4-[[3-(2-methylaminoethylamino)-1,1-dimethyl-3-oxo-propyl]amino]-4-oxo-butyl]phenyl]methyl]-4-methyl-phenyl]-1-(1-hydroxy-1-methyl-ethyl)-6,8-dioxabicyclo[3.2.1]octan-3-yl]acetate (0.12 g, 0.15 mmol) in anhydrous methanol (2 mL) was added solid sodium methoxide (41 mg, 0.75 mmol) at room temperature, and the mixture was stirred for 2 hours. The mixture was concentrated, and the residue was directly purified by TLC preparation [DCM/MeOH (v/v)=2/1] to give the title compound (60 mg, white solid) in 59% yield.

MS (ESI, pos. ion) m/z: 656.3[M+H]$^+$.

$^1$H NMR (400 MHz, DMSO-d$_6$) δ (ppm): 8.07 (br.s, 1H), 7.71 (t, 1H), 7.49 (s, 1H), 7.29 (s, 1H), 7.23 (d, 1H), 7.11-7.03 (m, 5H), 5.51 (d, 1H), 5.02 (d, 1H), 4.88 (d, 1H), 4.21 (s, 1H), 4.03 (d, 1H), 3.90 (s, 2H), 3.81 (d, 1H), 3.72 (d, 1H), 3.47-3.36 (m, 5H), 3.15 (m, 2H), 2.45 (s, 2H), 2.24 (s, 6H), 2.18 (s, 3H), 2.02 (t, 2H), 1.73 (m, 2H), 1.29 (s, 6H), 1.21 (s, 3H), 1.15 (s, 3H).

Example 5 N-[3-(dimethylamino)propyl]-2-methyl-2-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyrylamino]propionamide

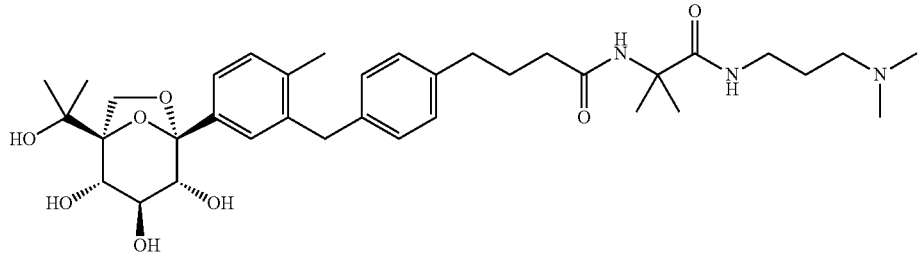 [SMILES: Cc1ccc([C@]23OC[C@](C(C)(C)O)(O2)[C@@H](O)[C@H](O)[C@H]3O)cc1Cc1ccc(CCCC(=O)NC(C)(C)C(=O)NCCCN(C)C)cc1]

Step 1: benzyl N-[2-[3-(Dimethylamino)propylamino]-1,1-dimethyl-2-oxo-ethyl]carbamate

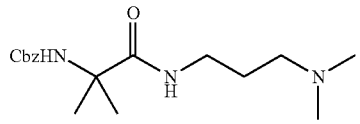 [SMILES: CN(C)CCCNC(=O)C(C)(C)NC(=O)OCc1ccccc1]

2-(Benzyloxycarbonylamino)-2-methyl-propionic acid (3.0 g, 13 mmol) was dissolved in dichloromethane (30 mL) at room temperature. The mixture was cooled to 0° C., and HATU (5.6 g, 14 mmol) and N,N-diisopropylethylamine (7.0 mL, 40 mmol) were added. The resulting mixture was stirred for 20 minutes. N,N-Dimethyl-1,3-propanediamine (1.7 g, 17 mmol) was added and the mixture was stirred overnight. The mixture was washed with water (20 mL), dried over anhydrous sodium sulfate, filtered by suction, concentrated, and the residue was purified by silica gel column chromatography [dichloromethane/anhydrous methanol (v/v)=30/1] to give the title compound (4.0 g, yellow oil) in 98% yield.

Step 2: 2-Amino-N-[3-(dimethylamino)propyl]-2-methyl-propionamide

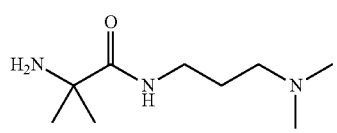

To a solution of benzyl N-[2-[3-(dimethylamino)propylamino]-1,1-dimethyl-2-oxo-ethyl] carbamate (4.0 g, 12 mmol) in anhydrous methanol (30 mL) was added 10% palladium/carbon (0.30 g, 0.28 mmol) at room temperature, and the mixture was stirred overnight under a hydrogen atmosphere. The mixture was filtered with suction and concentrated in vacuo to give the title compound (2.3 g, yellow oil) in 99% yield.

Step 3: 2-Amino-N-[3-(dimethylamino)propyl]-2-methyl-propionamide dihydrochloride

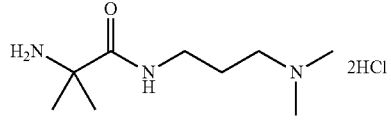

To a solution of 2-amino-N-[3-(dimethylamino)propyl]-2-methyl-propionamide (2.3 g, 12 mmol) in ethyl acetate (20 mL) was added HCl isopropanol solution (8 mL, 5 M) at room temperature, and the mixture was stirred for 1 hour. The mixture was filtered with suction, the filter cake was washed with ethyl acetate (20 mL), and dried in vacuo to give the title compound (2.5 g, white solid) in 78% yield.

MS (ESI, pos. ion) m/z: 188.2 [M+H]$^+$.

Step 4: [(1S,2S,3S,4R,5S)-2,4-diacetoxy-5-[3-[[4-[4-[[2-[3-(dimethylamino)propyl]-1,1-dimethyl-2-oxo-ethyl]amino]-4-oxo-butyl]phenyl]methyl]-4-methyl-phenyl]-1-(1-hydroxy-1-methyl-ethyl)-6,8-dioxabicyclo[3.2.1]octan-3-yl]acetate

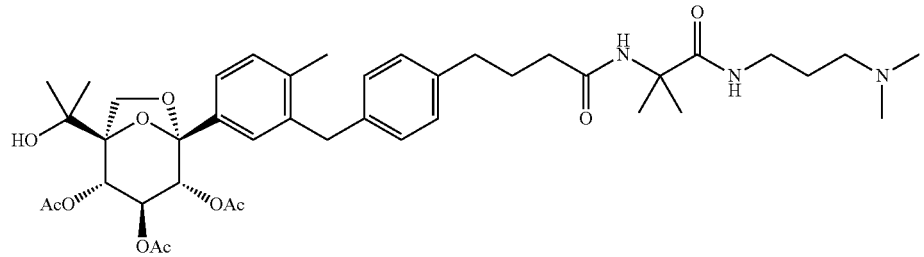

4-[4-[[2-Methyl-5-[(1S,2S,3S,4R,5S)-2,3,4-triacetoxy-1-(1-hydroxy-1-methyl-ethyl)-6,8-dioxabicyclo[3.2.1]octan-5-yl]phenyl]methyl]phenyl]butyric acid (0.10 g, 0.16 mmol) was dissolved in dichloromethane (5 mL) at room temperature, then the mixture was cooled to 0° C. HATU (80 mg, 0.21 mmol) and N,N-diisopropylethylamine (0.20 mL, 1.1 mmol) were added and the mixture was stirred for 20 minutes. 2-Amino-N-[3-(dimethylamino)propyl]-2-methyl-propionamide dihydrochloride (60 mg, 0.23 mmol) was added, and the mixture was warmed to room temperature and stirred overnight. The mixture was added with water (20 mL) and extracted with dichloromethane (40 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=8/1] to give the title compound (90 mg, white solid) in 80% yield.

MS (ESI, pos. ion) m/z: 782.6[M+H]⁺.

Step 5: N-[3-(Dimethylamino)propyl]-2-methyl-2-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyrylamino]propionamide

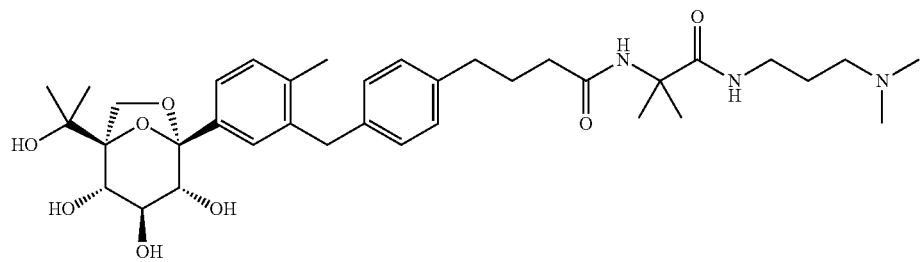 [SMILES: Cc1ccc([C@]23OC[C@](C(C)(C)O)(O2)[C@@H](O)[C@H](O)[C@H]3O)cc1Cc1ccc(CCCC(=O)NC(C)(C)C(=O)NCCCN(C)C)cc1]

To a solution of (1S,2S,3S,4R,5S)-2,4-diacetoxy-5-[3-[[4-[4-[[2-[3-(dimethylamino)propyl]-1,1-dimethyl-2-oxo-ethyl]amino]-4-oxo-butyl]phenyl]methyl]-4-methyl-phenyl]-1-(1-hydroxy-1-methyl-ethyl)-6,8-dioxabicyclo[3.2.1]octan-3-yl]acetate (90 mg, 0.11 mmol) in anhydrous methanol (2 mL) was added solid sodium methoxide (30 mg, 0.55 mmol) at room temperature, and the mixture was stirred for 2 hours. The mixture was concentrated, and the residue was directly purified by thin layer chromatography [DCM/MeOH (v/v)=2/1] to give the title compound (50 mg, white solid) in 66% yield.

MS (ESI, pos. ion) m/z: 656.3 [M+H]⁺.

¹H NMR (400 MHz, DMSO-d₆) δ (ppm): 7.95 (s, 1H), 7.70 (t, 1H), 7.29 (s, 1H), 7.23 (d, 1H), 7.12-7.04 (m, 5H), 5.53 (d, 1H), 5.04 (d, 1H), 4.89 (d, 1H), 4.21 (s, 1H), 4.04 (d, 1H), 3.91 (s, 2H), 3.81 (d, 1H), 3.73 (t, 1H), 3.54-3.38 (m, 4H), 3.09 (m, 2H), 2.90 (m, 2H), 2.61 (s, 6H), 2.18 (s, 3H), 2.11 (t, 2H), 1.78-1.67 (m, 4H), 1.29 (s, 6H), 1.21 (s, 3H), 1.16 (s, 3H).

Example 6 N-[2-[(3R)-3-fluoropyrrolidin-1-yl]ethyl]-2-methyl-2-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butyrylamino]propionamide

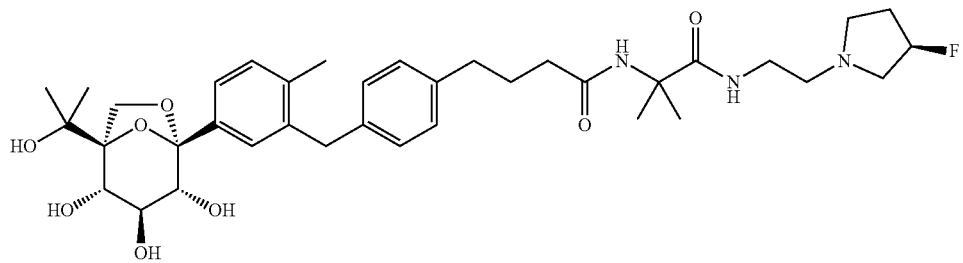 [SMILES: Cc1ccc([C@]23OC[C@](C(C)(C)O)(O2)[C@@H](O)[C@H](O)[C@H]3O)cc1Cc1ccc(CCCC(=O)NC(C)(C)C(=O)NCCN2CC[C@@H](F)C2)cc1]

Step 1: tert-Butyl N-[2-[(3R)-3-fluoropyrrolidin-1-yl]ethyl]carbamate

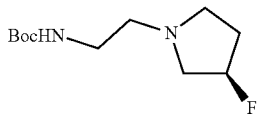 [SMILES: CC(C)(C)OC(=O)NCCN1CC[C@@H](F)C1]

(3R)-3-Fluoropyrrolidine hydrochloride (4.1 g, 33 mmol) was dissolved in dimethylsulfoxide (40 mL) at room temperature, and tert-butyl N-(2-bromoethyl)carbamate (6.9 g, 31 mmol) and N,N-diisopropylethylamine (11 mL, 64 mmol) were added. The resulting mixture was heated to 40° C. and stirred overnight. The mixture was added with water (150 mL) and extracted with ethyl acetate (100 mL×3). The combined organic phases were washed with saturated brine (50 mL), dried over anhydrous sodium sulfate, filtered by suction, concentrated, and the residue was purified by silica gel column chromatography [ethyl acetate/petroleum ether (v/v)=1/1] to obtain the title compound (3.0 g, yellow oil) in 42% yield.

Step 2: 2-[(3R)-3-fluoropyrrolidin-1-yl]ethylamine

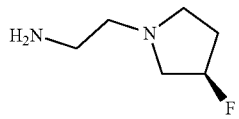

To a solution of tert-butyl N-[2-[(3R)-3-fluoropyrrolidin-1-yl]ethyl]carbamate (3.5 g, 15 mmol) in ethyl acetate (30 mL) was added HCl ethyl acetate solution (10 mL, 4M) at room temperature, and the mixture was stirred for 2 hours. The mixture was concentrated, and the residue was dissolved in methanol (30 mL). To the mixture was added solid sodium bicarbonate to adjust to pH=8-9. The mixture was filtered by suction, and concentrated to obtain the title compound (1.5 g, yellow oil) in 75% yield.

Step 3: Benzyl N-[2-[2-[(3R)-3-fluoropyrrolidin-1-yl]ethylamino]-1,1-dimethyl-2-oxo-ethyl]carbamate

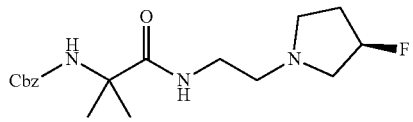 [SMILES: CC(C)(NC(=O)OCc1ccccc1)C(=O)NCCN1CC[C@@H](F)C1]

2-(Benzyloxycarbonylamino)-2-methyl-propionic acid (1.0 g, 4.2 mmol) was dissolved in dichloromethane (10 mL) at room temperature, and the mixture was cooled to 0° C. HATU (1.9 g, 4.7 mmol) and N,N-diisopropylethylamine (2.2 mL, 13 mmol) were added, and the resulting mixture was stirred for 20 minutes. 2-[(3R)-3-Fluoropyrrolidin-1-yl] ethylamine (0.7 g, 5.3 mmol) was added and the mixture was stirred overnight. The mixture was washed with water (20 mL), dried over anhydrous sodium sulfate, filtered by suction, concentrated, and the residue was purified by silica gel column chromatography [dichloromethane/anhydrous methanol (v/v)=30/1] to obtain the title compound (1.1 g, colorless oil) in 74% yield.

MS (ESI, pos. ion) m/z: 352.1[M+H]⁺.

Step 4: 2-Amino-N-[2-[(3R)-3-fluoropyrrolidin-1-yl]ethyl]-2-methyl-propionamide

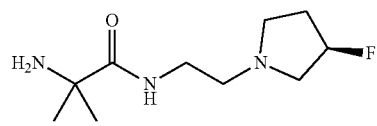

To a solution of benzyl N-[2-2-[(3R)-3-fluoropyrrolidin-1-yl]ethylamino]-1,1-dimethyl-2-oxo-ethyl]carbamate (1.1 g, 3.1 mmol) in anhydrous methanol (30 mL) was added 10% palladium/carbon (0.20 g, 0.21 mmol) at room temperature, and the mixture was stirred overnight under a hydrogen atmosphere. The mixture was filtered with suction and concentrated in vacuo to give the title compound (0.68 g, yellow oil) in 99% yield.

Step 5: 2-Amino-N-[2-[(3R)-3-fluoropyrrolidin-1-yl]ethyl]-2-methyl-propionamide dihydrochloride

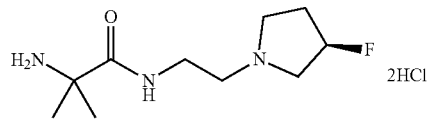

To a solution of 2-amino-N-[3-(dimethylamino)propyl]-2-methyl-propionamide (0.68 g, 3.1 mmol) in ethyl acetate (5 mL) was added HCl ethyl acetate solution (3 mL, 4 M) at room temperature, and the mixture was stirred for 1 hour. The mixture was filtered with suction, and the filter cake was washed with ethyl acetate (5 mL) and dried in vacuo to give the title compound (0.77 g, light yellow solid) in 85% yield.

MS (ESI, pos. ion) m/z: 218.1[M+H]⁺.

Step 6: [(1S,2S,3S,4R,5S)-2,4-diacetoxy-5-[3-[[4-[4-[[2-[2-[(3R)-3-fluoropyrrolidin-1-yl]ethylamino]-1,1-dimethyl-2-oxo-ethyl]amino]-4-oxo-butyl]phenyl]methyl]-4-methyl-phenyl]-1-(1-hydroxy-1-methyl-ethyl)-6,8-dioxabicyclo[3.2.1]octan-3-yl] acetate

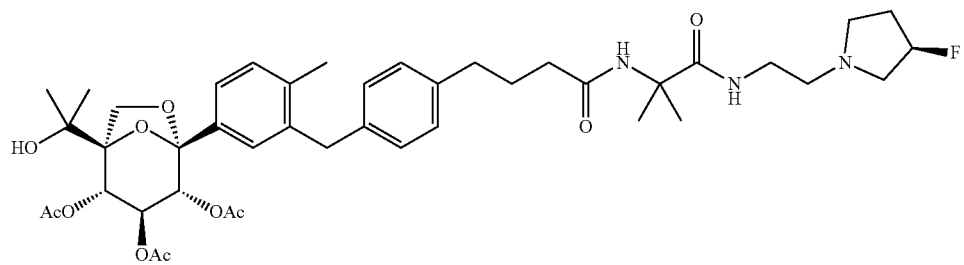 [SMILES: CC(=O)O[C@@H]1[C@@H](OC(C)=O)[C@@]2(c3ccc(C)c(Cc4ccc(CCCC(=O)NC(C)(C)C(=O)NCCN5CC[C@@H](F)C5)cc4)c3)OC[C@](C(C)(C)O)(O2)[C@H]1OC(C)=O]

4-[4-[[2-Methyl-5-[(1S,2S,3S,4R,5S)-2,3,4-tri acetoxy-1-(1-hydroxy-1-methyl-ethyl)-6,8-dioxabicyclo[3.2.1]octan-5-yl]phenyl]methyl]phenyl]butyric acid (0.15 g, 0.25 mmol) was dissolved in methyl chloride (5 mL) at room temperature, then the mixture was cooled to 0° C. HATU (0.18 g, 0.47 mmol) and N,N-diisopropylethylamine (0.22 mL, 1.3 mmol) were added and the mixture was stirred for 20 minutes. 2-Amino-N-[2-[(3R)-3-fluoropyrrolidin-1-yl]ethyl]-2-methyl-propionamide dihydrochloride (93 mg, 0.32 mmol) was added, and the mixture was stirred overnight. The mixture was added with water (20 mL) and extracted with dichloromethane (40 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=20/1] to obtain the title compound (0.15 g, white solid) in 75% yield.

MS (ESI, pos. ion) m/z: 812.7[M+H]$^+$.

Step 7: N-[2-[(3R)-3-Fluoropyrrolidin-1-yl]ethyl]-2-methyl-2-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butyrylamino]propionamide

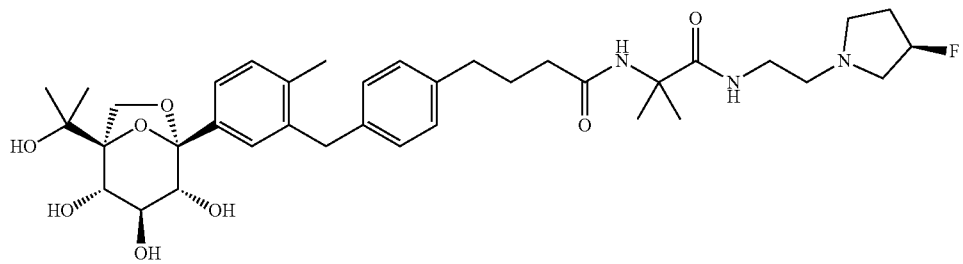 [SMILES: Cc1ccc([C@]23OC[C@](C(C)(C)O)(O2)[C@@H](O)[C@H](O)[C@H]3O)cc1Cc1ccc(CCCC(=O)NC(C)(C)C(=O)NCCN2CC[C@@H](F)C2)cc1]

To a solution of [(1S,2S,3S,4R,5S)-2,4-diacetoxy-5-[3-[[4-[4-[[2-[2-[(3R)-3-fluoropyrrolidin-1-yl]ethylamino]-1,1-dimethyl-2-oxo-ethyl]amino]-4-oxo-butyl]phenyl]methyl]-4-methyl-phenyl]-1-(1-hydroxy-1-methyl-ethyl)-6,8-dioxabicyclo[3.2.1]octan-3-yl]acetate (0.15 g, 0.18 mmol) in anhydrous methanol (2 mL) was added solid sodium methoxide (49 mg, 0.90 mmol) at room temperature, and the mixture was stirred for 2 hours. The mixture was concentrated and the residue was directly purified by TLC preparation [DCM/MeOH (v/v)=3/1] to give the title compound (100 mg, white solid) in 66% yield.

MS (ESI, pos. ion) m/z: 686.3[M+H]$^+$.

$^1$H NMR (400 MHz, DMSO-d$_6$) δ (ppm): 8.20 (br.s, 1H), 7.77 (br.s, 1H), 7.29 (s, 1H), 7.23 (d, 1H), 7.12-7.02 (m, 5H), 5.50 (d, 1H), 5.01 (d, 1H), 4.87 (d, 1H), 4.20 (s, 1H), 4.04 (d, 1H), 3.91 (s, 2H), 3.81 (d, 1H), 3.73 (t, 1H), 3.50-3.38 (m, 4H), 2.18 (s, 3H), 2.11 (t, 2H), 1.99 (m, 1H), 1.75 (m, 2H), 1.29 (s, 6H), 1.21 (s, 3H), 1.16 (s, 3H).

Example 7 N-[2-[(3R)-3-fluoropyrrolidin-1-yl]ethyl]-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butyrylamino]cyclohexyl formamide

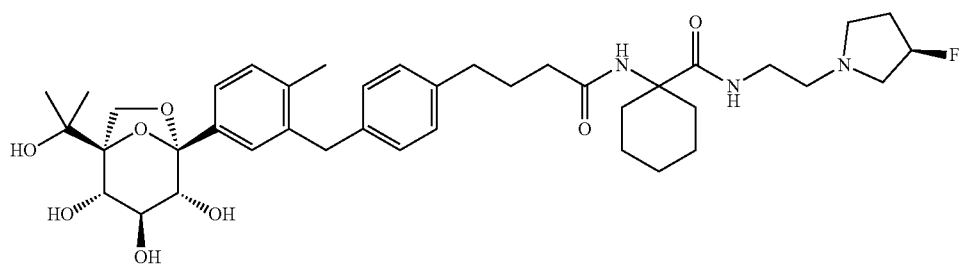 [SMILES: Cc1ccc([C@]23OC[C@](C(C)(C)O)(O2)[C@@H](O)[C@H](O)[C@H]3O)cc1Cc1ccc(CCCC(=O)NC2(C(=O)NCCN3CC[C@@H](F)C3)CCCCC2)cc1]

Step 1: 1-(benzyloxycarbonylamino)cyclohexanecarboxylic acid

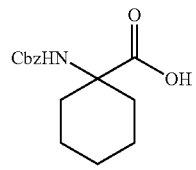

1-Aminocyclohexanecarboxylic acid (5.4 g, 38 mmol) was dissolved in dioxane (30 mL) at room temperature, then sodium carbonate (11.0 g, 104 mmol) and water (100 mL) were added. The resulting mixture was cooled to 0° C., then benzyl chloroformate (6.0 mL, 41 mmol) was added. The mixture was warmed to room temperature and stirred overnight. The mixture was washed with n-hexane (100 mL), the aqueous phases were adjusted to pH=2 with dilute hydrochloric acid (1 M), extracted with ethyl acetate (100 mL×2), and the combined organic phases were washed with saturated brine (100 mL), dried over anhydrous sodium sulfate, filtered by suction and concentrated to obtain the title compound (5.2 g, colorless oil) in 50% yield.

Step 2: Benzyl N-[1-[2-[(3R)-3-fluoropyrrolidin-1-yl]ethylcarbamoyl]cyclohexyl] carbamate

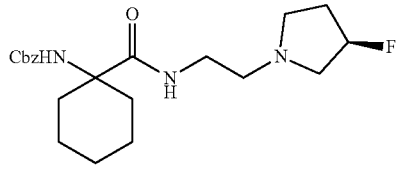 [SMILES: O=C(NC1(C(=O)NCCN2CC[C@@H](F)C2)CCCCC1)OCc1ccccc1]

1-(benzyloxycarbonylamino)cyclohexanecarboxylic acid (1.3 g, 4.7 mmol) was dissolved in dichloromethane (15 mL) at room temperature, then the mixture was cooled to 0° C. HATU (2.0 g, 5.0 mmol) and N,N-diisopropylethylamine (2.3 mL, 13 mmol) were added, and the resulting mixture was stirred for 20 minutes. 2-[(3R)-3-Fluoropyrrolidin-1-yl]ethylamine (0.70 g, 5.3 mmol) was added, and the mixture was warmed to room temperature and stirred overnight. The mixture was washed with water (20 mL), the organic phases were concentrated, and the residue was purified by silica gel column chromatography [dichloromethane/anhydrous methanol (v/v)=30/1] to give the title compound (1.6 g, colorless oil) in 87% yield.

MS (ESI, pos. ion) m/z: 392.2 [M+H]$^+$.

Step 3: 1-amino-N-[2-[(3R)-3-fluoropyrrolidin-1-yl]ethyl]cyclohexane carboxamide

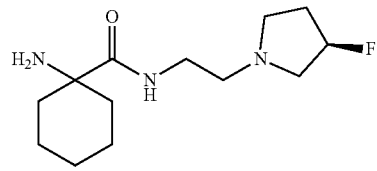 [SMILES: NC1(C(=O)NCCN2CC[C@@H](F)C2)CCCCC1]

To a solution of benzyl N-[1-[2-[(3R)-3-Fluoropyrrolidin-1-yl]ethylcarbamoyl] cyclohexyl]carbamate (1.6 g, 4.1 mmol) in anhydrous methanol (20 mL) was added 10% palladium/carbon catalyst (0.20 g, 0.19 mmol) at room temperature, and the mixture was stirred overnight under a hydrogen atmosphere. The mixture was filtered with suction and concentrated in vacuo to give the title compound (1.1 g, yellow oil) in 99% yield.

Step 4: 1-Amino-N-[2-[(3R)-3-fluoropyrrolidin-1-yl]ethyl]cyclohexane carboxamide dihydrochloride

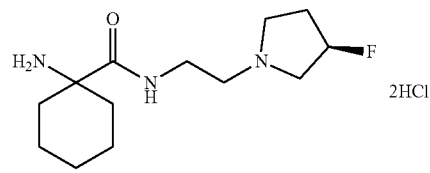 [SMILES: NC1(C(=O)NCCN2CC[C@@H](F)C2)CCCCC1]

To a solution of 1-amino-N-[2-[(3R)-3-fluoropyrrolidin-1-yl]ethyl]cyclohexane carboxamide (1.0 g, 3.9 mmol) in ethyl acetate (5 mL) was added HCl ethyl acetate solution (3 mL, 4 M) at room temperature, and the mixture was stirred for 1 hour. The mixture was filtered with suction, the filter cake was washed with ethyl acetate (5 mL), and dried in vacuo to give the title compound (1.1 g, white solid) in 86% yield.

MS (ESI, pos. ion) m/z: 258.1 [M+H]$^+$.

Step 5: [(1S,2S,3S,4R,5S)-2,4-Diacetoxy-5-[3-[[4-[4-[[1-[2-[(3R)-3-fluoropyrrolidine-1-yl]ethylcarbamoyl]cyclohexyl]amino]-4-oxo-butyl]phenyl]methyl]-4-methyl-phenyl]-1-(1-hydroxy-1-methyl-ethyl)-6,8-dioxabicyclo[3.2.1]octan-3-yl]acetate

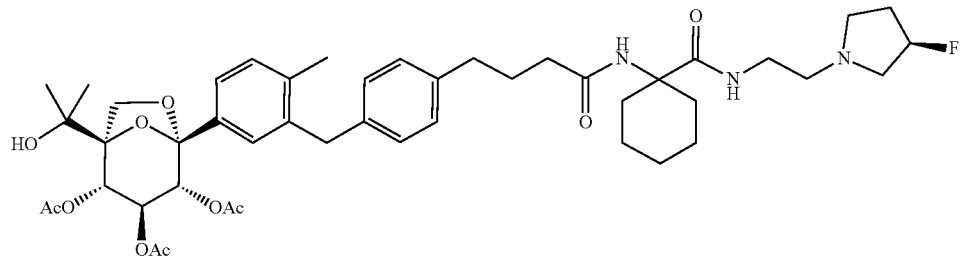 [SMILES: CC(=O)O[C@@H]1[C@@H](OC(C)=O)[C@@]2(c3ccc(C)c(Cc4ccc(CCCC(=O)NC5(C(=O)NCCN6CC[C@@H](F)C6)CCCCC5)cc4)c3)OC[C@](C(C)(C)O)(O2)[C@H]1OC(C)=O]

4-[4-[[2-Methyl-5-[(1S,2S,3S,4R,5S)-2,3,4-triacetoxy-1-(1-hydroxy-1-methyl-ethyl)-6,8-dioxabicyclo[3.2.1]octan-5-yl]phenyl]methyl]phenyl]butyric acid (0.15 g, 0.25 mmol) was dissolved in dichloromethane (5 mL) at room temperature, then the mixture was cooled to 0° C. HATU (0.12 g, 0.32 mmol) and N,N-diisopropylethylamine (0.22 mL, 1.3 mmol) were added and the mixture was stirred for 20 minutes. 1-amino-N-[2-[(3R)-3-fluoropyrrolidin-1-yl]ethyl]cyclohexane carboxamide dihydrochloride (110 mg, 0.32 mmol) was added, and the mixture was warmed to room temperature and stirred overnight. The mixture was added with water (10 mL) and extracted with dichloromethane (40 mL×3). The combined organic phases were washed with saturated brine (20 mL), dried over anhydrous sodium sulfate, filtered with suction, concentrated, and the residue was purified by silica gel column chromatography [dichloromethane/anhydrous methanol (v/v)=20/1] to obtain the title compound (0.18 g, white solid) in 86% yield.

MS (ESI, pos. ion) m/z: 852.7 [M+H]$^+$.

Step 6: N-[2-[(3R)-3-Fluoropyrrolidin-1-yl]ethyl]-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyrylamino] cyclohexyl formamide

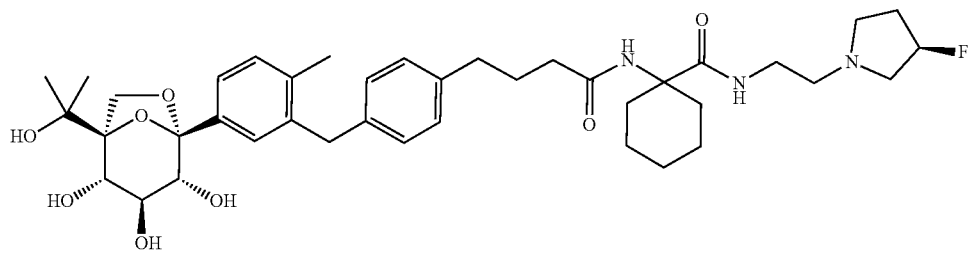 [SMILES: Cc1ccc([C@]23OC[C@](C(C)(C)O)(O2)[C@@H](O)[C@H](O)[C@H]3O)cc1Cc1ccc(CCCC(=O)NC2(C(=O)NCCN3CC[C@@H](F)C3)CCCCC2)cc1]

To a solution of [(1S,2S,3S,4R,5S)-2,4-diacetoxy-5-[3-[[4-[4-[[1-[2-[(3R)-3-fluoropyrrolidin-1-yl]ethylcarbamoyl]cyclohexyl]amino]-4-oxo-butyl]phenyl]methyl]-4-methyl-phenyl]-1-(1-hydroxy-1-methyl-ethyl)-6,8-di oxabicyclo[3.2.1]octan-3-yl]acetate (0.18 g, 0.21 mmol) in anhydrous methanol (2 mL) was added solid sodium methoxide (57 mg, 1.05 mmol) at room temperature, and the mixture was stirred for 2 hours. The mixture was concentrated, and the residue was directly purified by thin layer chromatography preparation [DCM/MeOH (v/v)=3/1] to give the title compound 7 (90 mg, white solid) in 58% yield.

MS (ESI, pos. ion) m/z: 726.3 [M+H]$^+$.

$^1$H NMR (400 MHz, DMSO-d$_6$) δ (ppm): 7.92 (br.s, 1H), 7.77 (br.s, 1H), 7.30 (s, 1H), 7.23 (d, 1H), 7.12-7.03 (m, 5H), 5.50 (d, 1H), 5.01 (d, 1H), 4.88 (d, 1H), 4.20 (s, 1H), 4.04 (d, 1H), 3.91 (s, 2H), 3.81 (d, 1H), 3.72 (t, 1H), 3.53-3.38 (m, 6H), 2.23-2.15 (m, 5H), 1.99 (m, 1H), 1.85 (d, 2H), 1.76 (m, 2H), 1.64 (m, 2H), 1.48 (m, 5H), 1.21 (s, 3H), 1.16 (s, 3H).

Example 8 N-(2-dimethylaminoethyl)-2-methyl-2-[methyl-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]amino]propionamide

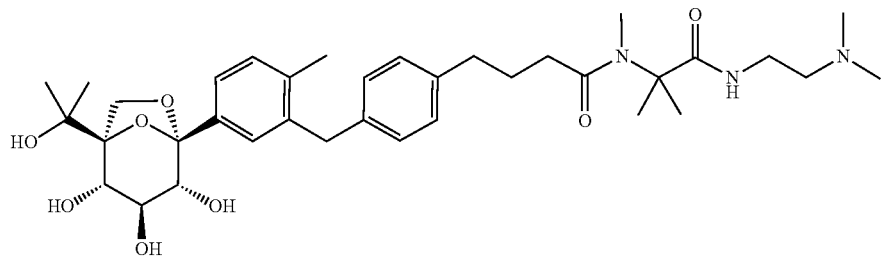 [SMILES: Cc1ccc([C@]23OC[C@](C(C)(C)O)(O2)[C@@H](O)[C@H](O)[C@H]3O)cc1Cc1ccc(CCCC(=O)N(C)C(C)(C)C(=O)NCCN(C)C)cc1]

Step 1: tert-Butyl N-[2-(2-dimethylaminoethyl-amino)-1,1,-dimethyl-2-oxo-ethyl]-N-methyl-formate

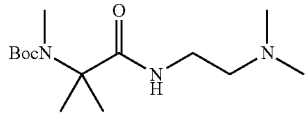

2-[-tert-Butoxycarbonyl(methyl)amino]-2-methylpropionic acid (2.6 g, 12 mmol) was dissolved in dichloromethane (40 mL) at room temperature, and the mixture was cooled to 0° C. HATU (5.8 g, 15 mmol) and N,N-diisopropylethylamine (6.3 mL, 36 mmol) were added, and the resulting mixture was stirred for 20 minutes. N,N-Dimethyl-1,2-ethylenediamine (1.6 g, 18 mmol) was added, and the resulting mixture was warmed to room temperature and stirred overnight. The resulting mixture was washed with water (30 mL), dried over anhydrous sodium sulfate, and filtered with suction. The filtrate was concentrated in vacuo and the residue was purified by silica gel column chromatography (DCM/anhydrous MeOH (v/v)=20/1) to give the title compound (2.0 g, yellow oil) in 58% yield.

MS (ESI, pos. ion) m/z: 288.1 [M+H]$^+$.

Step 2: N-(2-Dimethylaminoethyl)-2-methyl-2-(methylamino)propionamide dihydrochloride

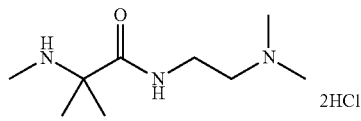

To a solution of tert-butyl N-[2-(2-dimethylaminoethyl-amino)-1,1,-dimethyl-2-oxo-ethyl]-N-methyl-formate (2.0 g, 7.0 mmol) in ethyl acetate (20 mL) was added HCl isopropanol solution (4 mL, 5M) at room temperature, and the resulting mixture was stirred overnight, cooled to 0° C. and stirred for 30 minutes. The mixture was filtered by suction, and the filter cake was washed with ethyl acetate (5 mL) and dried in vacuo to obtain the title compound (1.3 g, yellow solid) in 71% yield.

Step 3: [(1S,2S,3S,4R,5S)-2,4-Diacetoxy-5-[3-[[4-[4-[[2-(2-dimethylaminoethylamino)-1,1-dimethyl-2-oxo-ethyl]methyl-amino]-4-oxo-butyl]phenyl]methyl]-4-methyl-phenyl]-1-(1-hydroxy-1-methyl-ethyl)-6,8-dioxabicyclo[3.2.1]octan-3-yl]acetate

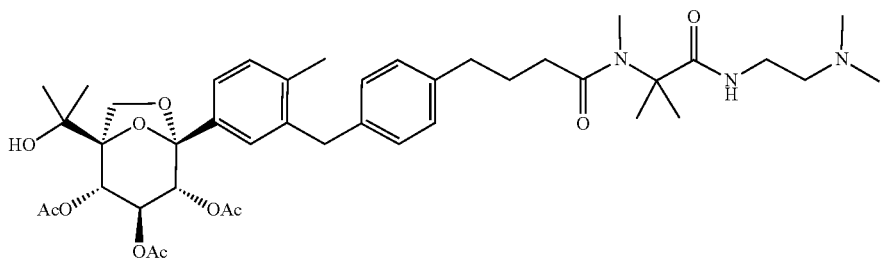 [SMILES: CC(=O)O[C@@H]1[C@@H](OC(C)=O)[C@@]2(c3ccc(C)c(Cc4ccc(CCCC(=O)N(C)C(C)(C)C(=O)NCCN(C)C)cc4)c3)OC[C@](C(C)(C)O)(O2)[C@H]1OC(C)=O]

4-[4-[[2-Methyl-5-[(1S,2S,3S,4R,5S)-2,3,4-triacetoxy-1-(1-hydroxy-1-methyl-ethyl)-6,7,8-dioxabicyclo[3.2.1]octan-5-yl]phenyl]methyl]phenyl]butyric acid (0.20 g, 0.33 mmol) was dissolved in dichloromethane (5 mL) at room temperature. The mixture was cooled to 0° C., then HATU (0.16 g, 0.40 mmol) and N,N-diisopropylethylamine (0.30 mL, 1.7 mmol) were added. The resulting mixture was stirred for 20 minutes. N-(2-Dimethylaminoethyl)-2-methyl-2-(methylamino)propionamide dihydrochloride (0.17 g, 0.66 mmol) was added, and the mixture was stirred overnight. The mixture was added with water (20 mL) and extracted with dichloromethane (40 mL×3). The combined organic phases were washed with saturated brine (20 mL), dried over anhydrous sodium sulfate, filtered with suction, concentrated, and the residue was purified by silica gel column chromatography [dichloromethane/anhydrous methanol (v/v)=8/1] to obtain the title compound (0.11 g, white solid) in 43% yield.

MS (ESI, pos. ion) m/z: 782.3[M+H]$^+$.

Step 4: N-(2-dimethylaminoethyl)-2-methyl-2-[methyl-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]amino]propionamide

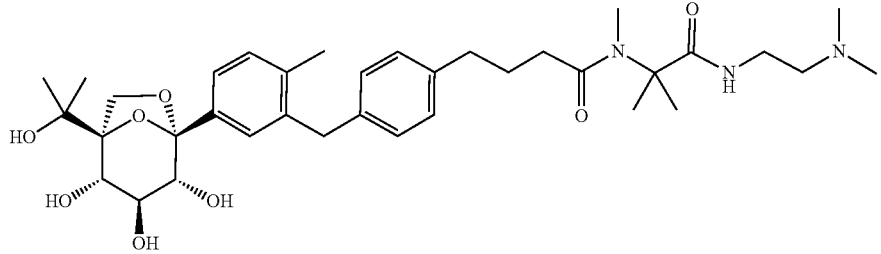 [SMILES: Cc1ccc([C@]23OC[C@](C(C)(C)O)(O2)[C@@H](O)[C@H](O)[C@H]3O)cc1Cc1ccc(CCCC(=O)N(C)C(C)(C)C(=O)NCCN(C)C)cc1]

To a solution of [(1S,2S,3S,4R,5S)-2,4-diacetoxy-5-[3-[[4-[4-[[2-(2-dimethylaminoethylamino)-1,1-dimethyl-2-oxo-ethyl]-methyl-amino]-4-oxo-butyl]phenyl]methyl]-4-methyl-phenyl]-1-(1-hydroxy-1-methyl-ethyl)-6,8-dioxabicyclo[3.2.1]octan-3-yl]acetate (0.11 g, 0.14 mmol) in anhydrous methanol (3 mL) was added solid sodium methoxide (38 mg, 0.70 mmol) at room temperature, and the mixture was stirred for 2 hours. The mixture was concentrated, and the residue was directly purified by preparative TLC [DCM/MeOH (v/v)=4/1] to give the title compound (55 mg, white solid) in 61% yield.

MS (ESI, pos. ion) m/z: 656.2 [M+H]$^+$.

$^1$H NMR (400 MHz, DMSO-d$_6$) δ (ppm): 8.71 (br.s, 1H), 7.85 (t, 1H), 7.30 (s, 1H), 7.23 (d, 1H), 7.12-7.04 (m, 5H), 5.50 (d, 1H), 5.01 (d, 1H), 4.88 (d, 1H), 4.20 (s, 1H), 4.04 (d, 1H), 3.91 (s, 2H), 3.81 (d, 1H), 3.75-3.69 (m, 1H), 3.45-3.35 (m, 5H), 3.18 (s, 3H), 3.10 (t, 2H), 2.81 (s, 6H), 2.18 (s, 3H), 2.12 (t, 2H), 1.75 (m, 2H), 1.29 (s, 6H), 1.21 (s, 3H), 1.16 (s, 3H).

Example 9 N-(2-Dimethylaminoethyl)-N,2-dimethyl-2-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl] propionamide Step 1: tert-Butyl N-[2-[2-dimethylaminoethyl(methyl)amino]-1,1,-dimethyl-2-oxo-ethyl]-formate

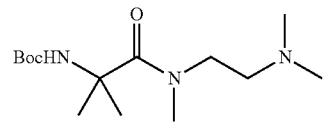

2-[-tert-Butoxycarbonyl(methyl)amino]-2-methylpropionic acid (2.0 g, 10 mmol) was dissolved in dichloromethane (30 mL) at room temperature, and the mixture was cooled to 0° C. HATU (4.7 g, 12 mmol) and N,N-diisopropylethylamine (5.2 mL, 30 mmol) were added, and the resulting mixture was stirred for 20 minutes. N,N',N'-Trimethyl-1,2-ethylenediamine (1.5 g, 15 mmol) was added, and the mixture was warmed to room temperature and stirred overnight. The resulting mixture was washed with water (30 mL), dried over anhydrous sodium sulfate, and filtered with suction. The filtrate was concentrated in vacuo and the residue was purified by silica gel column chromatography (DCM/anhydrous MeOH (v/v)=20/1) to give the title compound (1.6 g, yellow oil) in 56% yield.

MS (ESI, pos. ion) m/z: 288.0 [M+H]$^+$.

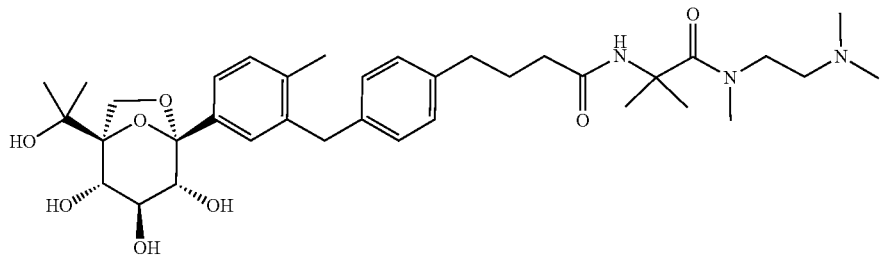 [SMILES: Cc1ccc([C@]23OC[C@](C(C)(C)O)(O2)[C@@H](O)[C@H](O)[C@H]3O)cc1Cc1ccc(CCCC(=O)NC(C)(C)C(=O)N(C)CCN(C)C)cc1]

Step 2: 2-Amino-N-(2-dimethylaminoethyl)-N,2-dimethyl-propionamide dihydrochloride

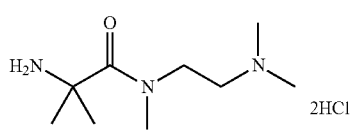

To a solution of tert-butyl N-[2-[2-dimethylaminoethyl(methyl)amino]-1,1,-dimethyl-2-oxo-ethyl]-carboxylate (1.6 g, 5.6 mmol) in ethyl acetate (20 mL) was added HCl isopropanol solution (4 mL, 5M). The mixture was stirred overnight, cooled to 0° C. and stirred for 30 minutes. The mixture was filtered with suction, and the filter cake was washed with ethyl acetate (5 mL) and dried in vacuo to obtain the title compound (1.0 g, yellow solid) in 69% yield.

Step 3: [(1S,2S,3S,4R,5S)-2,4-Diacetoxy-5-[3-[[4-[4-[[2-[2-dimethyl aminoethyl (methyl)amino]-1,1-dimethyl-2-oxo-ethyl]-amino]-4-oxo-butyl]phenyl]methyl]-4-methyl-phenyl]-1-hydroxy-1-methyl-ethyl)-6,8-dioxabicyclo[3.2.1]octan-3-yl]acetate

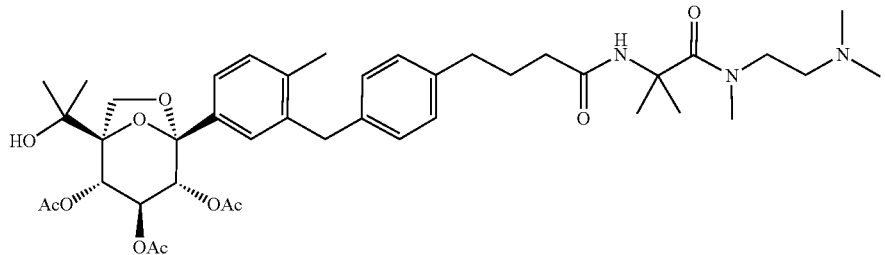 [SMILES: CC(=O)O[C@@H]1[C@@H](OC(C)=O)[C@@]2(c3ccc(C)c(Cc4ccc(CCCC(=O)NC(C)(C)C(=O)N(C)CCN(C)C)cc4)c3)OC[C@](C(C)(C)O)(O2)[C@H]1OC(C)=O]

4-[4-[[2-Methyl-5-[(1S,2S,3S,4R,5S)-2,3,4-triacetoxy-1-(1-hydroxy-1-methyl-ethyl)-6,7,8-dioxabicyclo[3.2.1]octan-5-yl]phenyl]methyl]phenyl]butyric acid (0.20 g, 0.33 mmol) was dissolved in dichloromethane (5 mL) at room temperature. The mixture was cooled to 0° C., then HATU (0.16 g, 0.40 mmol) and N,N-diisopropylethylamine (0.30 mL, 1.7 mmol) were added. The resulting mixture was stirred for 20 minutes. 2-Amino-N-(2-dimethylaminoethyl)-N,2-dimethyl-propionamide dihydrochloride (0.17 g, 0.66 mmol) was added and the mixture was stirred overnight. The mixture was added with water (20 mL) and extracted with dichloromethane (40 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=8/1] to obtain the title compound (0.13 g, white solid) in 50% yield.

MS (ESI, pos. ion) m/z: 782.2[M+H]⁺.

Step 4 N-(2-Dimethylaminoethyl)-N,2-dimethyl-2-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]propionamide

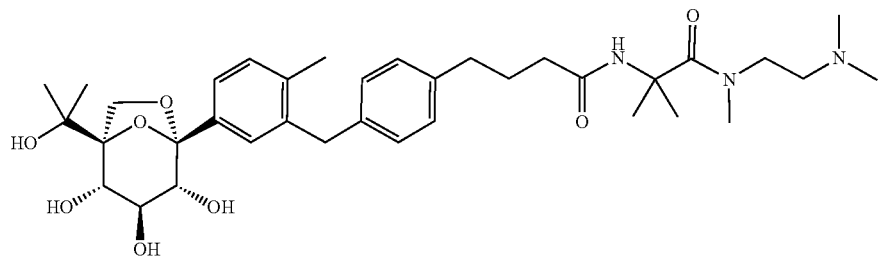 [SMILES: Cc1ccc([C@]23OC[C@](C(C)(C)O)(O2)[C@@H](O)[C@H](O)[C@H]3O)cc1Cc1ccc(CCCC(=O)NC(C)(C)C(=O)N(C)CCN(C)C)cc1]

To a solution of [(1S,2S,3S,4R,5S)-2,4-diacetoxy-5-[3-[[4-[4-[[2-[2-dimethylaminoethyl (methyl)amino]-1,1-dimethyl-2-oxo-ethyl]-amino]-4-oxo-butyl]phenyl]methyl]-4-methyl-phenyl]-1-(1-hydroxy-1-methyl-ethyl)-6,8-dioxabicyclo[3.2.1]octan-3-yl] acetate (0.13 g, 0.17 mmol) in anhydrous methanol (3 mL) was added solid sodium methoxide (46 mg, 0.85 mmol) at room temperature, and the mixture was stirred for 2 hours. The mixture was concentrated, and the residue was directly purified by TLC preparation [DCM/MeOH (v/v)=4/1] to give the title compound (42 mg, white solid) in 38% yield.

MS (ESI, pos. ion) m/z: 656.2 [M+H]$^+$.

$^1$H NMR (400 MHz, DMSO-d$_6$) δ (ppm): 8.65 (br.s, 1H), 8.02 (s, 1H), 7.31 (s, 1H), 7.24 (d, 1H), 7.12-7.04 (m, 5H), 5.49 (d, 1H), 5.00 (d, 1H), 4.85 (d, 1H), 4.20 (s, 1H), 4.04 (d, 1H), 3.90 (s, 2H), 3.81 (d, 1H), 3.73-3.69 (m, 1H), 3.44-3.35 (m, 5H), 3.10 (s, 3H), 3.06 (t, 2H), 2.80 (s, 6H), 2.16 (s, 3H), 2.12 (t, 2H), 1.72 (m, 2H), 1.28 (s, 6H), 1.21 (s, 3H), 1.16 (s, 3H).

Example 10 (2S)—N-(2-dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]azetidine-2-carboxamide

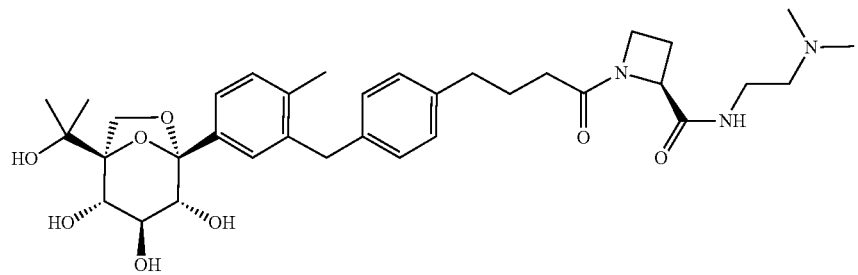 [SMILES: Cc1ccc([C@]23OC[C@](C(C)(C)O)(O2)[C@@H](O)[C@H](O)[C@H]3O)cc1Cc1ccc(CCCC(=O)N2CC[C@H]2C(=O)NCCN(C)C)cc1]

Step 1: tert-Butyl (2S)-2-(2-dimethylaminoethylcarbamoyl)azetidine-1-formate

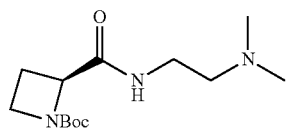 [SMILES: CN(C)CCNC(=O)[C@@H]1CCN1C(=O)OC(C)(C)C]

(2S)-1-tert-butoxycarbonylazetidine-2-carboxylic acid (3.0 g, 15 mmol) was dissolved in dichloromethane (50 mL) at room temperature, and the mixture was cooled to 0° C. HATU (7.1 g, 18 mmol) and N,N-diisopropylethylamine (7.9 mL, 45 mmol) were added, and the resulting mixture was stirred for 20 minutes. N,N-Dimethyl-1,2-ethylenediamine (2.0 g, 23 mmol) was added, and the resulting mixture was warmed to room temperature and stirred overnight. The resulting mixture was washed with water (30 mL), dried over anhydrous sodium sulfate, and filtered with suction. The filtrate was concentrated in vacuo and the residue was purified by silica gel column chromatography (DCM/anhydrous MeOH (v/v)=20/1) to give the title compound (2.6 g, yellow oil) in 64% yield.

MS (ESI, pos. ion) m/z: 272.0 [M+H]$^+$.

Step 2: (2S)—N-(2-Dimethylaminoethyl)azetidine-2-carboxamide dihydrochloride

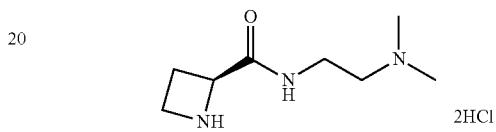

To a solution of tert-butyl (2S)-2-(2-dimethylaminoethylcarbamoyl)azetidine-1-formate (2.6 g, 9.6 mmol) in ethyl acetate (20 mL) was added HCl isopropanol solution (6 mL, 5M) at room temperature, and the mixture was stirred overnight, cooled to 0° C. and stirred for 30 minutes. The mixture was filtered by suction, and the filter cake was washed with ethyl acetate (10 mL) and dried in vacuo to obtain the title compound (1.7 g, yellow solid) in 72% yield.

Step 3: [(1S,2S,3S,4R,5S)-2,4-Diacetoxy-5-[3-[[4-[(2S)-2-(2-dimethyl aminoethyl carbamoyl)azetidine-1-yl]-4-oxo-butyl]phenyl]methyl]-4-methyl-phenyl]-1-(1-hydroxy-1-methyl-ethyl)-6,8-dioxabicyclo[3.2.1]octan-3-yl]acetate

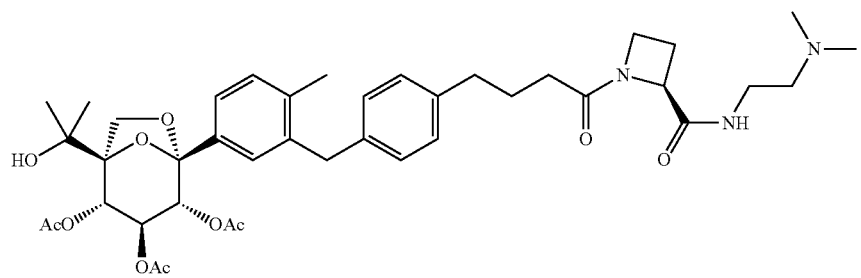

4-[4-[[2-Methyl-5-[(1S,2S,3S,4R,5S)-2,3,4-triacetoxy-1-(1-hydroxy-1-methyl-ethyl)-6,7,8-dioxabicyclo[3.2.1]octan-5-yl]phenyl]methyl]phenyl]butyric acid (0.20 g, 0.33 mmol) was dissolved in dichloromethane (5 mL) at room temperature. The mixture was cooled to 0° C., then HATU (0.16 g, 0.40 mmol) and N,N-diisopropylethylamine (0.30 mL, 1.7 mmol) were added. The resulting mixture was stirred for 20 minutes. (2S)—N-(2-Dimethylaminoethyl)azetidine-2-carboxamide dihydrochloride (0.16 g, 0.66 mmol) was added, and the resulting mixture was stirred overnight. The mixture was added with water (20 mL) and extracted with dichloromethane (40 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=8/1] to obtain the title compound (0.18 g, white solid) in 71% yield.

MS (ESI, pos. ion) m/z: 766.2[M+H]$^+$.

Step 4: (2S)—N-(2-Dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl] azetidine-2-carboxamide

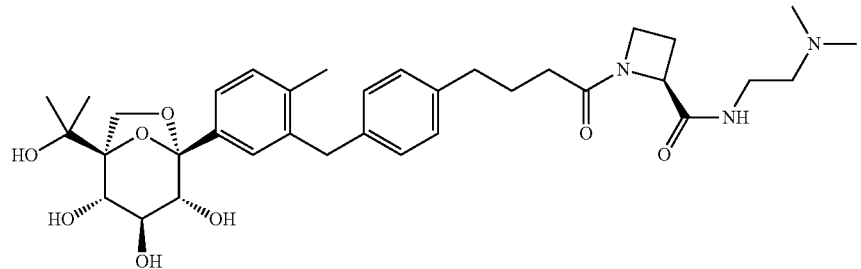 [SMILES: Cc1ccc([C@]23OC[C@](C(C)(C)O)(O2)[C@@H](O)[C@H](O)[C@H]3O)cc1Cc1ccc(CCCC(=O)N2CC[C@H]2C(=O)NCCN(C)C)cc1]

To a solution of [(1S,2S,3S,4R,5S)-2,4-diacetoxy-5-[3-[[4-[(2S)-2-(2-dimethylaminoethylcarbamoyl)azetidin-1-yl]-4-oxo-butyl]phenyl]methyl]-4-methyl-phenyl]-1-(1-hydroxy-1-methyl-ethyl)-6,8-dioxabicyclo[3.2.1]octan-3-yl] acetate (0.18 g, 0.23 mmol) in anhydrous methanol (5 mL) was added solid sodium methoxide (65 mg, 1.2 mmol) at room temperature, and the mixture was stirred for 2 hours. The mixture was concentrated, and the residue was directly purified by preparative TLC [DCM/MeOH (v/v)=4/1] to give the title compound (0.10 g, white solid) in 68% yield.

MS (ESI, pos. ion) m/z: 640.1 [M+H]$^+$.

$^1$H NMR (400 MHz, DMSO-d$_6$) δ (ppm): 9.21 (br.s, 1H), 8.18 (s, 1H), 7.29 (s, 1H), 7.22 (d, J=7.8 Hz, 1H), 7.13-7.02 (m, 5H), 5.55 (d, J=4.9 Hz, 1H), 5.07 (d, J=5.4 Hz, 1H), 4.93 (d, J=6.8 Hz, 1H), 4.24 (s, 1H), 4.20-4.15 (m, 1H), 4.03 (d, J=7.4 Hz, 1H), 3.92 (s, 2H), 3.82 (d, J=7.1 Hz, 1H), 3.75-3.68 (m, 1H), 3.54-3.37 (m, 4H), 3.06 (s, 2H), 2.76 (d, J=21.9 Hz, 6H), 2.60-2.52 (m, 2H), 2.39-2.26 (m, 2H), 2.18 (s, 3H), 2.07-1.95 (m, 2H), 1.88 (m, 1H), 1.77-1.72 (m, 2H), 1.21 (s, 3H), 1.15 (s, 3H).

Example 11 (2S)—N-(2-Dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl] pyrrolidine-2-carboxamide

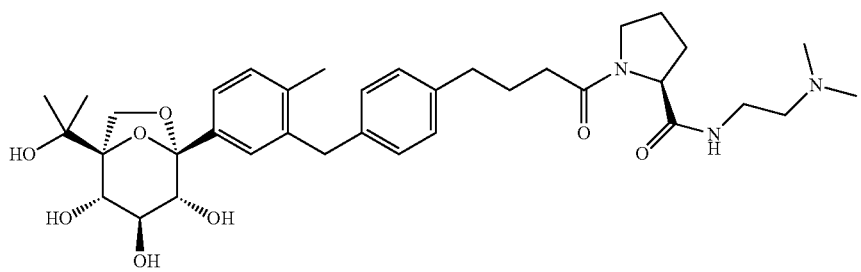 [SMILES: Cc1ccc([C@]23OC[C@](C(C)(C)O)(O2)[C@@H](O)[C@H](O)[C@H]3O)cc1Cc1ccc(CCCC(=O)N2CCC[C@H]2C(=O)NCCN(C)C)cc1]

119

Step 1: benzyl (2S)-2-(2-dimethylaminoethylcarbamoyl)pyrrolidine-1-formate

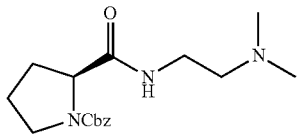 [SMILES: CN(C)CCNC(=O)[C@@H]1CCCN1C(=O)OCc1ccccc1]

(2S)-1-Benzyloxycarbonylpyrrolidine-2-carboxylic acid (4.0 g, 16 mmol) was dissolved in dichloromethane (50 mL) at room temperature, then the mixture was cooled to 0° C. HATU (7.2 g, 19 mmol) and N,N-diisopropylethylamine (8.4 mL, 48 mmol) were added, and the mixture was stirred for 20 minutes. N,N-Dimethyl-1,2-ethylenediamine (2.1 g, 24 mmol) was added, and the resulting mixture was warmed to room temperature and stirred overnight. The resulting mixture was washed with water (50 mL), dried over anhydrous sodium sulfate, and filtered with suction. The filtrate was concentrated in vacuo and the residue was purified by silica gel column chromatography (DCM/anhydrous MeOH (v/v)=30/1) to give the title compound (3.8 g, yellow oil) in 74% yield.

MS (ESI, pos. ion) m/z: 320.2 [M+H]$^+$.

Step 2: (2S)—N-(2-Dimethylaminoethyl)pyrrolidine-2-carboxamide

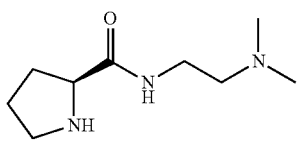

To a reaction flask were added benzyl (2S)-2-(2-dimethylaminoethylcarbamoyl) pyrrolidine-1-formate (3.8 g, 12 mmol), 10% palladium/carbon (0.50 g, 0.47 mmol), tetrahydrofuran (10 mL) and methanol (40 mL) at room temperature, and the mixture was stirred for 2 hours under a hydrogen atmosphere. The mixture was filtered by suction and concentrated to obtain the title compound (2.2 g, yellow oil) in 100% yield.

120

Step 3: (2S)—N-(2-Dimethylaminoethyl)pyrrolidine-2-carboxamide dihydrochloride

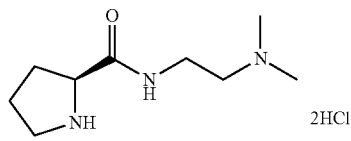

To a solution of (2S)—N-(2-dimethylaminoethyl)pyrrolidine-2-carboxamide (2.2 g, 12 mmol) in ethyl acetate (20 mL) was added HCl isopropanol solution (6 mL, 5M) at room temperature, and the mixture was stirred for 10 minutes, cooled to 0° C. and stirred for 30 minutes. The mixture was filtered by suction, and the filter cake was washed with ethyl acetate (20 mL) and dried in vacuo to obtain the title compound (2.8 g, yellow solid) in 92% yield.

Step 4: [(1S,2S,3S,4R,5S)-2,4-Diacetoxy-5-[3-[[4-[(2S)-2-(2-dimethylaminoethylcarbamoyl)pyrrolidin-1-yl]-4-oxo-butyl]phenyl]methyl]-4-methyl-phenyl]-1-(1-hydroxy-1-methyl-ethyl)-6,8-dioxabicyclo[3.2.1]octan-3-yl]acetate

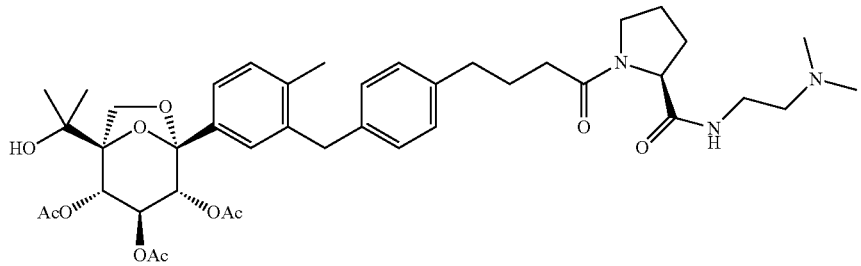 [SMILES: CC(=O)O[C@@H]1[C@@H](OC(C)=O)[C@@]2(c3ccc(C)c(Cc4ccc(CCCC(=O)N5CCC[C@H]5C(=O)NCCN(C)C)cc4)c3)OC[C@](C(C)(C)O)(O2)[C@H]1OC(C)=O]

4-[4-[[2-Methyl-5-[(1S,2S,3S,4R,5S)-2,3,4-triacetoxy-1-(1-hydroxy-1-methyl-ethyl)-6,7,8-dioxabicyclo[3.2.1]octan-5-yl]phenyl]methyl]phenyl]butyric acid (0.20 g, 0.33 mmol) was dissolved in dichloromethane (5 mL) at room temperature. The mixture was cooled to 0° C., then HATU (0.16 g, 0.40 mmol) and N,N-diisopropylethylamine (0.30 mL, 1.7 mmol) were added. The resulting mixture was stirred for 20 minutes. (2S)—N-(2-Dimethylaminoethyl)pyrrolidine-2-carboxamide dihydrochloride (0.17 g, 0.66 mmol) was added, and the mixture was stirred overnight. The mixture was added with water (20 mL) and extracted with dichloromethane (40 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=8/1] to obtain the title compound (0.20 g, white solid) in 79% yield.

MS (ESI, pos. ion) m/z: 780.2[M+H]$^+$.

Step 5: (2S)—N-(2-Dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]pyrrolidine-2-carboxamide

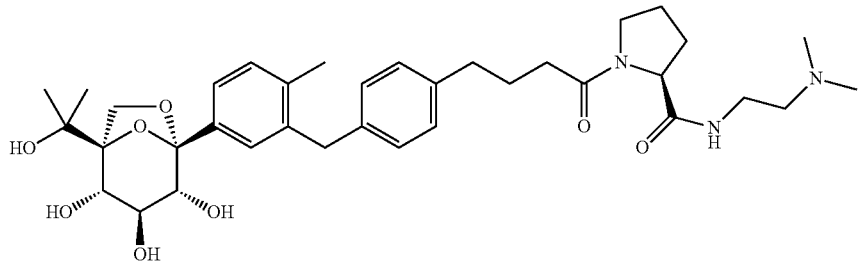 [SMILES: Cc1ccc([C@]23OC[C@](C(C)(C)O)(O2)[C@@H](O)[C@H](O)[C@H]3O)cc1Cc1ccc(CCCC(=O)N2CCC[C@H]2C(=O)NCCN(C)C)cc1]

To a solution of [(1S,2S,3S,4R,5S)-2,4-diacetoxy-5-[3-[[4-[(2S)-2-(2-dimethylaminoethylcarbamoyl)pyrrolidin-1-yl]-4-oxo-butyl]phenyl]methyl]-4-methyl-phenyl]-1-(1-hydroxy-1-methyl-ethyl)-6,8-dioxabicyclo[3.2.1]octan-3-yl] acetate (0.20 g, 0.26 mmol) in anhydrous methanol (5 mL) was added solid sodium methoxide (70 mg, 1.3 mmol) at room temperature, and the mixture was stirred for 2 hours. The mixture was concentrated, and the residue was directly purified by TLC preparation [DCM/MeOH (v/v)=4/1] to give the title compound (0.12 g, white solid) in 72% yield.

MS (ESI, pos. ion) m/z: 654.3[M+H]+.

$^1$H NMR (400 MHz, DMSO-$d_6$) δ (ppm): 9.80 (br.s, 1H), 8.17 (s, 1H), 7.28 (s, 1H), 7.22 (d, J=7.8 Hz, 1H), 7.12-7.02 (m, 5H), 5.55 (d, J=4.9 Hz, 1H), 5.06 (d, J=5.4 Hz, 1H), 4.92 (d, J=6.8 Hz, 1H), 4.22 (s, 1H), 4.20-4.14 (m, 1H), 4.03 (d, J=7.4 Hz, 1H), 3.91 (s, 2H), 3.81 (d, J=7.1 Hz, 1H), 3.74-3.68 (m, 1H), 3.54-3.37 (m, 4H), 3.05 (s, 2H), 2.71 (d, J=21.9 Hz, 6H), 2.57-2.52 (m, 2H), 2.35-2.24 (m, 2H), 2.17 (s, 3H), 2.07-1.95 (m, 2H), 1.90-1.81 (m, 2H), 1.80-1.71 (m, 3H), 1.21 (s, 3H), 1.15 (s, 3H).

Example 12 (2R)—N-(2-Dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]pyrrolidine-2-carboxamide

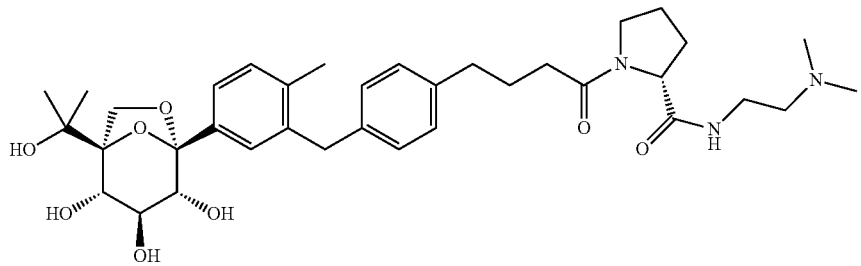 [SMILES: Cc1ccc([C@]23OC[C@](C(C)(C)O)(O2)[C@@H](O)[C@H](O)[C@H]3O)cc1Cc1ccc(CCCC(=O)N2CCC[C@@H]2C(=O)NCCN(C)C)cc1]

(2R)-1-Benzyloxycarbonylpyrrolidine-2-carboxylic acid instead of (2S)-1-benzyloxycarbonylpyrrolidine-2-carboxylic acid was used as the starting material, referring to the method described in Example 11, the title compound was obtained as white solid.

MS (ESI, pos. ion) m/z: 654.3[M+H]+.

$^1$H NMR (400 MHz, DMSO-$d_6$) δ (ppm): 9.96 (br.s, 1H), 8.15 (s, 1H), 7.29 (s, 1H), 7.22 (d, J=7.2 Hz, 1H), 7.17-6.96 (m, 5H), 5.55 (d, J=4.9 Hz, 1H), 5.06 (d, J=4.8 Hz, 1H), 4.91 (d, J=6.3 Hz, 1H), 4.22 (s, 1H), 4.18 (d, J=4.7 Hz, 1H), 4.03 (d, J=7.9 Hz, 1H), 3.91 (s, 2H), 3.81 (d, J=6.6 Hz, 1H), 3.72 (m, 1H), 3.56-3.37 (m, 4H), 3.01 (s, 2H), 2.66 (d, J=31.6 Hz, 6H), 2.58-2.52 (m, 2H), 2.32-2.23 (m, 2H), 2.17 (s, 3H), 2.06-1.93 (s, 2H), 1.88-1.80 (m, 2H), 1.80-1.68 (m, 3H), 1.21 (s, 3H), 1.15 (s, 3H).

Example 13 (2S,4S)—N-(2-dimethylaminoethyl)-4-hydroxy-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]pyrrolidine-2-carboxamide

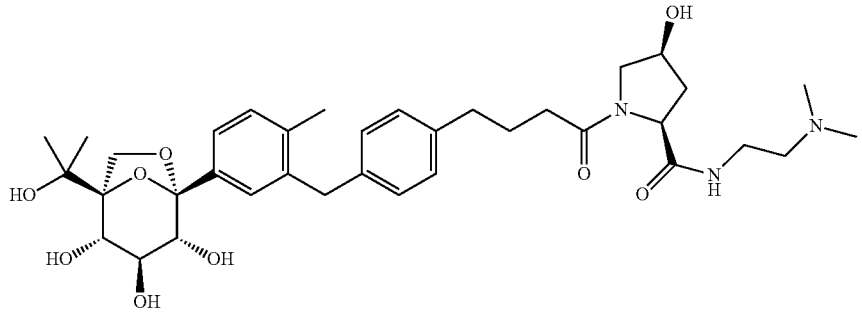 [SMILES: Cc1ccc([C@]23OC[C@](C(C)(C)O)(O2)[C@@H](O)[C@H](O)[C@H]3O)cc1Cc1ccc(CCCC(=O)N2C[C@@H](O)C[C@H]2C(=O)NCCN(C)C)cc1]

Step 1: benzyl (2S,4S)-2-(2-dimethylaminoethylcarbamoyl)-4-hydroxy-pyrrolidine-1-formate

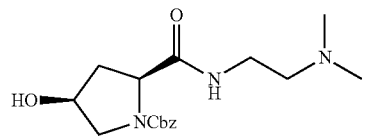 [SMILES: CN(C)CCNC(=O)[C@@H]1C[C@H](O)CN1C(=O)OCc1ccccc1]

(2S,4R)-1-benzyloxycarbonyl-4-hydroxy-pyrrolidine-2-carboxylic acid (5.0 g, 19 mmol) was dissolved in dichloromethane (80 mL) at room temperature, then the mixture was cooled to 0° C. HATU (8.7 g, 23 mmol), N,N-diisopropylethylamine (10 mL, 57 mmol) and N,N-dimethyl-1,2-ethylenediamine (2.4 g, 27 mmol) were added in turn, and the resulting mixture was warmed to room temperature and stirred overnight. The resulting mixture was washed with water (50 mL), dried over anhydrous sodium sulfate, and filtered with suction. The filtrate was concentrated in vacuo and the residue was purified by silica gel column chromatography (DCM/anhydrous MeOH (v/v)=15/1) to give the title compound (2.2 g, yellow oil) in 35% yield.
MS (ESI, pos. ion) m/z: 336.0 [M+H]+.

Step 2: (2S,4S)—N-(2-Dimethylaminoethyl)-4-hydroxy-pyrrolidine-2-carboxamide

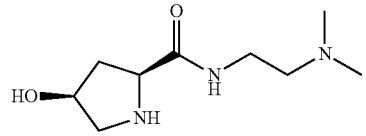

To the reaction flask were added benzyl (2S,4S)-2-(2-dimethylaminoethylcarbamoyl)-4-hydroxy-pyrrolidine-1-formate (2.2 g, 6.6 mmol), 10% palladium/carbon (0.50 g, 0.47 mmol), tetrahydrofuran (10 mL) and methanol (40 mL) at room temperature, and the mixture was stirred overnight under a hydrogen atmosphere. The mixture was filtered by suction and concentrated to obtain the title compound (1.3 g, yellow oil) in 100% yield.

Step 3: (2S,4S)—N-(2-Dimethylaminoethyl)-4-hydroxy-pyrrolidine-2-carboxamide dihydrochloride

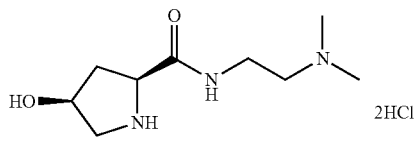

To a solution of (2S,4S)—N-(2-dimethyl aminoethyl)-4-hydroxy-pyrrolidine-2-carboxamide (1.3 g, 6.5 mmol) in ethyl acetate (15 mL) was added HCl isopropanol solution (2 mL, 5M) at room temperature, and the mixture was stirred for 30 minutes. The mixture was filtered by suction, and the filter cake was washed with ethyl acetate (5 mL) and dried in vacuo to obtain the title compound (0.95 g, white solid) in 53% yield.
MS (ESI, pos. ion) m/z: 202.0 [M+H]+.

Step 4: [(1S,2S,3S,4R,5S)-2,4-Diacetoxy-5-[3-[[4-[4-[(2S,4S)-2-(2-dimethylaminoethylcarbamoyl)-4-hydroxy-pyrrolidin-1-yl]-4-oxo-butyl]phenyl]methyl]-4-methyl-phenyl]-1-(1-hydroxy-1-methyl-ethyl)-6,8-dioxabicyclo[3.2.1]octan-3-yl]] acetate

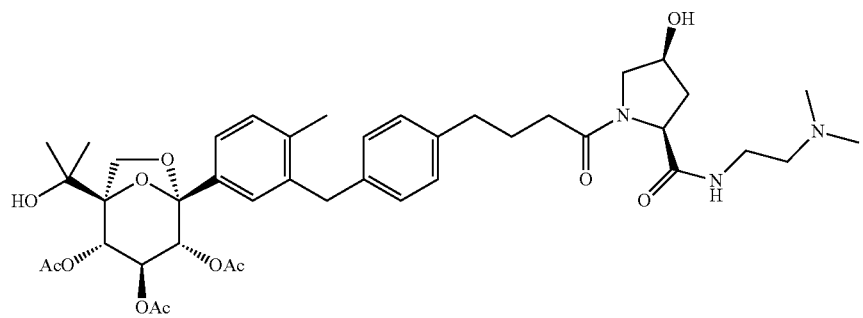 [SMILES: CC(=O)O[C@@H]1[C@@H](OC(C)=O)[C@@]2(c3ccc(C)c(Cc4ccc(CCCC(=O)N5C[C@@H](O)C[C@H]5C(=O)NCCN(C)C)cc4)c3)OC[C@](C(C)(C)O)(O2)[C@H]1OC(C)=O]

4-[4-[[2-methyl-5-[(1S,2S,3S,4R,5S)-2,3,4-triacetoxy-1-(1-hydroxy-1-methyl-ethyl)-6,7,8-dioxabicyclo[3.2.1]octan-5-yl]phenyl]methyl]phenyl]butyric acid (0.30 g, 0.49 mmol) was dissolved in dichloromethane (10 mL) at room temperature, then the mixture was cooled to 0° C. HATU (0.28 g, 0.74 mmol), N,N-diisopropylethylamine (0.50 mL, 2.9 mmol) and (2S,4S)—N-(2-dimethylaminoethyl)-4-hydroxy-pyrrolidine-2-carboxamide dihydrochloride (0.20 g, 0.74 mmol) were added in turn, and the resulting mixture was stirred overnight. The mixture was added with water (20 mL) and extracted with dichloromethane (20 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=7/1] to obtain the title compound (0.25 g, light yellow solid) in 64% yield.

MS (ESI, pos. ion) m/z: 796.2[M+H]⁺.

Step 5: (2S,4S)—N-(2-Dimethylaminoethyl)-4-hydroxy-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]pyrrolidine-2-carboxamide

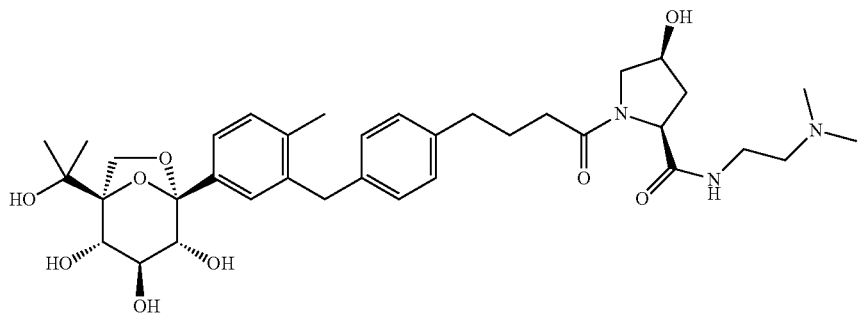 [SMILES: Cc1ccc([C@]23OC[C@](C(C)(C)O)(O2)[C@@H](O)[C@H](O)[C@H]3O)cc1Cc1ccc(CCCC(=O)N2C[C@@H](O)C[C@H]2C(=O)NCCN(C)C)cc1]

To a solution of [(1S,2S,3S,4R,5S)-2,4-diacetoxy-5-[3-[[4-[4-[(2S,4S)-2-(2-dimethylaminoethylcarbamoyl)-4-hydroxy-pyrrolidin-1-yl]-4-oxo-butyl]phenyl]methyl]-4-methyl-phenyl]-1-(1-hydroxy-1-methyl-ethyl)-6,8-dioxabicyclo[3.2.1]octan-3-yl]] acetate (0.25 g, 0.31 mmol) in anhydrous methanol (8 mL) was added solid sodium methoxide (70 mg, 1.3 mmol) at room temperature. The mixture was stirred for 2 hours. The mixture was concentrated, and the residue was directly purified by preparative TLC [DCM/MeOH (v/v)=4/1] to give the title compound (0.12 g, white solid) in 58% yield.

MS (ESI, pos. ion) m/z: 670.2[M+H]⁺.

¹H NMR (400 MHz, DMSO-d₆) δ (ppm): 9.37 (br.s, 1H), 8.16 (s, 1H), 7.27 (s, 1H), 7.22 (d, J=7.8 Hz, 1H), 7.11-7.02 (m, 5H), 5.55 (d, J=4.9 Hz, 1H), 5.05 (d, J=5.4 Hz, 1H), 4.92 (d, J=6.8 Hz, 1H), 4.35 (d, J=5.9 Hz, 1H), 4.21 (s, 1H), 4.20-4.15 (m, 1H), 4.02 (d, J=7.4 Hz, 1H), 3.90 (s, 2H), 3.80 (d, J=7.1 Hz, 1H), 3.76 (m, 1H), 3.73-3.68 (m, 1H), 3.54-3.38 (m, 4H), 3.18 (m, 1H), 3.04 (s, 2H), 2.70 (d, J=21.9 Hz, 6H), 2.55-2.51 (m, 2H), 2.38-2.25 (m, 3H), 2.17 (s, 3H), 2.10-1.98 (m, 2H), 1.71 (m, 1H), 1.21 (s, 3H), 1.15 (s, 3H).

Example 14 (2S,4R)—N-(2-Dimethylaminoethyl)-4-fluoro-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]pyrrolidine-2-carboxamide

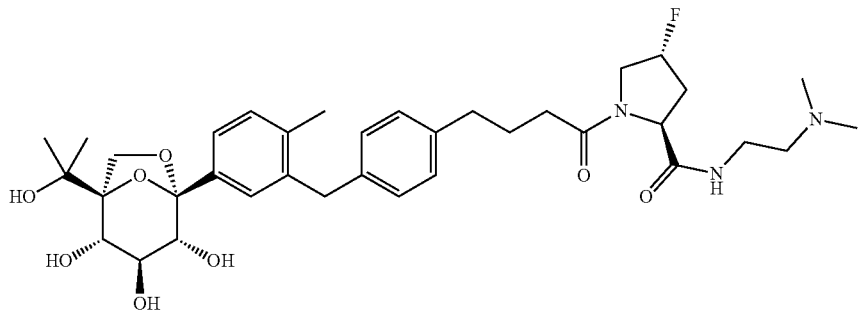 [SMILES: Cc1ccc([C@]23OC[C@](C(C)(C)O)(O2)[C@@H](O)[C@H](O)[C@H]3O)cc1Cc1ccc(CCCC(=O)N2C[C@H](F)C[C@H]2C(=O)NCCN(C)C)cc1]

Step 1: (2S,4R)-1-Benzyloxycarbonyl-4-fluoro-pyrrolidine-2-carboxylic acid

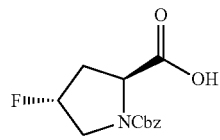 [SMILES: O=C(O)[C@@H]1C[C@@H](F)CN1C(=O)OCc1ccccc1]

(2S,4R)-4-Fluoro-pyrrolidine-2-carboxylic acid (3.0 g, 18 mmol) was dissolved in 1,4-dioxane (20 mL) at room temperature, then water (60 mL) and sodium carbonate (7.5 g, 71 mmol) were added in turn. The mixture was cooled to 0° C., and CbzCl (3.0 mL, 21 mmol) was added dropwise. The resulting mixture was stirred at room temperature overnight. The reaction was stopped, and the reaction solution was washed with n-hexane (100 mL). The aqueous phases were adjusted to pH=2 with 1 M dilute hydrochloric acid, extracted with ethyl acetate (100 mL), washed with saturated sodium chloride solution (100 mL), dried over anhydrous sodium sulfate, and concentrated in vacuo to obtain the title compound (4.7 g, colorless oil) in 99% yield.

Step 2: Benzyl (2S,4R)-2-(2-dimethylaminoethylcarbamoyl)-4-fluoro-pyrrolidine-1-formate

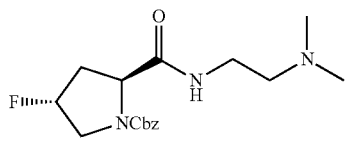 [SMILES: CN(C)CCNC(=O)[C@@H]1C[C@@H](F)CN1C(=O)OCc1ccccc1]

(2S,4R)-1-Benzyloxycarbonyl-4-fluoro-pyrrolidine-2-carboxylic acid (4.7 g, 18 mmol) was dissolved in dichloromethane (50 mL) at room temperature, then the mixture was cooled to 0° C. HATU (8.4 g, 22 mmol) and N,N-diisopropylethylamine (9.5 mL, 54 mmol) were added, and the resulting mixture was stirred for 20 minutes. N,N-Dimethyl-1,2-ethylenediamine (2.4 g, 27 mmol) was added, and the resulting mixture was warmed to room temperature and stirred overnight. The resulting mixture was washed with water (50 mL), dried over anhydrous sodium sulfate, and filtered with suction. The filtrate was concentrated in vacuo and the residue was purified by silica gel column chromatography (DCM/anhydrous MeOH (v/v)=20/1) to give the title compound (3.0 g, yellow oil) in 51% yield.
MS (ESI, pos. ion) m/z: 338.0 [M+H]⁺.

Step 3: (2S,4R)—N-(2-Dimethylaminoethyl)-4-fluoro-pyrrolidine-2-carboxamide

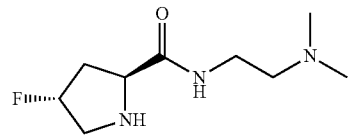

To a reaction flask were added benzyl (2S,4R)-2-(2-dimethylaminoethylcarbamoyl)-4-fluoro-pyrrolidine-1-formate (3.0 g, 8.9 mmol), 10% palladium/carbon (0.50 g, 0.47 mmol), tetrahydrofuran (10 mL) and methanol (40 mL) at room temperature. The mixture was stirred overnight under a hydrogen atmosphere. The mixture was filtered by suction and concentrated to obtain the title compound (1.8 g, yellow oil) in 100% yield.

Step 4: (2S,4R)—N-(2-Dimethyl aminoethyl)-4-fluoro-pyrrolidine-2-carboxamide dihydrochloride

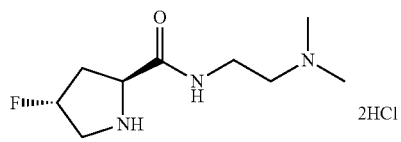

To a solution of (2S,4R)—N-(2-dimethylaminoethyl)-4-fluoro-pyrrolidine-2-carboxamide (1.8 g, 8.9 mmol) in ethyl acetate (20 mL) was added HCl isopropanol solution (3 mL, 5M) at room temperature. The mixture was stirred for 30 minutes. The mixture was filtered by suction, and the filter cake was washed with ethyl acetate (10 mL) and dried in vacuo to obtain the title compound (1.4 g, white solid) in 57% yield.
MS (ESI, pos. ion) m/z: 204.2 [M+H]⁺.

Step 5 [(1S,2S,3S,4R,5S)-2,4-Diacetoxy-5-[3-[[4-[4-[(2S,4R)-2-(2-dimethylaminoethylcarbamoyl)-4-fluoro-pyrrolidin-1-yl]-4-oxo-butyl]phenyl]methyl]-4-methyl-phenyl]-1-(1-hydroxy-1-methyl-ethyl)-6,8-dioxabicyclo[3.2.1]octan-3-yl]] acetate

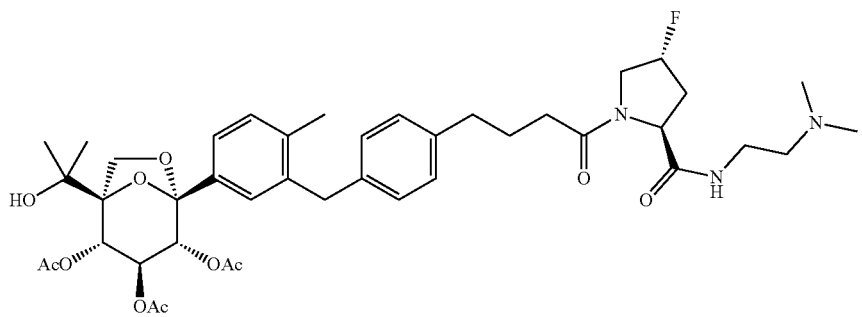 [SMILES: CC(=O)O[C@@H]1[C@@H](OC(C)=O)[C@@]2(c3ccc(C)c(Cc4ccc(CCCC(=O)N5C[C@H](F)C[C@H]5C(=O)NCCN(C)C)cc4)c3)OC[C@](C(C)(C)O)(O2)[C@H]1OC(C)=O]

4-[4-[[2-methyl-5-[(1S,2S,3S,4R,5S)-2,3,4-triacetoxy-1-(1-hydroxy-1-methyl-ethyl)-6,7,8-dioxabicyclo[3.2.1]octan-5-yl]phenyl]methyl]phenyl]butyric acid (0.33 g, 0.54 mmol) was dissolved in dichloromethane (10 mL) at room temperature, then the mixture was cooled to 0° C. HATU (0.26 g, 0.65 mmol) and N,N-diisopropylethylamine (0.50 mL, 2.9 mmol) were added, and the mixture was stirred for 20 minutes. (2S,4R)—N-(2-Dimethylaminoethyl)-4-fluoro-pyrrolidine-2-carboxamide dihydrochloride (0.30 g, 1.1 mmol) was added and the mixture was stirred overnight. The mixture was added with water (20 mL) and extracted with dichloromethane (20 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=8/1] to obtain the title compound (0.32 g, light yellow solid) in 75% yield.

MS (ESI, pos. ion) m/z: 798.2[M+H]$^+$.

Step 6: (2S,4R)—N-(2-dimethylaminoethyl)-4-fluoro-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]pyrrolidine-2-carboxamide

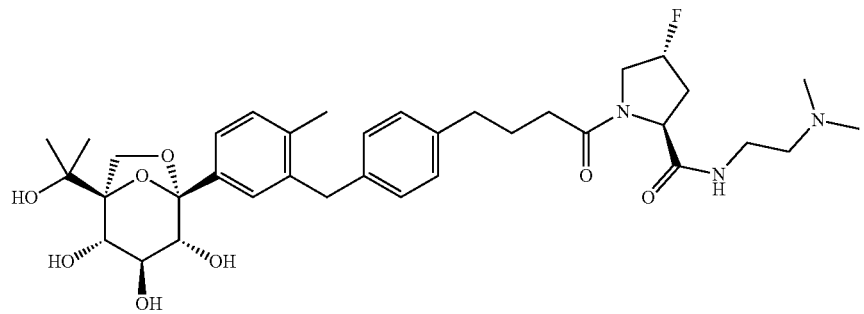 [SMILES: Cc1ccc([C@]23OC[C@](C(C)(C)O)(O2)[C@@H](O)[C@H](O)[C@H]3O)cc1Cc1ccc(CCCC(=O)N2C[C@H](F)C[C@H]2C(=O)NCCN(C)C)cc1]

To a solution of [(1S,2S,3S,4R,5S)-2,4-diacetoxy-5-[3-[[4-[4-[(2S,4R)-2-(2-dimethylaminoethylcarbamoyl)-4-fluoro-pyrrolidin-1-yl]-4-oxo-butyl]phenyl]methyl]-4-methyl-phenyl]-1-(1-hydroxy-1-methyl-ethyl)-6,8-dioxabicyclo[3.2.1]octan-3-yl]] acetate (0.32 g, 0.40 mmol) in anhydrous methanol (8 mL) was added solid sodium methoxide (0.11 g, 2.0 mmol) at room temperature. The mixture was stirred for 2 hours. The mixture was concentrated, and the residue was directly purified by preparative TLC [DCM/MeOH (v/v)=4/1] to give the title compound (0.17 g, white solid) in 63% yield.

MS (ESI, pos. ion) m/z: 672.3[M+H]$^+$.

$^1$H NMR (400 MHz, DMSO-d$_6$) δ (ppm): 9.45 (br.s, 1H), 8.37 (t, J=5.5 Hz, 1H), 7.29 (s, 1H), 7.23 (d, J=7.8 Hz, 1H), 7.12-7.00 (m, 5H), 5.44 (s, 0.5H), 5.30 (s, 0.5H), 5.56 (d, J=4.9 Hz, 1H), 5.08 (d, J=5.4 Hz, 1H), 4.93 (d, J=6.8 Hz, 1H), 4.24 (s, 1H), 4.21-4.16 (m, 1H), 4.04 (d, J=7.4 Hz, 1H), 3.92 (s, 2H), 3.83 (d, J=7.1 Hz, 1H), 3.76-3.69 (m, 1H), 3.56-3.38 (m, 4H), 3.07 (s, 2H), 2.77 (d, J=21.9 Hz, 6H), 2.36-2.18 (m, 3H), 2.35-2.24 (m, 2H), 2.17 (s, 3H), 2.14-1.94 (m, 2H), 1.76 (m, 2H), 1.21 (s, 3H), 1.15 (s, 3H).

Example 15 (2S)—N-(2-dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]piperidine-2-carboxamide

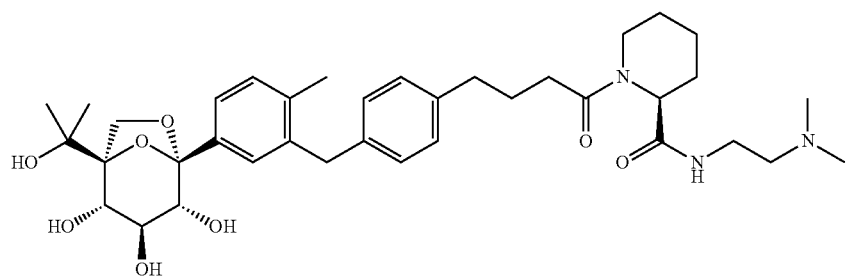 [SMILES: Cc1ccc([C@]23OC[C@](C(C)(C)O)(O2)[C@@H](O)[C@H](O)[C@H]3O)cc1Cc1ccc(CCCC(=O)N2CCCC[C@H]2C(=O)NCCN(C)C)cc1]

131

Step 1: tert-Butyl (2S)-2-(2-Dimethylaminoethylcarbamoyl)piperidine-1-formate

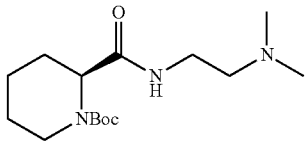 [SMILES: CN(C)CCNC(=O)[C@@H]1CCCCN1C(=O)OC(C)(C)C]

(2S)-1-tert-Butoxycarbonylpiperidine-2-carboxylic acid (3.7 g, 16 mmol) was dissolved in dichloromethane (50 mL) at room temperature, then the mixture was cooled to 0° C. HATU (7.2 g, 19 mmol) and N,N-diisopropylethylamine (8.4 mL, 48 mmol) was added and the resulting mixture was stirred for 20 minutes. N,N-Dimethyl-1,2-ethylenediamine (2.1 g, 24 mmol) was added, and the resulting mixture was warmed to room temperature and stirred overnight. The resulting mixture was washed with water (30 mL), dried over anhydrous sodium sulfate, and filtered with suction. The filtrate was concentrated in vacuo and the residue was purified by silica gel column chromatography (DCM/anhydrous MeOH (v/v)=20/1) to give the title compound (2.7 g, yellow oil) in 56% yield.

MS (ESI, pos. ion) m/z: 300.1 [M+H]$^+$.

132

Step 2: (2S)—N-(2-Dimethylaminoethyl)piperidine-2-carboxamide dihydrochloride

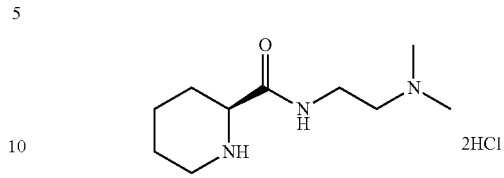

To a solution of tert-butyl (2S)-2-(2-dimethylaminoethylcarbamoyl)piperidine-1-formate (2.7 g, 9.0 mmol) in ethyl acetate (20 mL) was added HCl isopropanol solution (6 mL, 5M) at room temperature. The mixture was stirred overnight, cooled to 0° C. and stirred for 30 minutes. The mixture was filtered by suction, and the filter cake was washed with ethyl acetate (10 mL) and dried in vacuo to obtain the title compound (1.9 g, yellow solid) in 78% yield.

Step 3: [(1S,2S,3S,4R,5S)-2,4-Diacetoxy-5-[3-[[4-[(2S)-2-(2-dimethylaminoethylcarbamoyl)piperidin-1-yl]-4-oxo-butyl]phenyl]methyl]-4-methyl-phenyl]-1-(1-hydroxy-1-methyl-ethyl)-6,8-dioxabicyclo[3.2.1]octan-3-yl]acetate

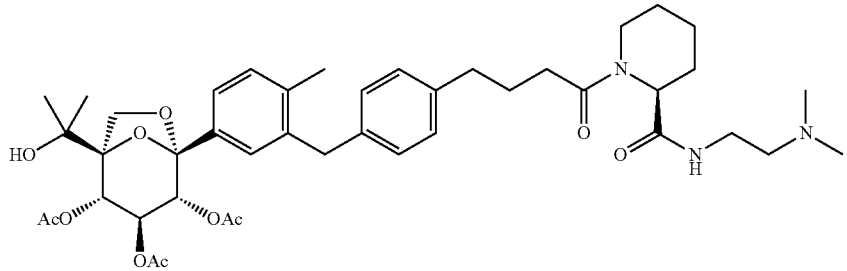 [SMILES: CC(=O)O[C@@H]1[C@@H](OC(C)=O)[C@@]2(c3ccc(C)c(Cc4ccc(CCCC(=O)N5CCCC[C@H]5C(=O)NCCN(C)C)cc4)c3)OC[C@](C(C)(C)O)(O2)[C@H]1OC(C)=O]

4-[4-[[2-methyl-5-[(1S,2S,3S,4R,5S)-2,3,4-triacetoxy-1-(1-hydroxy-1-methyl-ethyl)-6,7,8-dioxabicyclo[3.2.1]octan-5-yl]phenyl]methyl]phenyl]butyric acid (0.20 g, 0.33 mmol) was dissolved in dichloromethane (5 mL) at room temperature, then the mixture was cooled to 0° C. HATU (0.16 g, 0.40 mmol) and N,N-diisopropylethylamine (0.30 mL, 1.7 mmol) were added, and the mixture was stirred for 20 minutes. (2S)—N-(2-dimethylaminoethyl)piperidine-2-carboxamide dihydrochloride (0.18 g, 0.66 mmol) was added, and the mixture was stirred overnight. The mixture was added with water (20 mL) and extracted with dichloromethane (40 mL×3). The combined organic phases were washed with saturated brine (20 mL), dried over anhydrous sodium sulfate, filtered by suction, concentrated, and the residue was purified by silica gel column chromatography [dichloromethane/anhydrous methanol (v/v)=8/1] to obtain the title compound (0.14 g, white solid) in 53% yield.

MS (ESI, pos. ion) m/z: 794.3[M+H]$^+$.

Step 4: (2S)—N-(2-Dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octan-5-yl]phenyl]methyl]phenyl]butyryl]piperidine-2-carboxamide

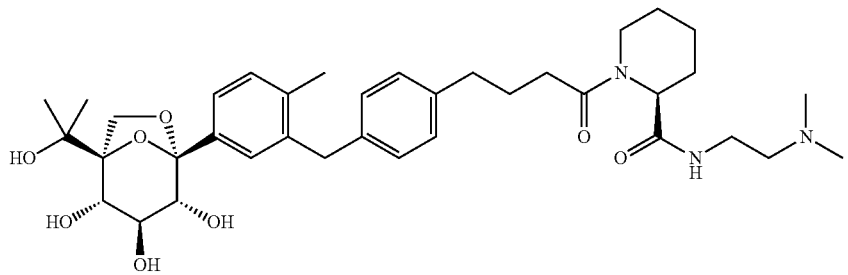 [SMILES: Cc1ccc([C@]23OC[C@](C(C)(C)O)(O2)[C@@H](O)[C@H](O)[C@H]3O)cc1Cc1ccc(CCCC(=O)N2CCCC[C@H]2C(=O)NCCN(C)C)cc1]

To a solution of [(1S,2S,3S,4R,5S)-2,4-diacetoxy-5-[3-[[4-[(2S)-2-(2-dimethylaminoethylcarbamoyl)piperidin-1-yl]-4-oxo-butyl]phenyl]methyl]-4-methyl-phenyl]-1-(1-hydroxy-1-methyl-ethyl)-6,8-dioxabicyclo[3.2.1]octan-3-yl] acetate (0.14 g, 0.18 mmol) in anhydrous methanol (5 mL) was added solid sodium methoxide (49 mg, 0.9 mmol) at room temperature. Then mixture was stirred for 2 hours. The mixture was concentrated, and the residue was directly purified by TLC preparation [DCM/MeOH (v/v)=4/1] to give the title compound (76 mg, white solid) in 63% yield.

MS (ESI, pos. ion) m/z: 668.2 [M+H]$^+$.

$^1$H NMR (400 MHz, DMSO-$d_6$) δ (ppm): 9.65 (br.s, 1H), 8.17 (s, 1H), 7.28 (s, 1H), 7.20 (d, J=7.8 Hz, 1H), 7.12-7.01 (m, 5H), 5.53 (d, J=4.9 Hz, 1H), 5.06 (d, J=5.4 Hz, 1H), 4.91 (d, J=6.8 Hz, 1H), 4.23 (s, 1H), 4.18-4.14 (m, 1H), 4.05 (d, J=7.3 Hz, 1H), 3.91 (s, 2H), 3.83 (d, J=7.0 Hz, 1H), 3.76-3.67 (m, 1H), 3.55-3.39 (m, 4H), 3.07 (s, 2H), 2.77 (d, J=21.7 Hz, 6H), 2.63-2.55 (m, 2H), 2.40-2.28 (m, 2H), 2.17 (s, 3H), 2.03-1.92 (m, 3H), 1.87-1.73 (m, 6H), 1.21 (s, 3H), 1.15 (s, 3H).

Test Example

1. Determination of SGLT1 Inhibitory Activity

Testing Purposes:

The following methods can be used to determine the inhibitory activity of the compounds described in the invention for SGLT1.

Test Materials:

$^{14}$C-AMG solution was purchased from PerkinElmer, Cat. No. NEZ080001MC;

α-methylglucoside was purchased from Sigma, Cat. No. M9376-100G;

N-methyl-D-glucosamine was purchased from Sigma, Cat. No. M2004-100G;

phloridzin was purchased from Sigma, Cat. No. P3449-1G;

96-well plate was purchased from Corning, Cat. No. 3903.

Test Method:

Mock-transfected FIP-in CHO cells (3×10$^4$ cells) and CHO cells expressing human SGLT1 gene were seeded into 96-well plates respectively. The cells were incubated for 12 hours. Each well of the 96-well plates was washed with 150 μL of sodium-free buffer once. To each well was added 50 μL of sodium-containing buffer containing test compounds having different concentrations and 0.5 μm [$^{14}$C]-AMG And the mixture in the well was incubated at 37° C. for 1 hour.

To each well was added 150 μL of precooled sodium-free buffer to terminate the reaction. The cell pellet was washed with sodium free buffer three times and the residual liquid in well was removed. To each well was added 20 μL of precooled 100 mM NaOH, and the 96-well plates were vibrated at 900 rpm for 5 minutes. Scintillation fluid (80 μL) was added to each well which was then vibrated at 600 rpm for 5 minutes. The amount of 14C-AMG was quantitatively detected using liquid scintillation. The results were shown in table 1:

TABLE 1

SGLT1 inhibitory activity of the compounds provided by the examples of the present invention

| Example No. | IC$_{50}$(SGLT1)/nM |
|---|---|
| Example 1 | 1.73 |
| Example 7 | 1.16 |
| Example 11 | 5.75 |

The test results show that the compounds of the present invention have a significant inhibitory effect on SGLT1.

2. Oral Glucose Tolerance Test and Glycosuria Excretion Test

Test Purpose:

The following methods were used to evaluate the effects of the compounds of the invention in improving oral glucose tolerance and promoting glycosuria excretion.

Test Materials:

The glucose was purchased from Cheng Du Kelong Chemical Reagent Company.

Urine sugar test was determined on Roche biochemical analyzer.

Blood glucose test was determined on Roche Accu-Chek Performa Blood Glucose Meter.

Test Method 1:

The weight and the blood glucose levels of C57BL/6 mice were measured after an overnight 15-hour fast. The mice were grouped by their weights and fasting plasma glucose levels. Each test group was administered with the corresponding test compound at a dose of 1 mg/kg once by gavage, and the blank control group was administered solvent. After 15 minutes, the blood glucose level (i.e., zero point blood glucose) of each group was measured, and then each group was administered glucose (2.5 g/kg) once immediately by gavage. The blood was drawn from the caudal vein of the C57BL/6 mice at 15, 30, 60 and 120 minutes after glucose administration and the blood glucose levels were measured continuously on blood-glucose meter. The rate of decrease of the area under the blood glucose curve (AUC$_{Glu\ 0\text{-}120}$ min) within 120 minutes after glucose administration was calculated.

After blood glucose level at 120 min time point was measured, each group was placed in a metabolism cage, and the urine was collected during 2.25 hours to 6 hours and 6 hours to 24 hours after drug administration with the metabolism cage as the unit. The urine volume of each metabolism cage at each time point was measured. The mice had free access to food and water during the urine collection. After urine collection, the supernatant was collected by centrifugation, and the urine glucose concentration of C57BL/6 mice at various time points was detected by Roche automatic biochemical analyzer.

Test Method 2:

The weight and the blood glucose levels of male SD rats were measured after an overnight 15-hour fast. The rats were grouped by their weights and fasting plasma glucose levels. Each test group was administered with the corresponding test compound at a dose of 1 mg/kg once by gavage, and the blank control group was administered solvent. After 30 minutes, the blood glucose level (i.e., zero point blood glucose) of each group was measured, and then each group was administered glucose (4.0 g/kg) immediately by gavage. The blood was drawn from the caudal vein of the SD rats at 15, 30 and 60 minutes after glucose administration and the blood glucose levels were measured continuously on blood-glucose meter. The rate of decrease of the area under the blood glucose curve ($AUC_{Glu\ 0-60}$ min) within 60 minutes after glucose administration was calculated.

After blood glucose level at 60 min time point was measured, each group was placed in a metabolism cage, and the urine was collected during 1.5 hours to 24 hours and 24 hours to 48 hours after drug administration with the metabolism cage as the unit. The urine volume of each metabolism cage at each time point was measured. The mice had free access to food and water during the urine collection. After urine collection, the supernatant was collected by centrifugation, and the urine glucose concentration of the SD rats at various time points was detected by Roche automatic biochemical analyzer.

The test results show that the compounds of the present invention are effective in reducing blood glucose levels.

The test results show that the compounds of the present invention have a significant effect in promoting urine glucose excretion.

3. Pharmacokinetic Evaluation after Intravenous or Oral Quantification of the Compounds of the Present Invention Test Purpose:

The following test were used to evaluate the pharmacokinetic properties of the compounds of the present invention in animals.

Test Method:

The SD rats were weighted after an overnight 15-hour fast. The rats were randomly grouped by their weights. The test compounds were dissolved in 5% DMSO+5% Koliphor HS 15+90% saline vehicle for administration. For the test group administered intravenously, the rats were given a dose of 1 mg/kg, 2 mg/kg, or 5 mg/kg; for the test group administered orally, the rats were given a dose of 5 mg/kg. Then, venous blood (approximately 0.2 mL) was taken at 0.083 hours before and at 0.083 (intravenous group only), 0.25, 0.5, 1.0, 2.0, 5.0, 7.0, and 24 hours after administration, placed in an $EDTAK_2$ anticoagulation tube, and centrifuged at 11000 rpm for 2 minutes. The plasma was collected and stored at 20° C. or 70° C. until LC/MS/MS analysis. The drug concentration in plasma was measured at each time point. The WinNonlin 6.3 software non-compartment model method was used to calculate the pharmacokinetic parameters, and the drug time curve was drawn.

The test results show that the compounds provided by the present invention exhibit excellent pharmacokinetic properties when administered intravenously or orally.

Reference throughout this specification to "an embodiment", "some embodiments", "one embodiment", "another example", "an example", "a specific example", or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example", or "in some examples" in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

The invention claimed is:

1. A compound having Formula (I) or a stereoisomer, a geometric isomer, a tautomer, an N-oxide, a solvate, a pharmaceutically acceptable salt, a dimer, or a trimer thereof,

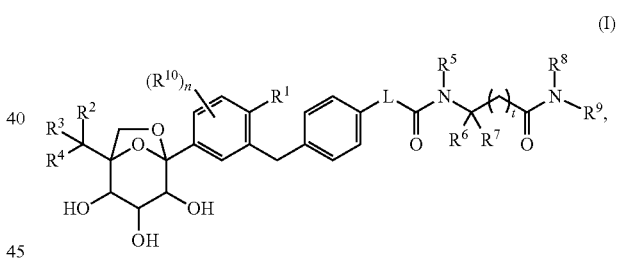

(I)

wherein,

L is —(CR$^a$R$^b$)$_q$—, —CH=CH—(CR$^a$R$^b$)$_p$—, —O—(CR$^a$R$^b$)$_p$—, —NH—(CR$^a$R$^b$)$_p$—, —S—(CR$^a$R$^b$)$_p$—, —S(=O)—(CR$^a$R$^b$)$_p$— or —S(=O)$_2$—(CR$^a$R$^b$)$_p$—;

q is 1, 2, 3, 4, 5 or 6;

p is 0, 1, 2, 3, 4, 5 or 6;

each R$^a$ and R$^b$ is independently H, D, F, Cl, Br, I, CN, NO$_2$, OH, NH$_2$, —C(=O) OH, —SH, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ alkylamino, C$_{1-6}$ haloalkoxy, C$_{3-6}$ cycloalkyl or 3-6 membered heterocyclyl; or, R$^a$ and R$^b$ together with the carbon atom to which they are attached, form a C$_{3-6}$ carbocycle or a 3-6 membered heterocycle;

R$^1$ is H, D, F, Cl, Br, I, OH, CN, NO$_2$, NH$_2$, C$_{1-6}$ alkyl, C$_{2-6}$ alkenyl, C$_{2-6}$ alkynyl, C$_{1-6}$ alkoxy, C$_{1-6}$ hydroxyalkyl, C$_{1-6}$ haloalkyl, C$_{1-6}$ haloalkoxy, C$_{1-6}$ alkylamino, C$_{1-6}$ alkylthio, C$_{3-6}$ cycloalkyl or C$_{3-6}$ cycloalkyl-C$_{1-4}$ alkylene, wherein each of C$_{1-6}$ alkyl, C$_{2-6}$ alkenyl, C$_{2-6}$ alkynyl, C$_{1-6}$ alkoxy, C$_{1-6}$ hydroxyalkyl, C$_{1-6}$ haloalkyl, C$_{1-6}$ haloalkoxy, C$_{1-6}$ alkylamino, C$_{1-6}$ alkylthio, C$_{3-6}$ cycloalkyl and C$_{3-6}$ cycloalkyl-C$_{1-4}$ alkylene is independently unsubstituted or substituted with 1, 2, 3 or 4 substituents, and the substituent is independently selected from D, F, Cl, Br, I, CN, $NO_2$, OH, $NH_2$, —C(=O) OH, —SH, $C_{1-6}$ alkyl, $C_{1-6}$ haloalkyl, $C_{1-6}$ alkoxy, $C_{1-6}$ alkylamino or $C_{1-6}$ haloalkoxy;

each of $R^2$ and $R^3$ is independently H, D, CN, OH, $NH_2$, —SH, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ alkylamino, $C_{3-6}$ cycloalkyl or 3-6 membered heterocyclyl, wherein each $C_{1-6}$ alkyl, $C_{2-6}$ alkenyl, $C_{2-6}$ alkynyl, $C_{1-6}$ alkoxy, $C_{1-6}$ alkylthio, $C_{1-6}$ alkylamino, $C_{3-6}$ cycloalkyl and 3-6 membered heterocyclyl is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

or, $R^2$ and $R^3$ together with the carbon atom to which they are attached, form carbonyl, or, $R^2$ and $R^3$ together with the carbon atom to which they are attached, form a $C_{3-6}$ carbocycle or a 3-6 membered heterocycle, wherein each of $C_{3-6}$ carbocycle and 3-6 membered heterocycle is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

$R^4$ is H, D, —$OR^{4a}$ or —$SR^{4b}$;

each of $R^{4a}$ and $R^{4b}$ is independently H, D, $C_{1-6}$ alkyl, $C_{3-6}$ cycloalkyl, $C_{3-6}$ cycloalkyl-$C_{1-4}$ alkylene, 5-6 membered heterocyclyl, (5-6 membered heterocyclyl)-$C_{1-4}$ alkylene, $C_{6-10}$ aryl, $C_{6-10}$ aryl-$C_{1-4}$ alkylene, 5-6 membered heteroaryl or (5-6 membered heteroaryl)-$C_{1-4}$ alkylene, wherein each $C_{1-6}$ alkyl, $C_{3-6}$ cycloalkyl, $C_{3-6}$ cycloalkyl-$C_{1-4}$ alkylene, 5-6 membered heterocyclyl, (5-6 membered heterocyclyl)-$C_{1-4}$ alkylene, $C_{6-10}$ aryl, $C_{6-10}$ aryl-$C_{1-4}$ alkylene, 5-6 membered heteroaryl and (5-6 membered heteroaryl)-$C_{1-4}$ alkylene is independently unsubstituted or substituted with 1, 2, 3 or 4 substituents, and the substituent is independently selected from D, F, Cl, Br, I, CN, $NO_2$, OH, $NH_2$, —C(=O) OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

each $R^{10}$ is independently H, D, F, Cl, Br, I, OH, CN, $NO_2$, $NH_2$, $C_{1-6}$ alkyl or $C_{1-6}$ alkoxy;

$R^5$ is H, D, $C_{1-6}$ alkyl, $C_{1-6}$ haloalkyl, $C_{3-8}$ cycloalkyl, 3-8 membered heterocyclyl, $C_{6-10}$ aryl or 5-8 membered heteroaryl, wherein each of $C_{1-6}$ alkyl, $C_{1-6}$ haloalkyl, $C_{3-8}$ cycloalkyl, 3-8 membered heterocyclyl, $C_{6-10}$ aryl and 5-8 membered heteroaryl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino, $C_{1-6}$ haloalkoxy, $C_{3-6}$ cycloalkyl, 5-6 membered heterocyclyl, $C_{6-10}$ aryl or 5-6 membered heteroaryl;

each of $R^6$ and $R^7$ is independently H, D, F, Cl, Br, I, CN, $NO_2$, OH, $NH_2$, $C_{1-6}$ alkyl, $C_{1-6}$ alkoxy, $C_{1-6}$ alkylamino, $C_{1-6}$ haloalkyl, $C_{1-6}$ haloalkoxy, $C_{3-8}$ cycloalkyl, 3-8 membered heterocyclyl, $C_{6-10}$ aryl or 5-8 membered heteroaryl, wherein each $C_{1-6}$ alkyl, $C_{1-6}$ alkoxy, $C_{1-6}$ alkylamino, $C_{1-6}$ haloalkyl, $C_{1-6}$ haloalkoxy, $C_{3-8}$ cycloalkyl, 3-8 membered heterocyclyl, $C_{6-10}$ aryl and 5-8 membered heteroaryl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino, $C_{1-6}$ haloalkoxy, $C_{3-6}$ cycloalkyl, 5-6 membered heterocyclyl, $C_{6-10}$ aryl or 5-6 membered heteroaryl;

or, $R^6$ and $R^7$ together with the carbon atom to which they are attached, form a $C_{3-8}$ carbocycle, a 3-8 membered heterocycle, a $C_{6-10}$ aromatic ring or a 5-8 membered heteroaromatic ring, wherein each of $C_{3-8}$ carbocycle, 3-8 membered heterocycle, $C_{6-10}$ aromatic ring and 5-8 membered heteroaromatic ring is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

or $R^5$ and $R^6$ together with the atom to which they are attached, or $R^5$ and $R^7$ together with the atom to which they are attached, form a 3-8 membered heterocycle or a 5-8 membered heteroaromatic ring, wherein each 3-8 membered heterocycle and 5-8 membered heteroaromatic ring is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

each of $R^8$ and $R^9$ is independently H, D, $R^eO$—$C_{1-4}$ alkylene, $R^dR^cN$—$C_{1-4}$ alkylene, $C_{1-8}$ alkyl, $C_{1-6}$ haloalkyl, $C_{3-8}$ cycloalkyl, $C_{3-8}$cycloalkyl-$C_{1-4}$ alkylene, 3-8 membered heterocyclyl, (3-8 membered heterocyclyl) —$C_{1-4}$ alkylene, $C_{6-10}$ aryl, $C_{6-10}$ aryl-$C_{1-4}$ alkylene, 5-8 membered heteroaryl or (5-8 membered heteroaryl)-$C_{1-4}$ alkylene, wherein each $C_{1-8}$ alkyl, $C_{1-6}$ haloalkyl, $C_{3-8}$ cycloalkyl, $C_{3-8}$cycloalkyl-$C_{1-4}$ alkylene, 3-8 membered heterocyclyl, (3-8 membered heterocyclyl) —$C_{1-4}$ alkylene, $C_{6-10}$ aryl, $C_{6-10}$ aryl-$C_{1-4}$ alkylene, 5-8 membered heteroaryl and (5-8 membered heteroaryl)-$C_{1-4}$ alkylene is independently unsubstituted or substituted with 1, 2, 3 or 4 substituents, and the substituent is independently selected from D, F, Cl, Br, I, CN, $NO_2$, =O, —$OR^e$, —$NR^cR^d$, —C(=O) $OR^e$, —C(=O) $NHR^f$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

or, $R^8$ and $R^9$ together with the nitrogen atom to which they are attached, form a 3-8 membered heterocycle or a 5-8 membered heteroaromatic ring, wherein each of 3-8 membered heterocycle and 5-8 membered heteroaromatic ring is independently unsubstituted or substituted with 1, 2, 3 or 4 substituents, and the substituent is independently selected from D, F, Cl, Br, I, CN, $NO_2$, =O, —$OR^e$, —$NR^cR^d$, —C(=O)$OR^e$, —C(=O)$NHR^f$, $C_{1-6}$ alkyl, $C_{2-6}$ alkenyl, $C^{2-6}$ alkynyl, $C_{1-6}$ haloalkyl, $C_{1-6}$ alkoxy, $C_{1-6}$ alkylamino or $C_{1-6}$ haloalkoxy;

each $R^c$, $R^d$, $R^e$ and $R^f$ is independently H, D, $C_{1-6}$ alkyl, $C_{1-6}$ haloalkyl, $C_{3-8}$ cycloalkyl, $C_{3-8}$cycloalkyl-$C_{1-4}$ alkylene, 3-8 membered heterocyclyl, (3-8 membered heterocyclyl) —$C_{1-4}$ alkylene, $C_{6-10}$ aryl, $C_{6-10}$ aryl-$C_{1-4}$ alkylene, 5-8 membered heteroaryl or (5-8 membered heteroaryl)-$C_{1-4}$ alkylene, wherein each $C_{1-6}$ alkyl, $C_{1-6}$ haloalkyl, $C_{3-8}$ cycloalkyl, $C_{3-8}$cycloalkyl-$C_{1-4}$ alkylene, 3-8 membered heterocyclyl, (3-8 membered heterocyclyl) —C$_{1-4}$ alkylene, C$_{6-10}$ aryl, C$_{6-10}$ aryl-C$_{1-4}$ alkylene, 5-8 membered heteroaryl and (5-8 membered heteroaryl)-C$_{1-4}$ alkylene is independently unsubstituted or substituted with 1, 2, 3 or 4 substituents, and the substituent is independently selected from D, F, Cl, Br, I, CN, NO$_2$, OH, —NH$_2$, =O, —C(=O) OH, —C(=O)NH$_2$, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ alkylamino or C$_{1-6}$ haloalkoxy;

or, R$^c$ and R$^d$ together with the nitrogen atom to which they are attached, form a 3-8 membered heterocycle or a 5-8 membered heteroaromatic ring, wherein each of 3-8 membered heterocycle and 5-8 membered heteroaromatic ring is independently unsubstituted or substituted with 1, 2, 3 or 4 substituents, and the substituent is independently selected from D, F, Cl, Br, I, CN, NO$_2$, =O, OH, —NH$_2$, —C(=O)OH, —C(=O)NH$_2$, C$_{1-6}$ alkyl, C$_{2-6}$ alkenyl, C$^{2-6}$ alkynyl, C$_{1-6}$ haloalkyl, C$_{1-6}$ alkoxy, C$_{1-6}$ alkylamino or C$_{1-6}$ haloalkoxy;

n is 0, 1, 2 or 3;

t is 0, 1, 2, 3, 4, 5 or 6; with the proviso that when R$^5$ and R$^8$ are both H, and R$^9$ is

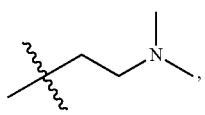 [SMILES: *CCN(C)C]

t is not 0.

2. The compound of claim 1 having Formula (II):

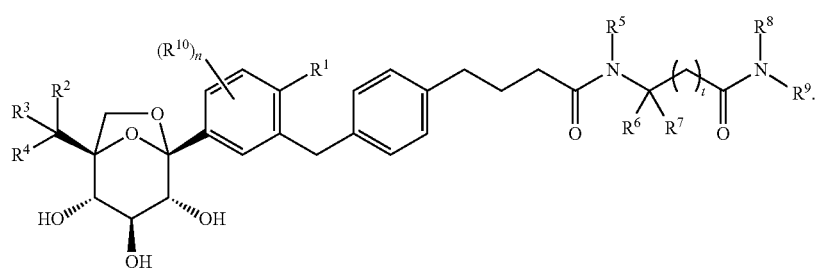

3. The compound of claim 1, wherein R$^1$ is H, D, F, Cl, Br, I, OH, CN, NO$_2$, NH$_2$, methyl, ethyl, n-propyl, isopropyl, propenyl, propynyl, methoxy, ethoxy, hydroxymethyl, trifluoromethyl, trifluoroethyl, monofluoromethyl, trifluoromethoxy, difluoromethoxy, methylamino, cyclopropyl, cyclobutyl, cyclopentyl, cyclohexyl or cyclopropyl-methylene, wherein each of methyl, ethyl, n-propyl, isopropyl, propenyl, propynyl, methoxy, ethoxy, hydroxymethyl, trifluoroethyl, monofluoromethyl, difluoromethoxy, methylamino, cyclopropyl, cyclobutyl, cyclopentyl, cyclohexyl and cyclopropyl-methylene is independently unsubstituted or substituted with 1, 2, 3, or 4 substituents, and the substituent is independently selected from D, F, Cl, Br, I, CN, NO$_2$, OH, NH$_2$, —C(=O) OH, —SH, methyl, ethyl, n-propyl, isopropyl, trifluoromethyl, methoxy, ethoxy, methylamino, trifluoromethoxy or difluoromethoxy.

4. The compound of claim 1, wherein each of R$^2$ and R$^3$ is independently H, D, CN, OH, NH$_2$, —SH, methyl, ethyl, n-propyl, isopropyl, vinyl, propynyl, methoxy, ethoxy, methylthio, methylamino, cyclopropyl, cyclobutyl, cyclopentyl, cyclohexyl or 5-6 membered heterocyclyl, wherein each methyl, ethyl, n-propyl, isopropyl, vinyl, propynyl, methoxy, ethoxy, methylthio, methylamino, cyclopropyl, cyclobutyl, cyclopentyl, cyclohexyl and 5-6 membered heterocyclyl is independently unsubstituted or substituted with 1, 2, 3 or 4 substituents, and the substituent is independently selected from D, F, Cl, Br, I, CN, NO$_2$, OH, NH$_2$, —C(=O) OH, —SH, =O, methyl, ethyl, n-propyl, isopropyl, trifluoromethyl, methoxy, ethyloxy, methylamino, trifluoromethoxy or difluoromethoxy;

or, R$^2$ and R$^3$ together with the carbon atom to which they are attached, form carbonyl, or, R$^2$ and R$^3$ together with the carbon atom to which they are attached, form cyclopropane, cyclobutane, cyclopentane, cyclohexane or a 5-6 membered heterocycle, wherein each of cyclopropane, cyclobutane, cyclopentane, cyclohexane and a 5-6 membered heterocycle is independently unsubstituted or substituted with 1, 2, 3 or 4 substituents, and the substituent is independently selected from D, F, Cl, Br, I, CN, NO$_2$, OH, NH$_2$, —C(=O) OH, —SH, =O, methyl, ethyl, n-propyl, isopropyl, trifluoromethyl, methoxy, ethoxy, methylamino, trifluoromethoxy or difluoromethoxy.

5. The compound of claim 1, wherein R$^4$ is H, D, —OR$^{4a}$ or —SR$^{4b}$;

each of R$^{4a}$ and R$^{4b}$ is independently H, D, methyl, ethyl, n-propyl, isopropyl, cyclopropyl, cyclobutyl, cyclopentyl, cyclohexyl, C$_{3-6}$ cycloalkyl-C$_{1-2}$ alkylene, tetrahydrofuranyl, tetrahydrothienyl, tetrahydropyranyl, piperidinyl, morpholinyl, thiomorpholinyl, piperazinyl, (5-6 membered heterocyclyl) —C$_{1-2}$ alkylene, phenyl, phenyl-C$_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl or (5-6 membered heteroaryl) —C$_{1-2}$ alkylene, wherein each methyl, ethyl, n-propyl, isopropyl, cyclopropyl, cyclobutyl, cyclopentyl, cyclohexyl, C$_{3-6}$ cycloalkyl-C$_{1-2}$ alkylene, tetrahydrofuranyl, tetrahydrothienyl, tetrahydropyranyl, piperidinyl, morpholinyl, thiomorpholinyl, piperazinyl, (5-6 membered heterocyclyl) —C$_{1-2}$ alkylene, phenyl, phenyl-C$_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl and (5-6 membered heteroaryl) —C$_{1-2}$ alkylene is independently unsubstituted or substituted with 1, 2, 3, or 4 substituents, and the substituent is independently selected from D, F, Cl, Br, I, CN, NO$_2$, OH, NH$_2$, —C(=O) OH, —SH, =O, methyl, ethyl, n-propyl, isopropyl, trifluoromethyl, methoxy, ethoxy, methylamino, trifluoromethoxy or difluoromethoxy.

6. The compound of claim 1, wherein $R^{10}$ is H, D, F, Cl, Br, I, OH, CN, $NO_2$, $NH_2$, methyl, ethyl, n-propyl, isopropyl, methoxy or ethoxy.

7. The compound of claim 1, wherein $R^5$ is H, D, $C_{1-4}$ alkyl, $C_{1-4}$ haloalkyl, $C_{3-6}$ cycloalkyl, 5-6 membered heterocyclyl, $C_{6-10}$ aryl or 5-6 membered heteroaryl, wherein each of $C_{1-4}$ alkyl, $C_{1-4}$ haloalkyl, $C_{3-6}$ cycloalkyl, 5-6 membered heterocyclyl, $C_{6-10}$ aryl and 5-6 membered heteroaryl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino, $C_{1-4}$ haloalkoxy, $C_{3-6}$ cycloalkyl, 5-6 membered heterocyclyl, $C_{6-10}$ aryl or 5-6 membered heteroaryl;

each of $R^6$ and $R^7$ is independently H, D, F, Cl, Br, I, CN, $NO_2$, OH, $NH_2$, $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl, 5-6 membered heterocyclyl, $C_{6-10}$ aryl or 5-6 membered heteroaryl, wherein each $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl, 5-6 membered heterocyclyl, $C_{6-10}$ aryl and 5-6 membered heteroaryl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino, $C_{1-4}$ haloalkoxy, $C_{3-6}$ cycloalkyl, 5-6 membered heterocyclyl, $C_{6-10}$ aryl or 5-6 membered heteroaryl;

or, $R^6$ and $R^7$ together with the carbon atom to which they are attached, form a $C_{3-6}$ carbocycle, a 5-6 membered heterocycle, a $C_{6-10}$ aromatic ring or a 5-6 membered heteroaromatic ring, wherein each of $C_{3-6}$ carbocycle, 5-6 membered heterocycle, $C_{6-10}$ aromatic ring and 5-6 membered heteroaromatic ring is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy;

or $R^5$ and $R^6$ together with the atom to which they are attached, or $R^5$ and $R^7$ together with the atom to which they are attached, form a 3-6 membered heterocycle or a 5-6 membered heterocycle, wherein each 3-6 membered heterocycle and 5-6 membered heterocycle is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy.

8. The compound of claim 1, wherein $R^5$ is H, D, methyl, ethyl, n-propyl, isopropyl, n-butyl, isobutyl, tert-butyl, trifluoromethyl, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each of methyl, ethyl, n-propyl, isopropyl, n-butyl, isobutyl, tert-butyl, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy, difluoromethoxy, cyclopropyl, cyclobutyl, cyclopentyl or phenyl;

each of $R^6$ and $R^7$ is independently H, D, F, Cl, Br, I, CN, $NO_2$, OH, $NH_2$, methyl, ethyl, n-propyl, isopropyl, n-butyl, isobutyl, tert-butyl, methoxy, ethoxy, methylamino, trifluoromethyl, trifluoromethoxy, difluoromethoxy, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each methyl, ethyl, n-propyl, isopropyl, n-butyl, isobutyl, tert-butyl, methoxy, ethoxy, methylamino, difluoromethoxy, cyclopropyl, cyclobutyl, cyclopentyl, cyclohexyl, pyrrolidinyl, tetrahydrofuranyl, tetrahydrothiophenyl, tetrahydropyranyl, tetrahydrothiopyranyl, piperidinyl, morpholinyl, thiomorpholyl, piperazinyl, phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents, and the substituent is independently selected from D, F, Cl, Br, I, CN, $NO_2$, OH, $NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy, difluoromethoxy, cyclopropyl, cyclobutyl, cyclopentyl or phenyl;

or, $R^6$ and $R^7$ together with the carbon atom to which they are attached, form cyclopropane, cyclobutane, cyclopentane, cyclohexane, pyrrolidine, tetrahydrofuran, tetrahydrothiophene, tetrahydropyran, tetrahydrothiopyran, piperidine, morpholine, thiomorpholine, piperazine, benzene ring, furan, pyrrole, pyridine, pyrazole, imidazole, triazole, tetrazole, oxazole, oxadiazole, 1,3,5-triazine, thiazole, thiophene, pyrazine, pyridazine or pyrimidine, wherein each of cyclopropane, cyclobutane, cyclopentane, cyclohexane, pyrrolidine, tetrahydrofuran, tetrahydrothiophene, tetrahydropyran, tetrahydrothiopyran, piperidine, morpholine, thiomorpholine, piperazine, benzene ring, furan, pyrrole, pyridine, pyrazole, imidazole, triazole, tetrazole, oxazole, oxadiazole, 1,3,5-triazine, thiazole, thiophene, pyrazine, pyridazine and pyrimidine is independently unsubstituted or substituted with 1, 2, 3, or 4 substituents, and the substituent is independently selected from D, F, Cl, Br, I, CN, $NO_2$, OH, $NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy or difluoromethoxy;

or $R^5$ and $R^6$ together with the atom to which they are attached, or $R^5$ and $R^7$ together with the atom to which they are attached, form aziridine, azetidine, pyrrolidine, pyrazolidine, imidazolidine, oxazolidine, thiazolidine, piperidine, morpholine, thiomorpholine, piperazine, pyrrole, pyridine, pyrazole, imidazole, triazole, tetrazole, oxazole, oxadiazole, 1,3,5-triazine, thiazole, pyrazine, pyridazine or pyrimidine, wherein each aziridine, azetidine, pyrrolidine, pyrazolidine, imidazolidine, oxazolidine, thiazolidine, piperidine, morpholine, thiomorpholine, piperazine, pyrrole, pyridine, pyrazole, imidazole, triazole, tetrazole, oxazole, oxadiazole, 1,3,5-triazine, thiazole, pyrazine, pyridazine and pyrimidine is independently unsubstituted or substituted with 1, 2, 3, or 4 substituents, and the substituent is independently selected from D, F, Cl, Br, I, CN, $NO_2$, OH, $NH_2$, =O, —C(=O) OH, —C(=O) $NH_2$, methyl, ethyl, n-propyl, isopropyl, vinyl, ethynyl, trifluoromethyl, methoxy, ethoxy, methylamino, trifluoromethoxy or difluoromethoxy.

9. The compound of claim 1, wherein each of $R^8$ and $R^9$ is independently H, D, $R^eO$—$C_{1-4}$ alkylene, $R^dR^cN$—$C_{1-4}$ alkylene, $C_{1-6}$ alkyl, $C_{1-4}$ haloalkyl, $C_{3-6}$ cycloalkyl, $C_{3-6}$cycloalkyl-$C_{1-2}$ alkylene, 5-6 membered heterocyclyl, (5-6 membered heterocyclyl) —$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene, wherein each of $C_{1-6}$ alkyl, $C_{1-4}$ haloalkyl, $C_{3-6}$ cycloalkyl, $C_{3-6}$cycloalkyl-$C_{1-2}$ alkylene, 5-6 membered heterocyclyl, (5-6 membered heterocyclyl) —$C_{1-2}$ alkylene, $C_{6-10}$ aryl, $C_{6-10}$ aryl-$C_{1-2}$ alkylene, 5-6 membered heteroaryl and (5-6 membered heteroaryl)-$C_{1-2}$ alkylene is independently unsubstituted or substituted with 1, 2, 3 or 4 substituents, and the substituent is independently selected from D, F, Cl, Br, I, CN, $NO_2$, =O, —$OR^e$, —$NR^cR^d$, —C(=O) $OR^e$, —C(=O) $NHR^f$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$haloalkoxy;

or, $R^8$ and $R^9$ together with the nitrogen atom to which they are attached, form a 3-6 membered heterocycle or a 5-6 membered heteroaromatic ring, wherein each of 3-6 membered heterocycle and 5-6 membered heteroaromatic ring is independently unsubstituted or substituted with 1, 2, 3 or 4 substituents, and the substituent is independently selected from D, F, Cl, Br, I, CN, $NO_2$, =O, —$OR^e$, —$NR^cR^d$, —C(=O)$OR^e$, —C(=O)$NHR^f$, $C_{1-4}$ alkyl, $C_{2-4}$ alkenyl, $C^{2-4}$ alkynyl, $C_{1-4}$ haloalkyl, $C_{1-4}$ alkoxy, $C_{1-4}$ alkylamino or $C_{1-4}$ haloalkoxy.

10. The compound of claim 1, wherein each of $R^8$ and $R^9$ is independently H, D, $R^dR^cN$—$C_{1-4}$ alkylene, methyl, ethyl, n-propyl, isopropyl, n-butyl, isobutyl, tert-butyl, n-pentyl, n-hexyl, trifluoromethyl, cyclopropyl, cyclobutyl, cyclopentyl, cyclohexyl, $C_{3-6}$ cycloalkyl-$C_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl) —$C_{1-2}$ alkylene, phenyl, $C_{6-10}$ aryl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl or (5-6 membered heteroaryl) —$C_{1-2}$ alkylene, wherein each methyl, ethyl, n-propyl, isopropyl, n-butyl, isobutyl, tert-butyl, n-pentyl, n-hexyl, cyclopropyl, cyclobutyl, cyclopentyl, cyclohexyl, $C_{3-6}$ cycloalkyl-$C_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl) —$C_{1-2}$ alkylene, phenyl, $C_{6-10}$ aryl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl and (5-6 membered heteroaryl) —$C_{1-2}$ alkylene is independently unsubstituted or substituted with 1, 2, 3, or 4 substituents, and the substituent is independently selected from D, F, Cl, Br, I, CN, $NO_2$, =O, —OH, —$NR^cR^d$, —C(=O)OH, —C(=O)$NH_2$, methyl, ethyl, n-propyl, vinyl, ethynyl, trifluoromethyl, methoxy, ethoxy, methylamino, trifluoromethoxy or difluoromethoxy;

or, $R^8$ and $R^9$ together with the nitrogen atom to which they are attached, form aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine or pyrimidine, wherein each of aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine and pyrimidine is independently unsubstituted or substituted with 1, 2, 3, or 4 substituents, and the substituent is independently selected from D, F, Cl, Br, I, CN, $NO_2$, =O, —OH, —$NR^cR^d$, —C (=O) OH, —C(=O) $NH_2$, methyl, ethyl, n-propyl, vinyl, ethynyl, trifluoromethyl, methoxy, ethoxy, methylamino, trifluoromethoxy or difluoromethoxy.

11. The compound of claim 1, wherein each $R^c$, $R^d$, $R^e$ and $R^f$ is independently H, D, $C_{1-4}$ alkyl, $C_{1-4}$ haloalkyl, $C_{3-6}$ cycloalkyl, $C_{3-6}$cycloalkyl-$C_{1-2}$ alkylene, 5-6 membered heterocyclyl, (5-6 membered heterocyclyl) —$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene, wherein each $C_{1-4}$ alkyl, $C_{1-4}$ haloalkyl, $C_{3-6}$ cycloalkyl, $C_{3-6}$cycloalkyl-$C_{1-2}$ alkylene, 5-6 membered heterocyclyl, (5-6 membered heterocyclyl) —$C_{1-2}$ alkylene, $C_{6-10}$ aryl, $C_{6-10}$ aryl-$C_{1-2}$ alkylene, 5-6 membered heteroaryl and (5-6 membered heteroaryl)-$C_{1-2}$ alkylene is independently unsubstituted or substituted with 1, 2, 3 or 4 substituents, and the substituent is independently selected from D, F, Cl, Br, I, CN, $NO_2$, OH, —$NH_2$, =O, —C(=O)OH, —C(=O)$NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy;

or, $R^c$ and $R^d$ together with the nitrogen atom to which they are attached, form a 3-6 membered heterocycle or a 5-6 membered heteroaromatic ring, wherein each of 3-6 membered heterocycle and 5-6 membered heteroaromatic ring is independently unsubstituted or substituted with 1, 2, 3 or 4 substituents, and the substituent is independently selected from D, F, Cl, Br, I, CN, $NO_2$, =O, OH, —$NH_2$, —C(=O)OH, —C(=O)$NH_2$, $C_{1-4}$ alkyl, $C_{2-4}$ alkenyl, $C^{2-4}$ alkynyl, $C_{1-4}$ haloalkyl, $C_{1-4}$ alkoxy, $C_{1-4}$ alkylamino or $C_{1-4}$ haloalkoxy.

12. The compound of claim 1, wherein each $R^c$, $R^d$, $R^e$ and $R^f$ is independently H, D, methyl, ethyl, n-propyl, isopropyl, n-butyl, isobutyl, tert-butyl, trifluoromethyl, cyclopropyl, cyclobutyl, cyclopentyl, cyclohexyl, $C_{3-6}$ cycloalkyl-$C_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl) —$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl or (5-6 membered heteroaryl) —$C_{1-2}$ alkylene, wherein each methyl, ethyl, n-propyl, isopropyl, n-butyl, isobutyl, tert-butyl, cyclopropyl, cyclobutyl, cyclopentyl, cyclohexyl, $C_{3-6}$ cycloalkyl-$C_{1-2}$ alkylene, pyrrolidinyl, pyrazolidinyl, imidazolidinyl, oxazolidinyl, thiazolidinyl, tetrahydrofuranyl, tetrahydrothienyl, tetrahydropyranyl, tetrahydrothiopyranyl, piperidinyl, morpholinyl, thiomorpholinyl, piperazinyl, (5-6 membered heterocyclyl) —C$_{1-2}$ alkylene, phenyl, phenyl-C$_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl and (5-6 membered heteroaryl) —C$_{1-2}$ alkylene is independently unsubstituted or substituted with 1, 2, 3, or 4 substituents, and the substituent is independently selected from D, F, Cl, Br, I, CN, NO$_2$, OH, —NH$_2$, =O, —C(=O) OH, —C(=O) NH$_2$, methyl, ethyl, n-propyl, isopropyl, vinyl, ethynyl, trifluoromethyl, methoxy, ethoxy, methylamino, trifluoromethoxy or difluoromethoxy;

or, R$^c$ and R$^d$ together with the nitrogen atom to which they are attached, form aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine or pyrimidine, wherein each of aziridine, azetidine, pyrrolidine, pyrazolidine, imidazolidine, oxazolidine, thiazolidine, piperidine, morpholine, thiomorpholine, piperazine, pyrazole, imidazole, triazole, tetrazole, oxazole, oxadiazole, 1,3,5-triazine, thiazole, pyrazine, pyridazine and pyrimidine is independently unsubstituted or substituted with 1, 2, 3, or 4 substituents, and the substituent is independently selected from D, F, Cl, Br, I, CN, NO$_2$, OH, NH$_2$, =O, —C(=O) OH, —C(=O) NH$_2$, methyl, ethyl, n-propyl, isopropyl, vinyl, ethynyl, trifluoromethyl, methoxy, ethoxy, methylamino, trifluoromethoxy or difluoromethoxy.

13. The compound of claim 1 having one of the following structures:

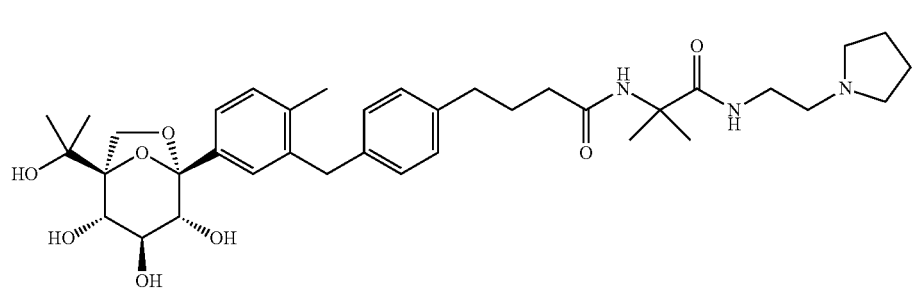

(1)

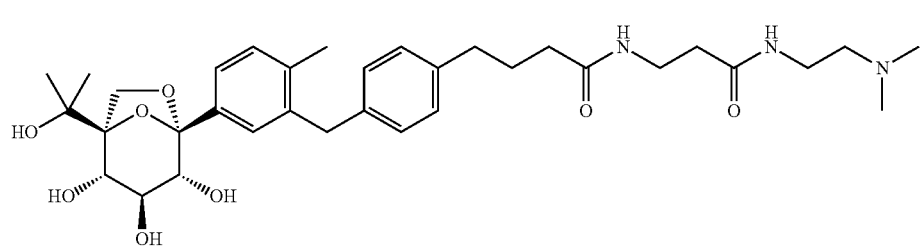

(2)

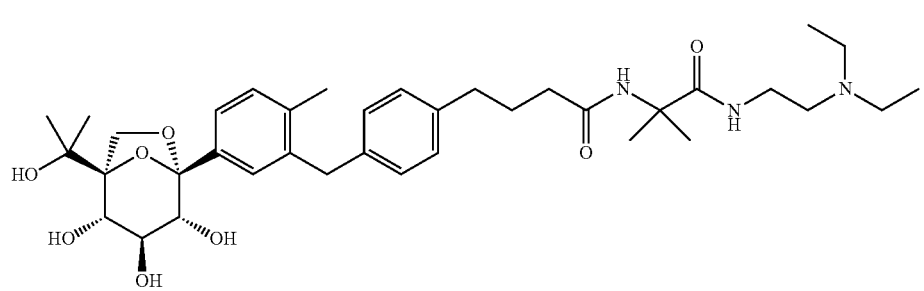

(3)

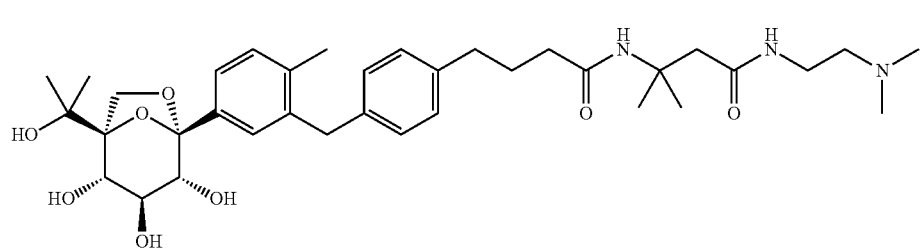

(4)

-continued
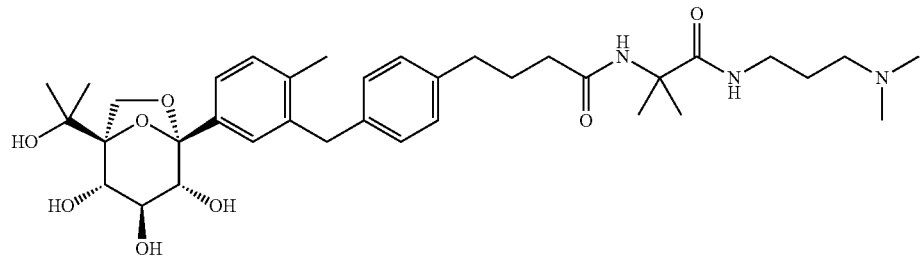
(5)
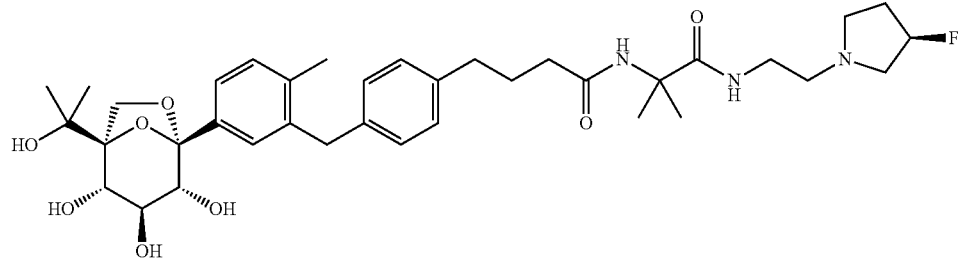
(6)
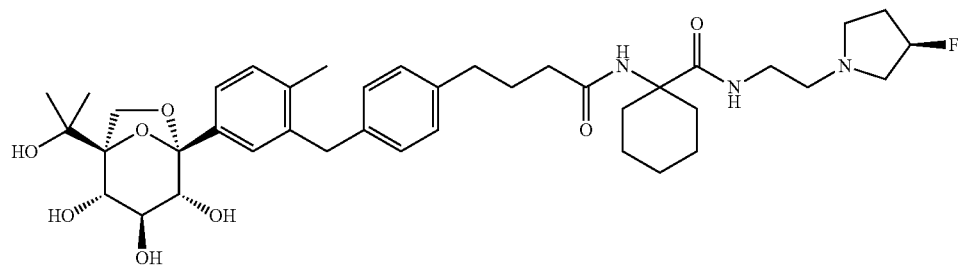
(7)
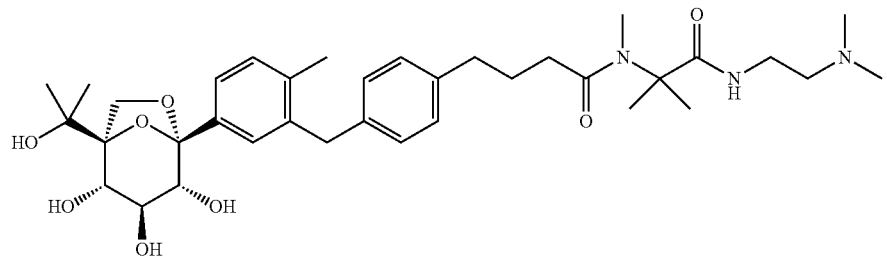
(8)
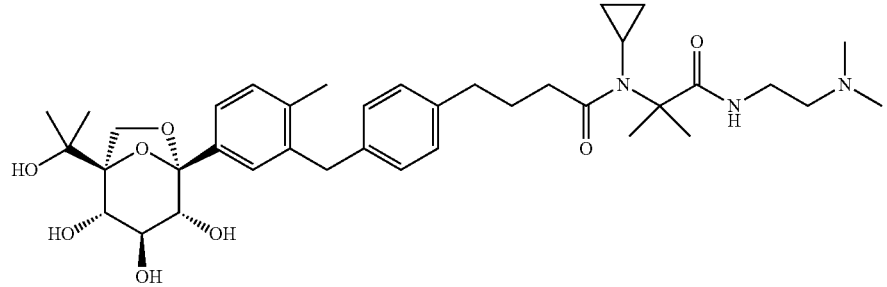
(9)
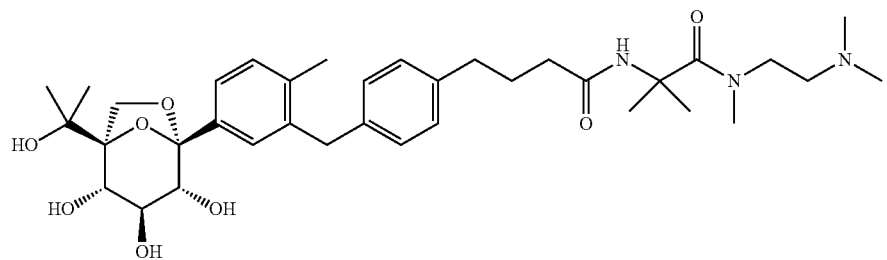
(10)

-continued
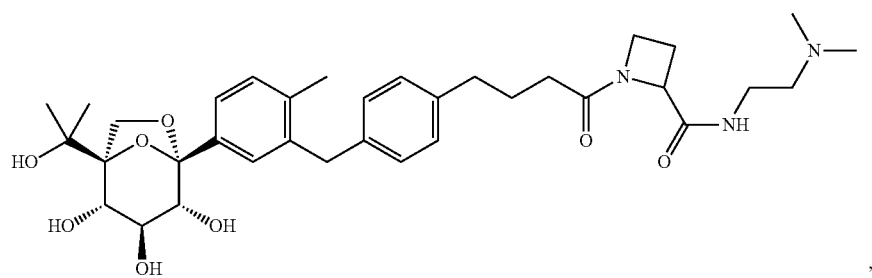
(11)
,
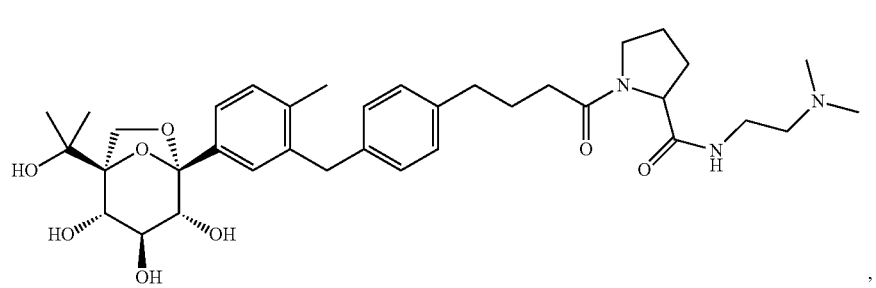
(12)
,
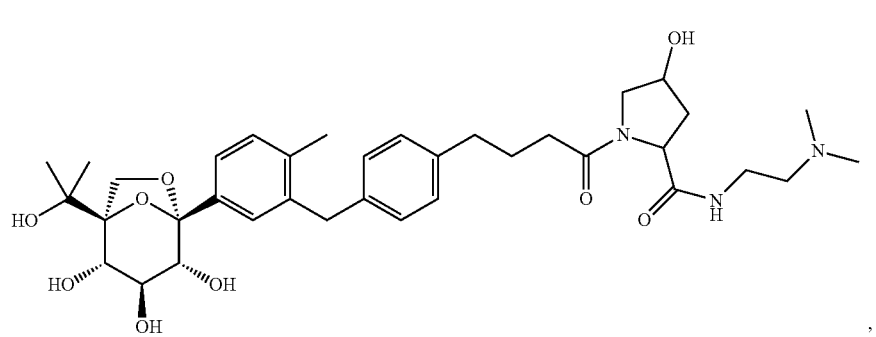
(13)
,
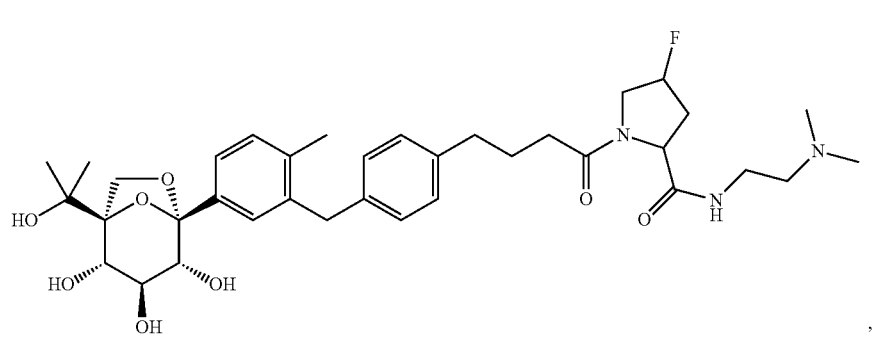
(14)
,
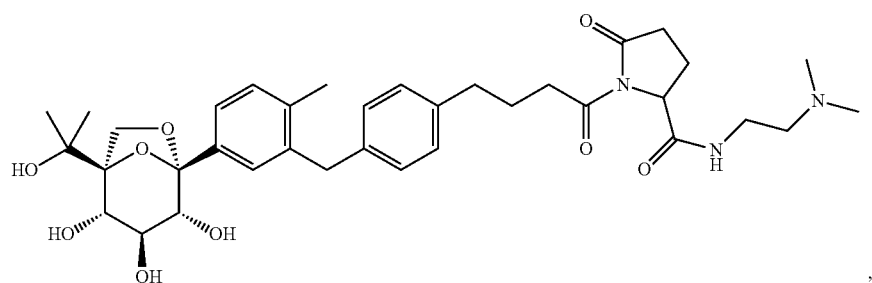
(15)
, -continued
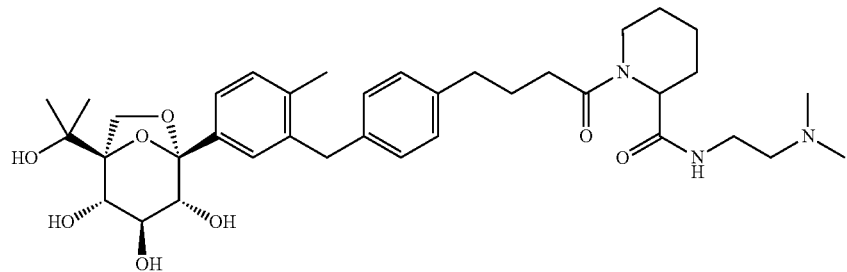
(16)
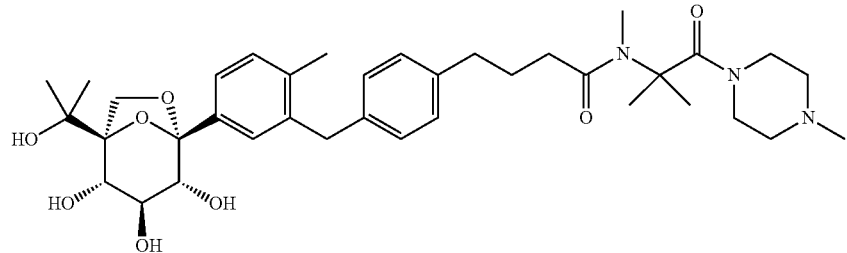
(17)
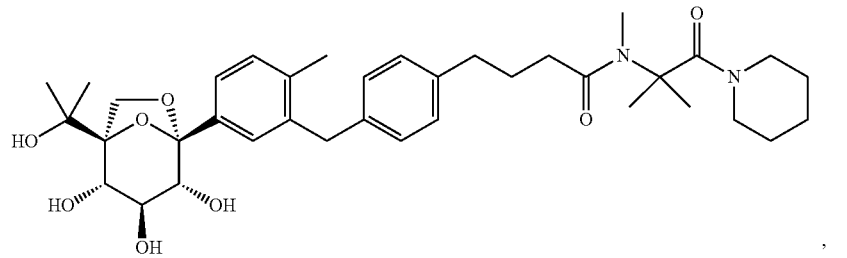
(18)
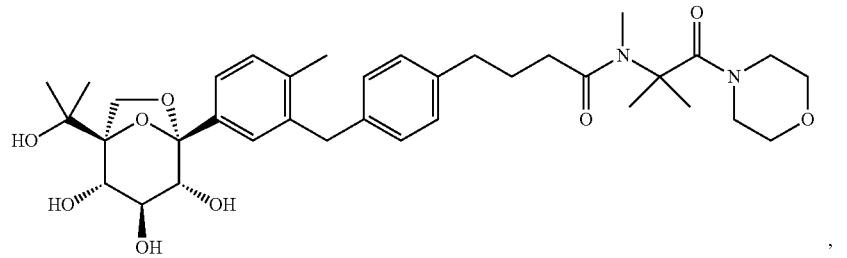
(19)
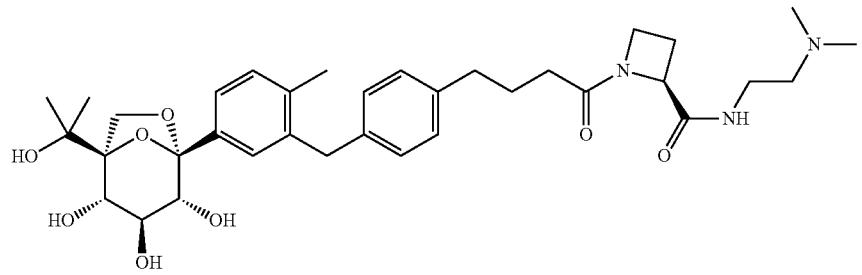
(20)
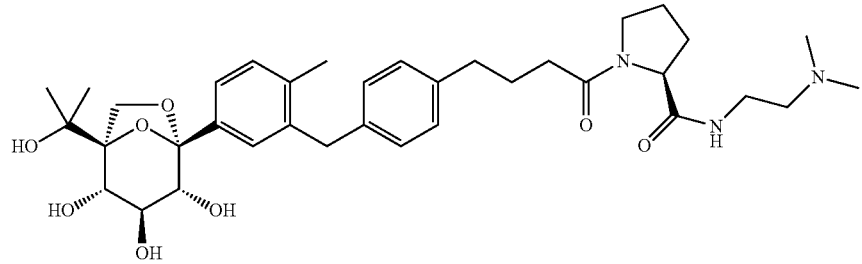
(21)

-continued

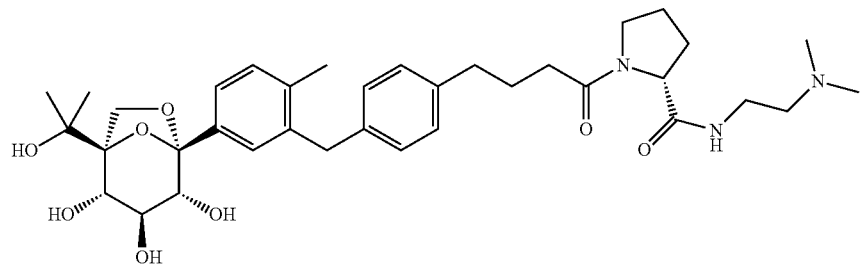

(22)

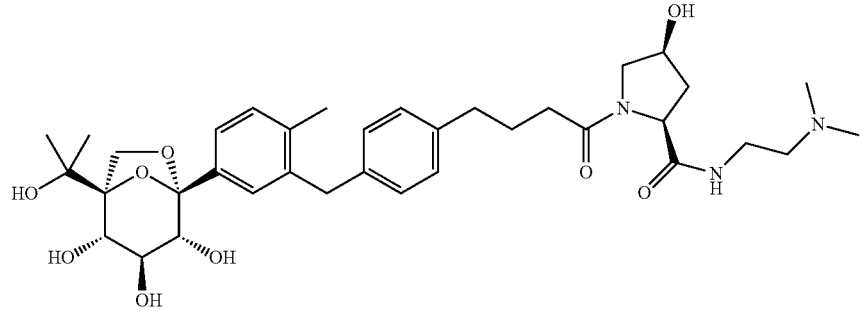

(23)

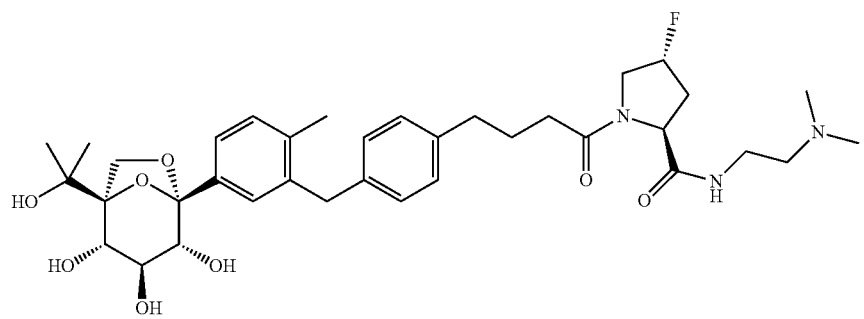

(24)

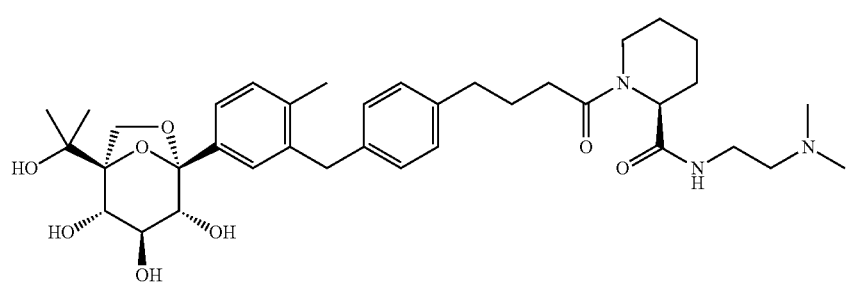

(25)

or a stereoisomer, a geometric isomer, a tautomer, an N-oxide, a solvate, a pharmaceutically acceptable salt, a dimer, or a trimer thereof.

14. A pharmaceutical composition comprising the compound of claim 1 and a pharmaceutically acceptable carrier, excipient, adjuvant, vehicle or a combination thereof.

15. The pharmaceutical composition of claim 14 further comprising one or more other additional therapeutic agents, wherein the other additional therapeutic agent is selected from an anti-diabetic drug, an anti-hyperglycemic drug, an anti-obesity drug, an anti-hypertensive drug, an appetite suppressant drug, a lipid-lowering drug, or a combination thereof.

16. The pharmaceutical composition of claim 15, wherein each anti-diabetic and anti-hyperglycemic drug is independently selected from a SGLT2 inhibitor, a biguanide drug, a sulfonylurea drug, a glucosidase inhibitor, a PPAR agonist, a αP2 inhibitor, PPARα/γ dual activator, a dipeptidyl peptidase IV inhibitor, a glinides drug, an insulin, a glucagon-like peptide-1 inhibitor, a PTP1B inhibitor, a glycogen phosphorylase inhibitor, a glucose-6-phosphatase inhibitor or a combination thereof; wherein the anti-obesity drug is selected from a central anti-obesity drug, a MCH receptor antagonist, a neuropeptide Y receptor antagonist, a cannabinoid receptor antagonist, a cerebrointestinal peptide antagonist, a lipase inhibitor, a (33 agonist, a 11β-HSD1 inhibitor, a DGAT-1 inhibitor, a peptide appetite inhibitor, a cholecystokinin agonist, a feeding inhibitor or a combination thereof; wherein the lipid-lowering drug is selected from a MTP inhibitor, a HMGCoA reductase inhibitor, a squalene synthase inhibitor, a betinic acid-type hypolipidemic drug, an ACAT inhibitor, a lipoxygenase inhibitor, a cholesterol absorption inhibitor, an ileum sodium ion/bile acid co-transporter inhibitor, an up-regulator of LDL receptor activity, a nicotinic hypolipidemic drug, a bile acid chelate, or a combination thereof; or wherein the lipid-lowering drug is selected from pravastatin, simvastatin, atorvastatin, fluvastatin, cerivastatin, atorvastatin, rosuvastatin, or a combination thereof.

17. A method of inhibiting SGLT1, or improving the intestinal environment, or treating a disease, lessening a disease symptom or delaying the progression or onset of a disease in a subject comprising administering to the subject a therapeutically effective amount of the compound of claim 1, wherein the disease is diabetes, diabetic complication, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders related to blood concentration, constipation, or high blood pressure;

wherein, the diabetic complication is diabetic retinopathy, diabetic neuropathy or diabetic nephropathy; the hyperlipidemia is hypertriglyceridemia.

18. A method of inhibiting SGLT1, or improving the intestinal environment, or preventing or treating a disease, lessening a disease symptom or delaying the progression or onset of a disease in a subject comprising administering to the subject a therapeutically effective amount of the pharmaceutical composition of claim 14, wherein the disease is diabetes, diabetic complication, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders related to blood concentration, constipation, or high blood pressure;

wherein, the diabetic complication is diabetic retinopathy, diabetic neuropathy or diabetic nephropathy; the hyperlipidemia is hypertriglyceridemia.

* * * * *